(12) United States Patent
Cohen et al.

(10) Patent No.: US 9,126,938 B2
(45) Date of Patent: Sep. 8, 2015

(54) PHOSPHATIDYLCHOLINE TRANSFER PROTEIN INHIBITORS

(75) Inventors: David Cohen, Chestnut Hill, MA (US); Neil Wagle, Brookline, MA (US); Gregory D. Cuny, Cambridge, MA (US); Jun Xian, Sharon, MA (US); Marcie Glicksman, Winchester, MA (US); Ross L. Stein, Cambridge, MA (US); Ekaterina Y. Shishova, Bryn Mawr, PA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 474 days.

(21) Appl. No.: 13/390,910

(22) PCT Filed: Aug. 17, 2010

(86) PCT No.: PCT/US2010/045752
§ 371 (c)(1),
(2), (4) Date: Jul. 5, 2012

(87) PCT Pub. No.: WO2011/022393
PCT Pub. Date: Feb. 24, 2011

(65) Prior Publication Data
US 2012/0264756 A1    Oct. 18, 2012

Related U.S. Application Data

(60) Provisional application No. 61/234,545, filed on Aug. 17, 2009.

(51) Int. Cl.
| | |
|---|---|
| *C07D 239/42* | (2006.01) |
| *A61K 31/505* | (2006.01) |
| *A61P 1/16* | (2006.01) |
| *A61P 3/04* | (2006.01) |
| *A61P 3/10* | (2006.01) |
| *A61P 9/10* | (2006.01) |
| *A61P 11/06* | (2006.01) |
| *C07D 213/60* | (2006.01) |

(Continued)

(52) U.S. Cl.
CPC .............. *C07D 213/60* (2013.01); *A61K 31/44* (2013.01); *A61K 31/505* (2013.01); *C07D 239/32* (2013.01); *C07D 239/42* (2013.01)

(58) Field of Classification Search
CPC ........................... C07D 239/42; A61K 31/505
USPC .................... 544/297, 327; 514/275, 256
See application file for complete search history.

(56) References Cited

U.S. PATENT DOCUMENTS
2012/0264756 A1    10/2012    Cohen et al.

FOREIGN PATENT DOCUMENTS
| | | |
|---|---|---|
| WO | WO 02/00196 | 1/2002 |
| WO | WO 2006/044682 | 4/2006 |

(Continued)

OTHER PUBLICATIONS

Kang et al., Trends Endocrinol Metab. Jul. 2010 ; 21(7): 449-456.*

(Continued)

*Primary Examiner* — Venkataraman Balasubramanian
(74) *Attorney, Agent, or Firm* — Fish & Richardson P.C.

(57) ABSTRACT

This invention relates to compounds of Formulas I, II, and III, and their use as inhibitors of phosphatidylcholine transfer protein (PC-TP). The invention further relates to pharmaceutical compositions and methods of treatment of disorders related to the inhibition of PC-TP using the compounds of Formulas I, II, and III. Such disorders include obesity and disorders associated with obesity.

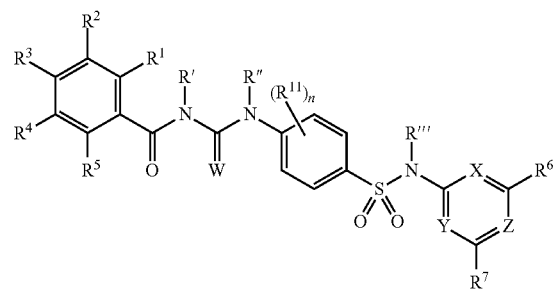

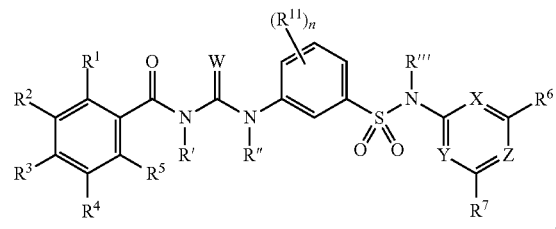

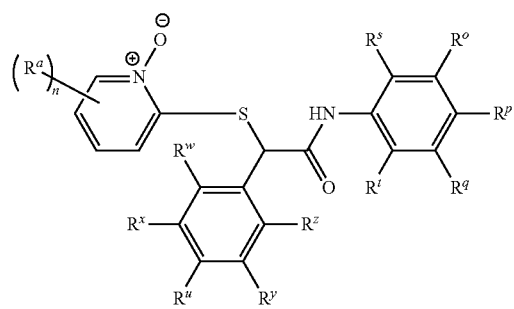

21 Claims, 3 Drawing Sheets

(51) Int. Cl.
A61K 31/44 (2006.01)
C07D 239/32 (2006.01)

(56) References Cited

FOREIGN PATENT DOCUMENTS

WO WO 2009/047558 4/2009
WO WO 2011/022393 2/2011

OTHER PUBLICATIONS

Ersoy et al.,Sci Signal. ; 6(286): ra64, pp. 1-22, 2004.*
Jia et al., Youji Huaxue (1993), 13(3), 250-2; CA 119: 203372, 1993, CAPLUS Abstract provided.*
Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ferrara, N, Oncology, 69 Suppl. 3, 11-16, 2005.*
Jain et al., Nature Clinical Practice Oncology, 3(1), 24-40, 2006.*
Gautschi et al., Clin. Cancer Res., 14(6), 1639-1648, 2008.*
Mountzios et al., Cancer Treatments Reviews, 34, 175-182, 2008.*
Qiu Y., Oncogene 19, 5651-5661,2000.*
Lima et al. Current Medicinal Chemistry, 2005, 12, 23-49 23.*
International Search Report and Written Opinion in International Application No. PCT/US2010/045752, mailed Apr. 28, 2011, 13 pages.
International Preliminary Report on Patentability in International Application No. PCT/US2010/045752, mailed Mar. 1, 2012, 8 pages.
Extended European Search Report in European Application No. EP 10810484.5, dated, May 24, 2013, 3 pages.
Berge et al., "Pharmaceutical Salts", Journal of Pharmaceutical Science, 66(1), 21 pages (1977).
Brawer et al., "Obesity and cancer," Prim Care, 2009, 36:509-531.
Breslow, "Mouse model of atherosclerosis," Science, 1996, 272:685-688.
Cypess et al., "Identification and importance of brown adipose tissue in adult humans," N. Engl. J. Med., 2009, 360:1509-1517
de Brouwer et al., "Clofibrate-induced relocation of phosphatidylcholine transfer protein to mitochondria in endothelial cells," Exp. Cell Res., 2002, 274:100-111.
Dolley et al., "Influences of the phosphatidylcholine transfer protein gene variants on the LDL peak particle size," Atherosclerosis, 2007, 195:297-302.
Greene et al., Protective Groups in Organic Synthesis, 4d. Ed., Wiley & Sons, 2007.
Kang et al., "Mice lacking phosphatidylcholine transfer protein/ StarD2 exhibit increased adaptive thermogenesis and enlarged mitochondria in brown adipose tissue," J Lipid Res., 2009.
Kanno et al., "Interacting proteins dictate function of the minimal Start domain phosphatidylcholine transfer protein/StarD2," J Biol Chem., 2007, 282:30728-30736.
Kanno et al., "Structure and function of phosphatidylcholine transfer protein (PC-TP)/StarD2," Biochim Biophys Acta., 2007, 1771:654-662 (Author Manuscript).
Leff, "Role of leukotrienes in bronchial hyperresponsiveness and cellular responses in airways," Am. J. Respir Crit. Care Med., 2000, 161:S125-S132.
Lemmetyinen et al., "Quenching of fluorescence of pyrene-substituted lecithin by tetracyanoquinodimethane in liposomes," Biophys. J., 1989, 55:885-895.

Levy et al., "Multi-pronged inhibition of airway hyper-responsiveness and inflammation by lipoxin A(4)," Nat. Med., 2002, 8:1018-1023.
Martin et al., "Diet-induced obesity alters AMP kinase activity in hypothalamus and skeletal muscle," J Biol. Chem., 2006, 281:18933-18941.
Mootha et al., "Integrated analysis of protein composition, tissue diversity, and gene regulation in mouse mitochondria," Cell, 2003, 115:629-640.
Ponting and Aravind, "Start: a lipid-binding domain in StAR, HD-ZIP and signaling proteins," Trends Biochem. Sci., 1999, 24:130-132.
Remington's Pharmaceutical Sciences, 17$^{th}$ ed., Mack Publishing Company, Easton, PA., 1985.
Roderick et al., "Structure of human phosphatidylcholine transfer protein in complex with its ligand," Nature Struct. Biol., 2002, 9:507-511.
Scapa et al., "Regulation of energy substrate utilization and hepatic insulin sensitivity by phosphatidylcholine transfer protein/Star D2," FASEB J, 2008, 22:2579-2590.
SciFinder Scholar search "W=O meta," conducted Jul. 28, 2009, 2 pages.
SciFinder Scholar search "W=O X=Y=N meta," conducted Jul. 28, 2009, 2 pages.
SciFinder Scholar search "W=S meta," conducted Jul. 28, 2009, 6 pages.
SciFinder Scholar search "W=S para," conducted Jul. 28, 2009, 45 pages.
SciFinder Scholar search "W=S X=Y=N para," conducted Jul. 28, 2009, 13 pages.
SciFinder Scholar search "W=S X=Z=N para," conducted Jul. 28, 2009, 8 pages.
Shishova et al., "Genetic Ablation or Chemical Inhibition of Phosphatidylcholine Transfer Protein Attenuates Diet-Induced Hepatic Glucose Production," Hepatology, 2011, 54(2):664-674.
van Marken Lichtenbelt et al., "Cold-activated brown adipose tissue in healthy men," N. Engl. J. Med., 2009, 360:1500-1508.
Van Paridon et al., "On the relationship between the dual specificity of the bovine brain phosphatidylinositol transfer protein and membrane phosphatidylinositol levels" Biochim Biophys Acta, 1987, 903:68-77.
Virtanen et al., "Functional brown adipose tissue in healthy adults," N. Engl. J. Med., 2009, 360:1518-1525.
Wagle et al., "Small molecule inhibitors of phosphatidylcholine transfer protein/StarD2 identified by high throughput screening," Anal. Biochem., 2008, 383:85-92.
Wang et al., "Homozygous disruption of Pctp modulates atherosclerosis in apolipoprotein E deficient mice," J Lipid Res., 2006, 47:2400-2407.
Wirtz, "Phospholipid Transfer Proteins," Ann. Rev. Biochem., 1991, 60:73-99.
Wu et al., "Impaired response of biliary lipid secretion to a lithogenic diet in phosphatidylcholine transfer protein-deficient mice," J Lipid Res., 2005, 46:422-431.
Yao et al., "Synthesis and structures of (S)-and (R)-2-[3-cyano-4-(2-thienyl)-5,6,7,8-tetrahydroquinolin-2-ylsulfanyl]-3-methyl-N-phenylbutyramide," J. Chem. Res., 2006, 1:3-5.
Zhi et al., "The deregulation of arachidonic acid metabolism-related genes in human esophageal squamous cell carcinoma," Int. J. Cancer, 2003, 106:327-333.
Heart Disease Health Center, "Atherosclerosis and Coronary Artery Disease," WebMD Medical Reference, http://www.webmd.com/heart-disease/atherosclerosis-and-coronary-artery-disease (2014).
Joslin Diabetes Center, "Joslin Study Finds Insulin Resistance Causes Gallstones," Joslin Diabetes Center News, http://www.joslin.org/news/joslin_study_finds_insulin_resistance_causes_gallstones.html (2008).

* cited by examiner

PHOSPHATIDYLCHOLINE TRANSFER PROTEIN INHIBITORS

FEDERALLY SPONSORED RESEARCH OR DEVELOPMENT

This invention was made with Government support under Grant Nos. R01 DK48873 and R01 DK56626 awarded by the National Institutes of Health. The Government has certain rights in the invention.

This application is a §371 National Stage Application of International Application PCT/US2010/045752, filed Aug. 17, 2010, which claims the benefit of priority of U.S. Provisional Appl. No. 61/234,545, filed Aug. 17, 2009, which is incorporated herein by reference in its entirety.

TECHNICAL FIELD

The present invention relates to inhibitors of phosphatidylcholine transfer protein (PC-TP), pharmaceutical compositions thereof, and methods of treatment of disorders related thereto.

BACKGROUND

Obesity has become an epidemic in the U.S. and other developed countries. As many as one-third of all Americans over 30 years of age are obese, based on the body mass index (BMI) criteria, and as many as one in three adults in the United States are attempting to loose weight. Each year, 30 billion dollars is spent on the treatment of obesity. Yet, despite this, less is known about the causes of obesity than is known about the causes of most other medical conditions. Accordingly, there is a need to develop new compounds for treatment of obesity and disorders associated with obesity. This invention addresses this need and others.

SUMMARY

The present invention provides, inter alia, compounds of Formulas I, II, or III:

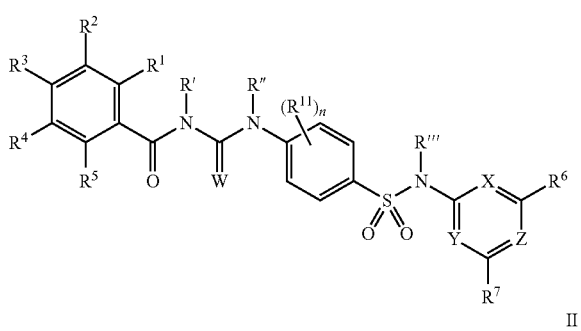

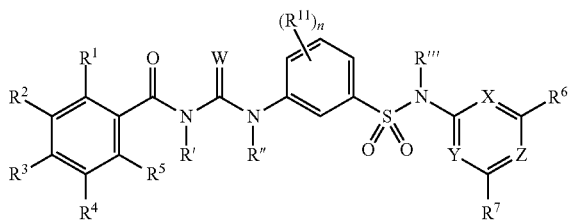

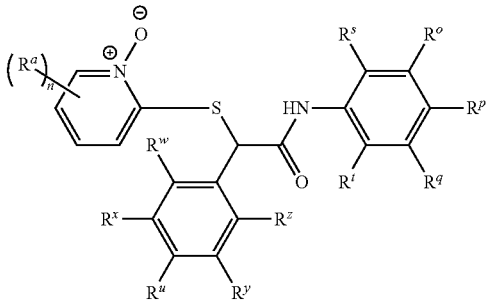

and their pharmaceutically acceptable salts, as well as pharmaceutical compositions comprising the compounds described herein.

The present invention further provides methods of treating obesity, disorders associated with obesity and disorders treatable with PC-TP inhibitors or reducing the risk of obesity using the compounds described herein, and their pharmaceutically acceptable salts. Also provided are methods of reducing a subject's risk of developing a disorder associated with obesity, disorders associated with obesity and disorders treatable with PC-TP inhibitors using the compounds described herein.

The present invention also provides compounds as described herein for use in treatment of obesity, disorders associated with obesity, and disorders treatable by PC-TP inhibitors or reducing the risk of obesity. The present invention further provides the use of the compounds described herein for the manufacture of a medicament for use in treatment of obesity, disorders associated with obesity, and disorders treatable by PC-TP inhibitors, or reducing the risk of obesity. In some embodiments, the disorders treatable by PC-TP inhibitor include, but are not limited to, type 2 diabetes, non-alcoholic fatty liver disease, asthma, hypertension, hyperlipidemia, coronary artery disease, arthritis, gallstones, osteoarthritis, atherosclerosis, sleep apnea, depression, cancer, and gastroesophagael reflux disease.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION

Figure 1:
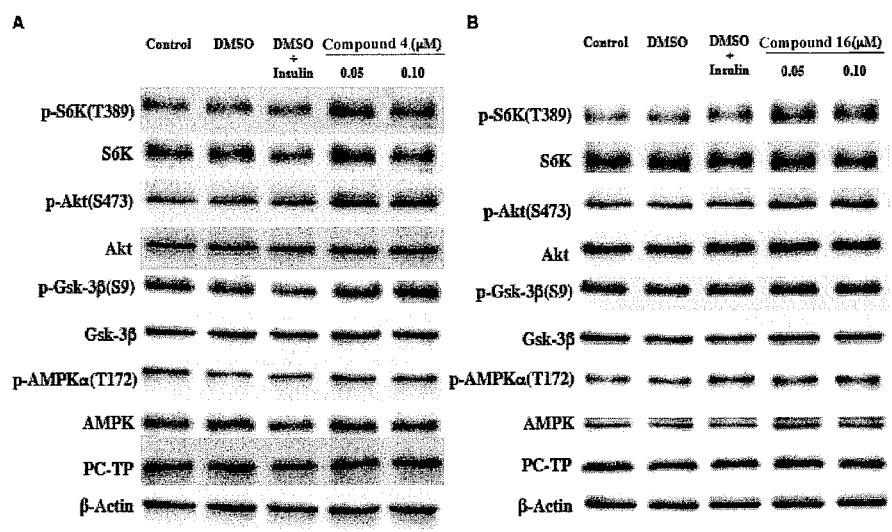
FIG. 1 depicts activation of the insulin-signaling pathway in human heptacycles for Compounds 4 and 16.

The present invention provides, inter alia:
(a) a compound of Formula I or II:

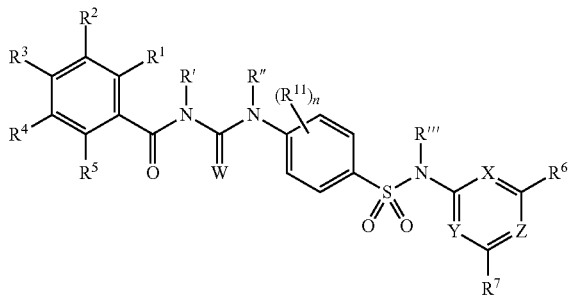

I

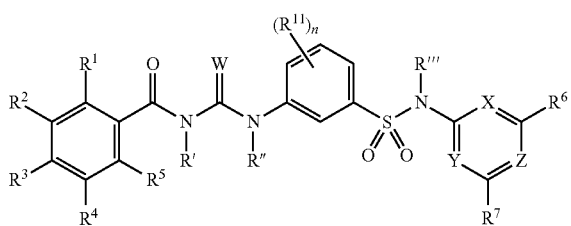

II wherein:

X is N or $CR^8$;

Y is N or $CR^9$;

Z is N or $CR^{10}$;

W is O or S;

R', R", and R'" are each independently selected from H and $C_{1-4}$ alkyl; wherein said $C_{1-4}$ alkyl is optionally substituted with di-$C_{1-4}$-alkylamino;

$R^1$, $R^2$, $R^3$, $R^4$, and $R^5$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;

or $R^1$ and $R^2$, together with the carbon atoms to which they are attached, form an phenyl or $C_{1-6}$ heteroaryl ring, which is optionally substituted with 1, 2, 3, or 4 independently selected $R^{a''}$ groups;

or $R^2$ and $R^3$, together with the carbon atoms to which they are attached, form an phenyl or $C_{1-6}$ heteroaryl ring, which is optionally substituted with 1, 2, 3, or 4 independently selected $R^{a''}$ groups;

or $R^3$ and $R^4$, together with the carbon atoms to which they are attached, form an phenyl or $C_{1-6}$ heteroaryl ring, which is optionally substituted with 1, 2, 3, or 4 independently selected $R^{a''}$ groups;

$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;

or $R^6$ and $R^8$, together with the carbon atoms to which they are attached, form an phenyl or $C_{1-6}$ heteroaryl ring, which is optionally substituted with 1, 2, 3, or 4 independently selected $R^{b''}$ groups;

or $R^6$ and $R^{10}$, together with the carbon atoms to which they are attached, form an phenyl or $C_{1-6}$ heteroaryl ring, which is optionally substituted with 1, 2, 3, or 4 independently selected $R^{b''}$ groups;

or $R^7$ and $R^9$, together with the carbon atoms to which they are attached, form an phenyl or $C_{1-6}$ heteroaryl ring, which is optionally substituted with 1, 2, 3, or 4 independently selected $R^{b''}$ groups;

or $R^7$ and $R^{10}$, together with the carbon atoms to which they are attached, form an phenyl or $C_{1-6}$ heteroaryl ring, which is optionally substituted with 1, 2, 3, or 4 independently selected $R^{b''}$ groups;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;

each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4;

(b) a compound of Formula III:

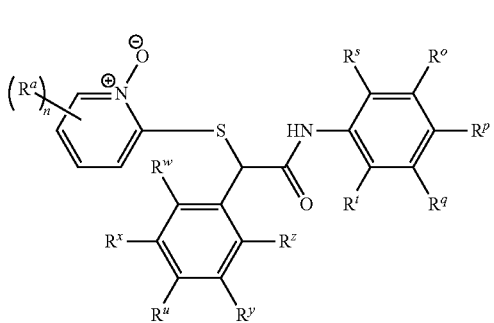

wherein:

each $R^a$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

or any two adjacent $R^a$ groups, together with the atoms to which they are attached, form a phenyl or $C_{1-6}$ heteroaryl group; each of which is optionally substituted by 1, 2, 3, or 4 independently selected $R^{a'}$ groups;

$R^s$, $R^t$, $R^o$, $R^p$, and $R^q$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl; wherein the $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, or 3 independently selected $R^{o'}$ groups;

$R^u$, $R^w$, $R^x$, $R^y$, and $R^z$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

or $R^y$ and $R^z$, together with the carbon atoms to which they are attached, form a phenyl ring or $C_{1-6}$ heteroaryl ring, each of which is optionally substituted by 1, 2, or 3 $R^g$ groups;

or $R^u$ and $R^y$, together with the carbon atoms to which they are attached, form a phenyl ring or $C_{1-6}$ heteroaryl ring, each of which is optionally substituted by 1, 2, or 3 $R^g$ groups;

each $R^{a'}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^g$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{o'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4;

or a pharmaceutically acceptable salt thereof.

In some embodiments, the present invention provides a compound as described above wherein R, R", and R''' are each independently selected from H and $C_{1-4}$ alkyl.

In some embodiments, $R^1$, $R^2$, $R^3$, $R^4$, and $R^5$ are each independently selected from H, halogen, cyano, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups.

In some embodiments, the compound is not selected from any of the compounds in Appendix I, or a pharmaceutically acceptable salt thereof. In some embodiments, the compound is not selected from compounds 2 and 3 of Table 1, or a pharmaceutically acceptable salt thereof. In some embodiments, the compound is not selected from any of the compounds in Appendix I and compounds 2 and 3 of Table 1, or a pharmaceutically acceptable salt thereof.

In some embodiments, the compound is a compound of Formula I:

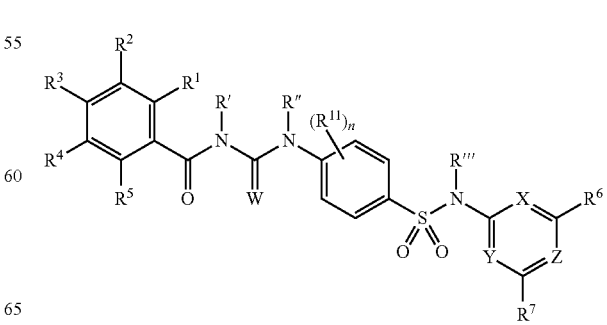

or a pharmaceutically acceptable salt thereof; wherein:
X is N or $CR^8$;
Y is N or $CR^9$;
Z is N or $CR^{10}$;
W is O;
R', R'', and R''' are each independently selected from H and $C_{1-4}$ alkyl; wherein said $C_{1-4}$ alkyl is optionally substituted by di-$C_{1-6}$-alkylamino;
$R^1$, $R^2$, $R^3$, $R^4$, and $R^5$ are each independently selected from H, halogen, cyano, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;

or $R^1$ and $R^2$, together with the carbon atoms to which they are attached, form an phenyl or $C_{1-6}$ heteroaryl ring, which is optionally substituted with 1, 2, 3, or 4 independently selected $R^{a''}$ groups;

or $R^2$ and $R^3$, together with the carbon atoms to which they are attached, form an phenyl or $C_{1-6}$ heteroaryl ring, which is optionally substituted with 1, 2, 3, or 4 independently selected $R^{a''}$ groups;

or $R^3$ and $R^4$, together with the carbon atoms to which they are attached, form an phenyl or $C_{1-6}$ heteroaryl ring, which is optionally substituted with 1, 2, 3, or 4 independently selected $R^{a''}$ groups;

$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;

or $R^6$ and $R^8$, together with the carbon atoms to which they are attached, form an phenyl or $C_{1-6}$ heteroaryl ring, which is optionally substituted with 1, 2, 3, or 4 independently selected $R^{b''}$ groups;

or $R^6$ and $R^{10}$, together with the carbon atoms to which they are attached, form an phenyl or $C_{1-6}$ heteroaryl ring, which is optionally substituted with 1, 2, 3, or 4 independently selected $R^{b''}$ groups;

or $R^7$ and $R^9$, together with the carbon atoms to which they are attached, form an phenyl or $C_{1-6}$ heteroaryl ring, which is optionally substituted with 1, 2, 3, or 4 independently selected $R^{b''}$ groups;

or $R^7$ and $R^{10}$, together with the carbon atoms to which they are attached, form an phenyl or $C_{1-6}$ heteroaryl ring, which is optionally substituted with 1, 2, 3, or 4 independently selected $R^{b''}$ groups;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;

each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4;

provided that:

(1) when the compound has Formula I, W is O, Z is CH, n is 0, $R^1$, $R^2$, $R^4$, $R^5$, $R^6$ and $R^7$ are each H, and either X is N and Y is CH, or X is CH and Y is N, then $R^3$ is other than chloro; and (2) when the compound has Formula I, W is O, X is N, Y is N, and Z is $CR^{10}$, then the following provisos apply:

(a) when $R^6$ and $R^7$ are each methyl or each H, $R^{10}$ is H, and $R^1$, $R^2$, $R^4$, and $R^5$ are H, then $R^3$ is not methoxy or chloro; and (b) when $R^6$ and $R^7$ are each methyl or each H and $R^{10}$ is H, then at least one of $R^1$, $R^2$, $R^3$, $R^4$, and $R^5$ is other than H.

In some embodiments, W is S. In some embodiments, W is O.

In some embodiments, n is 0.

In some embodiments, each $R^{11}$ is independently selected from halogen, $C_{1-4}$ alkyl and $C_{1-4}$ haloalkyl. In some embodiments, each $R^{11}$ is independently halogen.

In some embodiments, R', R'', and R''' are each independently selected from H and methyl. In some embodiments, R', R'', and R''' are each independently selected from H and methyl, provided at least two of R', R'', and R''' are H. In some embodiments, R', R'', and R''' are each independently selected from H and methyl, provided at least one of R', R'', and R''' is H. In some embodiments, R', R'', and R''' are each H.

In some embodiments, $R^1$, $R^2$, $R^3$, $R^4$, and $R^5$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylthio, $C_{1-6}$ alkylsulfinyl, and $C_{1-6}$ alkylsulfonyl. In some embodiments, $R^1$, $R^2$, $R^3$, $R^4$, and $R^5$ are each independently selected from H, halogen, cyano, nitro, and hydroxyl. In some embodiments, $R^1$, $R^2$, $R^3$, $R^4$, and $R^5$ are each independently selected from H and halogen. In some embodiments, $R^1$ and $R^3$ are each independently chloro.

In some embodiments, $R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylthio, and $C_{1-6}$ alkylsulfinyl, and $C_{1-6}$ alkylsulfonyl. In some embodiments, $R^6$, $R^7$, $R^8$, $R^9$, and $R^{10}$ are each independently selected from H, hydroxyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, and di-$C_{1-6}$-alkylamino. In some embodiments, $R^6$, $R^7$, $R^8$, $R^9$, and $R^{10}$ are each independently H and $C_{1-6}$ alkyl. In some embodiments, $R^6$, $R^7$, $R^8$, $R^9$, and $R^{10}$ are each independently H and methyl. In some embodiments, $R^6$ and $R^7$ are each independently methyl.

In some embodiments, $R^6$ and $R^7$ are each other than H. In some embodiments, either one or both of $R^6$ or $R^7$ is other H.

In some embodiments, X is N, Y is N, and Z is CH. In some embodiments, X is N, Y is CH, and Z is CH. In some embodiments, X is N, Y is CH, and Z is N. In some embodiments, X is CH, Y is CH, and Z is CH.

In some embodiments, the compound is a compound of Formula I, or a pharmaceutically acceptable salt thereof. In some embodiments, the compound is a compound of Formula II, or a pharmaceutically acceptable salt thereof.

In some embodiments:
X is N, Y is N, and Z is CH; or
X is N, Y is CH, and Z is CH; or
X is N, Y is CH, and Z is N; or
X is CH, Y is CH, and Z is CH;
R', R", and R''' are each independently selected from H and $C_{1-3}$ alkyl;
$R^1$, $R^2$, $R^3$, $R^4$, and $R^5$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylthio, $C_{1-6}$ alkylsulfinyl, and $C_{1-6}$ alkylsulfonyl;
$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylthio, and $C_{1-6}$ alkylsulfinyl, and $C_{1-6}$ alkylsulfonyl; and
n is 0.

In some embodiments:
X is N, Y is N, and Z is CH; or
X is N, Y is CH, and Z is CH; or
X is N, Y is CH, and Z is N; or
X is CH, Y is CH, and Z is CH;
R', R", and R''' are each independently selected from H and $C_{1-2}$ alkyl;
$R^1$, $R^2$, $R^3$, $R^4$, and $R^5$ are each independently selected from H, halogen, cyano, nitro, and hydroxyl;
$R^6$, $R^7$, $R^8$, $R^9$, and $R^{10}$ are each independently selected from hydroxyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, and di-$C_{1-6}$-alkylamino; and
n is 0.

In some embodiments:
X is N, Y is N, and Z is CH; or
X is N, Y is CH, and Z is CH; or
X is N, Y is CH, and Z is N; or
X is CH, Y is CH, and Z is CH;
R', R", and R''' are each independently selected from H and methyl;
$R^1$, $R^2$, $R^3$, $R^4$, and $R^5$ are each independently selected from H and halogen;
$R^6$, $R^7$, $R^8$, $R^9$, and $R^{10}$ are each independently H and $C_{1-6}$ alkyl; and
n is 0.

In some embodiments:
X is N, Y is N, and Z is CH; or
X is N, Y is CH, and Z is CH; or
X is N, Y is CH, and Z is N; or
X is CH, Y is CH, and Z is CH;
R', R", and R''' are each independently selected from H and methyl;
$R^1$, $R^2$, $R^3$, $R^4$, and $R^5$ are each independently selected from H and chloro;
$R^6$, $R^7$, $R^8$, $R^9$, and $R^{10}$ are each independently H and methyl; and
n is 0.

In some embodiments:
X is N, Y is N, and Z is CH; or
X is N, Y is CH, and Z is CH; or
X is N, Y is CH, and Z is N; or
X is CH, Y is CH, and Z is CH;
R', R", and R''' are each independently selected from H and $C_{1-3}$ alkyl;
$R^1$, $R^2$, $R^3$, $R^4$, and $R^5$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, $C_{1-6}$ alkylcarbamyl, alkylcarbamyl, $C_{1-6}$ alkoxycarbonyl, $C_{1-6}$ alkylcarbonyl, $C_{1-6}$ alkylthio, $C_{1-6}$ alkylsulfinyl, and $C_{1-6}$ alkylsulfonyl;
$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, $C_{1-6}$ alkylcarbamyl, alkylcarbamyl, $C_{1-6}$ alkoxycarbonyl, $C_{1-6}$ alkylcarbonyl, $C_{1-6}$ alkylthio, and $C_{1-6}$ alkylsulfinyl, and $C_{1-6}$ alkylsulfonyl; provided that one or both of $R^6$ and $R^7$ are other than H; and
n is 0.

In some embodiments:
X is N, Y is N, and Z is CH; or
X is N, Y is CH, and Z is CH; or
X is N, Y is CH, and Z is N; or
X is CH, Y is CH, and Z is CH;
R', R", and R''' are each independently selected from H and $C_{1-2}$ alkyl;
$R^1$, $R^2$, $R^3$, $R^4$, and $R^5$ are each independently selected from H, halogen, cyano, nitro, and hydroxyl;
$R^6$, $R^7$, $R^8$, $R^9$, and $R^{10}$ are each independently selected from hydroxyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, and di-$C_{1-6}$-alkylamino; provided that one or both of $R^6$ and $R^7$ are other than H; and
n is 0.

In some embodiments:
X is N, Y is N, and Z is CH; or
X is N, Y is CH, and Z is CH; or
X is N, Y is CH, and Z is N; or
X is CH, Y is CH, and Z is CH;
R', R", and R''' are each independently selected from H and methyl;
$R^1$, $R^2$, $R^3$, $R^4$, and $R^5$ are each independently selected from H and halogen;
$R^6$, $R^7$, $R^8$, $R^9$, and $R^{10}$ are each independently H and $C_{1-6}$ alkyl; provided that one or both of $R^6$ and $R^7$ are other than H; and
n is 0.

In some embodiments:
X is N, Y is N, and Z is CH; or
X is N, Y is CH, and Z is CH; or
X is N, Y is CH, and Z is N; or
X is CH, Y is CH, and Z is CH;
R', R", and R'" are each independently selected from H and methyl;
$R^1$, $R^2$, $R^3$, $R^4$, and $R^5$ are each independently selected from H and chloro;
$R^6$, $R^7$, $R^8$, $R^9$, and $R^{10}$ are each independently H and methyl; provided that one or both of $R^6$ and $R^7$ are other than H; and
n is 0.

In any of the preceding embodiments, the compound may be a compound of Formula Ia:

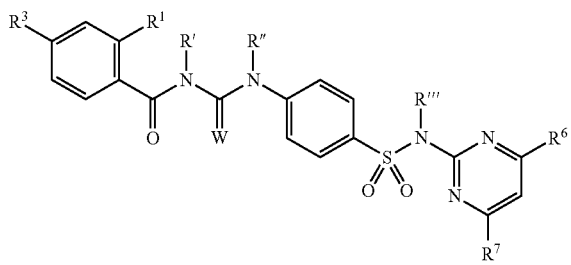

Ia or a pharmaceutically acceptable salt thereof.

In any of the preceding embodiments, the compound may be a compound of Formula Ib:

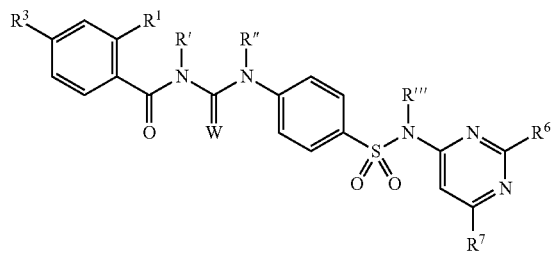

Ib or a pharmaceutically acceptable salt thereof. In some embodiments, W is S. In some embodiments, W is O.

In any of the preceding embodiments, the compound may be a compound of Formula Ic:

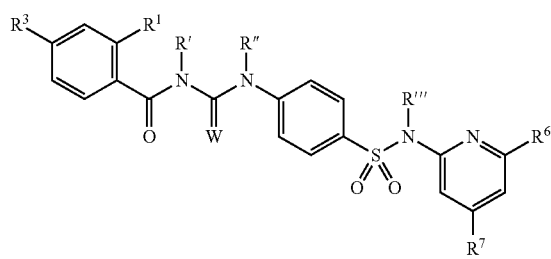

Ic or a pharmaceutically acceptable salt thereof. In some embodiments, W is S. In some embodiments, W is O.

In any of the preceding embodiments, the compound may be a compound of Formula Id:

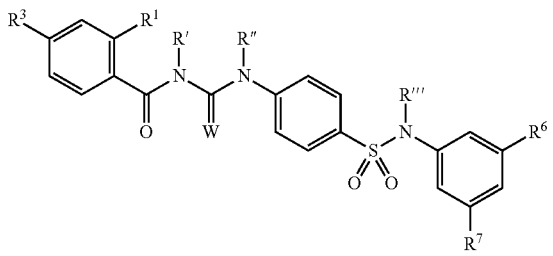

Id or a pharmaceutically acceptable salt thereof. In some embodiments, W is S. In some embodiments, W is O.

In any of the preceding embodiments, the compound may be a compound of Formula Ie:

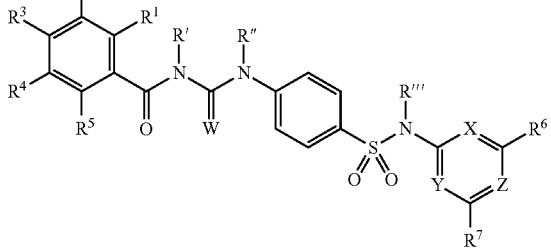

Ie or a pharmaceutically acceptable salt thereof. In some embodiments, W is S. In some embodiments, W is O.

In any of the preceding embodiments, the compound may be a compound of Formula If:

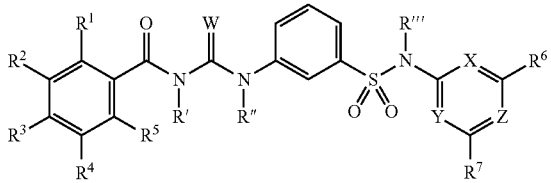

If or a pharmaceutically acceptable salt thereof. In some embodiments, W is S. In some embodiments, W is O.

In some of the preceding embodiments, when the compound has Formula I, W is O, Z is CH, n is 0, $R^1$, $R^2$, $R^4$, $R^5$, $R^6$ and $R^7$ are each H, and either X is N and Y is CH, or X is CH and Y is N, then $R^3$ is other than chloro.

In some of the preceding embodiments, when the compound has Formula I, W is O, Z is CH, n is 0, $R^1$, $R^2$, $R^4$, $R^5$, $R^6$ and $R^7$ are each H, and either X is N and Y is CH, or X is CH and Y is N, then $R^3$ is other than halogen.

In some of the preceding embodiments, when the compound has Formula I, W is O, Z is CH, n is 0, $R^6$ and $R^7$ are each H and either X is N and Y is CH, or X is CH and Y is N, then $R^1$, $R^2$, $R^3$, $R^4$, and $R^5$ are other than halogen.

In some embodiments, the compound is a compound of Formula I, or a pharmaceutically acceptable salt thereof, wherein:

X is N and Y is CH; or
X is CH and Y is N;
Z is CH;
W is O;
R', R", and R''' are each independently selected from H and $C_{1-4}$ alkyl;
$R^1$, $R^2$, $R^3$, $R^4$, and $R^5$ are each independently selected from H, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, alkylcarbamyl, $C_{1-6}$ alkoxycarbonyl, $C_{1-6}$ alkylcarbonyl, $C_{1-6}$ alkylcarbonylamino, alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;
$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, $C_{1-6}$ alkylcarbamyl, alkylcarbamyl, $C_{1-6}$ alkoxycarbonyl, $C_{1-6}$ alkylcarbonyl, $C_{1-6}$ alkylcarbonylamino, alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, alkylcarbamyl, $C_{1-6}$ alkoxycarbonyl, $C_{1-6}$ alkylcarbonyl, $C_{1-6}$ alkylcarbonylamino, alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;
each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, alkylcarbamyl, $C_{1-6}$ alkoxycarbonyl, $C_{1-6}$ alkylcarbonyl, $C_{1-6}$ alkylcarbonylamino, alkylcarbonylamino, $C_{1-6}$ alkylthio, $C_{1-6}$ alkylsulfinyl, and $C_{1-6}$ alkylsulfonyl;
each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;
each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and
n is an integer selected from 0, 1, 2, 3, and 4.

In some of the preceding embodiments, when W is S, X is $CR^8$, Y is $CR^9$, and Z is $CR^{10}$, then the compound does not have Formula I.

In some of the preceding embodiments, when W is S, X is $CR^8$, Y is $CR^9$, and Z is $CR^{10}$, then the compound does not have Formula I.

In some of the preceding embodiments, when the compound has Formula II, W is S, X is $CR^8$, Y is $CR^9$, and Z is $CR^{10}$, then the following provisos apply:

(a) n is 0;
(b) if one of $R^1$ or $R^5$ is chloro and four of $R^1$, $R^2$, $R^3$, $R^4$, and $R^5$ are H, then at least one of $R^6$ and $R^7$ is other than trifluoromethyl;
(c) if one of $R^1$ or $R^5$ is bromo and four of $R^1$, $R^2$, $R^3$, $R^4$, and $R^5$ are H, then at least one of $R^8$ or $R^9$ is other than methoxy;
(d) if one of $R^2$ or $R^4$ is nitro and four of $R^1$, $R^2$, $R^3$, $R^4$, and $R^5$ are H, then at least one of $R^6$ and $R^7$ is other than chloro;
(e) if

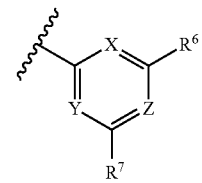

is 2-bromo-5-methylphenyl, then

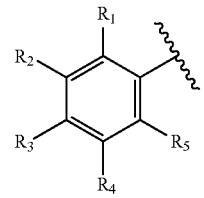

is not naphth-2-yl; and (f) if $R^2$ and $R^4$ are each methoxy and $R^1$, $R^3$, and $R^5$ are each H, then

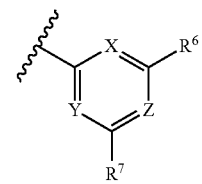

is not 2-bromo-5-methylphenyl.

In some of the preceding embodiments, when the compound has Formula II, W is S, X is $CR^8$, Y is $CR^9$, and Z is $CR^{10}$, then the following provisos apply:

(a) n is 0;
(b) if one of $R^1$ or $R^5$ is halogen and four of $R^1$, $R^2$, $R^3$, $R^4$, and $R^5$ are H, then at least one of $R^6$ and $R^7$ is other than $C_{1-4}$ haloalkyl;
(c) if one of $R^1$ or $R^5$ is halogen and four of $R^1$, $R^2$, $R^3$, $R^4$, and $R^5$ are H, then at least one of $R^8$ or $R^9$ is other than $C_{1-4}$ alkoxy;
(d) if one of $R^2$ or $R^4$ is nitro and four of $R^1$, $R^2$, $R^3$, $R^4$, and $R^5$ are H, then at least one of $R^6$ and $R^7$ is other than halogen;
(e) if

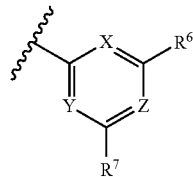

is 2-(halogen)-5-($C_{1-4}$ alkyl)phenyl, then

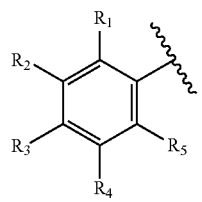

is not a naphthalene ring; and
(f) if $R^2$ and $R^4$ are each $C_{1-4}$ alkoxy and $R^1$, $R^3$, and $R^5$ are each H, then

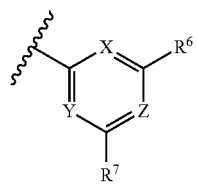

is not 2-(halogen)-5-($C_{1-4}$ alkyl)phenyl.

In some embodiments, the compound is a compound of Formula II, or a pharmaceutically acceptable salt thereof, wherein:

W is S;
X is $CR^8$, Y is $CR^9$, and Z is $CR^{10}$;
R', R", and R'" are each independently selected from H and $C_{1-4}$ alkyl;
$R^1$, $R^2$, $R^3$, $R^4$, and $R^5$ are each independently selected from H, halogen, cyano, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;

$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{2-6}$ alkenyl, $C_{2-6}$ alkynyl, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{2-6}$ alkenyl, $C_{2-6}$ alkynyl, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;

each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and n is 0.

In some of the preceding embodiments, X is not $CR^8$, Y is not $CR^9$, and Z is not $CR^{10}$.

In some of the preceding embodiments, when the compound has Formula I, W is O, X is N, Y is N, and Z is $CR^{10}$, then the following provisos apply:
(a) when $R^6$ and $R^7$ are each methyl or each H, $R^{10}$ is H, and $R^1$, $R^2$, $R^4$, and $R^5$ are H, then $R^3$ is not methoxy or chloro;
(b) when $R^6$ and $R^7$ are each methyl or each H and $R^{10}$ is H, then at least one of $R^1$, $R^2$, $R^3$, $R^4$, and $R^5$ is other than H; and
(c) when $R^{10}$ is bromo, $R^6$ and $R^7$ each H, and at least four of $R^1$, $R^2$, $R^3$, $R^4$, and $R^5$ are H, then $R^1$ or $R^5$ is other than nitro.

In some of the preceding embodiments, when the compound has Formula I, W is O, X is N, Y is N, and Z is $CR^{10}$, where $R^{10}$ is H or halogen, then the following provisos apply:

(a) when $R^6$ and $R^7$ are each methyl or each H, $R^{10}$ is H, and $R^1$, $R^2$, $R^4$, and $R^5$ are H, then $R^3$ is not $C_{1-3}$ alkoxy or halogen;

(b) when $R^6$ and $R^7$ are each methyl or each H and $R^{10}$ is H, then at least one of $R^1$, $R^2$, $R^3$, $R^4$, and $R^5$ is other than H; and (c) when $R^{10}$ is bromo, $R^6$ and $R^7$ each H, and at least four of $R^1$, $R^2$, $R^3$, $R^4$, and $R^5$ are H, then $R^1$ or $R^5$ is other than nitro.

In some of the preceding embodiments, when the compound has Formula I, W is O, X is N, Y is N, and Z is $CR^{10}$, where $R^{10}$ is H or halogen, then $R^1$, $R^2$, $R^3$, $R^4$, and $R^5$ are not selected from halogen, nitro, or $C_{1-3}$ alkoxy.

In some embodiments, the compound is a compound of Formula I, or a pharmaceutically acceptable salt thereof, wherein:

W is O;

X is N, Y is N, and Z is $CR^{10}$;

R', R'', and R''' are each independently selected from H and $C_{1-4}$ alkyl;

$R^1$, $R^2$, $R^3$, $R^4$, and $R^5$ are each independently selected from H, halogen, cyano, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;

$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$ alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;

each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4;

provided that when $R^6$ and $R^7$ are each methyl or each H; and $R^{10}$ is H; then at least one of $R^1$, $R^2$, $R^3$, $R^4$, and $R^5$ is other than H.

In some of the preceding embodiments, when the compound has Formula I, W is S, X is N, Y is CH, and Z is N, then the following provisos apply:

(a) $R^7$ is not methoxy; and (b) the compound is not selected from 4-chloro-N-(4-(N-(6-methylpyrimidin-4-yl)sulfamoyl(phenylcarbamothioyl) benzamide or N-(4-(N-(2,6-dimethylpyrimidin-4-yl)sulfamoyl(phenylcarbamothioyl)-3,4-difluorobenzamide; or a pharmaceutically acceptable salt thereof.

In some of the preceding embodiments, when the compound has Formula I, W is S, X is N, Y is CH, and Z is N, then the following provisos apply:

(a) $R^7$ is not methoxy;

(b) when $R^7$ is methyl, $R^6$ is H, and $R^1$, $R^2$, $R^4$, and $R^5$ are H, then $R^3$ is other than chloro; and (c) when $R^6$ and $R^7$ are each methyl and $R^3$ is fluoro, then at least one of $R^2$ or $R^4$ is other than fluoro.

In some of the preceding embodiments, when the compound has Formula I, W is S, X is N, Y is CH, and Z is N, then the following provisos apply:

(a) $R^7$ is not $C_{1-4}$ alkoxy; and (b) when $R^6$ or $R^7$ are methyl, then $R^3$ is other than halogen.

In some embodiments, when the compound is a compound of Formula I, or a pharmaceutically acceptable salt thereof, wherein:

W is S;

X is N, Y is $CR^9$, and Z is N;

R', R'', and R''' are each independently selected from H and $C_{1-4}$ alkyl;

$R^1$, $R^2$, $R^3$, $R^4$, and $R^5$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;

$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, alkylcarbamyl, $C_{1-6}$ alkoxycarbonyl, $C_{1-6}$ alkylcarbonyl, $C_{1-6}$ alkylcarbonylamino, alkylcarbonylamino, $C_{1-6}$ alkylthio, $C_{1-6}$ alkylsulfinyl, and $C_{1-6}$ alkylsulfonyl;

each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;

each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4;

provided that:

(a) when Y is CH, $R^7$ is methyl, $R^6$ is H, and $R^1$, $R^2$, $R^4$, and $R^5$ are H, then $R^3$ is other than halogen; and (b) when Y is CH, $R^6$ and $R^7$ are each methyl and $R^3$ is fluoro, then at least one of $R^2$ or $R^4$ is other than halogen.

In some of the preceding embodiments, when the compound has Formula I, W is S, X is N, Y is N, and Z is CH, then the following provisos apply:

(a) when $R^6$ and $R^7$ are each methyl and at least two of $R^1$, $R^2$, $R^3$, $R^4$, and $R^5$ are H, then the remaining $R^1$, $R^2$, $R^3$, $R^4$, and $R^5$ are not selected from nitro, $C_{1-4}$ alkyl, $C_{1-6}$ alkoxy, methoxycarbonyl, and phenyl; wherein said $C_{1-6}$ alkoxy is optionally substituted by a $C_{1-4}$ alkoxy;

(b) when $R^6$ and $R^7$ are each methyl or each H, then at least one of $R^2$, $R^3$, $R^4$, and $R^5$ is other than H;

(c) when $R^6$ and $R^7$ are each H and at least four of $R^1$, $R^2$, $R^3$, $R^4$, and $R^5$ are other than H, then the remaining $R^1$, $R^2$, $R^3$, $R^4$, or $R^5$ are not selected from halogen;

(d) when $R^6$ and $R^7$ are each methyl, the moiety

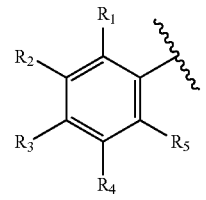

is 2,4-disubstituted with groups other than H, the remaining positions are unsubstituted, and $R^1$ us chloro, then $R^3$ is other than chloro;

(e) when $R^6$ and $R^7$ are each methyl, the moiety

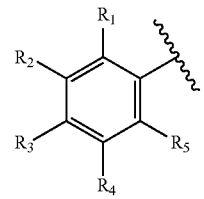

is 2,5-disubstituted with groups other than H, the remaining positions are unsubstituted, and $R^1$ is chloro, then $R^4$ is other than bromo, iodo, or chloro;

(f) when $R^6$ and $R^7$ are each methyl, the moiety

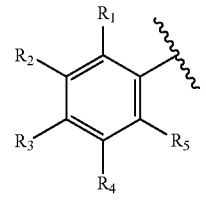

is 3,4-disubstituted with groups other than H, the remaining positions are unsubstituted, and $R^2$ is chloro or fluoro, then $R^3$ is other than chloro or fluoro;

(g) when $R^6$ and $R^7$ are each methyl and at least four of $R^1$, $R^2$, $R^3$, $R^4$ and $R^5$ are H, then the remaining $R^1$, $R^2$, $R^3$, $R^4$ or $R^5$ is not halogen;

(h) when one of $R^6$ and $R^7$ is methyl and the other of $R^6$ and $R^7$ is H, and at least four of $R^1$, $R^2$, $R^3$, $R^4$, and $R^5$ are H, then $R^3$ is other than methyl.

(i) when $R^6$ and $R^7$ are each methyl, then the moiety

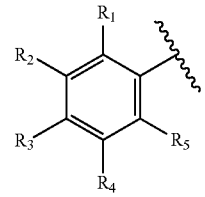

is not a naphthalene ring, which is optionally substituted by methoxy.

In some of the preceding embodiments, when the compound has Formula I, W is S, X is N, Y is N, and Z is CH, then the following provisos apply:

(a) when $R^6$ and $R^7$ are each methyl, then $R^1$, $R^2$, $R^3$, $R^4$, and $R^5$ are not selected from nitro, $C_{1-4}$ alkyl, $C_{1-6}$ alkoxy, $C_{1-6}$ alkoxycarbonyl, and phenyl; wherein said $C_{1-4}$ alkyl, $C_{1-6}$ alkoxy, $C_{1-6}$ alkoxycarbonyl are each optionally substituted by 1, 2, 3, or 4 independently selected $R^{a'}$ groups;

(b) when $R^6$ and $R^7$ are each methyl or each H, then at least one of $R^1$, $R^2$, $R^3$, $R^4$, and $R^5$ is other than H, methyl, or ethyl.

(c) when $R^6$ and $R^7$ are each H, then $R^1$, $R^2$, $R^3$, $R^4$, and $R^5$ are not selected from halogen;

(d) when $R^6$ and $R^7$ are each methyl, the moiety

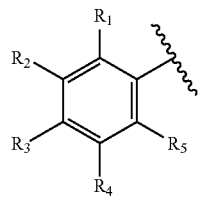

is 2,4-disubstituted with groups other than H, the remaining positions are unsubstituted, and $R^1$ is halogen, then $R^3$ is other than halogen;

(e) when $R^6$ and $R^7$ are each methyl, the moiety

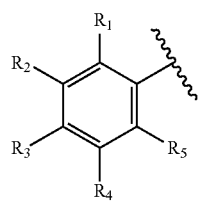

is 2,5-disubstituted with groups other than H, the remaining positions are unsubstituted, and $R^1$ is halogen, then $R^4$ is other than halogen;

(f) when $R^6$ and $R^7$ are each methyl, the moiety

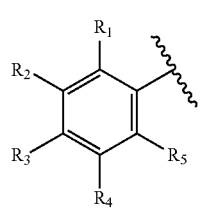

is 3,4-disubstituted with groups other than H, the remaining positions are unsubstituted, and $R^2$ is halogen, then $R^3$ is other than halogen;

(g) when $R^6$ and $R^7$ are each methyl and at least four of $R^1$, $R^2$, $R^3$, $R^4$ and $R^5$ are H, then the remaining $R^1$, $R^2$, $R^3$, $R^4$ or $R^5$ is not halogen;

(h) when one of $R^6$ and $R^7$ is methyl and the other of $R^6$ and $R^7$ is H, and at least four of $R^1$, $R^2$, $R^3$, $R^4$, and $R^5$ are H, then $R^3$ is other than $C_{1-3}$ alkyl; and (i) when $R^6$ and $R^7$ are each methyl, then the moiety

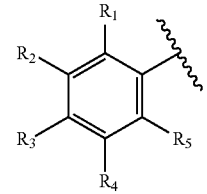

is not a naphthalene ring, which is optionally substituted by $C_{1-3}$ alkoxy.

In some of the preceding embodiments, when the compound has Formula I, W is S, X is N, Y is N, and Z is CH, then the following provisos apply:

(a) when $R^6$ and $R^7$ are each methyl, then $R^1$, $R^2$, $R^3$, $R^4$, and $R^5$ are not selected from halogen, nitro, $C_{1-4}$ alkyl, $C_{1-6}$ alkoxy, $C_{1-6}$ alkoxycarbonyl, and phenyl; wherein said $C_{1-4}$ alkyl, $C_{1-6}$ alkoxy, $C_{1-6}$ alkoxycarbonyl are each optionally substituted by 1, 2, 3, or 4 independently selected $R^{a'}$ groups;

(b) when $R^6$ and $R^7$ are each methyl or each H, then at least one of $R^1$, $R^2$, $R^3$, $R^4$, and $R^5$ is other than H, methyl or ethyl;

(c) when $R^6$ and $R^7$ are each H, then $R^1$, $R^2$, $R^3$, $R^4$, and $R^5$ are not selected from halogen;

(d) when one of $R^6$ and $R^7$ is methyl and the other of $R^6$ and $R^7$ is H, and at least four of $R^1$, $R^2$, $R^3$, $R^4$, and $R^5$ are H, then $R^3$ is other than $C_{1-4}$ alkyl; and (e) when $R^6$ and $R^7$ are each methyl, then the moiety

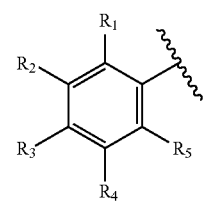

is does not form an optionally substituted fused aryl or heteroaryl ring.

In some embodiments, when the compound is a compound of Formula I, or a pharmaceutically acceptable salt thereof, wherein:

W is S;

X is N, Y is N, and Z is $CR^{10}$;

R', R", and R'" are each independently selected from H and $C_{1-4}$ alkyl;

$R^1$, $R^2$, $R^3$, $R^4$, and $R^5$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$- alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;

$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-6}$-alkyl, phenyl, phenyl-$C_{1-6}$-alkyl, $C_{1-6}$ heteroaryl, and $C_{1-6}$ heteroaryl-$C_{1-6}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;

each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4;

provided that:

(a) when Z is CH, $R^6$ and $R^7$ are each methyl and at least two of $R^1$, $R^2$, $R^3$, $R^4$, and $R^5$ are H, then the remaining $R^1$, $R^2$, $R^3$, $R^4$, and $R^5$ are not selected from nitro, $C_{1-4}$ alkyl, $C_{1-6}$ alkoxy, methoxycarbonyl, and phenyl; wherein said $C_{1-6}$ alkoxy is optionally substituted by a $C_{1-4}$ alkoxy;

(b) when Z is CH, $R^6$ and $R^7$ are each methyl or each H, then at least one of $R^1$, $R^2$, $R^3$, $R^4$, and $R^5$ is other than H;

(c) when Z is CH, $R^6$ and $R^7$ are each H and at least four of $R^1$, $R^2$, $R^3$, $R^4$, and $R^5$ are other than H, then the remaining $R^1$, $R^2$, $R^3$, $R^4$, or $R^5$ are not selected from halogen;

(d) when Z is CH, $R^6$ and $R^7$ are each methyl, the moiety

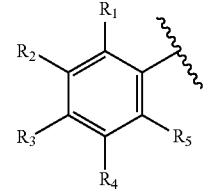

is 2,4-disubstituted with groups other than H, the remaining positions are unsubstituted, and $R^1$ is chloro, then $R^3$ is other than chloro;

(e) when Z is CH, $R^6$ and $R^7$ are each methyl, the moiety

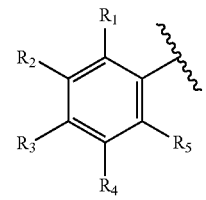

is 2,5-disubstituted with groups other than H, the remaining positions are unsubstituted, and $R^1$ is chloro, then $R^4$ is other than bromo, iodo, or chloro;

(f) when Z is CH, $R^6$ and $R^7$ are each methyl, the moiety

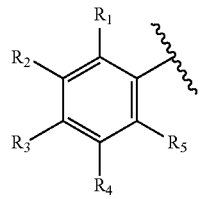

is 3,4-disubstituted with groups other than H, the remaining positions are unsubstituted, and $R^2$ is chloro or fluoro, then $R^3$ is other than chloro or fluoro;

(g) when Z is CH, $R^6$ and $R^7$ are each methyl and at least four of $R^1$, $R^2$, $R^3$, $R^4$ and $R^5$ are H, then the remaining $R^1$, $R^2$, $R^3$, $R^4$ or $R^5$ is not halogen; and (h) when Z is CH, one of $R^6$ and $R^7$ is methyl and the other of $R^6$ and $R^7$ is H, and at least four of $R^1$, $R^2$, $R^3$, $R^4$, and $R^5$ are H, then $R^3$ is other than methyl.

Each of the preceding provisos can be presented separately or in any suitable combination.

The present invention further provides a compound of Formula III:

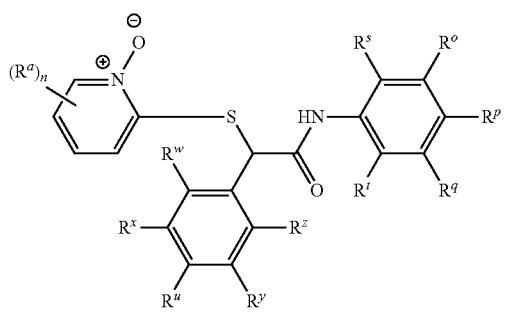

or a pharmaceutically acceptable salt thereof; wherein:

each $R^a$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

or any two adjacent $R^a$ groups, together with the atoms to which they are attached, form a phenyl or $C_{1-6}$ heteroaryl group; each of which is optionally substituted by 1, 2, 3, or 4 independently selected $R^{a'}$ groups;

$R^s$, $R^t$, $R^o$, $R^p$, and $R^q$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl; wherein the $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, or 3 independently selected $R^{o'}$ groups;

$R^u$, $R^w$, $R^x$, $R^y$, and $R^z$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

or $R^y$ and $R^z$, together with the carbon atoms to which they are attached, form a phenyl ring or $C_{1-6}$ heteroaryl ring, each of which is optionally substituted by 1, 2, or 3 $R^g$ groups;

or $R^u$ and $R^y$, together with the carbon atoms to which they are attached, form a phenyl ring or $C_{1-6}$ heteroaryl ring, each of which is optionally substituted by 1, 2, or 3 $R^g$ groups;

each $R^{a'}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^g$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{o'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4.

In some embodiments, the compound is not selected from compounds 18, 19, and 28 of Table 1, or a pharmaceutically acceptable salt thereof.

In some embodiments, n is 0.

In some embodiments, each $R^a$ is independently selected from halogen, cyano, nitro, hydroxyl, $C_{1-3}$ alkyl, $C_{1-3}$ haloalkyl, $C_{1-3}$ alkoxy, and $C_{1-3}$ haloalkoxy, amino, $C_{1-3}$ alkylamino, and di-$C_{1-3}$-alkylamino. In some embodiments, each $R^a$ is independently selected from halogen, cyano, nitro, hydroxyl, $C_{1-3}$ alkyl, $C_{1-3}$ haloalkyl, and $C_{1-3}$ alkoxy.

In some embodiments, $R^s$, $R^t$, $R^o$, $R^p$, and $R^q$ are each independently selected from H, halogen, cyano, nitro, hydroxyl, carboxyl, amino, $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-6}$-alkylamino, and $C_{1-6}$ alkylsulfonyl. In some embodiments, $R^s$, $R^t$, $R^o$, $R^p$, and $R^q$ are each independently selected from H, halogen, cyano, nitro, hydroxyl, carboxyl, amino, $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-6}$-alkylamino, and $C_{1-6}$ alkylsulfonyl. In some embodiments, $R^s$, $R^t$, $R^o$, $R^p$, and $R^q$ are each independently selected from H, halogen, $C_{1-6}$ alkyl, $C_{1-6}$ haloalkyl, $C_{1-6}$ alkoxy, and $C_{1-6}$ haloalkoxy. In some embodiments, $R^s$, $R^t$, $R^o$, $R^p$, and $R^q$ are each independently selected from H, halogen, $C_{1-6}$ alkyl, $C_{1-6}$ haloalkyl, and $C_{1-6}$ alkoxy. In some embodiments, $R^s$, $R^t$, $R^o$, $R^p$, and $R^q$ are each independently selected from H, chloro, methyl, trifluoromethyl, and methoxy.

In some embodiments, $R^u$, $R^w$, $R^x$, $R^y$, and $R^z$ are each independently selected from H, halogen, cyano, nitro, hydroxyl, carboxyl, amino, $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-6}$-alkylamino, and $C_{1-6}$ alkylsulfonyl; or $R^y$ and $R^z$, together with the carbon atoms to which they are attached, form a phenyl ring; or $R^u$ and $R^y$, together with the carbon atoms to which they are attached, form a phenyl ring. In some embodiments, $R^u$, $R^w$, $R^x$, $R^y$, and $R^z$ are each independently selected from H, halogen, $C_{1-6}$ alkyl, $C_{1-6}$ haloalkyl, $C_{1-6}$ alkoxy, and $C_{1-6}$ haloalkoxy; or $R^y$ and $R^z$, together with the carbon atoms to which they are attached, form a phenyl ring; or $R^u$ and $R^y$, together with the carbon atoms to which they are attached, form a phenyl ring. In some embodiments, $R^u$, $R^w$, $R^x$, $R^y$, and $R^z$ are each independently selected from H, halogen, and $C_{1-6}$ alkoxy; or $R^y$ and $R^z$, together with the carbon atoms to which they are attached, form a phenyl ring; or $R^u$ and $R^y$, together with the carbon atoms to which they are attached, form a phenyl ring. In some embodiments, $R^u$, $R^w$, $R^x$, $R^y$, and $R^z$ are each independently selected from H, chloro, and methoxy; or $R^y$ and $R^z$, together with the carbon atoms to which they are attached, form a phenyl ring; or $R^u$ and $R^y$ together with the carbon atoms to which they are attached, form a phenyl ring.

In some embodiments:

$R^s$, $R^t$, $R^o$, $R^p$, and $R^q$ are each independently selected from H, halogen, cyano, nitro, hydroxyl, carboxyl, amino, $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-6}$-alkylamino, and $C_{1-6}$ alkylsulfonyl; and $R^u$, $R^w$, $R^x$, $R^y$, and $R^z$ are each independently selected from H, halogen, cyano, nitro, hydroxyl, carboxyl, amino, $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-6}$-alkylamino, and $C_{1-6}$ alkylsulfonyl;

or $R^y$ and $R^z$, together with the carbon atoms to which they are attached, form a phenyl ring;

or $R^u$ and $R^y$, together with the carbon atoms to which they are attached, form a phenyl ring.

In some embodiments:

$R^s$, $R^t$, $R^o$, $R^p$, and $R^q$ are each independently selected from H, halogen, $C_{1-6}$ alkyl, $C_{1-6}$ haloalkyl, $C_{1-6}$ alkoxy, and $C_{1-6}$ haloalkoxy;

$R^u$, $R^w$, $R^x$, $R^y$, and $R^z$ are each independently selected from H, halogen, $C_{1-6}$ alkyl, $C_{1-6}$ haloalkyl, $C_{1-6}$ alkoxy, and $C_{1-6}$ haloalkoxy;

or $R^y$ and $R^z$, together with the carbon atoms to which they are attached, form a phenyl ring; and or $R^u$ and $R^y$, together with the carbon atoms to which they are attached, form a phenyl ring.

In some embodiments:

$R^s$, $R^t$, $R^o$, $R^p$, and $R^q$ are each independently selected from H, halogen, $C_{1-6}$ alkyl, $C_{1-6}$ haloalkyl, and $C_{1-6}$ alkoxy; and $R^u$, $R^w$, $R^x$, $R^y$, and $R^z$ are each independently selected from H, halogen, and $C_{1-6}$ alkoxy;

or $R^y$ and $R^z$, together with the carbon atoms to which they are attached, form a phenyl ring;

or $R^u$ and $R^y$, together with the carbon atoms to which they are attached, form a phenyl ring.

In some embodiments:

$R^s$, $R^t$, $R^o$, $R^p$, and $R^q$ are each independently selected from H, chloro, methyl, trifluoromethyl, and methoxy; and $R^u$, $R^w$, $R^x$, $R^y$, and $R^z$ are each independently selected from H, chloro, and methoxy;

or $R^y$ and $R^z$, together with the carbon atoms to which they are attached, form a phenyl ring;

or $R^u$ and $R^y$, together with the carbon atoms to which they are attached, form a phenyl ring;

In any of the preceding embodiments, the compound may be a compound of Formula IIIa

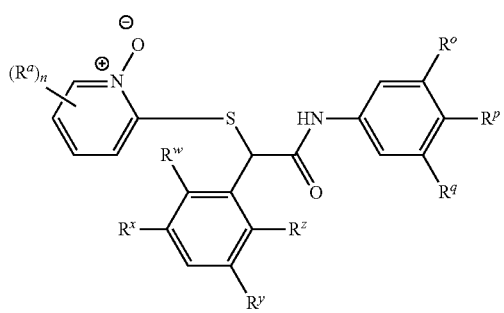

IIIa or a pharmaceutically acceptable salt thereof. In some embodiments, n is 0.

In any of the preceding embodiments, the compound may be a compound of Formula IIIb:

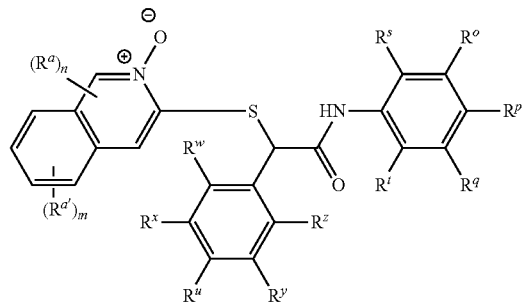

IIIb or a pharmaceutically acceptable salt thereof, wherein n is 1 or 2; and m is an integer selected from 1, 2, 3, and 4.

At various places in the present specification, substituents of compounds are disclosed in groups or in ranges. It is specifically intended that the compounds include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

For compounds in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

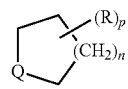

then it is understood that substituent R can occur p number of times on the ring, and R can be a different moiety at each occurrence. It is understood that each R group may replace any hydrogen atom attached to a ring atom, including one or both of the $(CH_2)_n$ hydrogen atoms. Further, in the above example, should the variable Q be defined to include hydrogens, such as when Q is the to be $CH_2$, NH, etc., any floating substituent such as R in the above example, can replace a hydrogen of the Q variable as well as a hydrogen in any other non-variable component of the ring. Unless otherwise indicated, should floating substituent R appear on a fused ring system, the substituent may replace a hydrogen atom at any ring atom in the fused ring system.

The compounds described herein can be asymmetric (e.g., having one or more stereocenters). All stereoisomers, such as enantiomers and diastereomers, are intended unless otherwise indicated. Compounds described herein that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds described herein may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein further include hydrates and solvates, as well as anhydrous and non-solvated forms. Compounds described herein can also include all isotopes of atoms occurring in the intermediates or final compounds. Isotopes include those atoms having the same atomic number but different mass numbers. For example, isotopes of hydrogen include tritium and deuterium.

The compounds can also include salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents.

The compounds also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

As used herein, the phrase "optionally substituted" means unsubstituted or substituted. As used herein, the term "substituted" means that a hydrogen atom is removed and replaced by a substitutent. It is understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, or 1 to 4 carbon atoms. Examples of alkyl moieties include, but are not limited to, chemical groups such as methyl, ethyl, n-propyl, isopropyl, n-butyl, tert-butyl, isobutyl, sec-butyl, 2-methyl-1-butyl, n-pentyl, 3-pentyl, n-hexyl, 1,2,2-trimethylpropyl, n-heptyl, n-octyl, and the like.

As used herein, "$C_{n-m}$ alkenyl", employed alone or in combination with other terms, refers to an alkyl group having one or more double carbon-carbon bonds and n to m carbon atoms. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl", employed alone or in combination with other terms, refers to an alkyl group having one or more triple carbon-carbon bonds, which may also optionally have one or more double carbon-carbon bonds, and having n to m carbon atoms. In some embodiments, the alkynyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, the term "$C_{n-m}$ alkoxy", employed alone or in combination with other terms, refers to an group of formula —O-alkyl, having n to m carbon atoms. Example alkoxy groups include methoxy, ethoxy, propoxy (e.g., n-propoxy and isopropoxy), t-butoxy, and the like.

As used herein, the term "amino", employed alone or in combination with other terms, refers to a group of formula —$NH_2$.

As used herein, the term "$C_{n-m}$ alkylamino", employed alone or in combination with other terms, refers to a group of formula —NH(alkyl), wherein the alkyl group has n to m carbon atoms. In some embodiments, the alkyl group has 1 to 6, 1 to 4, or 1 to 3 carbon atoms.

As used herein, the term "di-$C_{n-m}$ alkylamino", employed alone or in combination with other terms, refers to a group of formula —N(alkyl)$_2$, wherein each alkyl group independently has n to m carbon atoms. In some embodiments, each alkyl group has 1 to 6, 1 to 4, or 1 to 3 carbon atoms.

As used herein, the term "$C_{n-m}$ alkoxycarbonyl", employed alone or in combination with other terms, refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl", employed alone or in combination with other terms, refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylthio", employed alone or in combination with other terms, refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl", employed alone or in combination with other terms, refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl", employed alone or in combination with other terms, refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbamyl", employed alone or in combination with other terms, refers to a group of formula —C(O)NH-alkyl, wherein the alkyl group has n to m carbon atoms. In some embodiments, the alkyl group has 1 to 6, 1 to 4, or 1 to 3 carbon atoms.

As used herein, the term "di-$C_{n-m}$ alkylcarbamyl", employed alone or in combination with other terms, refers to a group of formula —C(O)N(alkyl)$_2$, wherein each alkyl group independently has n to m carbon atoms. In some embodiments, each alkyl group has 1 to 6, 1 to 4, or 1 to 3 carbon atoms.

As used herein, the term "$C_{n-m}$ alkylcarbonylamine", employed alone or in combination with other terms, refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "di-$C_{n-m}$ alkylcarbonylamine", employed alone or in combination with other terms, refers to a group of formula —N(alkyl)C(O)-alkyl, wherein each alkyl group independently has n to m carbon atoms. In some embodiments, each alkyl group has 1 to 6, 1 to 4, or 1 to 3 carbon atoms.

As used herein, the term "carbamyl", employed alone or in combination with other terms, refers to a —C(O)NH$_2$ group.

As used herein, the term "carbonyl", employed alone or in combination with other terms, refers to a —C(O)— group.

As used herein, the term "carboxy", employed alone or in combination with other terms, refers to a group of formula —C(O)OH.

As used herein, the term "cyano", employed alone or in combination with other terms, refers to a group of formula —CN.

As used herein, the terms "halo" and "halogen", employed alone or in combination with other terms, refer to fluoro, chloro, bromo, and iodo. In some embodiments, halogen is fluoro.

As used herein, the term "$C_{n-m}$ haloalkyl", employed alone or in combination with other terms, refers to an alkyl group having from n to m carbon atoms and one halogen atom to 2x+1 halogen atoms which may be the same or different, where "x" is the number of carbon atoms in the alkyl group. In some embodiments, the halogen atoms are fluoro atoms. In some embodiments, the alkyl group has 1 to 6 or 1 to 4 carbon atoms. An example of a haloalkyl group is —CF$_3$.

As used herein, "$C_{n-m}$ haloalkoxy", employed alone or in combination with other terms, refers to a group of formula —O-haloalkyl, wherein the haloalkyl group has n to m carbon atoms. In some embodiments, the alkyl group has 1 to 6 or 1 to 4 carbon atoms. An example haloalkoxy group is —OCF$_3$.

As used herein, the term "$C_{n-m}$ cycloalkyl", employed alone or in combination with other terms, refers to a non-aromatic cyclic hydrocarbon moiety, which may optionally contain one or more alkenylene or alkynylene groups as part of the ring structure, and which has n to m ring member carbon atoms. Cycloalkyl groups can include mono- or polycyclic (e.g., having 2, 3, or 4 fused, bridged, or spiro rings) ring systems. The term "cycloalkyl" also includes bridgehead cycloalkyl groups and spirocycloalkyl groups. As used herein, "bridgehead cycloalkyl groups" refers to non-aromatic cyclic hydrocarbon moieties containing at least one bridgehead carbon, such as admantan-1-yl. As used herein, "spirocycloalkyl groups" refers to non-aromatic hydrocarbon moieties containing at least two rings fused at a single carbon atom, such as spiro[2.5]octane and the like. In some embodiments, the cycloalkyl group has 3 to 14 ring members, 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is admanatan-1-yl.

As used herein, the term "$C_{n-m}$ cycloalkylene" refers to a divalent cycloalkyl group having n to m carbon atoms.

As used herein, the term "$C_{n-m}$ cycloalkyl-$C_{o-p}$ alkyl", employed alone or in combination with other terms, refers to a group of formula -alkylene-cycloalkyl, wherein the cycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the cycloalkyl portion has 3 to 14 ring members, 3 to 10 ring members, or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "x-membered cycloalkyl ring" refers to a monocyclic cycloalkyl ring having x ring members.

As used herein, the term "$C_{n-m}$ heterocycloalkyl", "$C_{n-m}$ heterocycloalkyl ring", or "$C_{n-m}$ heterocycloalkyl group", employed alone or in combination with other terms, refers to non-aromatic ring or ring system, which may optionally contain one or more alkenylene or alkynylene groups as part of the ring structure, which has at least one heteroatom ring member independently selected from nitrogen, sulfur and oxygen, and which has n to m ring member carbon atoms. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 hetereoatoms independently selected from nitrogen, sulfur and oxygen. Also included in the definition of heterocycloalkyl are moieties that have one or more aromatic rings (e.g., heteroaryl or aryl rings) fused (e.g., having a bond in common with) to the non-aromatic ring, for example, 1,2,3,4-tetrahydroquinoline and the like. Heterocycloalkyl groups can also include bridgehead heterocycloalkyl groups and spiroheterocycloalkyl groups. As used herein, "bridgehead heterocycloalkyl group" refers to a heterocycloalkyl moiety containing at least one bridgehead atom, such as azaadmantan-1-yl and the like. As used herein, "spiroheterocycloalkyl group" refers to a heterocycloalkyl moiety containing at least two rings fused at a single atom, such as [1,4-dioxa-8-aza-spiro [4.5]decan-N-yl] and the like. In some embodiments, the heterocycloalkyl group has 3 to 20 ring-forming atoms, 3 to 10 ring-forming atoms, or about 3 to 8 ring forming atoms. The carbon atoms or hetereoatoms in the ring(s) of the heterocycloalkyl group can be oxidized to form a carbonyl, or sulfonyl group (or other oxidized linkage) or a nitrogen atom can be quaternized. In some embodiments, the heterocycloalkyl portion is a $C_{2-7}$ monocyclic heterocycloalkyl group.

As used herein, the term "x-membered heterocycloalkyl ring" refers to a monocyclic heterocycloalkyl ring having x ring members.

As used herein, the term "$C_{n-m}$ heterocycloalkyl-$C_a$ alkyl", employed alone or in combination with other terms, refers to a group of formula -alkylene-heterocycloalkyl, wherein the heterocycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heterocycloalkyl portion has 3 to 14 ring members, 3 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "$C_{n-m}$ aryl", employed alone or in combination with other terms, refers to a monocyclic or polycyclic (e.g., having 2, 3 or 4 fused rings) aromatic hydrocarbon moiety having n to m ring member carbon atoms, such as, but not limited to, phenyl, 1-naphthyl, 2-naphthyl, anthracenyl, phenanthrenyl, and the like. Also included in the definition of aryl are moieties that have one or more cycloalkyl or heterocycloalkyl rings fused (i.e., having a bond in common with) to the aryl ring. In some embodiments, aryl groups have from 6 to 14 carbon atoms, about 6 to 10 carbon atoms, or about 6 carbons atoms. In some embodiments, the aryl group is a monocyclic or bicyclic group.

As used herein, the term "$C_{n-m}$ aryl-$C_{o-p}$-alkyl", employed alone or in combination with other terms, refers to a group of formula -alkylene-aryl, wherein the aryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the aryl portion is phenyl. In some embodiments, the aryl group is a monocyclic or bicyclic group. In some embodiments, the arylalkyl group is benzyl.

As used herein, the term "$C_{n-m}$ heteroaryl", "$C_{n-m}$ heteroaryl ring", or "$C_{n-m}$ heteroaryl group", employed alone or in combination with other terms, refers to a monocyclic or polycyclic (e.g., having 2, 3 or 4 fused rings) aromatic hydrocarbon moiety, having one or more heteroatom ring members independently selected from nitrogen, sulfur and oxygen and having n to m ring member carbon atoms. Also included in the definition of heteroaryl are moieties that have one or more cycloalkyl or heterocycloalkyl rings fused (i.e., having a bond in common with) to the aryl ring. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. The carbon atoms or hetereoatoms in the ring(s) of the heteroaryl group can be oxidized to form a carbonyl, or sulfonyl group (or other oxidized linkage) or a nitrogen atom can be quaternized, provided the aromatic nature of the ring is preserved for at least one ring of the heteroaryl moiety. In some embodiments, the heteroaryl group has 5 to 10 carbon atoms.

As used herein, the term "x-membered heteroaryl ring" refers to a monocyclic heteroaryl ring having x ring members.

As used herein, the term "$C_{n-m}$ heteroaryl-$C_{o-p}$-alkyl", employed alone or in combination with other terms, refers to a group of formula -alkylene-heteroaryl, wherein the heteroaryl portion has n to m ring member carbon atoms and the alkylene portion has to p carbon atoms. In some embodiments, the alkylene portion has 1 to 4, 1 to 3, 1 to 2, or 1 carbon atom(s). In some embodiments, the alkylene portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

As used herein, the term "oxo" refers to a group of formula "=O".

The term "protecting group" includes, but are not limited to, the protecting groups described in Greene, et al., Protective Groups in Organic Synthesis, 4d. Ed., Wiley & Sons, 2007, which is incorporated herein by reference in its entirety.

Unless otherwise indicated herein, the point of attachment of a substituent is generally in the last portion of the name (e.g., arylalkyl is attached through the alkylene portion of the group).

Methods, Pharmaceutical Formulations and Dosage Forms

Certain compounds described herein are PC-TP inhibitors. PC-TP (also referred to as StarD2) is a soluble phosphatidylcholine-binding protein and a member of the steroidogenic acute regulatory protein-related transfer (START) domain superfamily (Ponting, C. P., and Aravind, L. 1999. START: a lipid-binding domain in StAR, HD-ZIP and signalling proteins. *Trends Biochem. Sci.* 24:130-132; Roderick, S. L., Chan, W. W., Agate, D. S., Olsen, L. R., Vetting, M. W., Rajashankar, K. R., and Cohen, D. E. 2002. Structure of human phosphatidylcholine transfer protein in complex with its ligand. *Nature Struct. Biol.* 9:507-511). Expression of PC-TP is accentuated in highly oxidative tissues in the mouse, including liver, brown fat, heart, and muscle (Kanno, K., Wu, M. K., Scapa, E. F., Roderick, S. L., and Cohen, D. E. 2007. Structure and function of phosphatidylcholine transfer protein (PC-TP)/StarD2. *Biochim. Biophys. Acta* 1771:654-662). Among the phenotypes of mice with homozygous disruption of the Pctp gene (Pctp$^{-/-}$) are increased hepatic insulin sensitivity and redistribution of body fat, both of which appear to be attributable to preferential use of fatty acids over glucose as energy substrates (Scapa, E. F., Pocai, A., Wu, M. K., Gutierrez-Juarez, R., Glenz, L., Kanno, K., Li, H., Biddinger, S., Jelicks, L. A., Rossetti, L., and Cohen, D. E. 2008. Regulation of energy substrate utilization and hepatic insulin sensitivity by phosphatidylcholine transfer protein/StarD2. *FASEB J* 22:2579-259). Mice that lack expression of both PC-TP and apolipoprotein E (ApoE) are relatively resistant to atherosclerosis when compared with ApoE-deficient mice (Wang, W. J., Baez, J. M., Maurer, R., Dansky, H. M., and Cohen, D. E. 2006. Homozygous disruption of Pctp modulates atherosclerosis in apolipoprotein E deficient mice. *J. Lipid Res.* 47:2400-2407). Moreover, an unbiased genetic screen of a well-characterized human population revealed that a coding region polymorphism in the Pctp gene is associated with larger, less atherogenic low-density lipoprotein (LDL) particles (Dolley, G., Berthier, M. T., Lamarche, B., Despres, J. P., Bouchard, C., Perusse, L., and Vohl, M. C. 2007. Influences of the phosphatidylcholine transfer protein gene variants on the LDL peak particle size. *Atherosclerosis* 195:297-302). PC-TP was identified, and has been characterized extensively based on its in vitro activity (Wirtz, K. W. 1991. Phospholipid Transfer Proteins. *Annu. Rev. Biochem.* 60:73-99), which is to bind and catalyze the intermembrane exchange of phosphatidylcholines, but no other lipid.

Recently, yeast two-hybrid screening (Kanno, K., Wu, M. K., Agate, D. A., Fanelli, B. K., Wagle, N., Scapa, E. F., Ukomadu, C., and Cohen, D. E. 2007. Interacting proteins dictate function of the minimal START domain phosphatidylcholine transfer protein/StarD2. *J. Biol. Chem.* 282: 30728-30736) has led to the suggestion that the function(s) of PC-TP in vivo may be dictated at least in part by interacting proteins. One such protein is thioesterase superfamily member 2 (Them2), which is mitochondrial associated (Mootha, V. K., Bunkenborg, J., Olsen, J. V., Hjerrild, M., Wisniewski, J. R., Stahl, E., Bolouri, M. S., Ray, H. N., Sihag, S., Kamal, M., Patterson, N., Lander, E. S., and Mann, M. 2003. Integrated analysis of protein composition, tissue diversity, and gene regulation in mouse mitochondria. *Cell* 115:629-640; Wei, J., Kang, H. W. and Cohen, D. E. 2009. Thioesterase superfamily member 2 (Them2)/acyl-CoA thioesterase 13 (Acot13): A homotetrameric hotdog fold thioesterase with selectivity for long chain fatty acyl-CoAs. Biochem. J. 421, 311-322) and exhibits acyl-coenzyme A (CoA) thioesterase activity (Kanno, Wei supra). This suggests the possibility that PC-TP may participate in mitochondrial fatty acid metabolism (de Brouwer, A. P., Westerman, J., Kleinnijenhuis, A., Bevers, L. E., Roelofsen, B., and Wirtz, K. W. A. 2002. Clofibrate-induced relocation of phosphatidylcholine transfer protein to mitochondria in endothelial cells. *Exp. Cell Res.* 274:100-111; Kanno, K., Wu, M. K., Scapa, E. F., Roderick, S. L., and Cohen, D. E. 2007. Structure and function of phosphatidylcholine transfer protein (PC-TP)/StarD2. *Biochim. Biophys. Acta* 1771:654-662). The observation that it also interacts with developmentally expressed transcription factor Pax3 raises the possibility that PC-TP could also regulate transcription in certain cell types (Kanno supra).

It has been demonstrated that Pctp$^{-/-}$ mice are protected against diet-induced diabetes and allergen-induced asthma (infra). This suggests that the compounds described herein could be effective in the treatment of asthma. Finally, the Cohen laboratory has demonstrated that brown fat functions more efficiently in Pctp$^{-/-}$ mice (Kang H, Ribich S, Kim B W, Hagen S J, Bianco A C, Cohen D E. "Mice lacking phosphatidylcholine transfer protein/StarD2 exhibit increased adaptive thermogenesis and enlarged mitochondria in brown adipose tissue", *J Lipid Res* 2009, in press.). Three recently published studies (van Marken Lichtenbelt et al., 2009. *N. Engl. J. Med.* 360:1500-1508; Cypess et al., 2009. *N. Engl. J. Med.* 360: 1509-1517; and Virtanen et al., 2009. *N. Engl. J. Med.* 360: 1518-1525) have shown that brown fat plays an important role in energy utilization in adult humans (which was not previously appreciated) and may protect against obesity. Compounds that increase brown fat efficiency there are likely to have utility as anti-obesity agents.

The methods described herein include methods for the treatment of obesity, reducing the risk of obesity, treating disorders associated with obesity, and treating disorders treatable by a PC-TP inhibitor. In some embodiments, the methods include treating or reducing the risk of obesity in a patient or individual in need thereof. Generally, the methods include administering a therapeutically effective amount of therapeutic compound as described herein, to a subject who is in need of, or who has been determined to be in need of, such treatment. The methods can include a step of selecting a subject on the basis of the presence of obesity or a symptom of a disorder associated with obesity. The methods include administering a therapeutically effective amount of a compound of Formula I, II, or III, or any embodiment thereof, or a pharmaceutically acceptable salt thereof, to the individual. In some embodiments, the disorders treatable by a PC-TP inhibitor include type 2 diabetes, non-alcoholic fatty liver disease, asthma, hypertension, hyperlipidemia, coronary artery disease, arthritis, gallstones, osteoarthritis, atherosclerosis, sleep apnea, depression, cancer, and gastroesophagael reflux disease. Cancers in include esophageal squamous (Zhi, H., Zhang, J., Hu, G., Lu, J., Wang, X., Zhou, C., Wu, M. and Liu, Z. 2003. The deregulation of arachidonic acid metabolism-related genes in human esophageal squamous cell carcinoma. Int. J. Cancer 106, 327-333) and cancers related to obesity (Brawer, R., Brisbon, N. and Plumb, J. 2009. Obesity and cancer. Prim. Care 36, 509-531).

The present invention also provides a compound of Formula I, II, or III, or any embodiment thereof, or a pharmaceutically acceptable salt thereof, for use in a method of treating obesity, disorders associated with obesity, and disorders treatable by PC-TP inhibitors, or reducing risk of obesity, in an individual.

The present invention also provides use of a compound of Formula I, II, or III, or any embodiment thereof, or a pharmaceutically acceptable salt thereof, for the manufacture of a medicament for use in treatment of obesity, disorders associated with obesity, and disorders treatable by a PC-TP inhibitor, or reducing risk of obesity, in an individual.

The present invention also provides kits including one or more compounds of Formula I, II, or III, or any embodiment thereof, or pharmaceutically acceptable salts thereof; and instructions, wherein the instructions include a direction to administer a therapeutically effective amount of the compound or the salt to an individual in need of treatment of obesity, disorders associated with obesity, and disorders treatable by a PC-TP inhibitor, or reducing risk of obesity in an individual.

The present invention further provides pharmaceutical compositions including one or more compounds according to Formula I, II, or III, or any embodiment thereof, or pharmaceutically acceptable salts thereof, and a pharmaceutically acceptable carrier.

As used herein, the term "treating" or "treatment" refers to one or more of (1) preventing the disease; for example, preventing (i.e., reducing the risk of developing) a disease, condition or disorder in an individual who may be predisposed to the disease, condition or disorder but does not yet experience or display the pathology or symptomatology of the disease; (2) inhibiting the disease; for example, inhibiting (e.g., slowing progression of) a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein "body mass index (BMI)" refers to a mathematical formula used to assess relative body weight. BMI is generally used to define overweight and obesity. BMI may be calculated using the formula 'weight (kg)/Height2 (m).' BMI may be determined by a clinician or may be estimated by a subject using standard tables.

As used herein, "obesity" refers to a disorder in a subject, where the subject's weight exceeds their ideal weight, according to standard tables by 20% or more, e.g., 25%, 30%, 40%, and 50% or more. Obesity may also mean an individual with a body mass index (BMI) of 30 or more, e.g., 30-35 and 35-40 or more. For example, a subject diagnosed with class I obesity has a BMI range of 30-34.9. A subject with class II obesity has a BMI range of 35.0-39.9. A subject with class III obesity has a BMI greater than 40.

As used herein, "overweight" refers to a subject with a BMI range of 25.0-29.9.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. For example, a therapeutic amount is one that achieves the desired therapeutic effect, e.g., weight loss, e.g., sufficient weight loss to reduce the subject's risk of developing an obesity-related disorder.

In some embodiments, a therapeutically effective amount ranges from about 0.001 to 30 mg/kg body weight, for example, about 0.01 to 25 mg/kg body weight, about 0.1 to 20 mg/kg body weight, or about 1 to 10 mg/kg, 2 to 9 mg/kg, 3 to 8 mg/kg, 4 to 7 mg/kg, or 5 to 6 mg/kg body weight. In some embodiments, the compound may be administered one or several times per day or per week for between about 1 to 10 weeks, for example, between 2 to 8 weeks, between about 3 to 7 weeks, or about 4, 5, or 6 weeks.

When employed as pharmaceuticals, the compounds described herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds described herein in combination with one or more pharmaceutically acceptable carriers (excipients). In making the compositions, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds described herein may be milled using known milling procedures such as wet milling to obtain a particle size appropriate for tablet formation and for other formulation types. Finely divided (nanoparticulate) preparations of the compounds described herein can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions can be formulated so as to provide quick, sustained or delayed release of the active ingredient after administration to the patient by employing procedures known in the art.

The compositions can be formulated in a unit dosage form, each dosage containing from about 5 to about 1000 mg (1 g), or about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds described herein can vary according to, for example, the particular use for which the treatment is made, the manner of administration of the compound, the health and condition of the patient, and the judgment of the prescribing physician. The proportion or concentration of a compound in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Preparation of the Compounds

The compounds described herein can be prepared in a variety of ways known to one skilled in the art of organic synthesis, such as by the methods shown in the Schemes below. For example, compounds of Formula I or II can be prepared starting from a benzamide of formula S1 as shown in Scheme 1. Accordingly, the benzamide of formula S1 is converted to a ketoisocyanate or ketothioisocyanate of formula S2 by methods known in the art. The compound of formula S2 can then be reacted with an appropriate aniline of formula S3 to give the compound of Formula I or II.

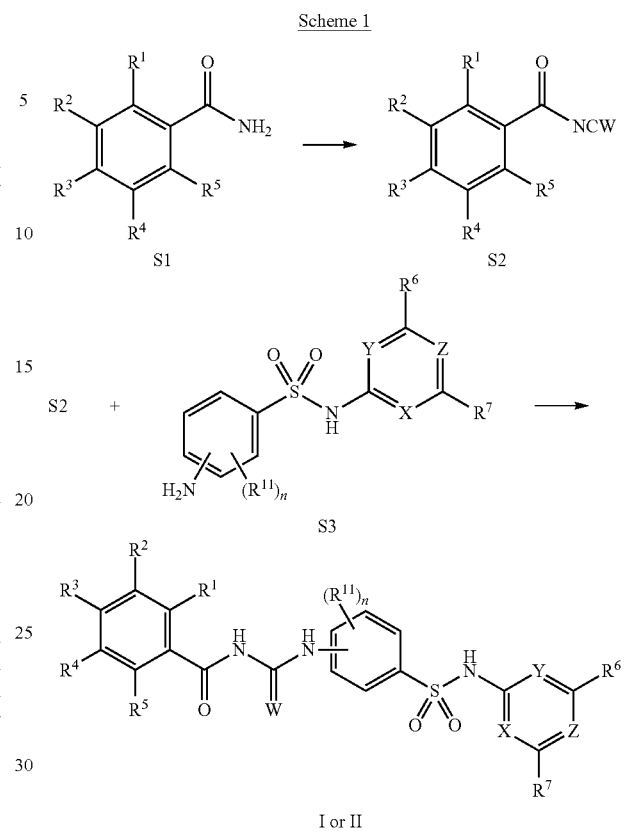

Compounds of Formula III can be prepared starting from an α-hydroxycarboxylic acid of formula S4 as shown in Scheme 2. Accordingly, the α-hydroxycarboxylic acid of formula S4 is converted to an α-chloroacyl chloride of formula S5. The compound of formula S5 can then be reacted with an aniline of formula S6 to give an α-chloroamide of formula S7. The α-chloroamide of formula S7 can then be reacted with a 2-thio-pyridine N-oxide of formula S8 to give the compound of Formula III.

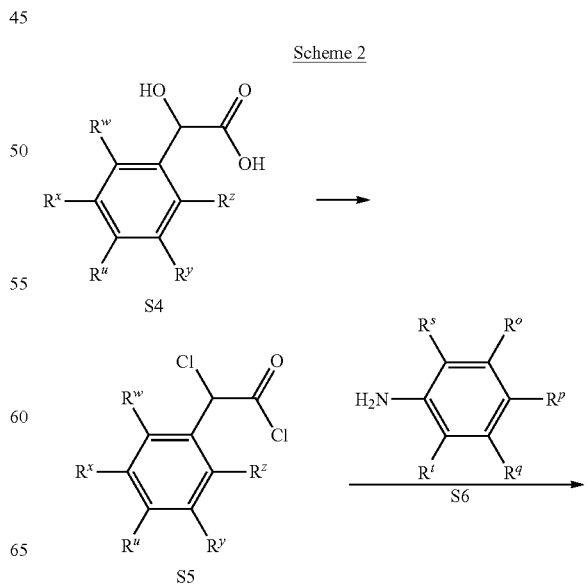

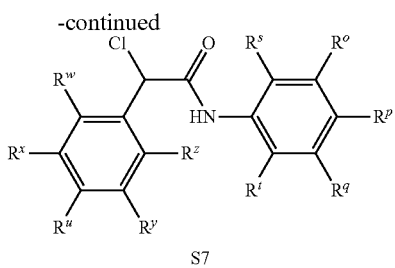

S7

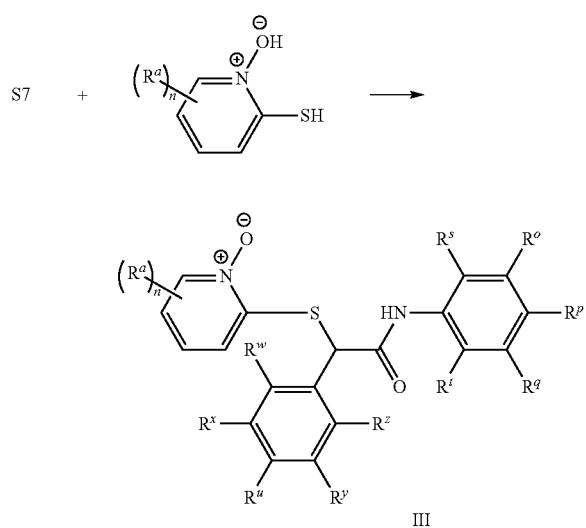

III

The compounds may be conveniently prepared by employing standard synthetic methods and procedures known to those skilled in the art from commercially available starting materials, compounds known in the literature, or readily prepared intermediates. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds.

The processes can be monitored according to any suitable method known in the art. For example, product formation can be monitored by spectroscopic means, such as nuclear magnetic resonance spectroscopy (e.g., $^1$H or $^{13}$C NMR) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods may be adjusted as necessary in light of the various substituents.

The reactions can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, 1,1,1-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide and ionic liquids can also be used as solvents.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments, the compounds can be substantially isolated. By "substantially isolated" is meant that the compound is at least partially or substantially separated from the environment in which it was formed or detected. Partial separation can include, for example, a composition enriched in the compound or intermediate, or salt thereof. Substantial separation can include compositions containing at least about 50%, at least about 60%, at least about 70%, at least about 80%, at least about 90%, at least about 95%, at least about 97%, or at least about 99% by weight of a compound described herein, or salt thereof. Methods for isolating compounds and their salts are routine in the art.

As used herein, the expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

PC-TP Inhibition

The compounds in Table 1 and 2 were assayed for their ability to inhibit PC-TP and StarD10, respectively, using a known assay method (see Wagle et al., 2008. *Anal. Biochem.* 383:85-92, which is incorporated herein by reference in its entirety). Further, certain compounds were also tested for their ability to inhibit StarD7 (see Table 2). The activity of the compounds at PC-TP and StarD10/StarD7, respectively, when tested at 5-10 microM is shown in Tables 1 and 2.

TABLE 1

| # | Name | Structure | Activity |
|---|------|-----------|----------|
| 1 | 2,4-dichloro-N-(4-(N-(4,6-dimethyl-pyrimidin-2-yl)sulfamoyl)phenylcarbamothioyl)benzamide | 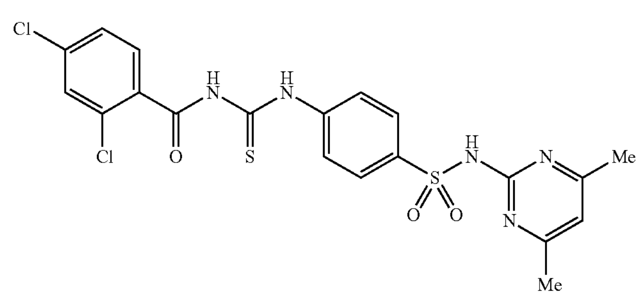 | 3.2 µM |

TABLE 1-continued

| # | Name | Structure | Activity |
|---|------|-----------|----------|
| 2 | N-(4-(N-(4,6-dimethylpyrimidin-2-yl)sulfamoyl)phenylcarbamothioyl)-4-fluorobenzamide | 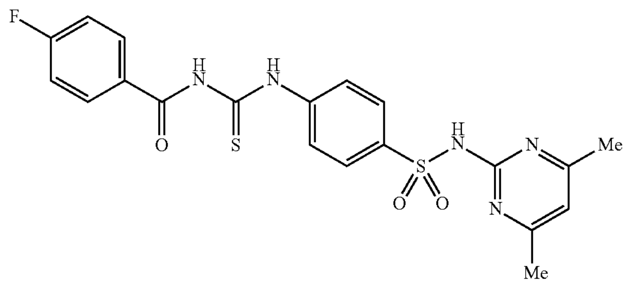 [SMILES: Cc1cc(C)nc(NS(=O)(=O)c2ccc(NC(=S)NC(=O)c3ccc(F)cc3)cc2)n1] | 55% inhibition at 100 μM |
| 3 | N-(4-(N-(4,6-dimethylpyrimidin-2-yl)sulfamoyl)phenylcarbamothioyl)benzamide | 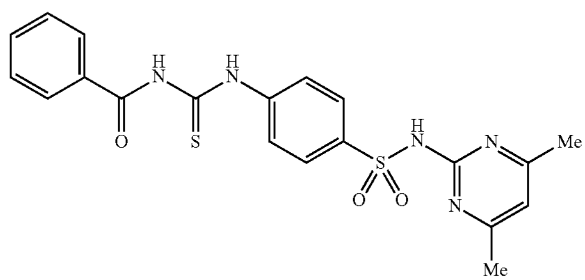 [SMILES: Cc1cc(C)nc(NS(=O)(=O)c2ccc(NC(=S)NC(=O)c3ccccc3)cc2)n1] | 45% inhibition at 100 μM |
| 4 | 2,4-dichloro-N-(4-(N-(4,6-dimethylpynmidin-2-yl)sulfamoyl)phenylcarbamoyl)benzamide | 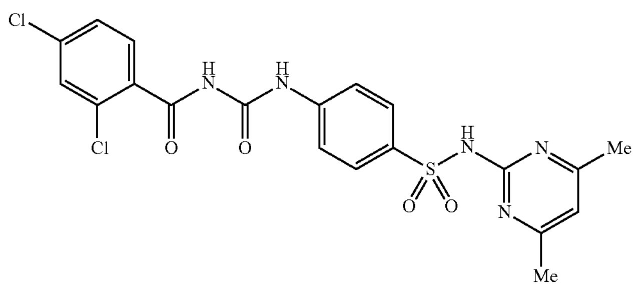 [SMILES: Cc1cc(C)nc(NS(=O)(=O)c2ccc(NC(=O)NC(=O)c3ccc(Cl)cc3Cl)cc2)n1] | 4.1 μM |
| 5 | 2-chloro-N-(4-(N-(4,6-dimethylpyrimidin-2-yl)sulfamoyl)phenylcarbamoyl)benzamide | 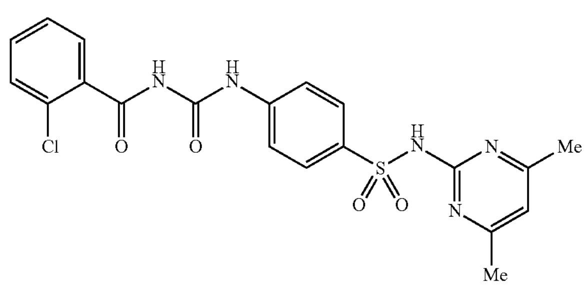 [SMILES: Cc1cc(C)nc(NS(=O)(=O)c2ccc(NC(=O)NC(=O)c3ccccc3Cl)cc2)n1] | 30 μM |
| 6 | 4-chloro-N-(4-(N-(4,6-dimethylpyrimidin-2-yl)sulfamoyl)phenylcarbamoyl)benzamide | 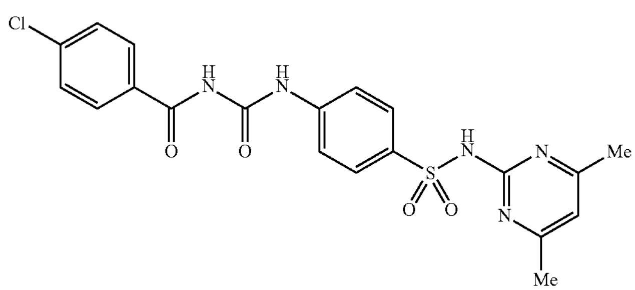 [SMILES: Cc1cc(C)nc(NS(=O)(=O)c2ccc(NC(=O)NC(=O)c3ccc(Cl)cc3)cc2)n1] | 26 μM |

TABLE 1-continued

| # | Name | Structure | Activity |
|---|------|-----------|----------|
| 7 | 2,4-dichloro-N-(4-(N-(4,6-dimethylpyridin-2-yl)sulfamoyl)phenylcarbamoyl)benzamide | 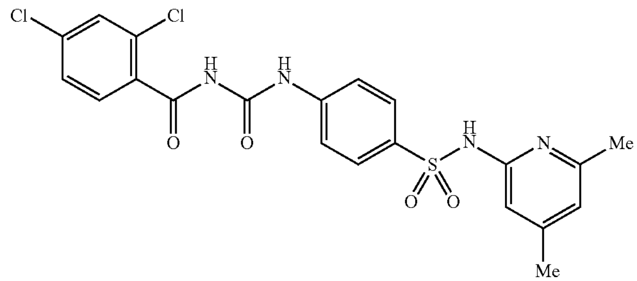 [SMILES: Cc1cc(C)nc(NS(=O)(=O)c2ccc(NC(=O)NC(=O)c3ccc(Cl)cc3Cl)cc2)c1] | 5.0 μM |
| 8 | 2,4-dichloro-N-(3-(N-(4,6-dimethylpyrimidin-2-yl)sulfamoyl)phenylcarbamoyl)benzamide | 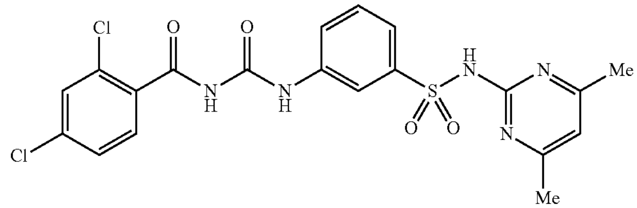 [SMILES: Cc1cc(C)nc(NS(=O)(=O)c2cccc(NC(=O)NC(=O)c3ccc(Cl)cc3Cl)c2)n1] | 6.5 μM |
| 9 | 2,3-dichloro-N-(4-(N-(4,6-dimethylpyrimidin-2-yl)sulfamoyl)phenylcarbamoyl)benzamide | 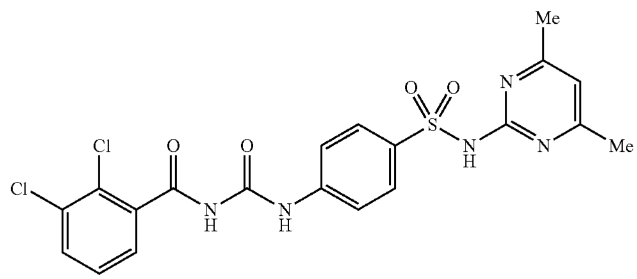 [SMILES: Cc1cc(C)nc(NS(=O)(=O)c2ccc(NC(=O)NC(=O)c3cccc(Cl)c3Cl)cc2)n1] | 3.2 μM |
| 10 | 3,4-dichloro-N-(4-(N-(4,6-dimethylpyrimidin-2-yl)sulfamoyl)phenyl-carbamoyl)benzamide | 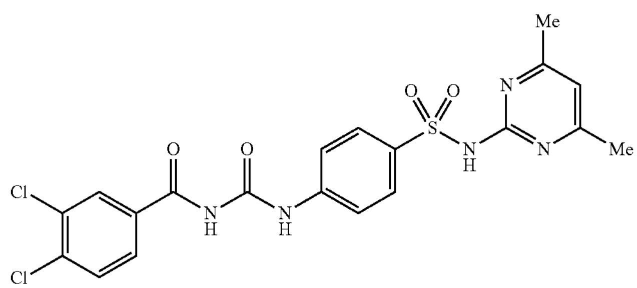 [SMILES: Cc1cc(C)nc(NS(=O)(=O)c2ccc(NC(=O)NC(=O)c3ccc(Cl)c(Cl)c3)cc2)n1] | 30 μM |
| 11 | 2,4-dichloro-N-((4-(N-(4,6-dimethylpyrimidin-2-yl)sulfamoyl)phenyl)(methyl)carbamoyl)benzamide | 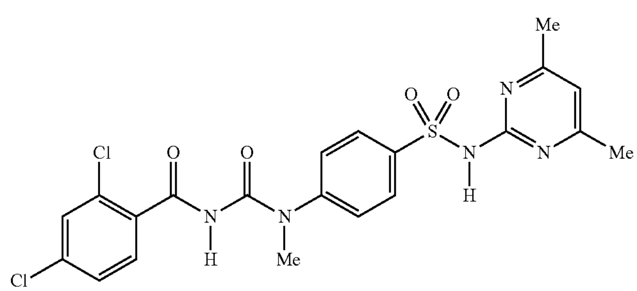 [SMILES: Cc1cc(C)nc(NS(=O)(=O)c2ccc(N(C)C(=O)NC(=O)c3ccc(Cl)cc3Cl)cc2)n1] | >50 μM |

TABLE 1-continued

| # | Name | Structure | Activity |
|---|------|-----------|----------|
| 12 | 2,4-dichloro-N-(4-(N-(4,6-dimethylpyrimidin-2-yl)-N-methylsulfamoyl)phenylcarbamoyl)benzamide | 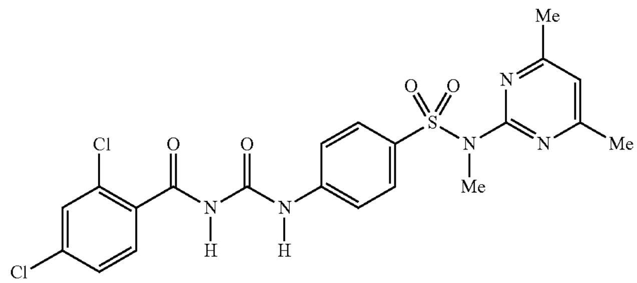 [SMILES: Cc1cc(C)nc(N(C)S(=O)(=O)c2ccc(NC(=O)NC(=O)c3ccc(Cl)cc3Cl)cc2)n1] | 2.3 μM |
| 13 | 2,4-dichloro-N-(4-(N-(2,6-dimethylpyrimidin-4-yl)sulfamoyl)phenylcarbamoyl)benzamide | 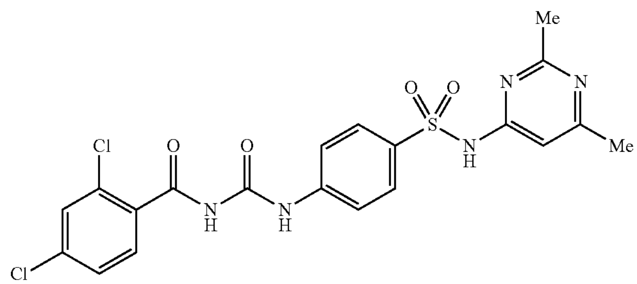 [SMILES: Cc1cc(NS(=O)(=O)c2ccc(NC(=O)NC(=O)c3ccc(Cl)cc3Cl)cc2)nc(C)n1] | 2.3 μM |
| 14 | 2,4-dichloro-N-(4-N-(3,5-dimethylphenyl)sulfamoyl)phenylcarbamoyl)benzamide | 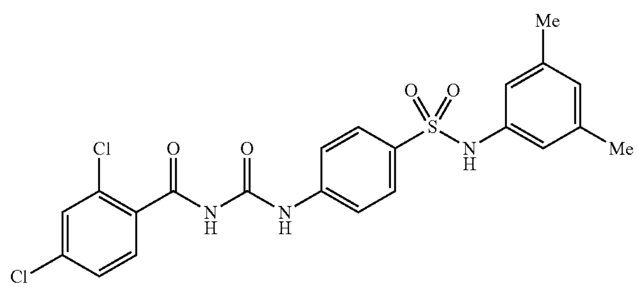 [SMILES: Cc1cc(C)cc(NS(=O)(=O)c2ccc(NC(=O)NC(=O)c3ccc(Cl)cc3Cl)cc2)c1] | 20 μM |
| 15 | 2,4-dichloro-N-(4-(N-(4,6-dimethylpyrimidin-2-yl)sulfamoyl)phenylcarbamoyl)-N-methylbenzamide | 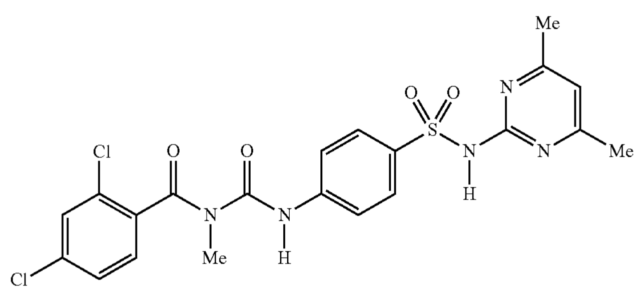 [SMILES: Cc1cc(C)nc(NS(=O)(=O)c2ccc(NC(=O)N(C)C(=O)c3ccc(Cl)cc3Cl)cc2)n1] | 8.0 μM |
| 16 | 2-(2-(3,5-dichlorophenylamino)-2-oxo-1-phenylethylthio)pyridine 1-oxide | 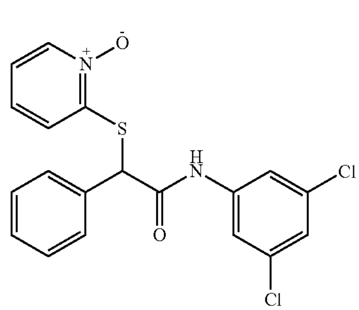 | 3.6 μM |

TABLE 1-continued

| # | Name | Structure | Activity |
|---|------|-----------|----------|
| 17 | 2-(2-(3-chloro-4-methoxyphenylamino)-2-oxo-1-phenylethylthio)pyridine 1-oxide | 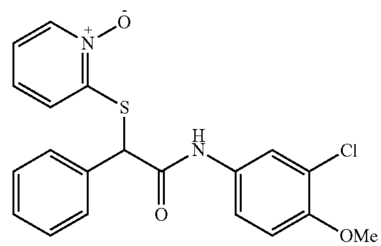 | 20 μM |
| 18 | 2-(2-(3-chloro-4-methylphenylamino)-2-oxo-1-phenylethylthio)pyridine 1-oxide | 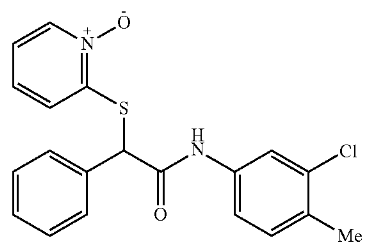 | 100 μM |
| 19 | 2-(2-oxo-1-phenyl-2-(3-(trifluoromethyl)phenylamino)ethylthio)pyridine 1-oxide | 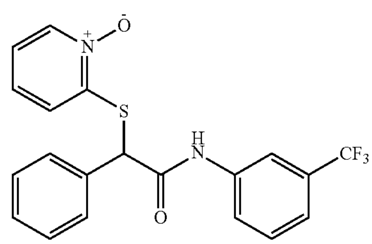 | 11 μM |
| 20 | 2-(2-(3,5-bis(trifluoromethyl)phenylamino)-2-oxo-1-phenylethylthio)pyridine 1-oxide | 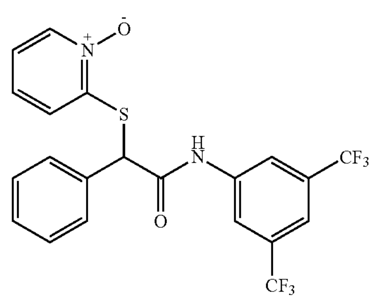 | 13 μM |
| 21 | 2-(1-(2-chlorophenyl)-2-(3,5-dichlorophenylamino)-2-oxoethylthio)pyridine 1-oxide | 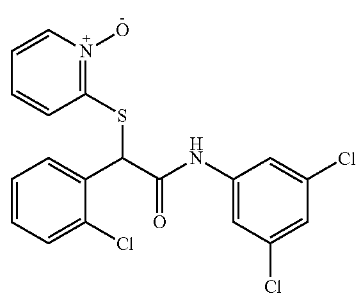 | 15 μM |

TABLE 1-continued

| # | Name | Structure | Activity |
|---|------|-----------|----------|
| 22 | 2-(2-(3,5-dichlorophenylamino)-1-(2-methoxyphenyl)-2-oxoethylthio)pyridine 1-oxide | 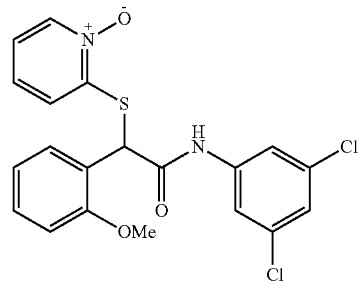 | 4.1 μM |
| 23 | 2-(2-(3,5-dichlorophenylamino)-1-(naphthalen-1-yl)-2-oxoethylthio)pyridine 1-oxide | 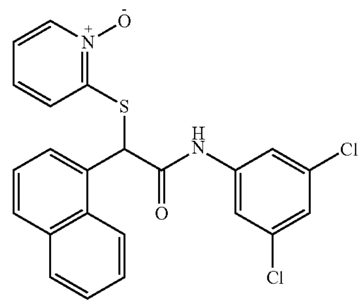 | 12 μM |
| 24 | 3-(2-(3,5-dichlorophenylamino)-2-oxo-1-phenylethylthio)isoquinoline 2-oxide | 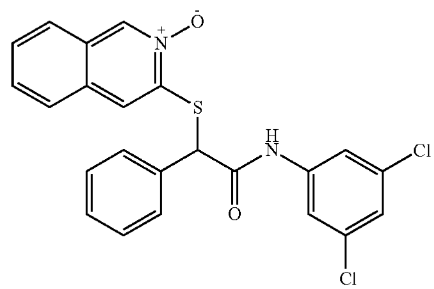 | 25% inhibition at 30 μM |
| 25 | 2-(2-(3,5-dichlorophenylamino)-1-(4-methoxyphenyl)-2-oxoethylthio)pyridine 1-oxide | 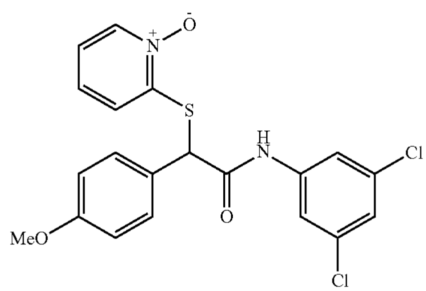 | 30% at 50 μM |
| 26 | 2-(2-(3,5-dichlorophenylamino)-1-(naphthalen-2-yl)-2-oxoethylthio)pyridine 1-oxide | 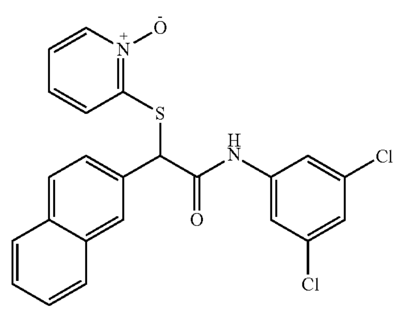 | 20% at 50 μM |

TABLE 1-continued

| # | Name | Structure | Activity |
|---|------|-----------|----------|
| 28 | 2-(2-(4-chloro-2-(trifluoromethyl)phenylamino)-2-oxo-1-phenylethylthio)pyridine 1-oxide | 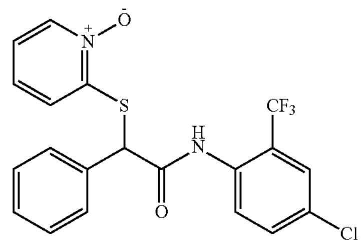 | ~50 μM |
| 29 | 2,4-dichloro-N-(2-(diethylamino)ethyl)-N-((4-(N-(4,6-dimethylpyrimidin-2-yl)sulfamoyl)phenyl)carbamoyl)benzamide | 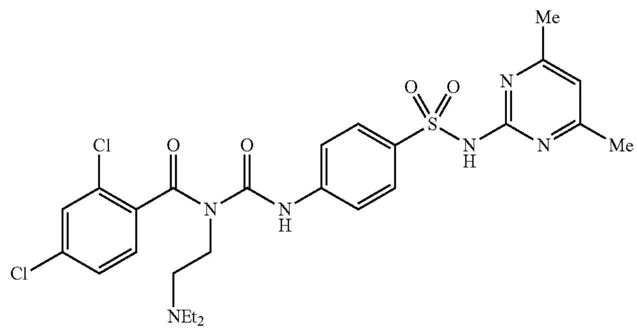 | High fluoroescense |
| 30 | 2,4-dichloro-N-((4-(N-(2-(diethylamino)ethyl)-N-(4,6-dimethylpyrimidin-2-yl)sulfamoyl)phenyl)carbamoyl)benzamide | 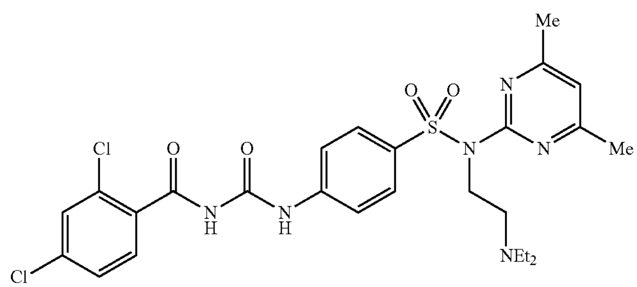 | High fluorescense |
| 31 | 2-(2-(2-chloro-5-(trifluoromethyl)phenylamino)-2-oxo-1-phenylethylthio)pyridine 1-oxide | 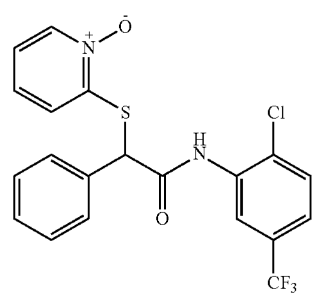 | >100 μM |
| 32 | 2-(2-(2-ethoxyphenylamino)-2-oxo-1-phenylethylthio)pyridine 1-oxide | 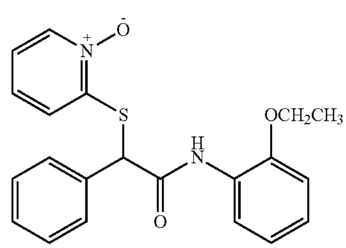 | >100 μM |

TABLE 1-continued

| # | Name | Structure | Activity |
|---|------|-----------|----------|
| 33 | 2-(2-(2-chlorophenylamino)-2-oxo-1-phenylethylthio)pyridine 1-oxide | 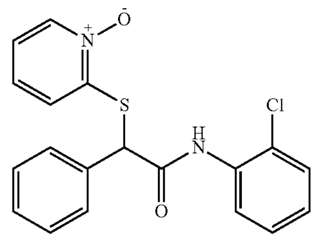 | 15 μM |
| 34 | 2-(2-(2-methoxyphenylamino)-2-oxo-1-phenylethylthio)pyridine 1-oxide | 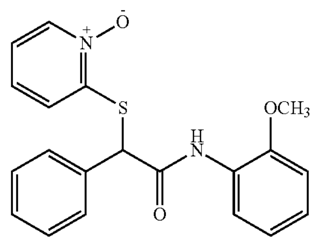 | 4 μM |

TABLE 2

| Compound # | StarD10 IC$_{50}$ (μM) | StarD7 IC$_{50}$ (μM) |
|---|---|---|
| 4 | 12 | 63 |
| 8 | 14 | |
| 9 | 39 | |
| 12 | 11 | |
| 13 | 20 | |
| 15 | 17 | |
| 16 | 20 | 66 |
| 33 | 23 | |
| 34 | 15 | |

Example 2

Pctp$^{-/-}$ Mice are Protected Against Diet-Induced Diabetes and Non-Alcoholic Fatty Liver Disease (NAFLD)

Considering that type 2 diabetes is characterized by hepatic insulin resistance with increased hepatic glucose production and is frequently accompanied by NAFLD, Pctp$^{-/-}$ mice were tested for resistance to diet induced diabetes and the accumulation of hepatic triglycerides. Male Pctp$^{-/-}$ and wild type control mice were fed a high fat diet (HF; 60% kcal from fat) for 8 to 18 weeks. Percentages of body fat and lean muscle mass were determined by magnetic resonance imaging. Fasting plasma glucose concentrations were monitored as mice became diabetic. Rates of hepatic glucose production and glucose clearance from the plasma were quantified in hyperinsulinemic euglycemic clamp studies as described (Scapa, E. F., Pocai, A., Wu, M. K., Gutierrez-Juarez, R., Glenz, L., Kanno, K., Li, H., Biddinger, S., Jelicks, L. A., Rossetti, L., and Cohen, D. E. 2008. Regulation of energy substrate utilization and hepatic insulin sensitivity by phosphatidylcholine transfer protein/StarD2. *FASEB J* 22:2579-259). Liver samples were harvested for measurements of hepatic triglyceride concentrations. Both genotypes of mice consumed the same amounts of food, gained weight equally, and became obese. After 18 weeks of HF feeding, body fat and lean muscle mass did not differ in Pctp$^{-/-}$ and wild type mice. In wild type mice, fasting plasma glucose concentrations increased 1.9 fold between 8 and 12 weeks of HF feeding and then leveled off. The absence of PC-TP expression was associated with 25%, 46%, and 17% reductions in plasma glucose at 8, 12, and 18 weeks respectively. Clamp studies performed at 18 weeks of HF feeding revealed a 46% decrease in hepatic glucose production rates, but no difference in rates of glucose clearance. Hepatic triglyceride concentrations (mg/g liver) were reduced in Pctp$^{-/-}$ mice at 8 weeks, but not 12 weeks.

Example 3

Pctp$^{-/-}$ Mice are Protected Against Allergen-Induced Asthma

Mice lacking PC-TP and their wild type littermate controls were sensitized using intraperitoneal injection of ovalbumin. Mice were then challenged with the same allergen by an aerosolized route prior to collecting bronchalveolar lavage fluid (Levy, B. D., De Sanctis, G. T., Devchand, P. R., Kim, E., Ackerman, K., Schmidt, B. A., Szczeklik, W., Drazen, J. M. and Serhan, C. N. 2002. Multi-pronged inhibition of airway hyper-responsiveness and inflammation by lipoxin A(4). Nat. Med. 8, 1018-1023). In the absence of PC-TP, concentrations of cysteinyl leukotrienes decreased, with concentrations of lipoxin A$_4$ (LXA$_4$) tending to decline as well. There was a 40% reduction in the number of eosinophils and modest increase in macrophages. Polymorphonuclear neutrophils were not prominent in either cohort at the time of bronchoalveolar lavage sampling. This pattern of leukocyte trafficking in the lung coupled with decrements in cysteinyl leukotrienes, which are potent mediators of airway constriction (Leff, A. R. 2000. Role of leukotrienes in bronchial hyperresponsiveness and cellular responses in airways. Am. J. Respir. Crit. Care Med. 161, S125-S132), suggests that the airway inflammation was already in the process of resolving in the animals lacking PC-TP.

An interpretation of these data is that the reduction of eosinophils in mice lacking PC-TP was attributable to increased clearance by macrophages. Decreased levels of both cysteinyl leukotrienes and LXA$_4$ are consistent with the possibility that PC-TP is an important regulator of eicosanoid formation. Of note, decreases in $LXA_4$ in mice lacking also suggest that lipoxin-independent pathways contributed to the accelerated resolution of allergic inflammation.

Example 4

Animal Model for Asthma

Allergic airway inflammation and airway hyper-responsiveness are induced in mice lacking PC-TP and wild type littermate control mice as described (Levy, B. D., De Sanctis, G. T., Devchand, P. R., Kim, E., Ackerman, K., Schmidt, B. A., Szczeklik, W., Drazen, J. M. and Serhan, C. N. 2002. Multi-pronged inhibition of airway hyper-responsiveness and inflammation by lipoxin A(4). Nat. Med. 8, 1018-1023). Briefly, 5 week-old male mice are injected i.p. with 10 μg ovalbumin plus 1 mg aluminum hydroxide on days 0 and 7. On day 14, mice are exposed to aerosolized ovalbumin (6% for 20 min) for 4 consecutive days. Following aerosol exposure on day 18, mice are studied immediately (time 0), then every 2 hours for the first 6 hours, followed by 12 hours, 24 hours, 72 hours and 7 days. At the end of treatment periods, mice are subjected to bilateral bronchoalveolar lavage using 2 aliquots of 1 ml phosphate buffered saline containing 0.6 mM EDTA. For histological analysis, separate groups of mice are sacrificed in order to harvest lungs. Separate groups of mice are also subjected to measurements of lung resistance using a Flexivent System. In this model, inhibitors are administered before, during and after challenge with allergen in order to determine whether these compounds prevent, attenuate or promote resolution of asthma.

Cells obtained by bronchoalveolar lavage are pelleted, resuspended and counted using a hemocytometer. Cells are concentrated onto a microscope slide and stained by Wright-Giemsa staining. The distribution of polymorphonuclear neutrophils, eosinophils, macrophages and lymphocytes are determined by counting ≥200 cells/sample. T lymphocytes are analyzed by fluorescence assisted cells sorting to determine the proportion of $CD4^+$, $CD8^+$ and $CD4^+$ T cells that express markers characteristic of T-regulatory cells (CD25 and FoxP3).

Cell-free bronchoalveolar fluid are used to measure lipid and peptide mediators. Selected eicosanoids are measured by ELISA [Levy, 2001 #2577] and as necessary, HPLC or mass spectrometry. In order to probe for potential differences in the lymphocytic response, concentrations of specific Th2 cytokines, interleukin-5 (IL-5) and IL-13 are measured. Measurements of serum ovalbumin-specific and total IgE concentrations are correlated with the cellular composition of the inflammatory response.

For the measurement of airway resistance, a thoracotomy are performed while the mouse is being mechanically ventilated. Thereafter, respiratory status are closely monitored while geometrically increasing doses of methacholine chloride (a bronchoconstrictor and congener of acetylcholine) are administered via in-line nebulizer. These experiments determine whether PC-TP expression influences airway hyper-responsiveness, as is suggested by the changes in eicosanoids and inflammatory infiltrate.

To assess the possibility that PC-TP influences eosinophil trafficking, the capacity of eosinophils to accumulate in vivo in response to chemoattractants are measured. Briefly, prostaglandin $E_2$ plus leukotriene $B_4$ in acetone are applied topically on the inside of ears of PC-TP-deficient and wild type mice. After 13-16 h, 6 mm diameter skin punch biopsies are taken. Samples are homogenized and analyzed for eosinophil peroxidase as a measure of tissue eosinophil concentration.

Example 5

Animal Model for Atherosclerosis

Mice with gene disruption of apoE or the low density lipoprotein receptor (LDLr) genes develop atherosclerosis when placed on a Western-type diet (Breslow, J. L. 1996. Mouse models of atherosclerosis. Science 272, 685-688). Mice lacking both apoE and PC-TP generally develop less atherosclerosis than apoE mice alone (Wang, W. J., Baez, J. M., Maurer, R., Dansky, H. M., and Cohen, D. E. 2006. Homozygous disruption of Pctp modulates atherosclerosis in apolipoprotein E deficient mice. *J. Lipid Res.* 47:2400-2407). Mice lacking apoE or LDLr are fed a western diet. These mice are treated with PC-TP inhibitors during the period when they develop atherosclerosis to assess their capacity to prevent atherosclerosis. The dosing, frequency and route of administration of compounds depends upon pharmacokinetics of the compounds, but ideal compounds will be given no more frequently than once per day. The compounds are also tested for the capacities to treat atherosclerosis by waiting until atherosclerosis is established in these models before administering them. Mice lacking both PC-TP and apoE or LDLr (which can be readily prepared by breeding) serve as positive controls for the capability of the inhibitors to prevent atherosclerosis. However, they cannot serve as positive controls for atherosclerosis treatment because the gene is chronically absent in these mice. Nevertheless, negative controls administered vehicle alone may provide the requisite information about whether the PC-TP inhibitors are effective at atherosclerosis treatment. The effectiveness of inhibitors will be assessed by quantification of atherosclerosis and influence on plasma lipids as we have previously described (Wang, W. J., Baez, J. M., Maurer, R., Dansky, H. M., and Cohen, D. E. 2006. Homozygous disruption of Pctp modulates atherosclerosis in apolipoprotein E deficient mice. *J. Lipid Res.* 47:2400-2407).

Example 6

Animal Model for Type 2 Diabetes and Obesity

When fed a high fat diet, FVB/NJ mice develop both diabetes and obesity (Martin, T. L., Alquier, T., Asakura, K., Furukawa, N., Preitner, F. and Kahn, B. B. 2006. Diet-induced obesity alters AMP kinase activity in hypothalamus and skeletal muscle. J. Biol. Chem. 281, 18933-18941). Because mice lacking PC-TP were crossed to this genetic background (Wu, M. K., Hyogo, H., Yadav, S., Novikoff, P. M. and Cohen, D. E. 2005. Impaired response of biliary lipid secretion to a lithogenic diet in phosphatidylcholine transfer protein-deficient mice. J. Lipid Res. 46, 422-431), this model has been used to demonstrate that the absence of PC-TP expression protects against diabetes and obesity in the setting of 8 weeks of high fat feeding (see above). These mice are used to test inhibitor compounds for the prevention and treatment of diabetes and obesity by initiating treatment at the time that high fat feeding commences or by administering them once diabetes and obesity are established. The effectiveness of compounds in preventing and treating obesity is assessed by measuring weights, food consumption and body fat distribution as we have described (Scapa, E. F., Pocai, A., Wu, M. K., Gutierrez-Juarez, R., Glenz, L., Kanno, K., Li, H., Biddinger, S., Jelicks, L. A., Rossetti, L., and Cohen, D. E.

2008. Regulation of energy substrate utilization and hepatic insulin sensitivity by phosphatidylcholine transfer protein/StarD2. *FASEB J.* 22:2579-259). The influence of inhibitors on diabetes will be assessed in detailed studies of glucose metabolism as we have described (Scapa, E. F., Pocai, A., Wu, M. K., Gutierrez-Juarez, R., Glenz, L., Kanno, K., Li, H., Biddinger, S., Jelicks, L. A., Rossetti, L., and Cohen, D. E. 2008. Regulation of energy substrate utilization and hepatic insulin sensitivity by phosphatidylcholine transfer protein/StarD2. *FASEB J* 22:2579-259).

Example 7

PC-TP Inhibitors Enhance the Insulin Signaling Pathway in Human Hepatocytes, Even in the Absence of Insulin Cultured primary human hepatocytes (commercially obtained) were serum starved overnight followed by 60 minute exposure to A) Compound 4 or B) Compound 16 at the indicated concentrations. Inhibitors were dissolved in DMSO. Negative controls included Control (no additions) and DMSO alone. The positive control included DMSO plus insulin (50 nM) for 30 minutes. Cells were harvested and lysates were subjected to immunoblot analyses using antibodies, as indicated. Both inhibitors activated insulin signaling at doses of 0.05 and 0.10 µM. Results are shown in FIG. 1.

Example 8

Surface Plasmon Resonance of Compound 8 Binding to PC-TP

Figure 2:
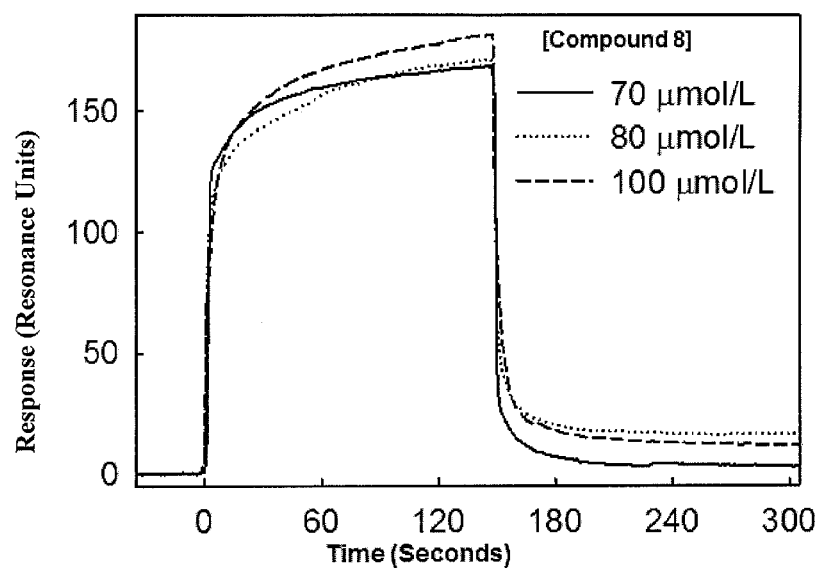
FIG. 2 depicts the results of a surface plasmon resonance study of Compound 8 binding to PC-TP.

Compound 8 was injected into a Biacore 3000 surface plasmon resonance instrument with purified recombinant His-tag PC-TP immobilized to a carboxymethyl dextran 5 (CM %) chip for 150 s and allowed to dissociate. Each sensogram was overlaid and zeroed on the y-axis to the average baseline before injection. The start injection time for each sample was set to zero on the x-axis (see FIG. 2). The $K_D$ value was 5.0 µM.

Example 9

Displacement Assay of PC-TP Using a Pyrene-Labeled PC

Competition between the small molecule inhibitors and fluorescent pyrene-labeled phosphatidylcholine (PyrPC) for binding to PC-TP was measured using Pyr-PC fluorescent vesicles quenched with tetracyanoquinodimethane (TCNQ) (Lemmetyinen H. et al. 1989). Upon mixing of quenched Pyr-PC vesicles with purified recombinant PC-TP, the rise in Pyr-PC fluorescence reflects binding of fluorescently labeled phosphatidylcholine molecules to the active site of PC-TP. If the small molecule inhibitors enter the active site and prevent binding of phosphatidylcholine to PC-TP by competing the Pyr-PC, this should reduce the observed increase in Pyr-PC fluorescence.

The fluorescence of PyrPC monomer was measured at 392 nm on SpectraMax M5 plate-reader with excitation was set at 345 nm. Pyrene-labeled PC vesicles contained PyrPC, egg PC, and TCNQ in a molar ratio of 40:20:60. For PC and PyrPC competition assays, we used unlabeled PC vesicles composed of egg PC and TCNQ in a molar ratio of 55:45 or PC vesicles of varied lipid concentrations and PyrPC vesicles quenched with TCNQ (55:45). In order to determine the affinity of PC-TP for Compound 4 relative to PyrPC, PyrPC lipid binding was measured using varying concentrations of inhibitor 5, 20, 50, and 75 µM and a fixed amount of PyrPC (36 µM). To determine the affinity of eggPC compared to PyrPC, we varied the concentration of egg PC in the assay as follows: 5, 11, 22, 27, 33, and 44 µM, and a fixed amount of PyrPC (44 µM). The wells where unlabeled PC concentration was less than 44 µM were supplemented with additional amounts of TCNQ to keep the concentration of the quencher equal in all the wells. In another assay, multiple egg PC:TCNQ vesicles of varied lipid concentration were prepared separately as follows, 10:20, 40:20, 60:20, 80:20 molar ratios of PC:TCNQ and binding competition for PC-TP was tested against PyrPC:TCNQ vesicles (40:40). PC-TP concentration was kept constant at 300 nM. In the displacement assay, the increase in pyrene monomer fluorescence (ΔF) is proportional to the amount of [Pyr], pyrene-labeled PC bound to PC-TP. The maximal fluorescence increase ($\Delta F_{max}$) at pyrene monomer emission peak (~380-394 nm) is observed in the absence of inhibitor ([inh]=0) or unlabeled lipid ([PC]=0). The fluorescence reading of wells with PyrPC vesicles alone and Pyr-PC vesicles with inhibitor (highest background fluorescence) were used as control and subtracted as background. Increasing Compound 4 concentration resulted in diminishing fluorescence of pyrene monomer suggesting that the inhibitor entered and bound to the active site and thus, prevented Pyr-PC from binding to PC-TP. In contrast, no change in fluorescence was observed upon addition of an inactive compound, which was also found to have no inhibitory effect on PC transfer activity.

Figure 3:
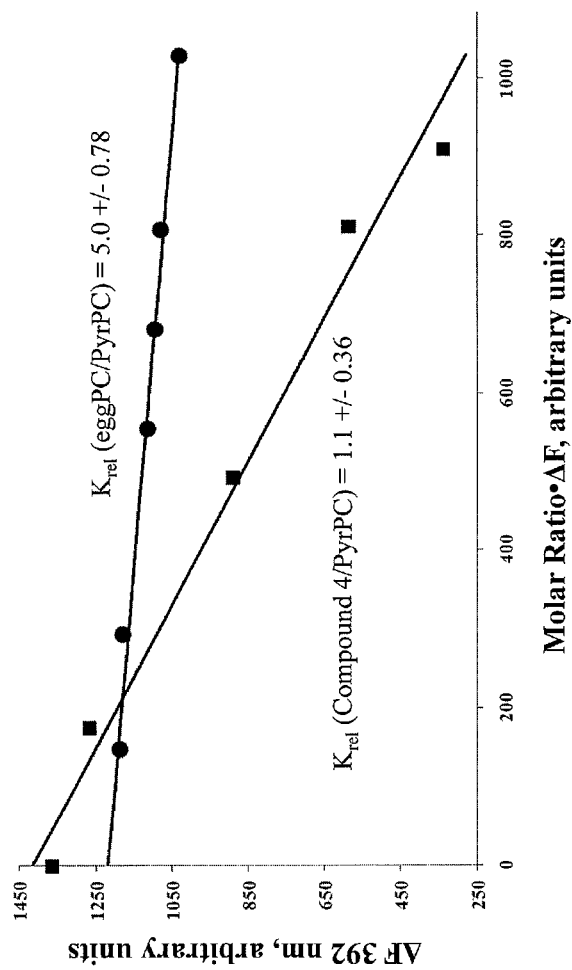
FIG. 3 depicts results from a displacement assay of PC-TP using a Pyrene-labeled PC for Compound 4.

As described in Van Paridon et al. 1987, by plotting ΔF as a function of ΔF·[inh]/[Pyr] (■) or ΔF·[PC]/[Pyr] (●), a straight line is obtained with a slope of $-1/K_{rel}$, where $K_{rel}$ is relative affinity constant (FIG. 3). The $K_{rel}$ value is estimated by least-squares fitting of the data. From the plot $K_{rel}$ (Compound 4/PyrPC) was estimated as 1.1+/-0.36, whereas $K_{rel}$ (PC/PyrPC)=5.0+/-0.78 (Note: the above $K_{rel}$ values are averaged $K_{rel}$ values obtained from multiple experiments). Therefore, $K_{rel}$ (Compound 4/PC) can be calculated as $K_{rel}$ (Compound 4/PyrPC)/$K_{rel}$ (PC/PyrPC)=0.22. These findings suggest that the inhibitor is capable of displacing PC from the active site of PC-TP.

References: Lemmetyinen H., Yliperttula M., Mikkola J., Kinnunen P. Quenching of fluorescence of pyrene-substituted lecithin by tetracyanoquinodimethane in liposomes. *Biophys. J.,* 55 (1989) 885-895; Van Paridon P. A., Gadella T. W. J., Somerharju P. J., Wirtz K. W. A. On the relationship between the dual specificity of the bovine brain phosphatidylinositol transfer protein and membrane phosphatidylinositol levels. *Biochim. Biophys. Acta,* 903 (1987) 68-77.

Example 10

Preparation of Compounds of Formula I

Compounds of Formula I can be formed as shown below in Scheme A1 or Scheme A2.

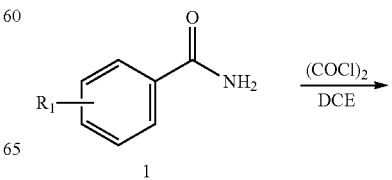

Scheme A1

-continued

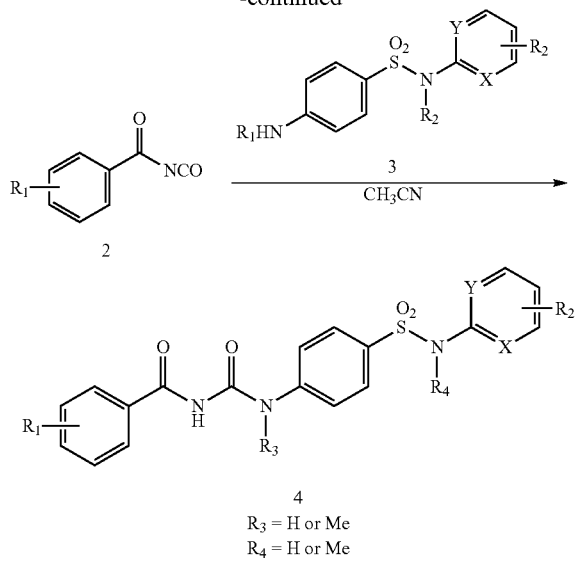

R₃ = H or Me
R₄ = H or Me

To a solution of 1 (1 mmol) in dichloroethane (DCE; 15 mL) was added oxalyl chloride (500 μL). The mixture was then heated at 80° C. for 18 h before being concentrated to dry. Toluene (10 mL×2) was added to the residue and concentrated until a white solid formed. This solid, 2, was used in next step without further purification.

A mixture of 2 and 3 (1 mmol) in CH₃CN was heated at 80° C. for 5 h. The formed solid was collected by filtration and purified by prep-HPLC to give 4 as white solid.

The following are ¹H NMR spectra of representative examples prepared utilizing the procedure described in Scheme A1:

(Compound 1): ¹H NMR (d₆-DMSO, 500 MHz) δ 12.38 (s, 1H), 12.12 (s, 1H), 8.01 (d, 2H, J=9.0 Hz), 7.90 (d, 2H, J=9.0 Hz), 7.77 (d, 1H, J=2.0 Hz), 7.67 (d, 1H, J=7.0 Hz), 7.57 (dd, 1H, J=2.0, 7.0 Hz), 6.78 (s, 1H), 2.26 (s, 6H).

(Compound 5): ¹H NMR (CDCl₃, 500 MHz) δ 10.85 (s, 1H), 8.70 (s, 1H), 8.01 (d, 2H, J=9.0 Hz), 7.65-7.25 (m, 7H), 6.55 (s, 1H), 2.28 (s, 6H).

(Compound 6): ¹H NMR (d₆-DMSO, 500 MHz) δ 11.20 (s, 1H), 11.00 (s, 1H), 8.1-7.90 (m, 4H), 7.78-7.62 (m, 4H), 6.75 (s, 1H), 2.28 (s, 6H).

(Compound 7): ¹H NMR (d₆-DMSO, 500 MHz) δ 11.3 (s, 1H), 10.5 (s, 1H), 8.40 (s, 1H), 7.80 (2, 7H), 6.80 (s, 1H), 6.40 (s, 1H), 2.18 (s, 3H), 2.10 (s, 3H).

(Compound 8): ¹H NMR (d₆-DMSO, 500 MHz) δ 11.2 (s, 1H), 10.38 (s, 1H), 8.4 (s, 1H), 7.80 (d, 2H, J=2.0 Hz), 7.73-7.50 (m, 5H), 6.78 (s, 1H), 2.28 (s, 6H).

(Compound 4): ¹H NMR (d₆-DMSO, 500 MHz) δ 11.38 (s, 1H), 10.55 (s, 1H), 7.98 (d, 2H, J=2.0 Hz), 7.80-7.5 (m, 6H), 6.78 (s, 1H), 2.28 (s, 6H).

(Compound 11): ¹H NMR (d₆-DMSO, 500 MHz) δ 10.6 (s, 1H), 7.95 (d, 2H, J=2.0 Hz), 7.60-7.30 (m, 5H), 6.68 (s, 1H), 3.26 (s, 3H), 2.30 (s, 6H).

(Compound 9): ¹H NMR (d₆-DMSO, 500 MHz) δ 10.48 (s, 1H), 7.95 (d, 2H, J=2.0 Hz), 7.75-7.40 (m, 5H), 6.75 (s, 1H), 2.25 (s, 6H).

(Compound 12): ¹H NMR (d₆-DMSO, 500 MHz) δ 8.00 (d, 2H, J=2.0 Hz), 7.75-7.55 (m, 5H), 6.82 (s, 1H), 3.55 (s, 3H), 2.28 (s, 6H).

(Compound 10): ¹H NMR (d₆-DMSO, 500 MHz) δ 8.2 (s, 1H), 8.0-7.70 (m, 7H), 6.75 (s, 1H), 2.22 (s, 6H).

(Compound 13): ¹H NMR (d₆-DMSO, 500 MHz) δ 10.5 (s, 1H), 10.0 (s, 1H), 7.75-7.45 (m, 7H), 6.75 (s, 2H), 6.65 (s, 1H), 2.15 (s, 6H).

(Compound 14): ¹H NMR (d₆-DMSO, 500 MHz) δ 10.5 (s, 1H), 7.9-7.55 (m, 8H), 2.35 (s, 3H), 2.25 (s, 3H).

Scheme A2

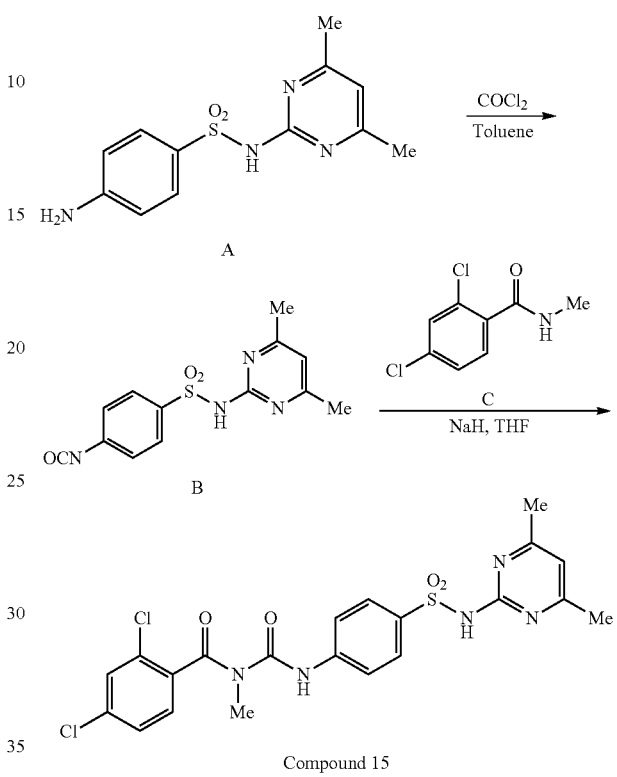

Compound 15

To a suspension of A (278 mg, 1 mmol) in toluene (5 mL) was added phosgene (20% in toluene, 2 mL). The mixture was stirred 30 min at room temperature and then was heated at 80° C. for 2 h before being concentrated to dryness. Toluene (10 mL×2) was added to the residue and concentrated. This solid, B, was used in next step without further purification.

To a solution of C (102 mg, 0.5 mmol) in THF (5 mL) was added NaH (30 mg, 0.75 mmol). The mixture was stirred at room temperature for 30 min, then B (152 mg, 0.5 mmol) was added. The resulted mixture was heated at 80° C. for 5 h. The formed solid was collected by filtration and purified by prep-HPLC to give Compound 15 as white solid (120 mg, 47%).

(Compound 15): ¹H NMR (d₆-DMSO, 400 MHz) δ 10.6 (s, 1H), 7.84 (d, 2H, J=8.4 Hz), 7.54-7.50 (m, 6H), 3.18 (s, 3H), 2.13 (s, 6H).

Example 9

Preparation of Compounds of Formula III

Compounds of Formula III can be formed as shown below in Scheme B.

Scheme B

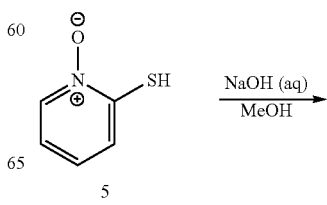

5

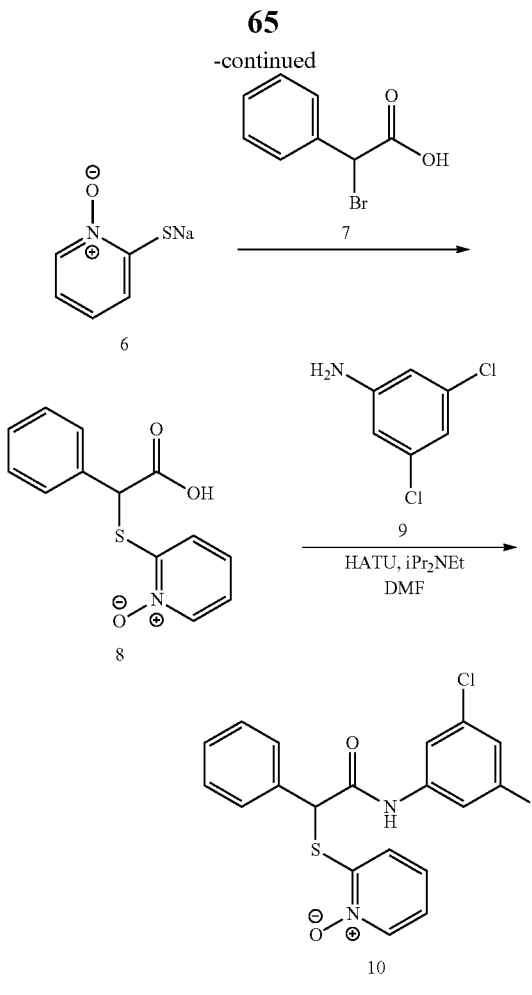

To a solution of 5 (2 mmol) in MeOH (15 mL) was added NaOH (6N, 333 μL). The reaction was stirred at room temperature for 30 min. The solution of 6 was used directed for the next step.

To a solution of 6 was added 7 (2 mmol) and the resulting solution was stirred at 70° C. for 30 min. The resulted mixture was neutralized with KHSO$_4$ (350 mg, 3 mmol) in H$_2$O (20 mL) and then concentrated to partially remove the solvents. The solid residue was filtered to give 8 as a white crystalline solid.

A mixture of 8 (1 mmol), 9 (1.2 mmol), HATU (460 mg, 1.2 mmol), and iPr$_2$NEt (350 μL, 2 mmol) in DMF (10 mL) was stirred at room temperature for 18 h. After diluting with water the reaction mixture was extracted with ethyl acetate. The organic later was dried over anhydrous sodium sulfate, filtered and concentrated. The residue was purified by prep-HPLC to give 10 as a white solid.

The following are $^1$H NMR spectra of representative examples prepared utilizing the procedure described in Scheme B:

(Compound 16): $^1$H NMR (d$_6$-DMSO, 500 MHz) δ 11.38 (s, 1H), 8.33 (d, 1H, J=6.0 Hz), 7.69 (d, 2H, J=2.0 Hz), 7.65 (d, 2H, J=2.0 Hz), 7.67 (d, 1H, J=7.5 Hz), 7.43-7.40 (m, 2H), 7.37-7.34 (m, 3H), 7.32-7.31 (m, 1H), 7.24-7.22 (m, 1H), 5.66 (s, 1H).

(Compound 17): $^1$H NMR (d$_6$-DMSO, 500 MHz) δ 11.2 (s, 1H), 8.36 (d, 1H), 7.70-7.63 (m, 4H), 7.47-7.22 (m, 7H), 5.58 (s, 1H).

(Compound 20): $^1$H NMR (d$_6$-DMSO, 500 MHz) δ 11.30 (s, 1H), 8.33 (d, 1H, J=7.0 Hz), 8.25 (s, 1H), 7.80 (s, 1H), 7.63-7.61 (m, 2H), 7.42-7.22 (m, 6H), 5.53 (s, 1H).

(Compound 24): $^1$H NMR (CDCl$_3$, 500 MHz) δ 10.7 (s, 1H), 8.85 (s, 1H), 7.75-7.25 (m, 12H), 7.00 (s, 1H), 5.35 (s, 1H).

(Compound 21): $^1$H NMR (d$_6$-DMSO, 500 MHz) δ 11.0 (s, 1H), 8.38 (d, 1H, J=7.0 Hz), 7.64-7.22 (m, 10H), 5.70 (s, 1H).

(Compound 23): $^1$H NMR (d$_6$-DMSO, 500 MHz) δ 10.89 (s, 1H), 8.55 (d, 1H, J=7.0 Hz), 8.20-8.18 (m, 1H), 7.98-7.40 (m, 12H), 6.45 (s, 1H).

(Compound 26): $^1$H NMR (d$_6$-DMSO, 500 MHz) δ 11.0 (s, 1H), 8.30 (d, 1H, J=7.0 Hz), 8.10 (s, 1H), 7.98-7.20 (m, 12H), 5.65 (s, 1H).

(Compound 22): $^1$H NMR (d$_6$-DMSO, 500 MHz) δ 10.88 (s, 1H), 8.38 (d, 1H, J=7.0 Hz), 7.72 (s, 2H), 7.55-7.00 (m, 8H), 5.70 (s, 1H), 3.92 (s, 3H).

Compounds 33 and 34 were synthesized by a method analogous to that for Compounds 21 and 22.

Compounds 2, 18, 19, and 28 were obtained from Ryan Scientific (Mt. Pleasant, S.C.). Compound 3 was obtained from ChemBridge (San Diego, Calif.). Compounds 31 and 32 were purchased from Enamine Compound 29. 2,4-dichloro-N-(2-(diethylamino)ethyl)-N-((4-(N-(4,6-dimethylpyrimidin-2-yl)sulfamoyl)phenyl)carbamoyl)benzamide

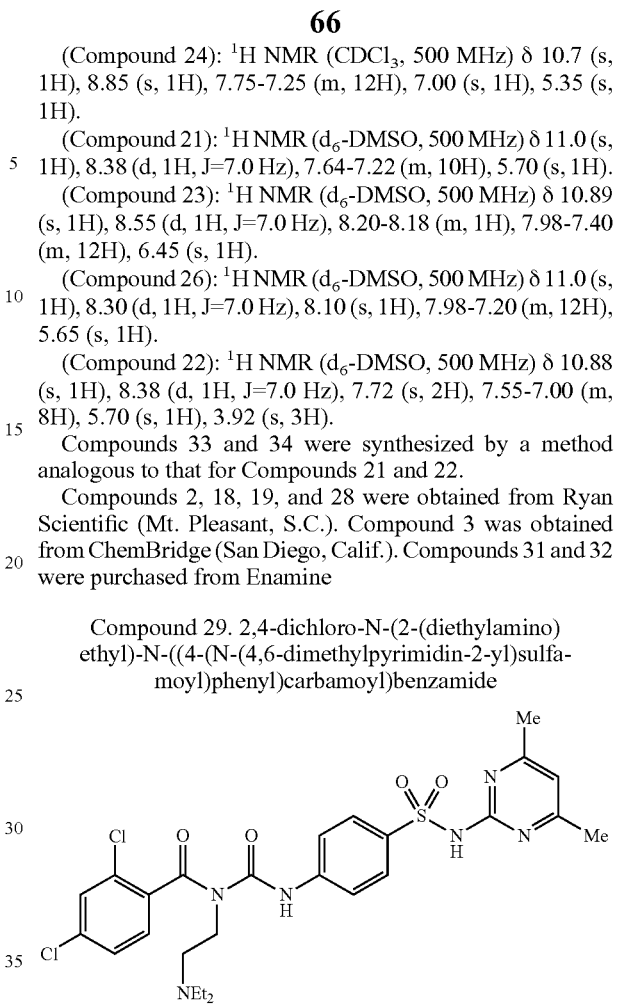

The compound was prepared as in the scheme below. Reagents and conditions: 2-chloro-N,N-diethylethylamine hydrochloride, tetrabutyl-ammonium bromide (TBAB), NaOH, Toluene, H$_2$O, 100° C., 14 hours, 33%.

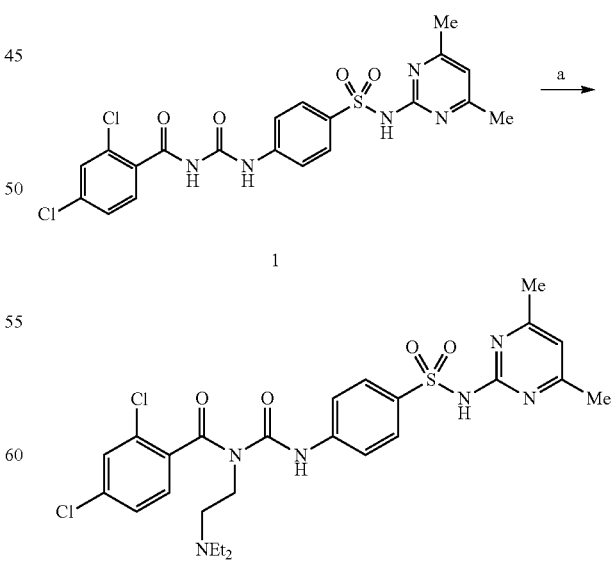

A mixture of corresponding benzenesulfonamide (1) (100 mg, 0.20 mmol), 2-chloro-N,N-diethylamine hydrochloride (42 mg, 0.24 mmol), TBAB (65 mg, 0.20 mmol), sodium hydroxide (24 mg, 0.61 mmol), toluene 2 mL, and water 2 mL was stirred at reflux for 14 hours. After cooling, the mixture was diluted with water and extracted with ethyl acetate. The combined organic layers were washed with brine, dried over magnesium sulfate and evaporated in vacuo. The residue was chromatographed on a silica gel column eluting with 5% methanol in dichloromethane to give 2 (40 mg, 33%). $^1$H NMR (500 MHz, CDCl$_3$) δ 8.20-8.12 (m, 3H), 7.78-7.70 (m, 3H), 7.48 (d, J=2.0 Hz, 1H), 7.38 (dd, J=2.0, 8.5 Hz, 1H), 6.57 (s, 1H), 4.32-4.22 (m, 2H), 2.92 (t, J=7.5 Hz, 2H), 2.70 (q, J=7.0 Hz, 4H), 2.30 (s, 6H), 1.13 (t, J=7.0 Hz, 6H).

Compound 30. 2,4-dichloro-N-((4-(N-(2-(diethylamino)ethyl)-N-(4,6-dimethylpyrimidin-2-yl)sulfamoyl)phenyl)carbamoyl)benzamide The compound was prepared as in the scheme below.

ethanol (20 mL), and water (10 mL) was heated at 100° C. for 2 hours. After cooling, the mixture was filtered through celite, extracted with ethyl acetate, washed with brine, dried over magnesium sulfate and evaporated in vacuo. The residue was used directly without further purification.

(c) To a solution of 2,4-dichlorobenzamide (380 mg, 2 mmol) in 1,2-dichloroethane was added oxalyl chloride (1.0 mL, 11.4 mmol). The mixture was then heated at 80° C. for 18 hours before being concentrated to dryness. Toluene (20 mL×2) was added to the residue and concentrated until 4, a white solid formed. This solid was used in next step without further purification.

(d) A solution of 2 (1.0 mmol) and 4 (0.2 mmol) in 8 mL of acetonitrile was heated at 95° C. for 48 hours. After cooling, the mixture was concentrated. The residue was chromatographed on a silica gel column eluting with 5% Methanol in dichloromethane to give 5 (30 mg, 25% in 4 steps).

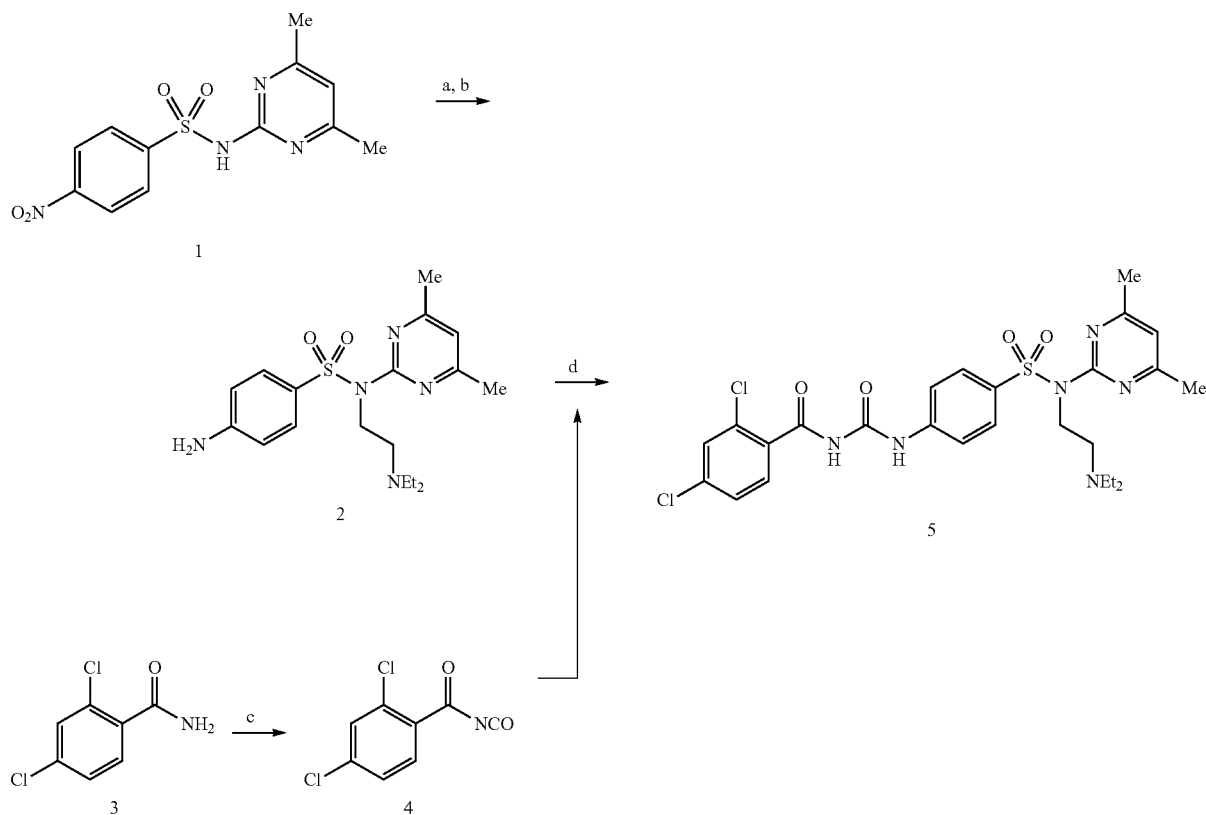

Reagents and conditions: (a) 2-chloro-N,N-diethylethylamine hydrochloride, tetrabutyl-ammonium bromide (TBAB), NaOH, Toluene, H$_2$O, 100° C., 12 hours; (b) iron, HCl, ethanol, H$_2$O, 100° C., 2 h; (c) oxalyl chloride, ClCH$_2$CH$_2$Cl, 80° C., 18 hours; (d) CH$_3$CN, 80° C., 5 hours.

(a) 2-chloro-N,N-diethylethylamine hydrochloride, tetrabutyl-ammonium bromide (TBAB), NaOH, Toluene, H$_2$O, 100° C., 14 hours, 33%. Concentrated mixture was used in next step without further purification.

(b) A mixture of compound obtained above (0.162 mmol), iron (360 mg, 0.63 mmol), NH$_4$Cl (182 mg, 0.34 mmol),

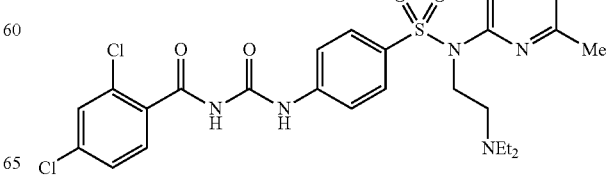

$^1$H NMR (500 MHz, CDCl$_3$) δ 8.20-8.05 (m, 2H), 7.85-7.30 (m, 5H), 6.63 (d, J=2.0 Hz, 1H), 4.56 (t, J=7.0 Hz, 2H), 3.45 (brs, 2H), 3.18 (brs, 4H), 2.33 (s, 6H), 1.48 (brs, 6H).

A number of embodiments of the invention have been described. Nevertheless, it will be understood that various modifications may be made without departing from the spirit and scope of the invention. Accordingly, other embodiments are within the scope of the following claims.

APPENDIX 1

Answer 1:

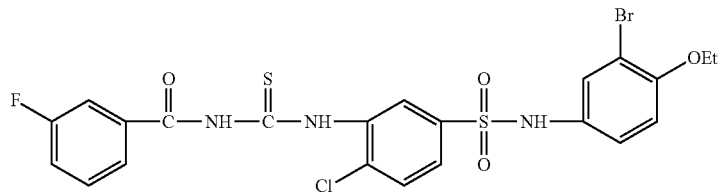

Answer 2:

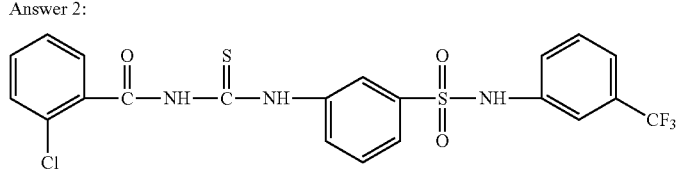 [SMILES: O=C(NC(=S)Nc1cccc(S(=O)(=O)Nc2cccc(C(F)(F)F)c2)c1)c1ccccc1Cl]

Answer 3:

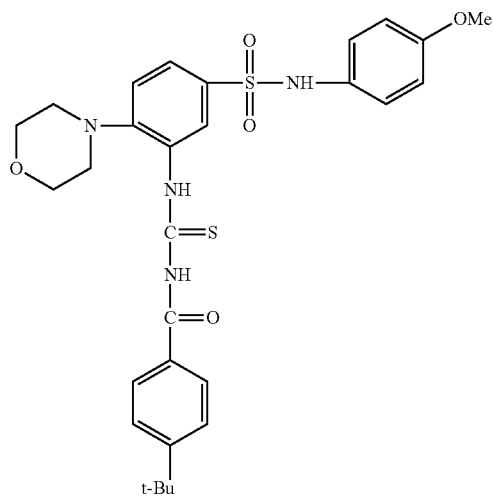

Answer 4:

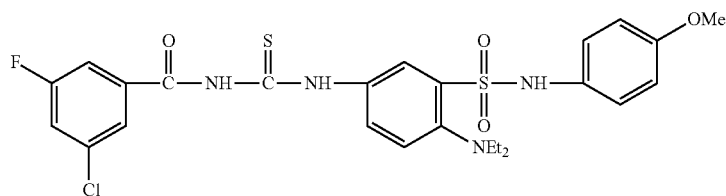

Answer 5:

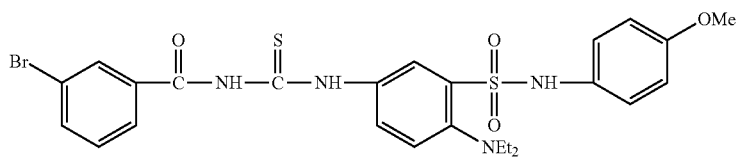

Answer 6:
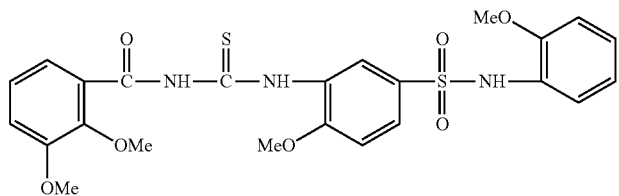
Answer 7:
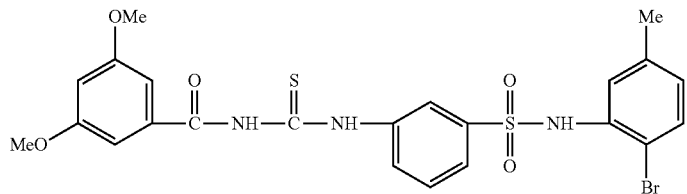
Answer 8:
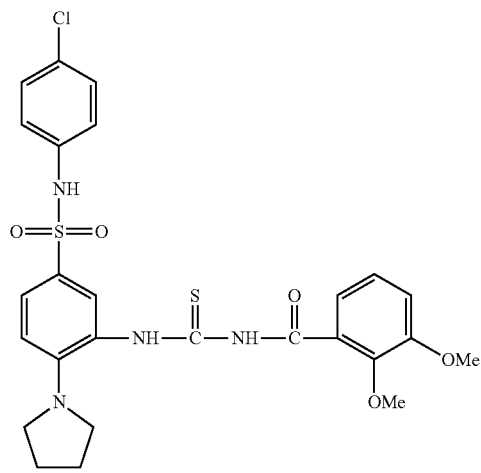
Answer 9:
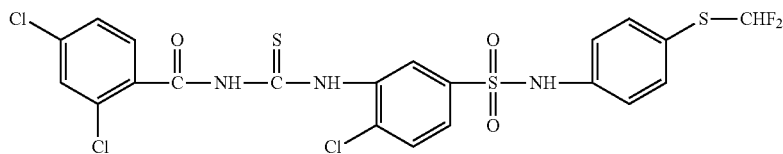
Answer 10:
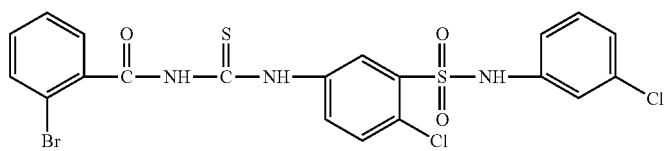
Answer 11:
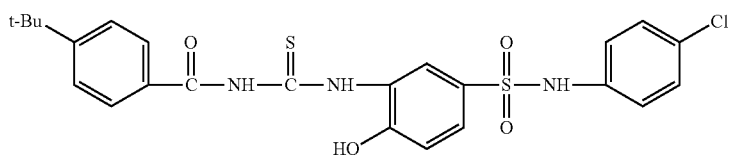

Answer 12:
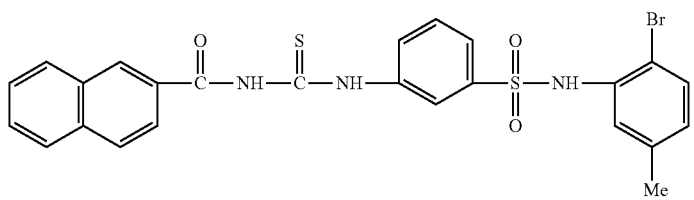
Answer 13:
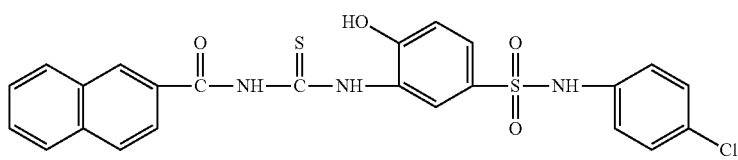
Answer 14:
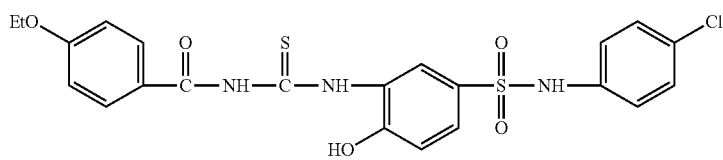
Answer 15:
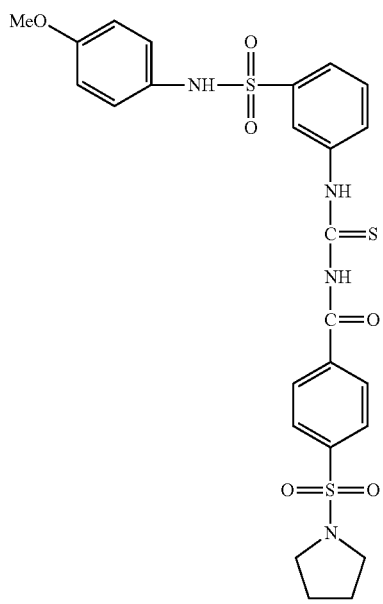
Answer 16:
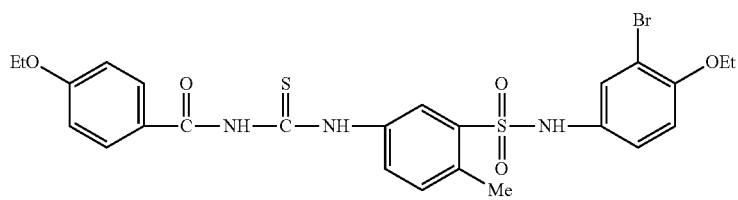

Answer 17:
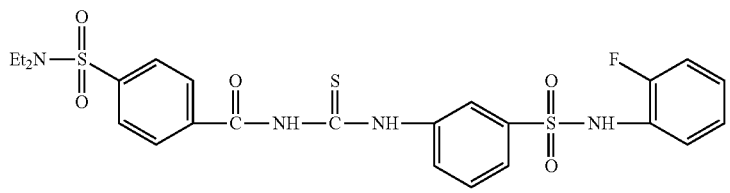
Answer 18:
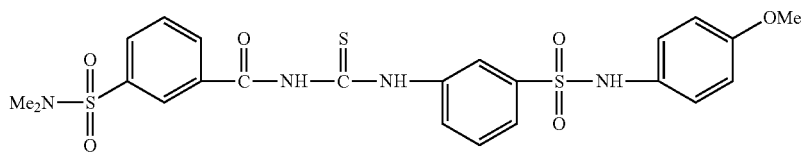
Answer 19:
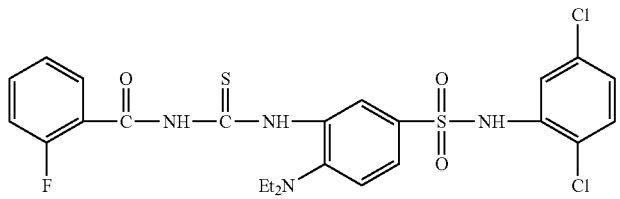
Answer 20:
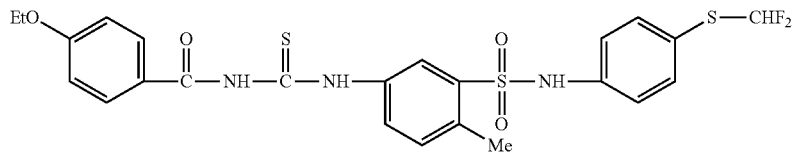
Answer 21:
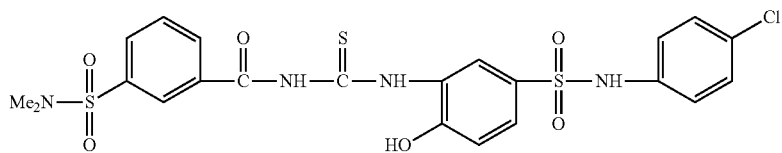

Answer 22:
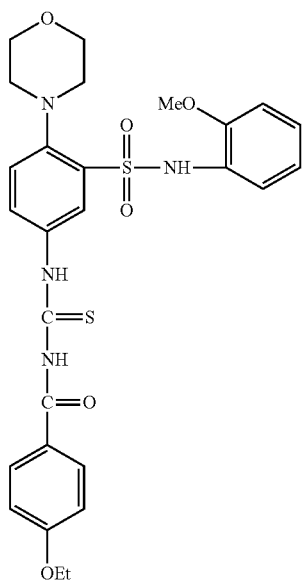
Answer 23:
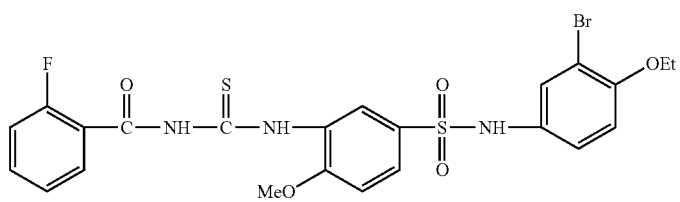
Answer 24:
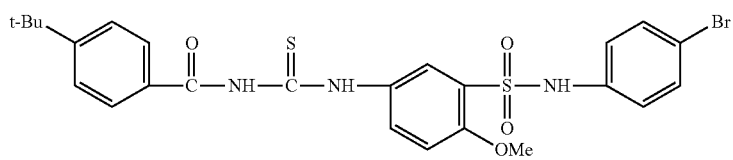
Answer 25:
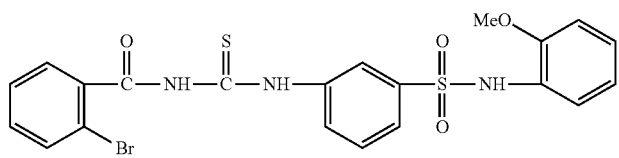
Answer 26:
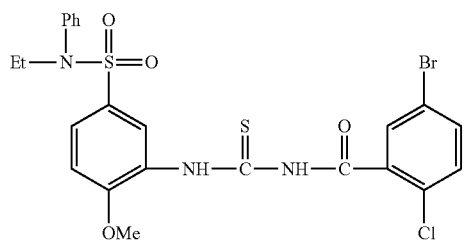

Answer 27:
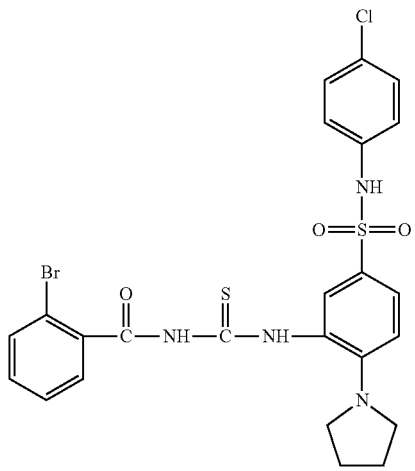
Answer 28:
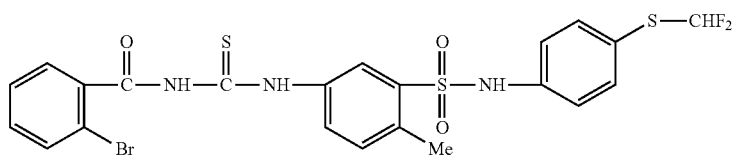
Answer 29:
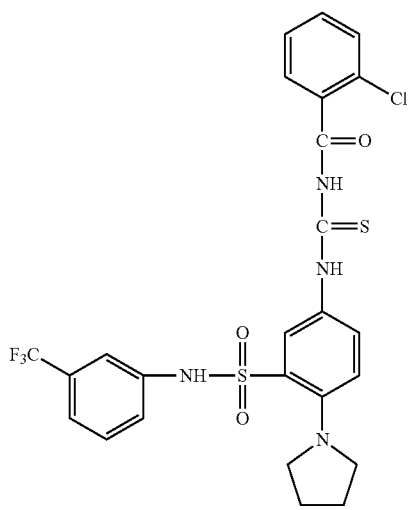
Answer 30:
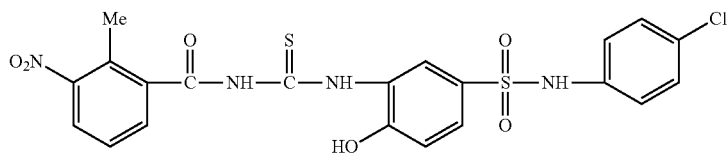
Answer 31:
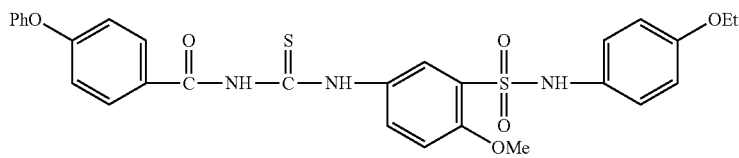

Answer 32:
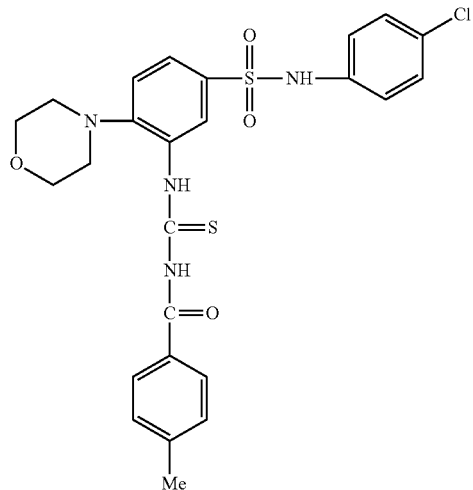
Answer 33:
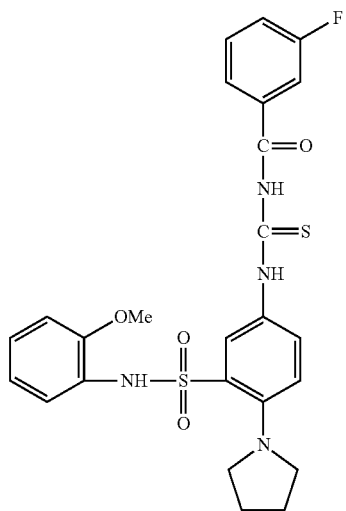
Answer 34:
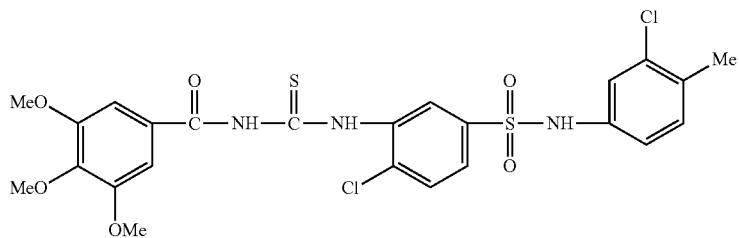
Answer 35:
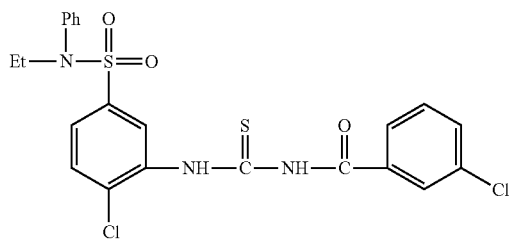

-continued
Answer 36:
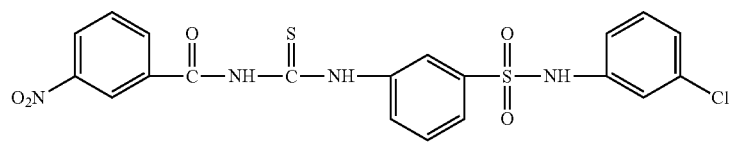
Answer 37:
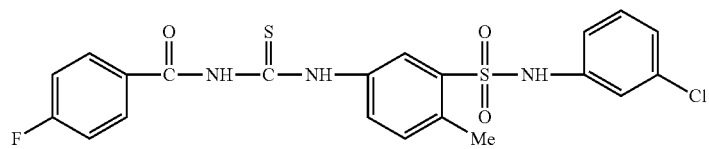
Answer 38:
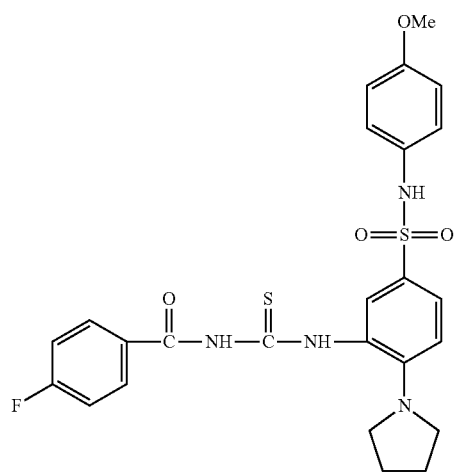
Answer 39:
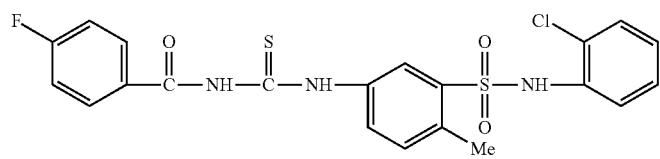
Answer 40:
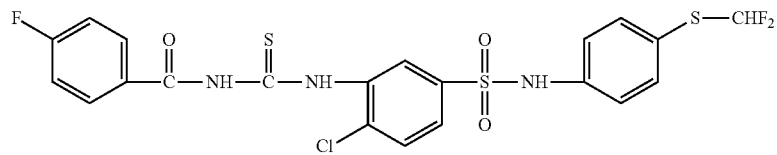
Answer 41:
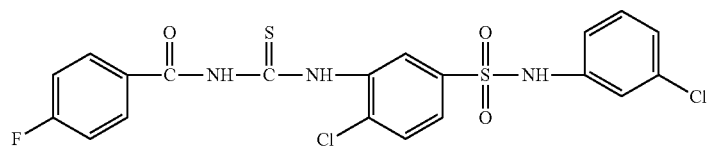

Answer 42:
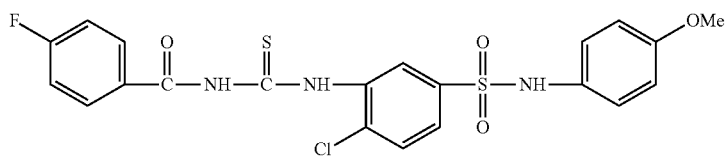
Answer 43:
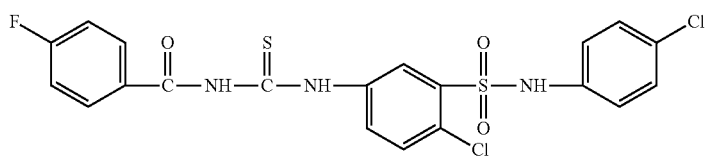
Answer 44:
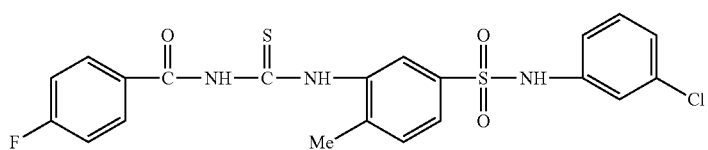
Answer 45:
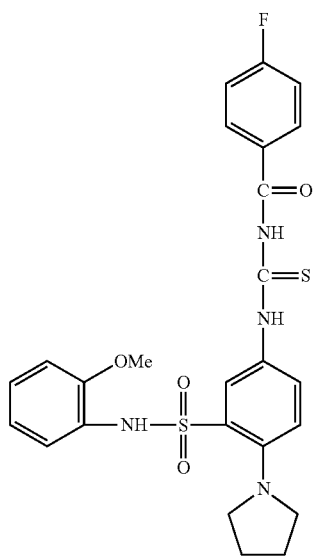
Answer 1:
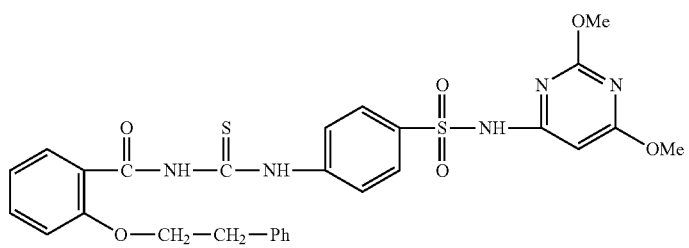

Answer 2:
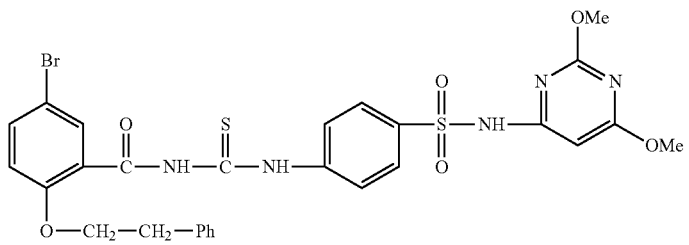
Answer 3:
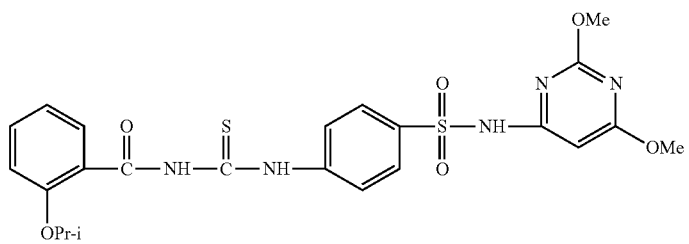
Answer 4:
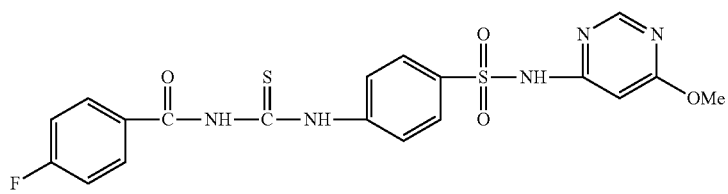
Answer 5:
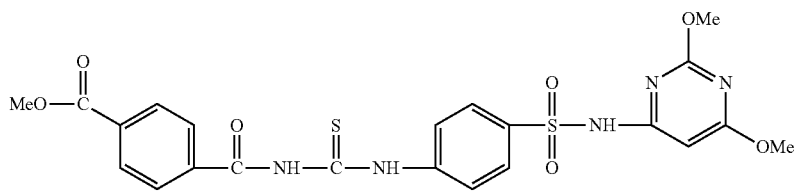
Answer 6:
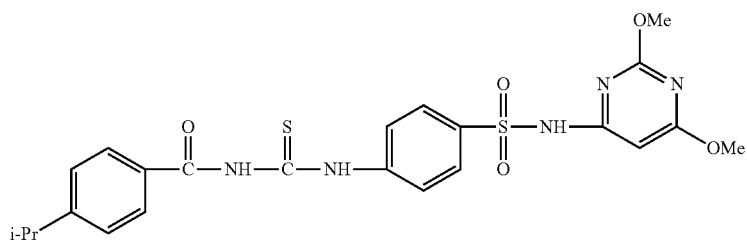
Answer 7:
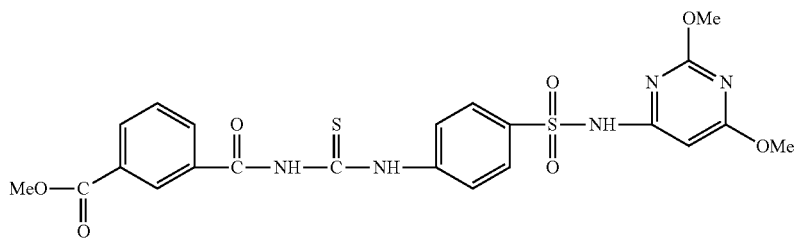

Answer 8:
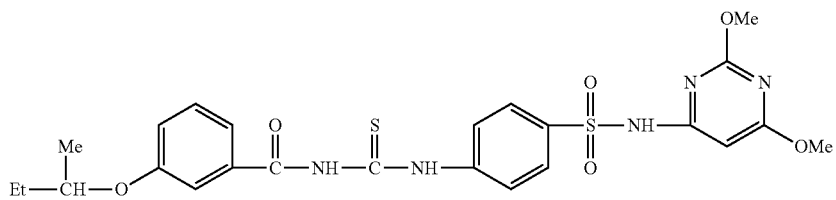
Answer 9:
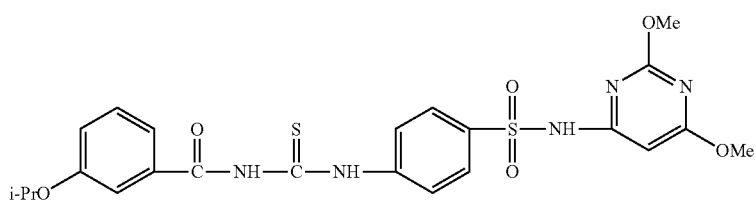
Answer 10:
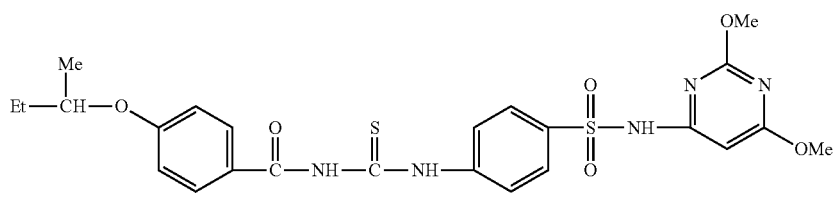
Answer 11:
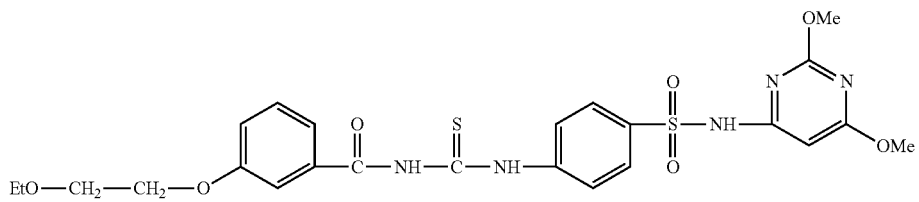
Answer 12:
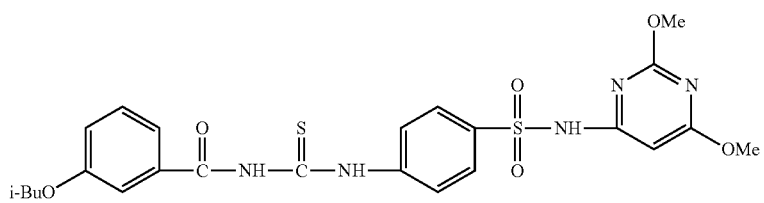
Answer 13:
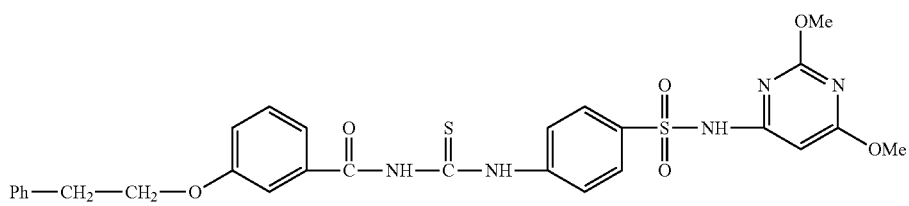

Answer 14:
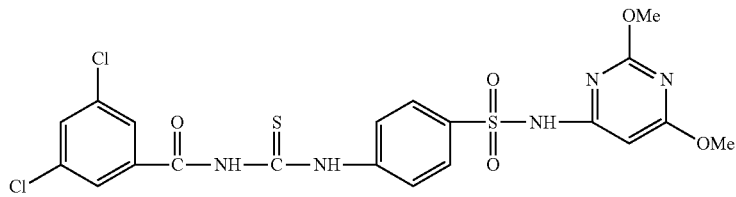
Answer 15:
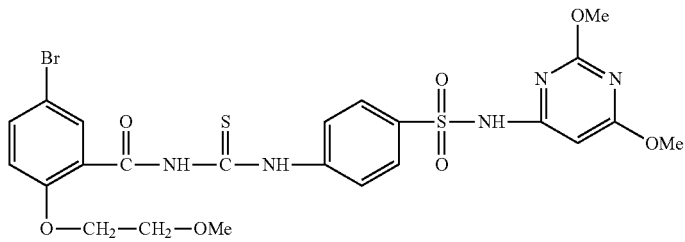
Answer 16:
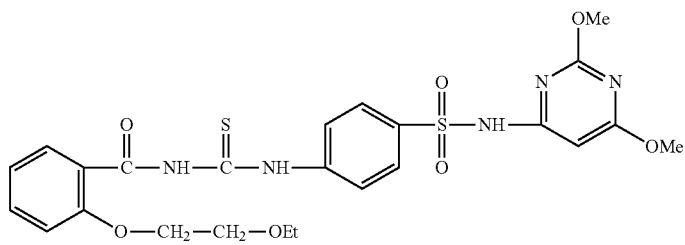
Answer 17:
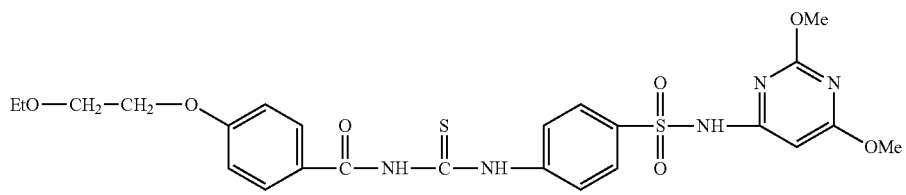
Answer 18:
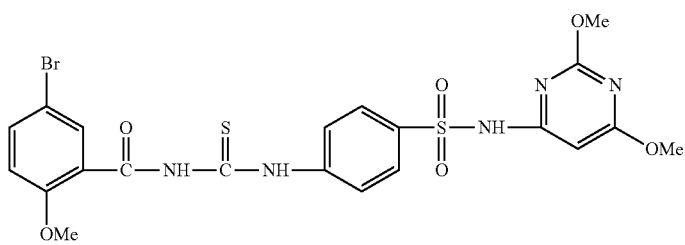
Answer 19:
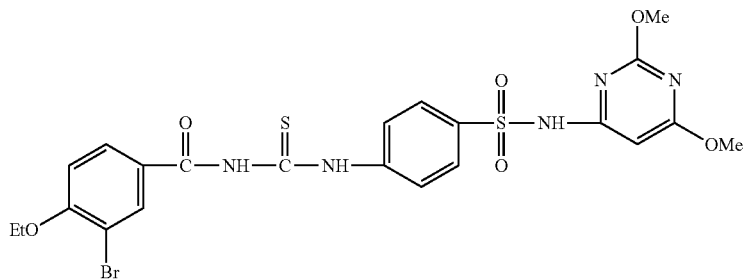

Answer 20:
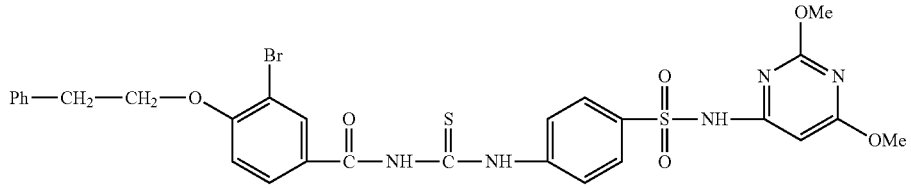
Answer 21:
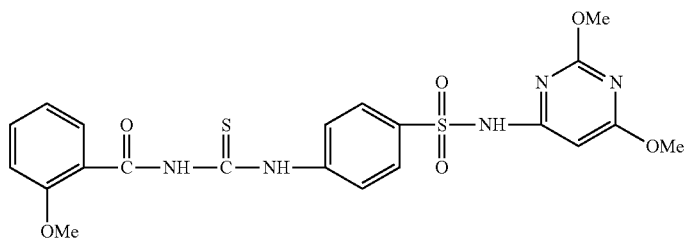
Answer 22:
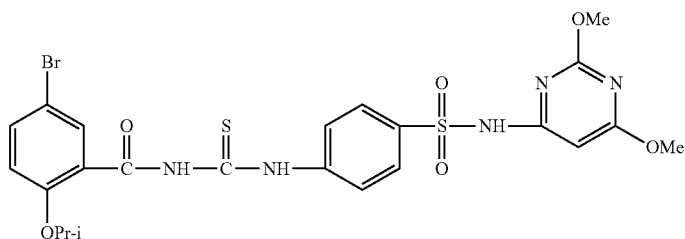
Answer 23:
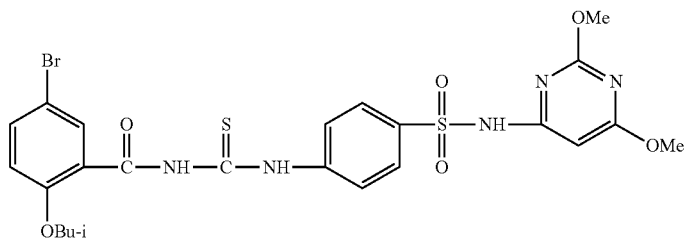
Answer 24:
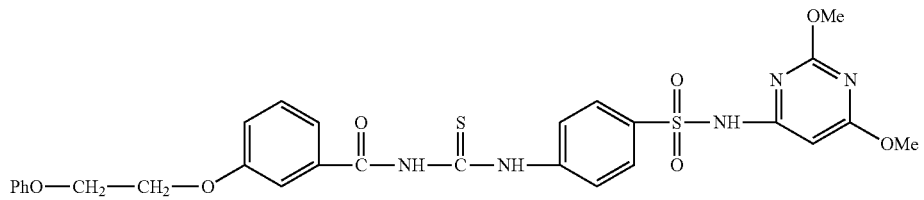
Answer 25:
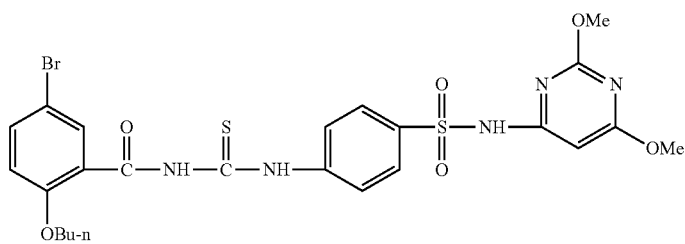

-continued
Answer 26:
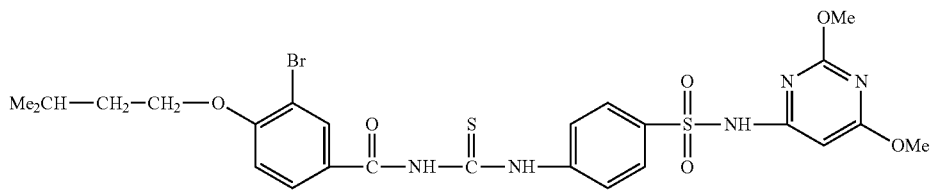
Answer 27:
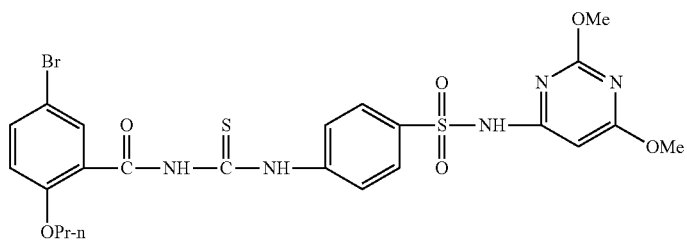
Answer 28:
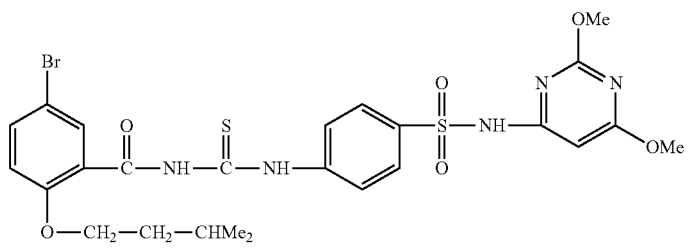
Answer 29:
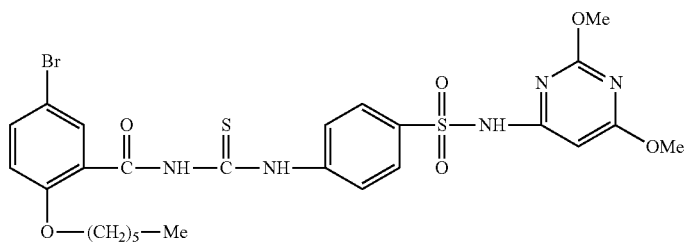
Answer 30:
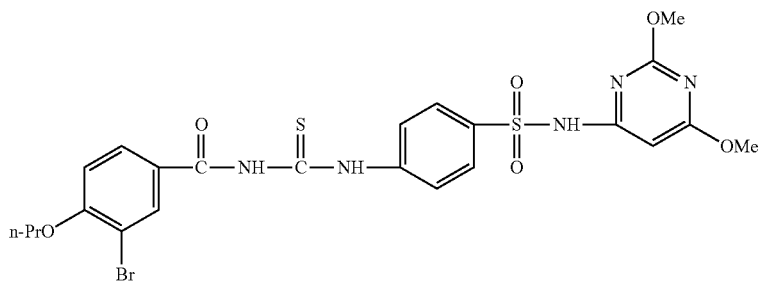
Answer 31:
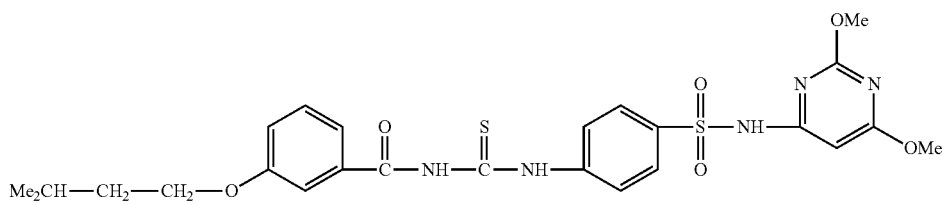

Answer 32:
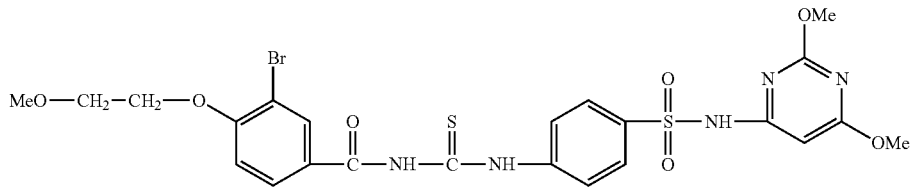
Answer 33:
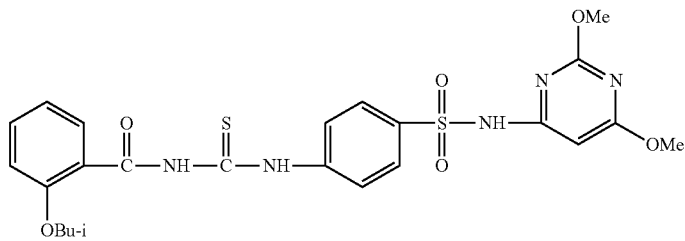
Answer 34:
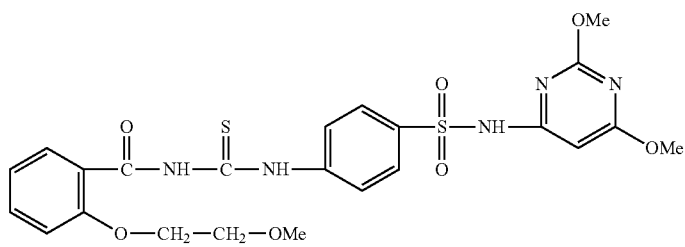
Answer 35:
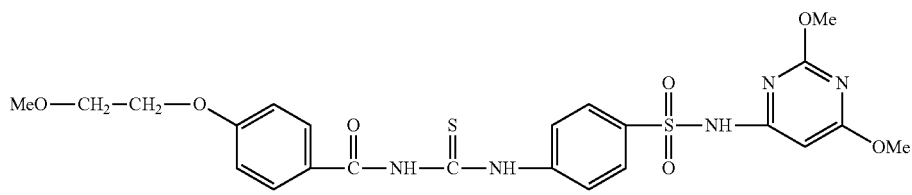
Answer 36:
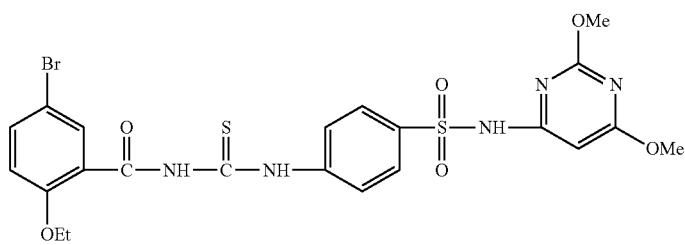
Answer 37:
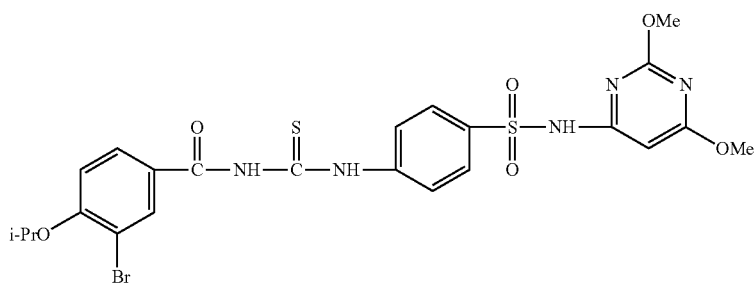

Answer 38:
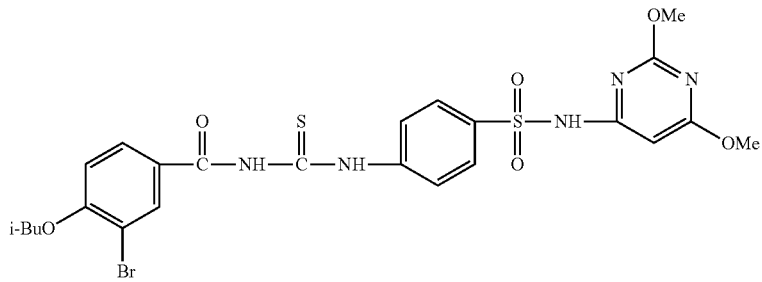
Answer 39:
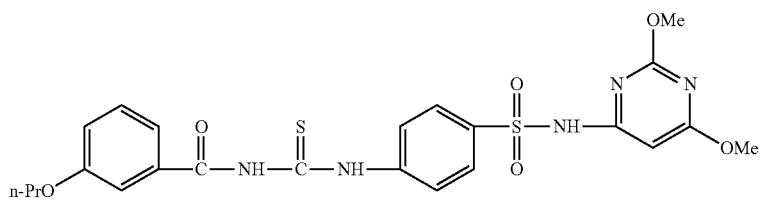
Answer 40:
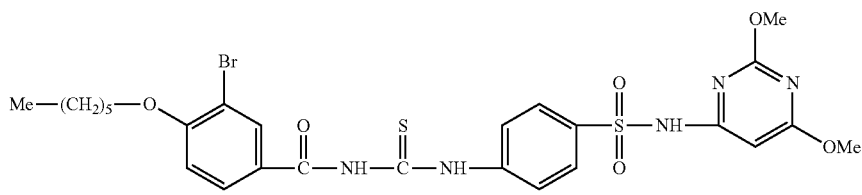
Answer 41:
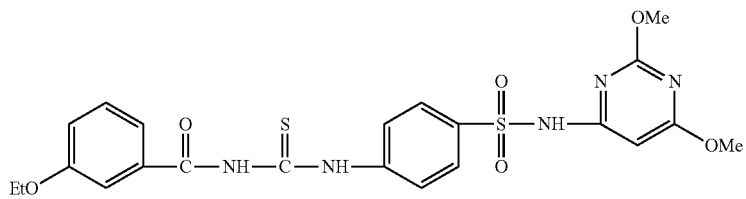
Answer 42:
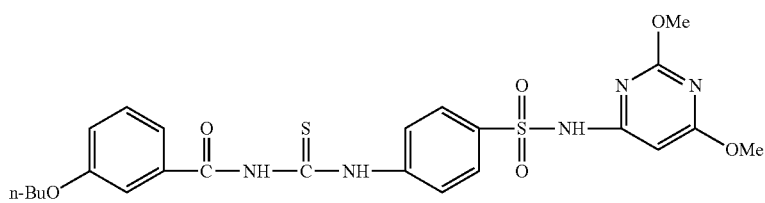
Answer 43:
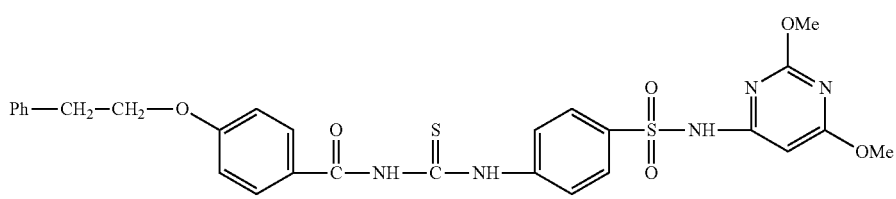

Answer 44:
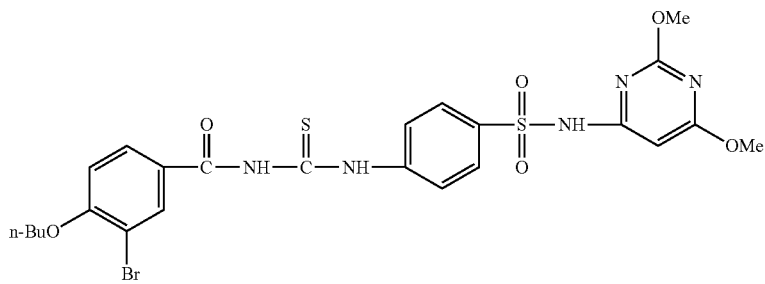
Answer 45:
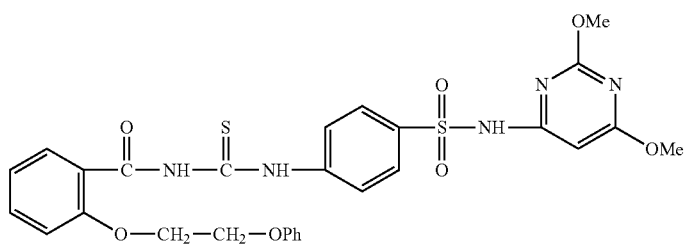
Answer 46:
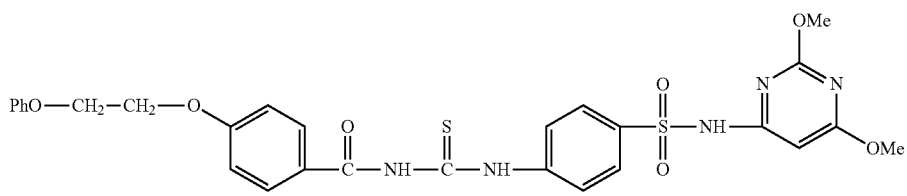
Answer 47:
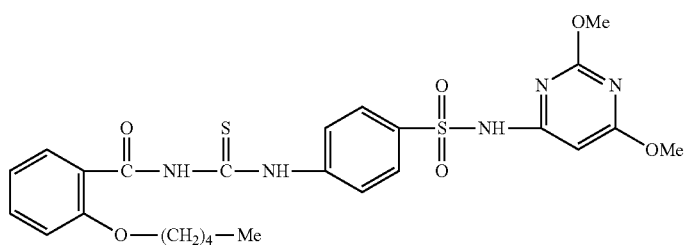
Answer 48:
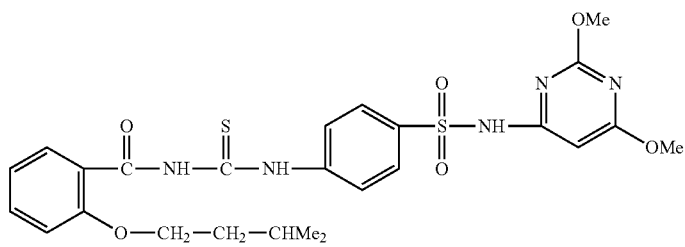

Answer 49:
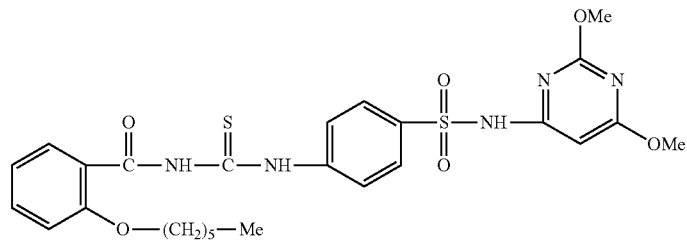
Answer 50:
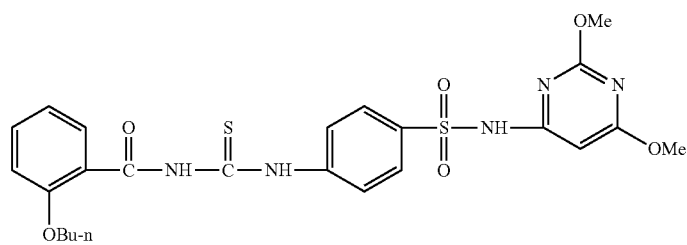
Answer 51:
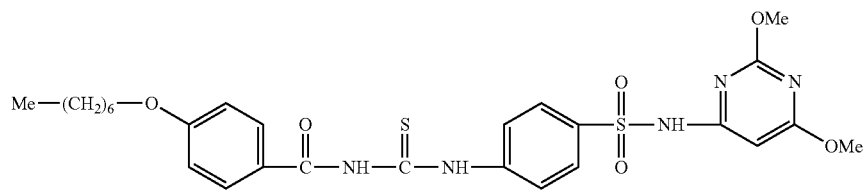
Answer 52:
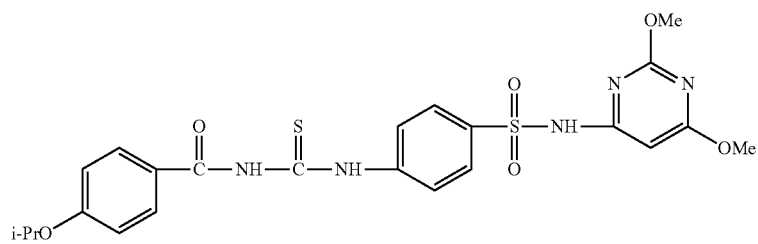
Answer 53:
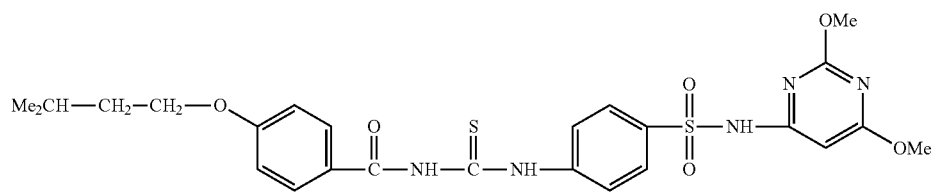
Answer 54:
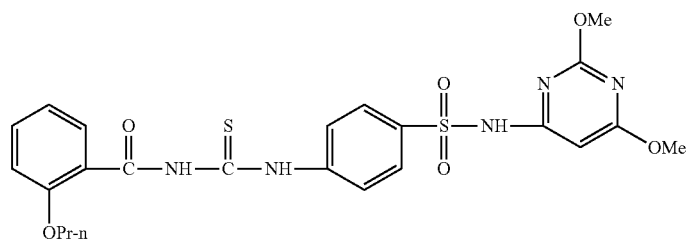

Answer 55:
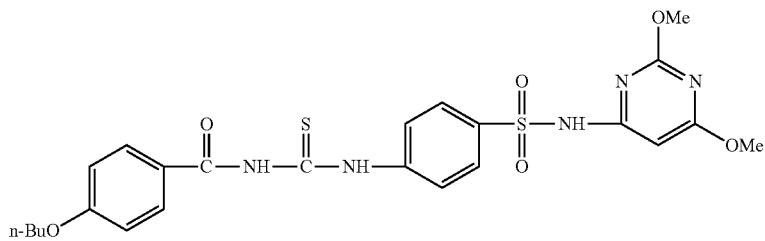
Answer 56:
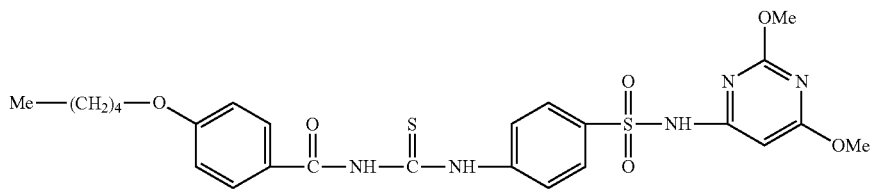
Answer 57:
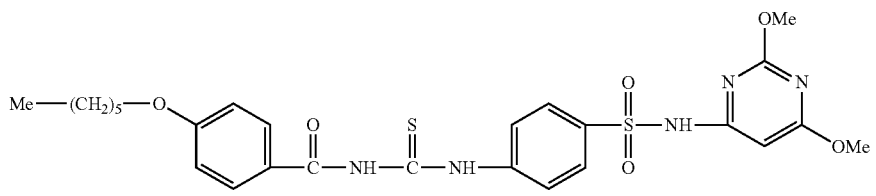
Answer 58:
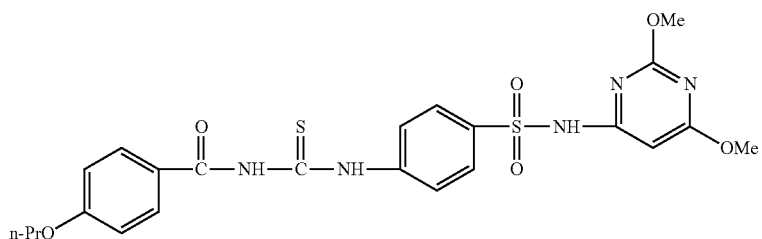
Answer 59:
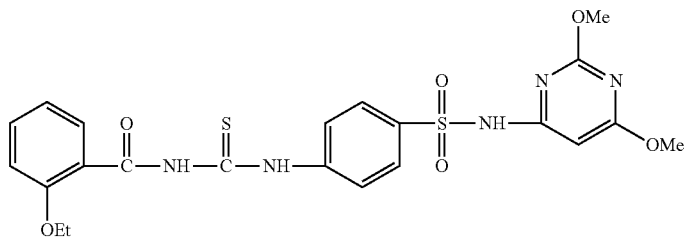
Answer 60:
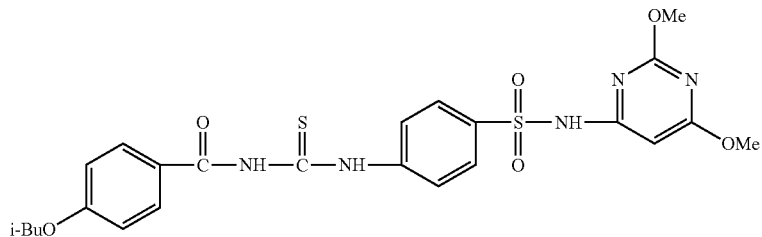

Answer 61:
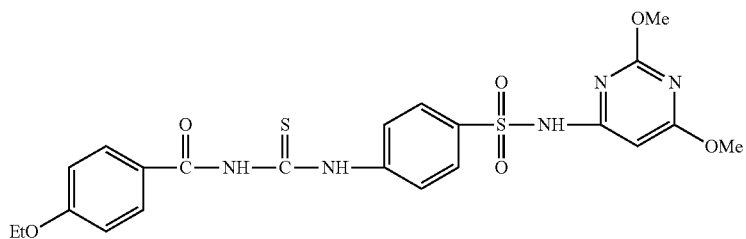
Answer 62:
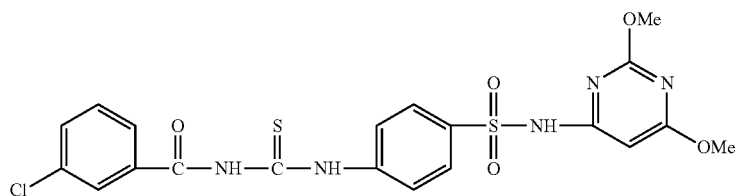
Answer 63:
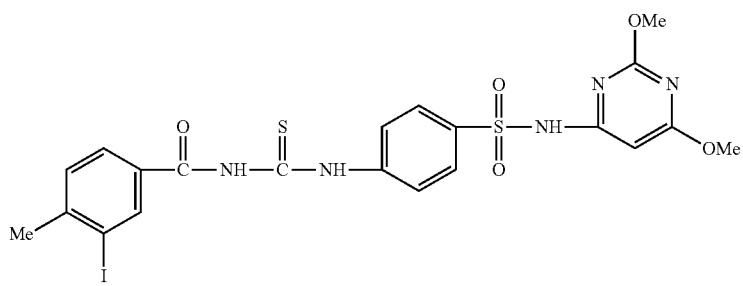
Answer 64:
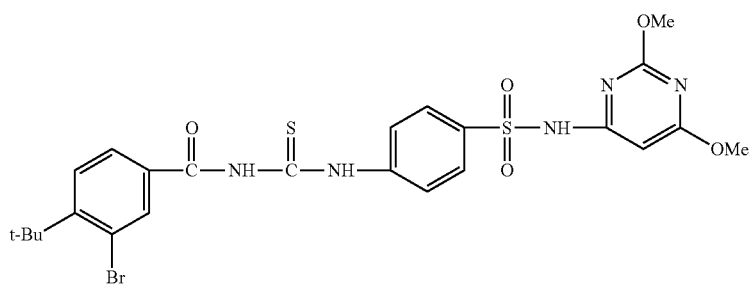
Answer 65:
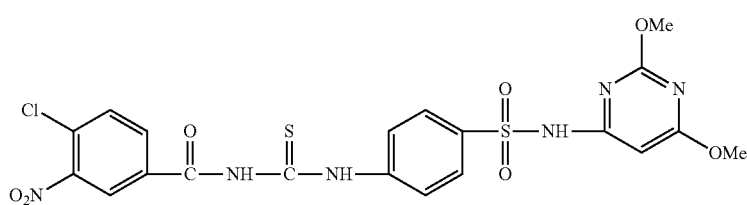

Answer 66:
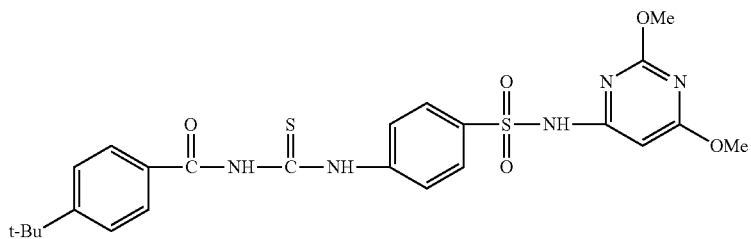
Answer 67:
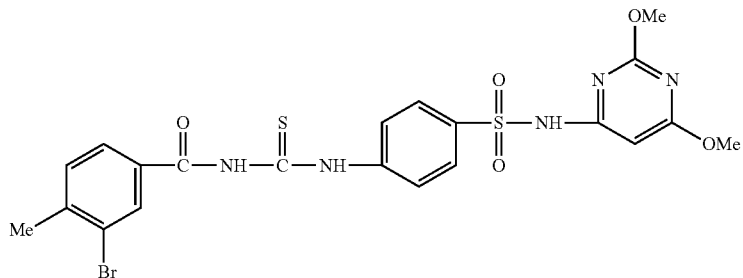
Answer 68:
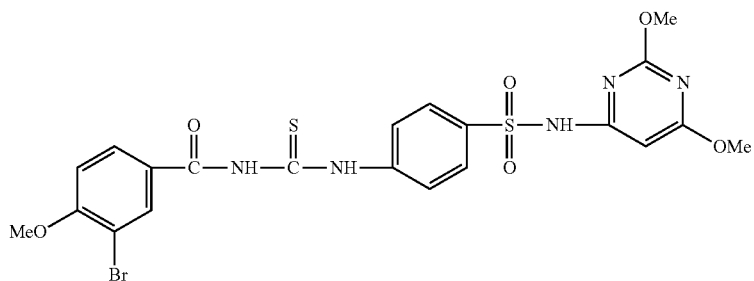
Answer 69:
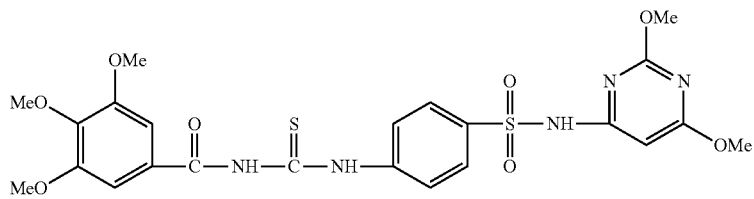
Answer 70:
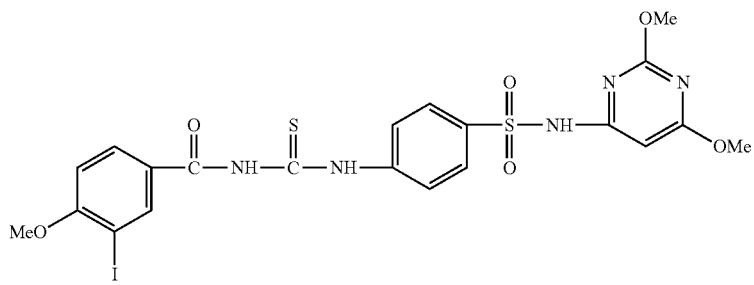

-continued
Answer 71:
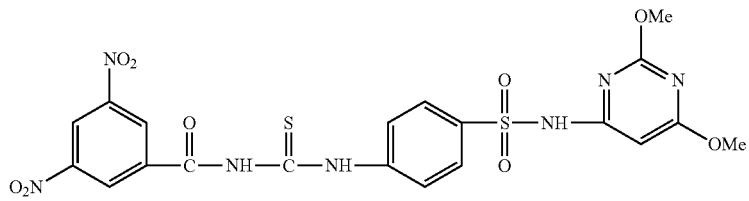
Answer 72:
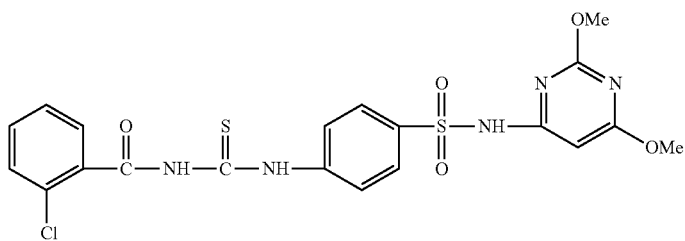
Answer 73:
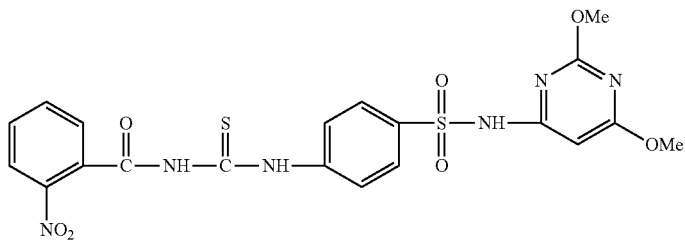
Answer 74:
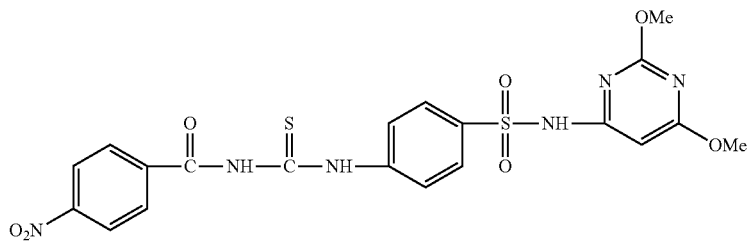
Answer 75:
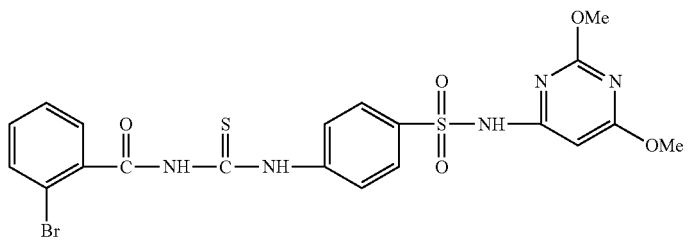
Answer 76:
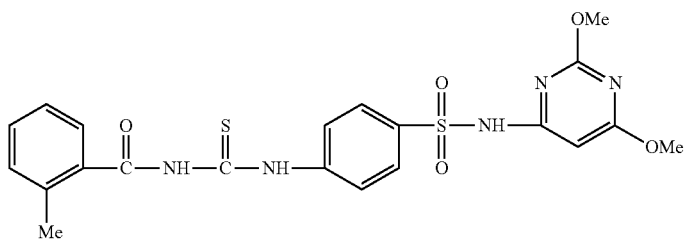

Answer 77:
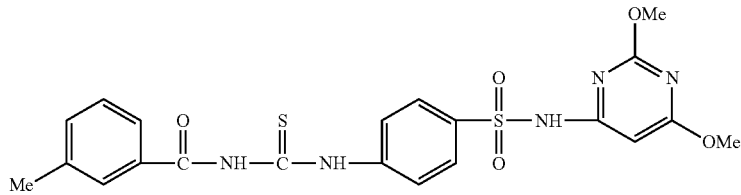
Answer 78:
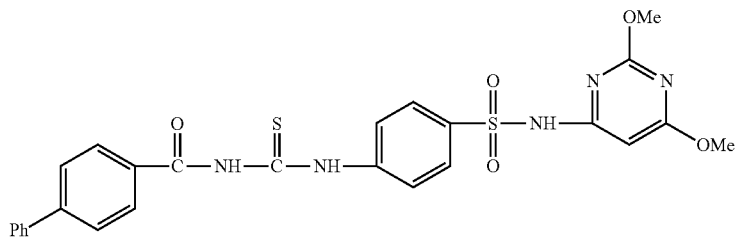
Answer 79:
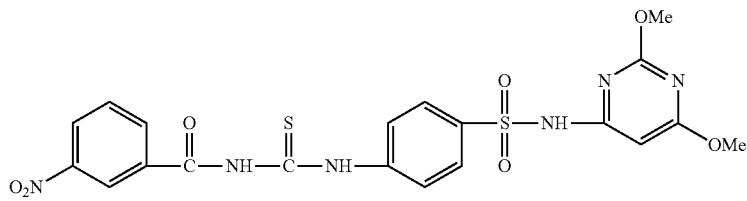
Answer 80:
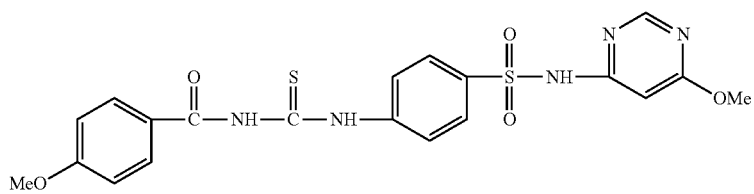
Answer 81:
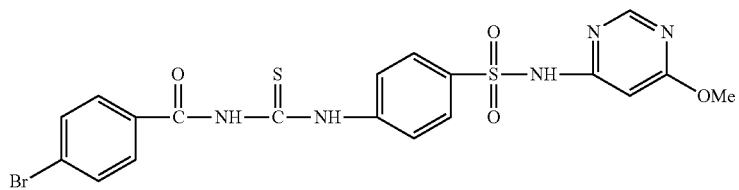
Answer 82:
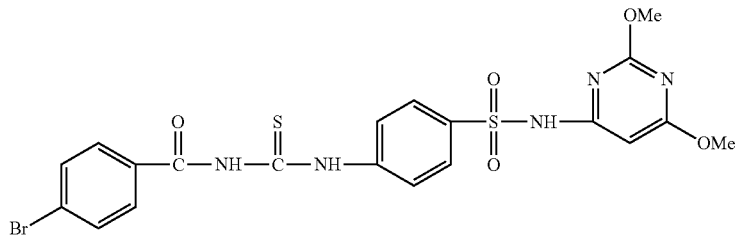

Answer 83:
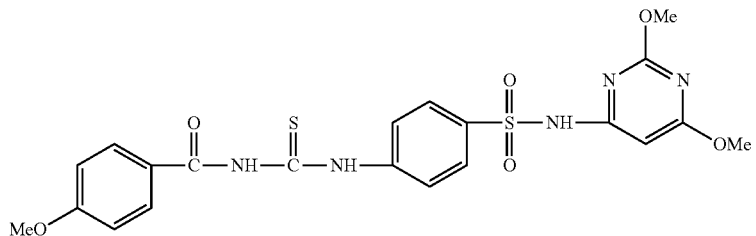
Answer 84:
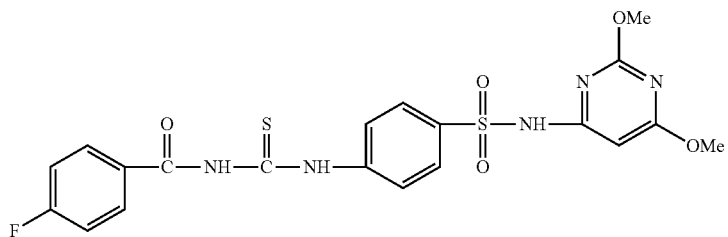
Answer 85:
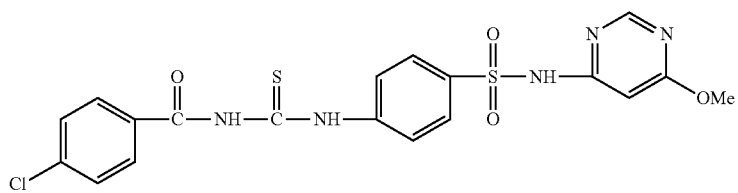
Answer 86:
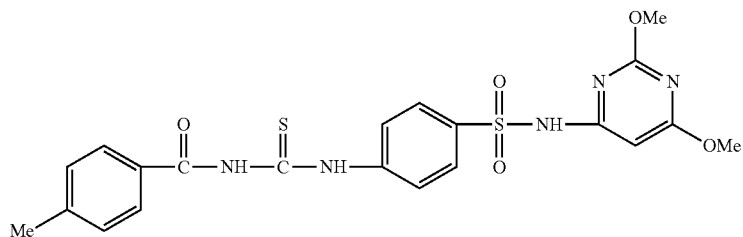
Answer 87:
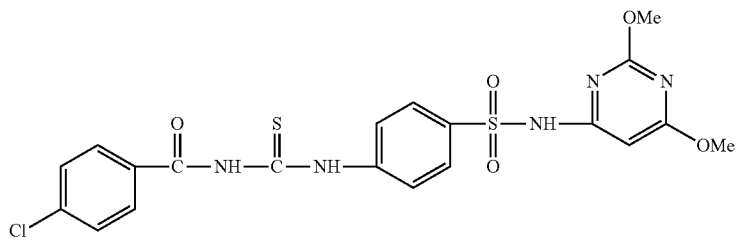
Answer 88:
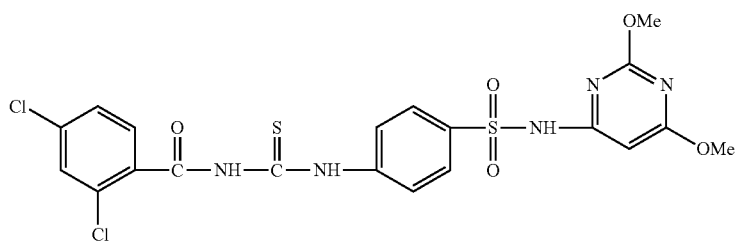

-continued
Answer 89:
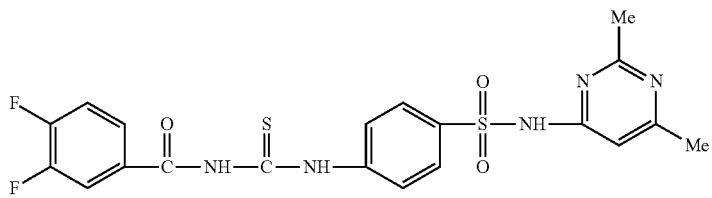
Answer 90:
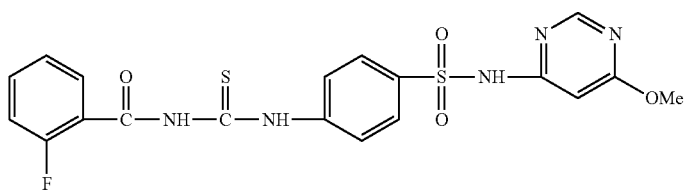
Answer 91:
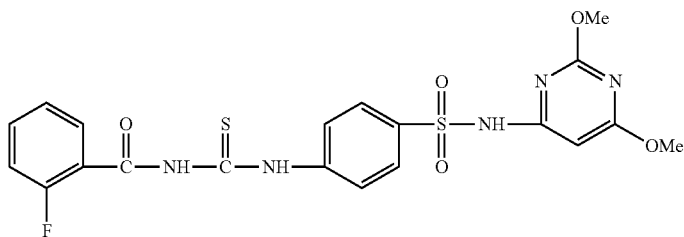
Answer 92:
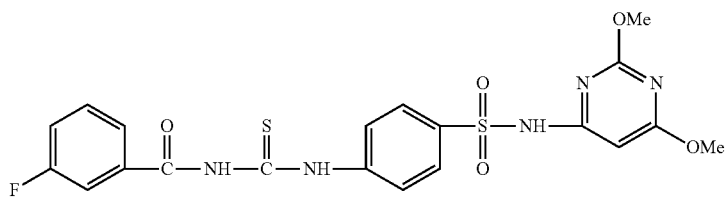
Answer 93:
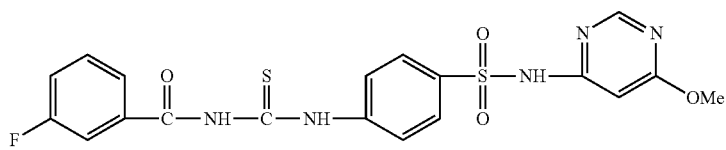
Answer 94:
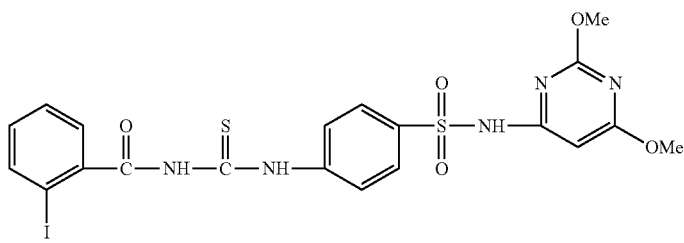

Answer 95:
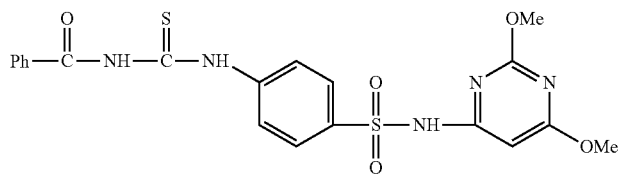
Answer 96:
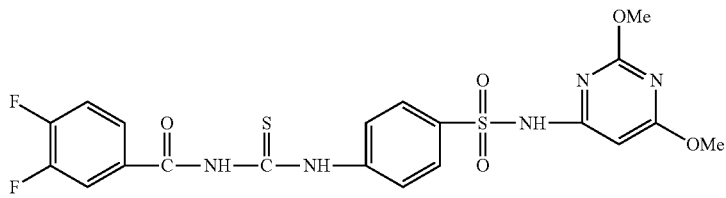
Answer 97:
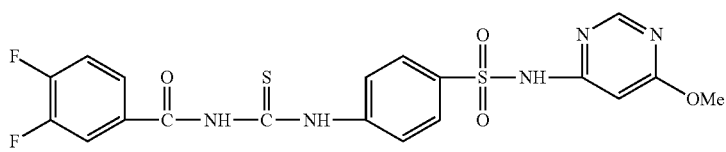
Answer 1:
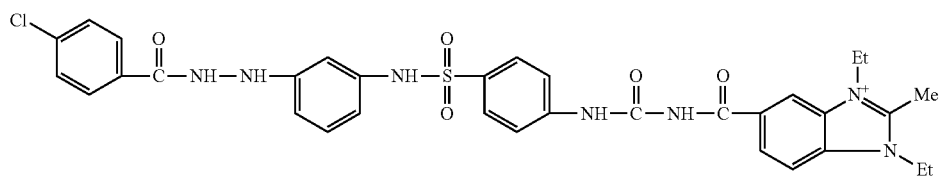
Answer 2:
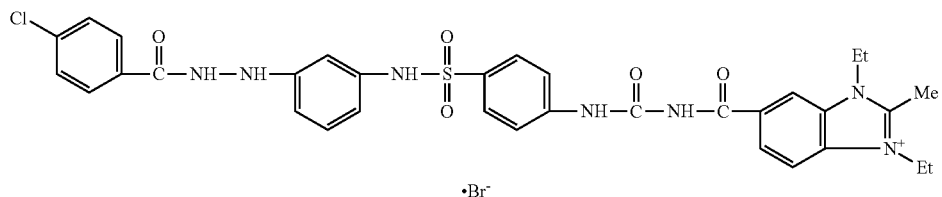
•Br⁻
Answer 1:
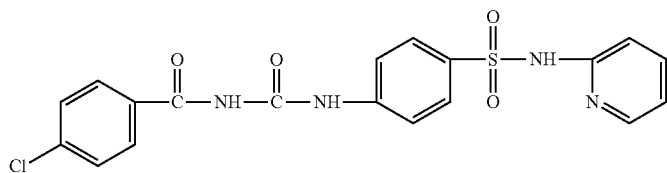
Answer 1:
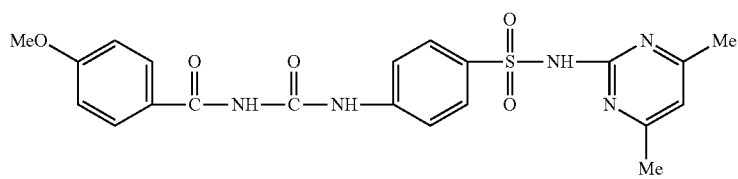

-continued
Answer 2:
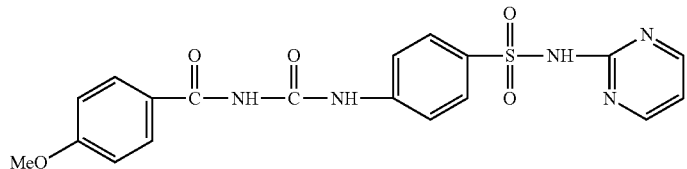
Answer 3:
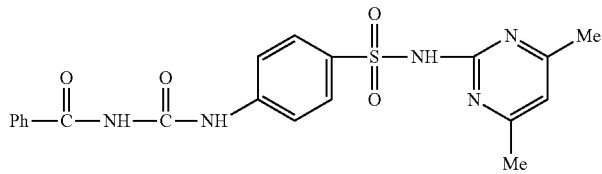
Answer 4:
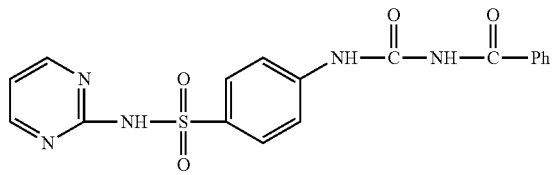
Answer 5:
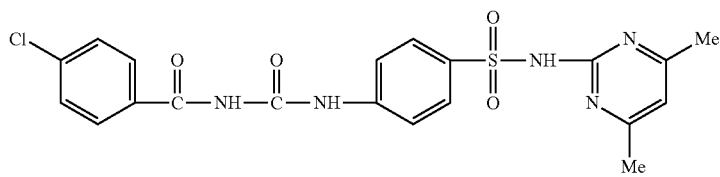
Answer 6:
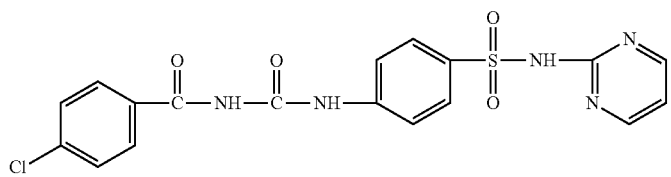
Answer 7:
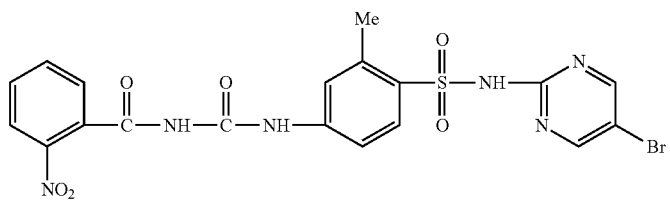
Answer 1:
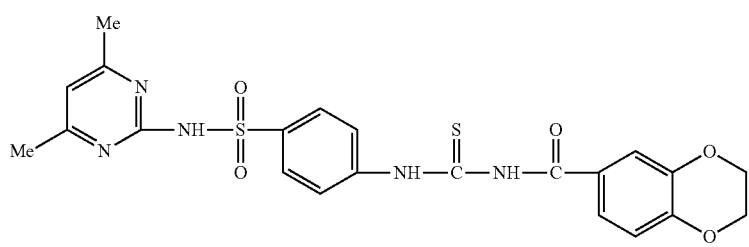

Answer 2:
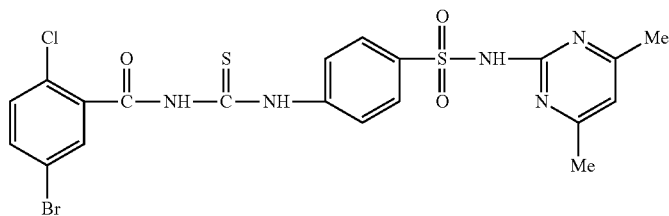
Answer 3:
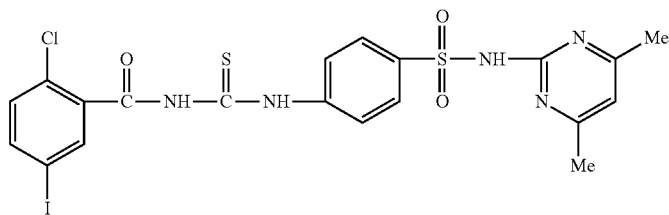
Answer 4:
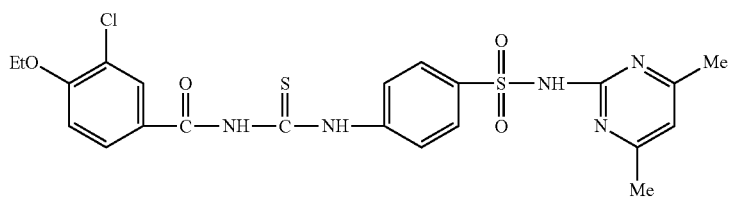
Answer 5:
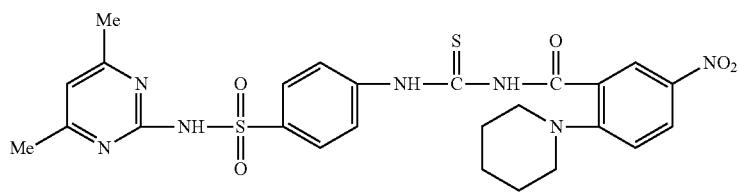
Answer 6:
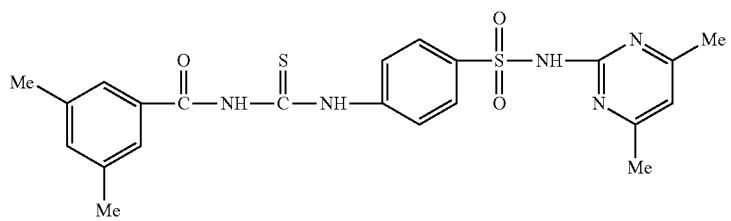

Answer 7:
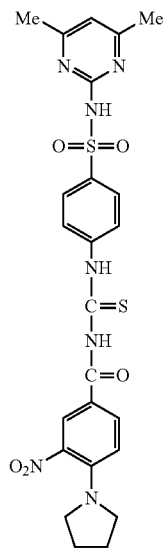
Answer 8:
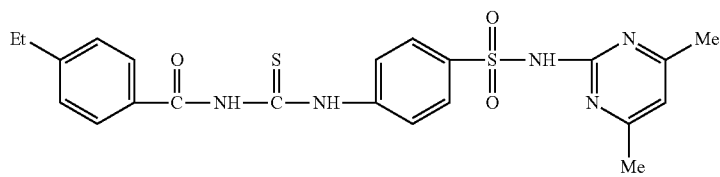
Answer 9:
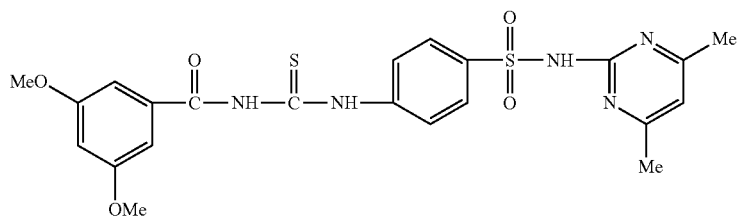
Answer 10:
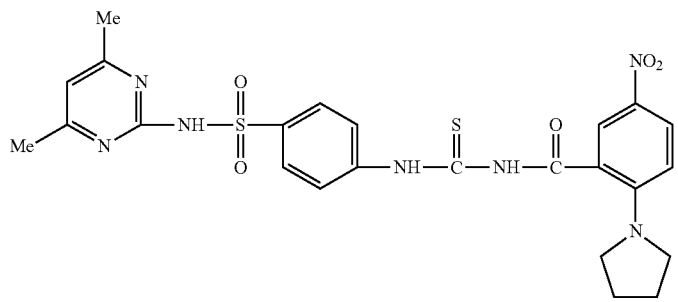
Answer 11:
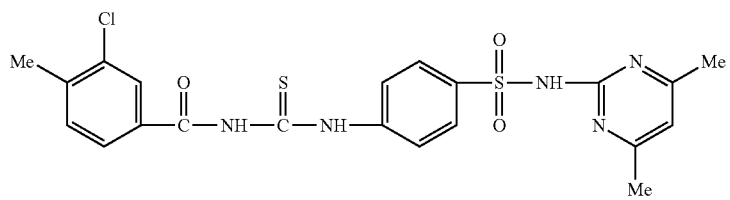

Answer 12:
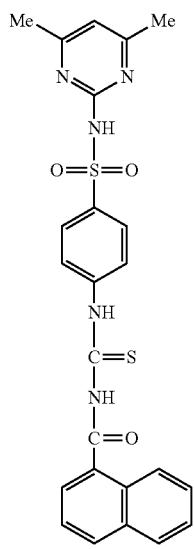
Answer 13:
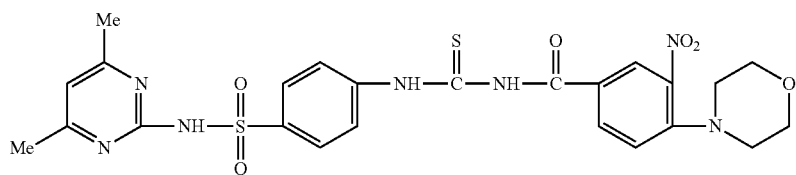
Answer 14:
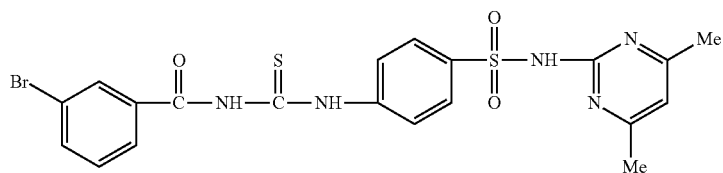
Answer 15:
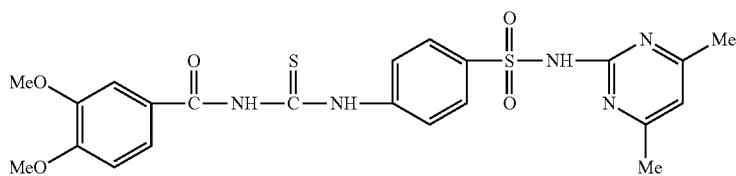
Answer 16:
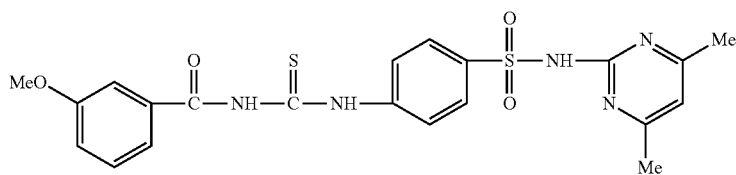

Answer 17:
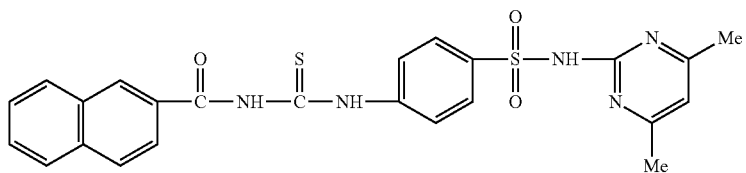
Answer 18:
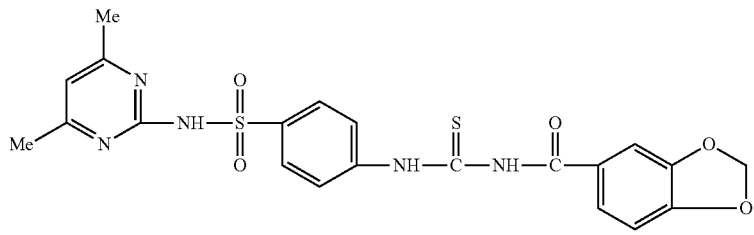
Answer 19:
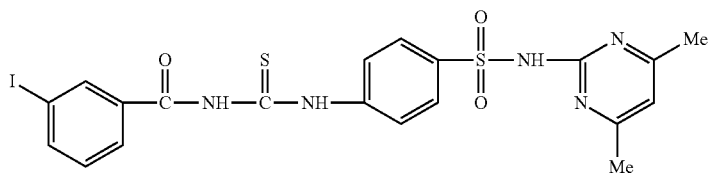
Answer 20:
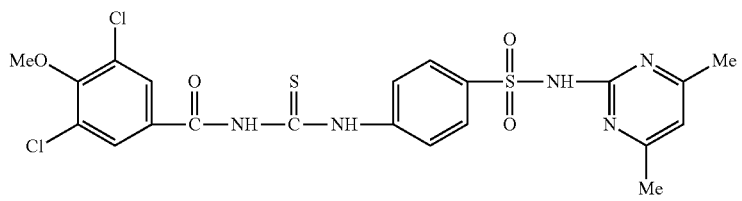
Answer 21:
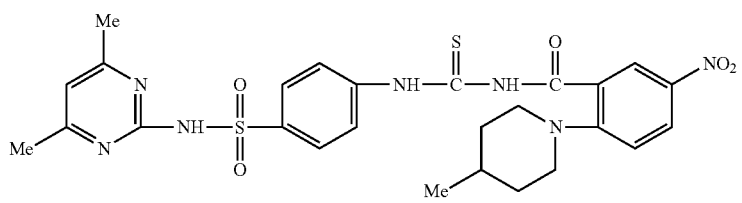
Answer 22:
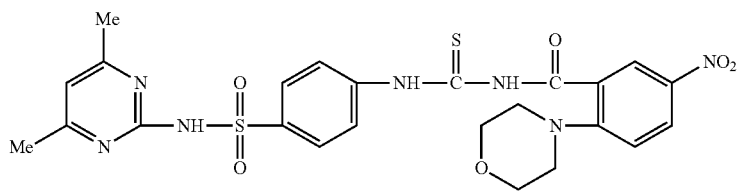
Answer 23:
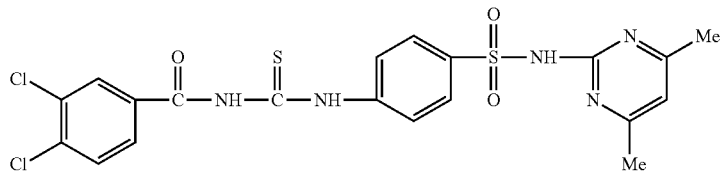

Answer 24:
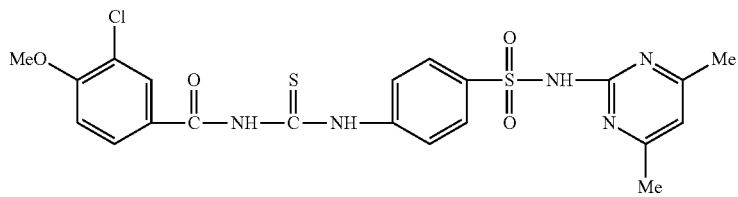
Answer 25:
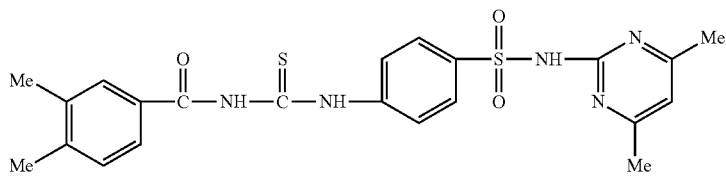
Answer 26:
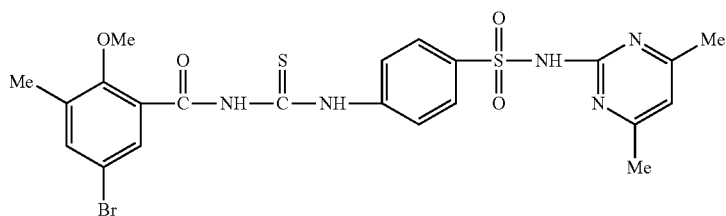
Answer 27:
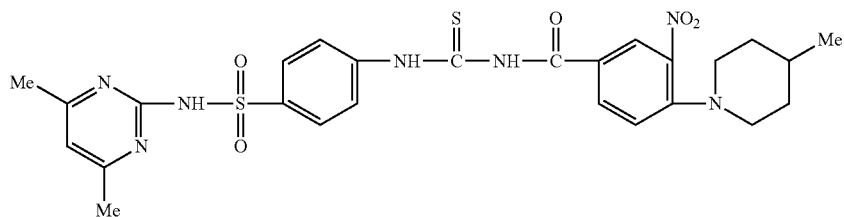
Answer 28:
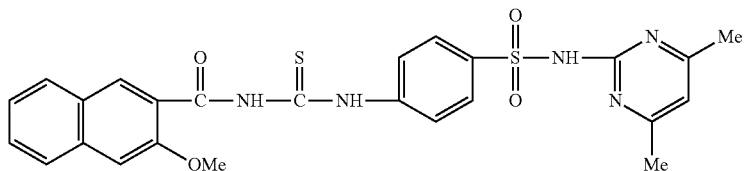
Answer 29:
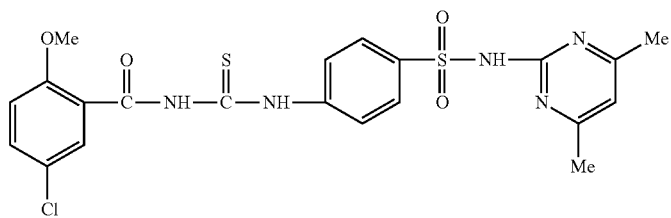

Answer 30:
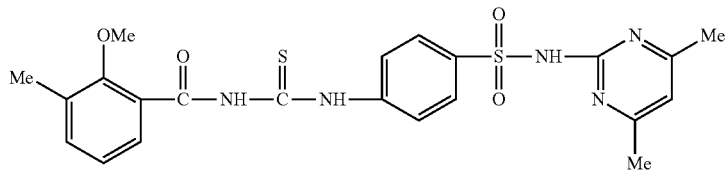
Answer 31:
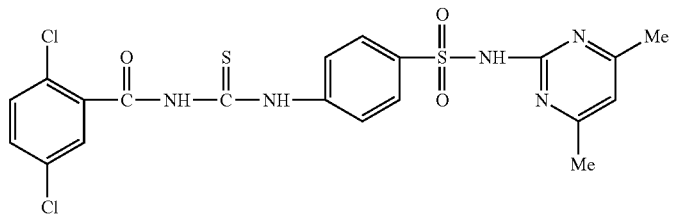
Answer 32:
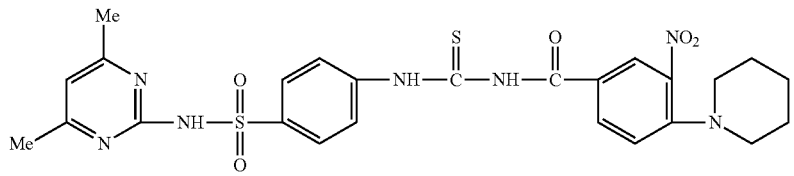
Answer 33:
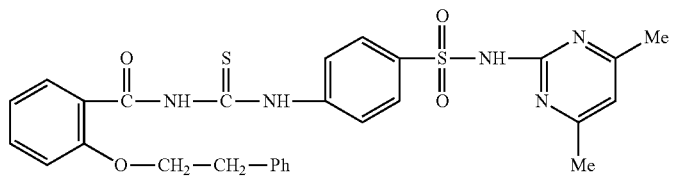
Answer 34:
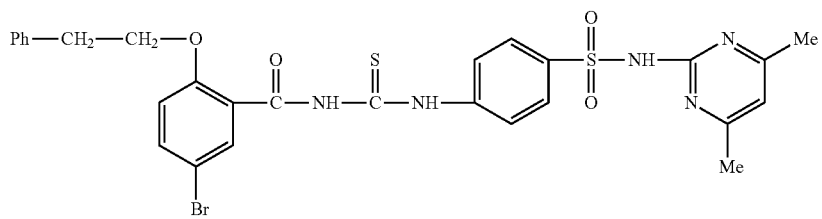
Answer 35:
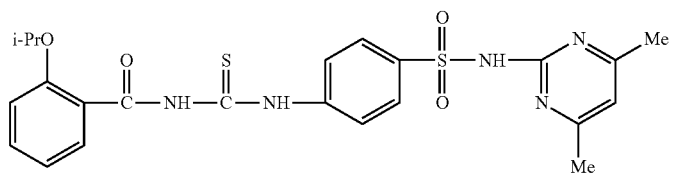
Answer 36:
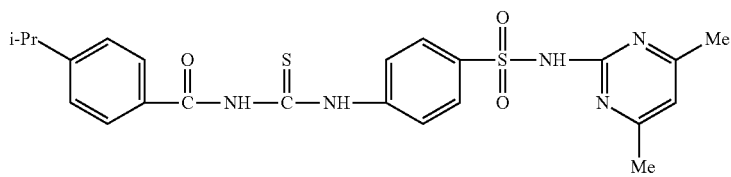

-continued
Answer 37:
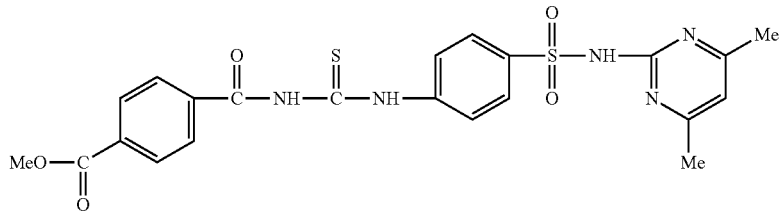
Answer 38:
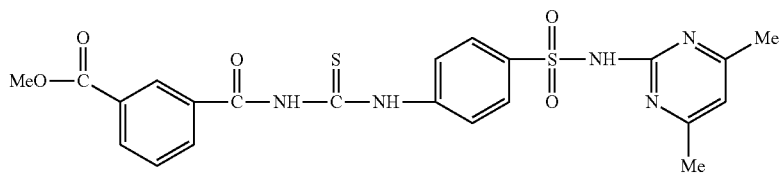
Answer 39:
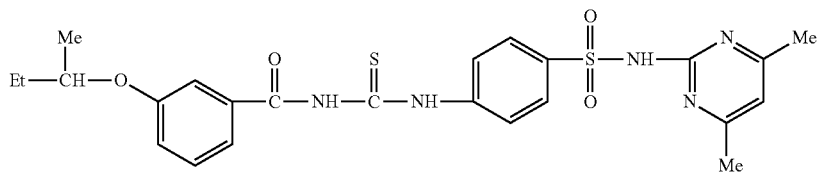
Answer 40:
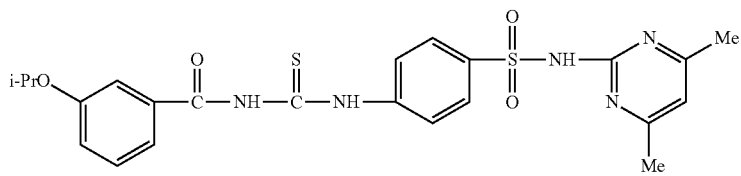
Answer 41:
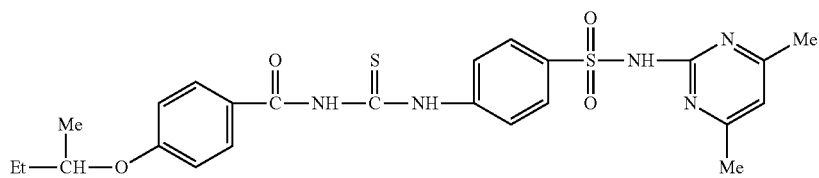
Answer 42:
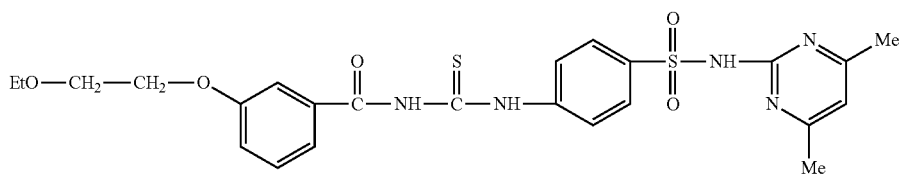
Answer 43:
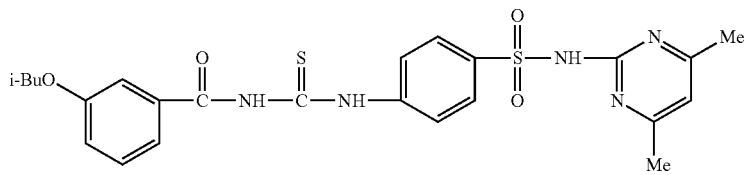

-continued
Answer 44:
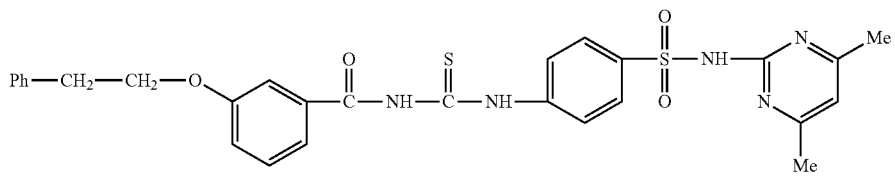
Answer 45:
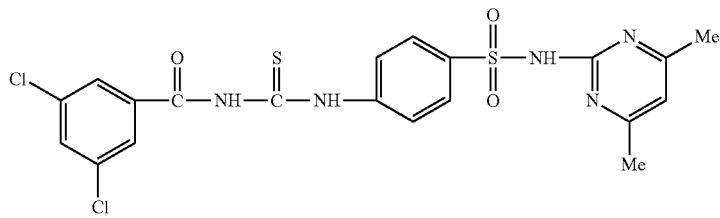
Answer 46:
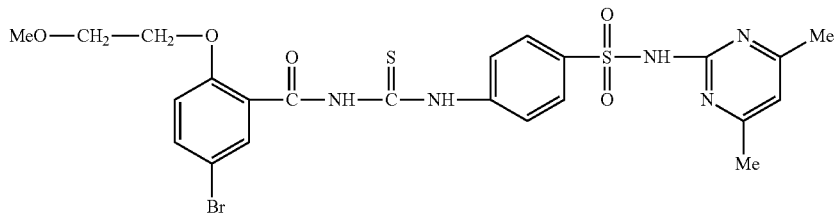
Answer 47:
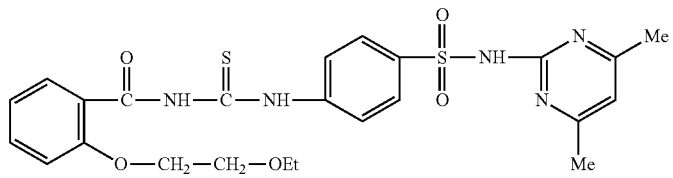
Answer 48:
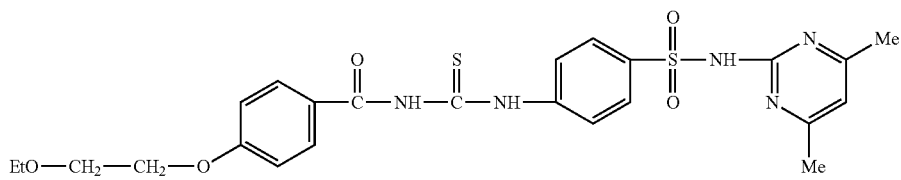
Answer 49:
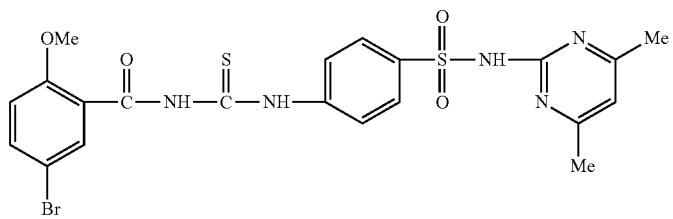

Answer 50:
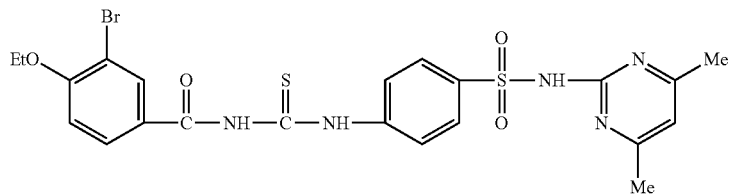
Answer 51:
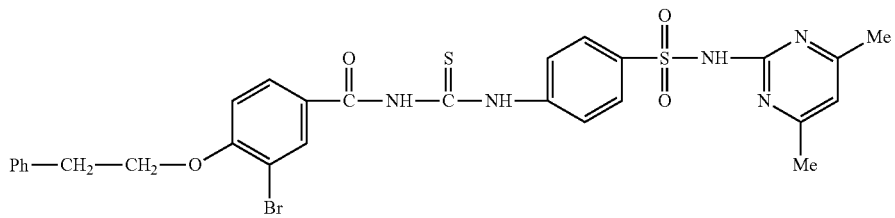
Answer 52:
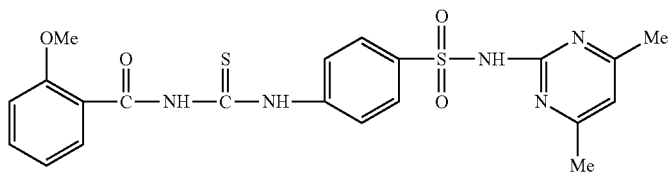
Answer 53:
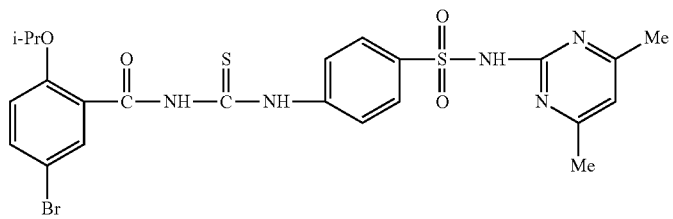
Answer 54:
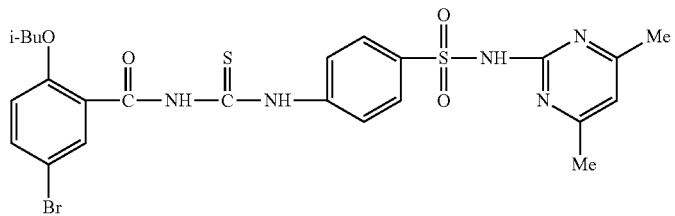
Answer 55:
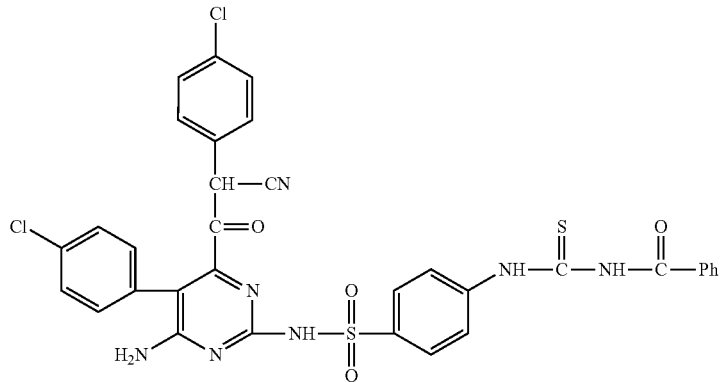

Answer 56:
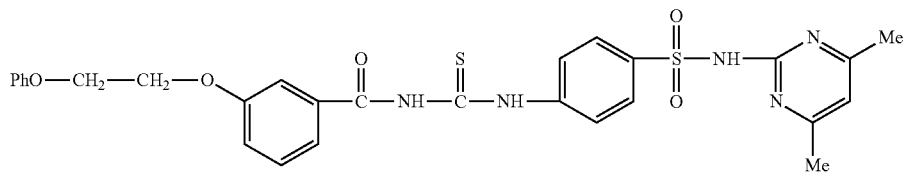
Answer 57:
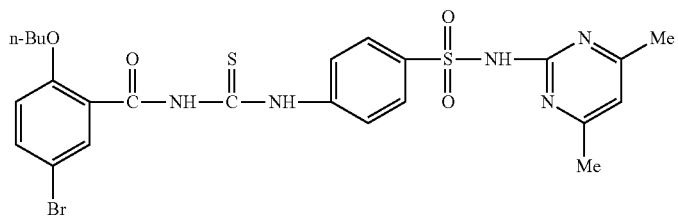
Answer 58:
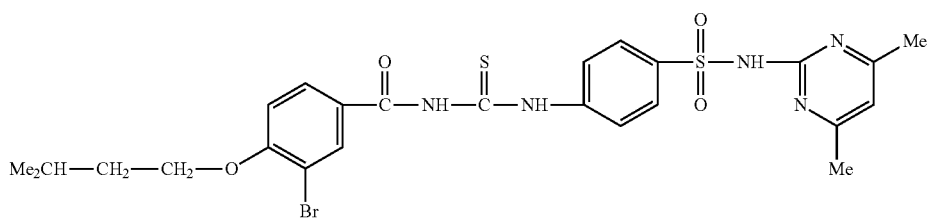
Answer 59:
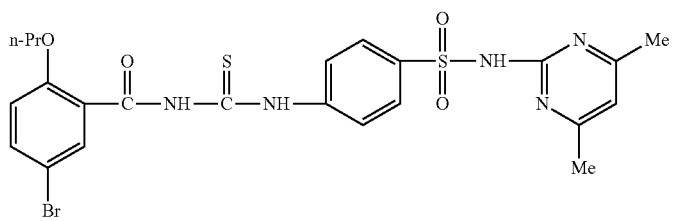
Answer 60:
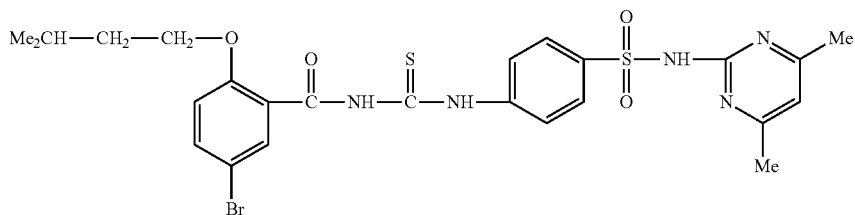
Answer 61:
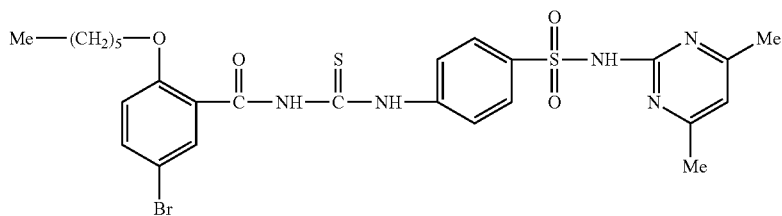

Answer 62:
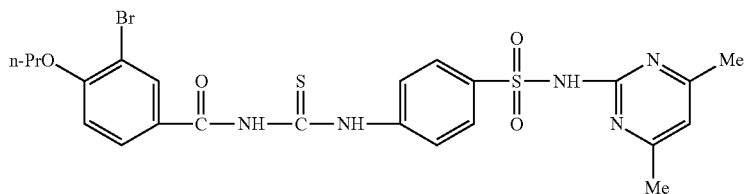
Answer 63:
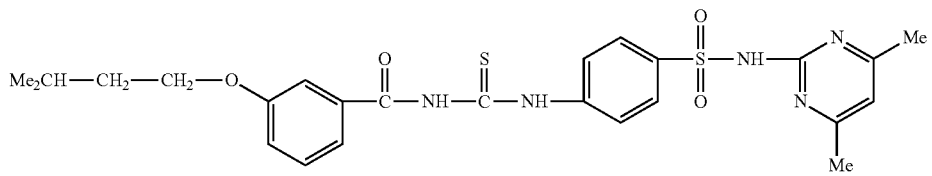
Answer 64:
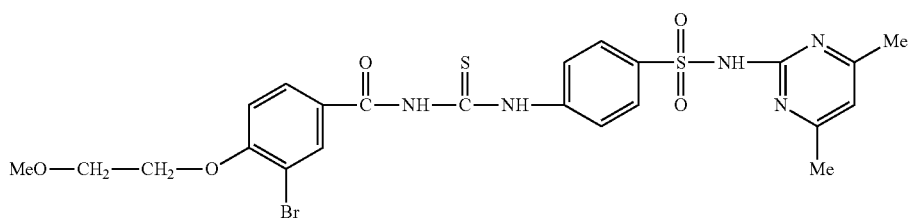
Answer 65:
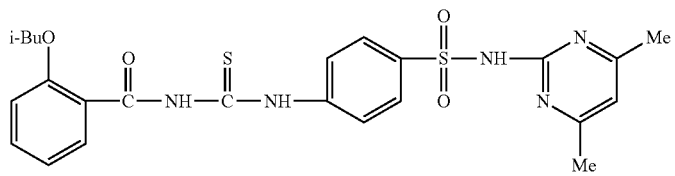
Answer 66:
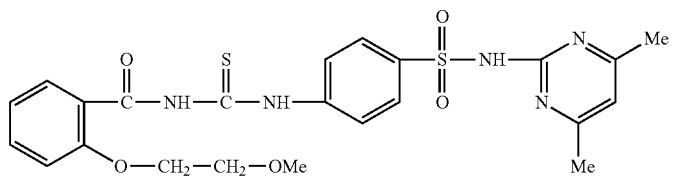
Answer 67:
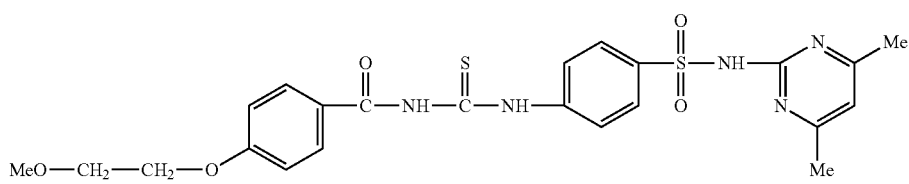
Answer 68:
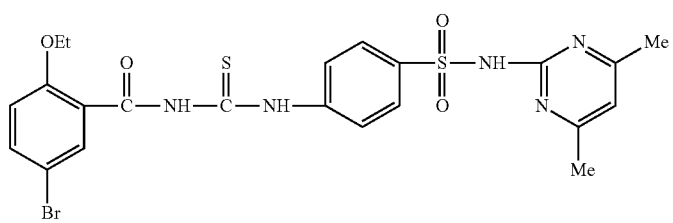

Answer 69:
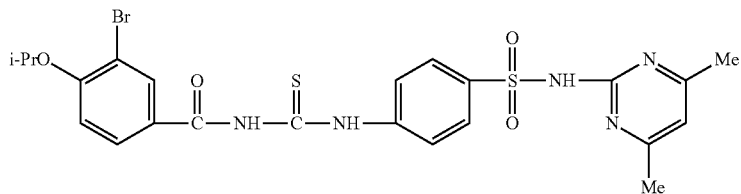
Answer 70:
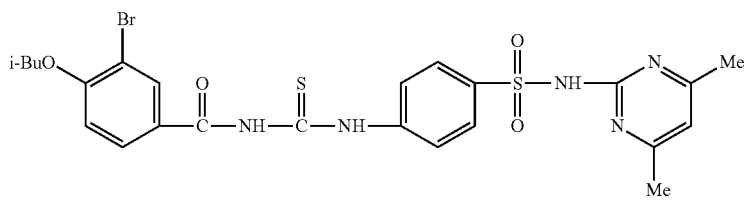
Answer 71:
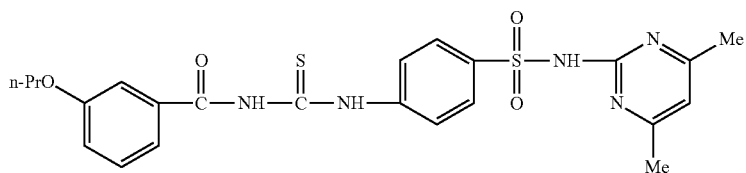
Answer 72:
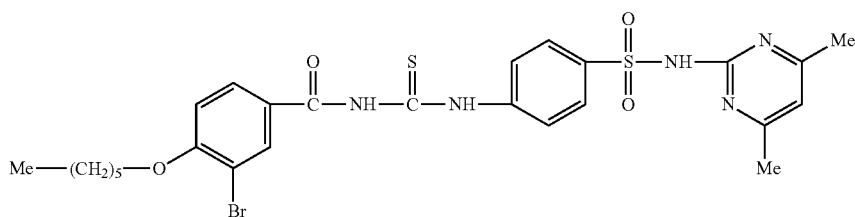
Answer 73:
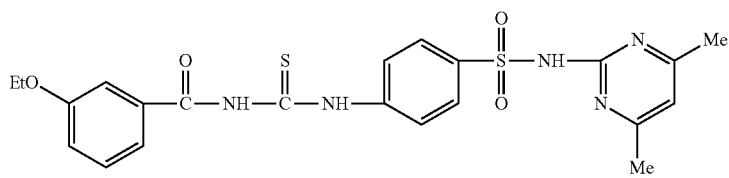
Answer 74:
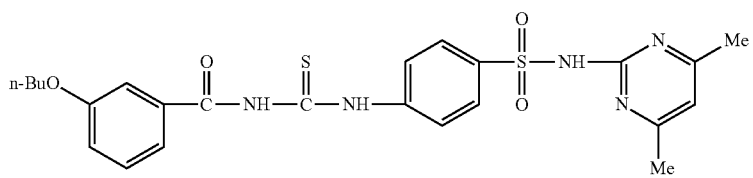
Answer 75:
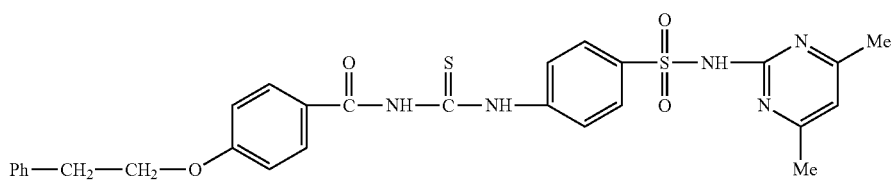

Answer 76:
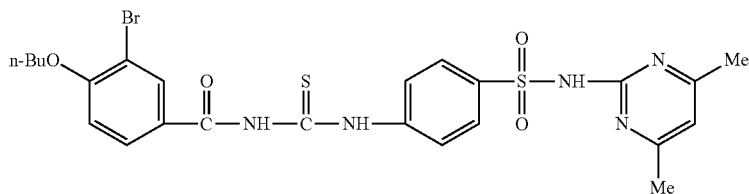
Answer 77:
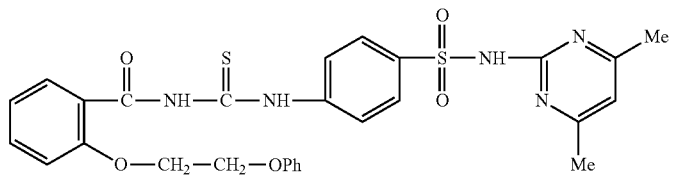
Answer 78:
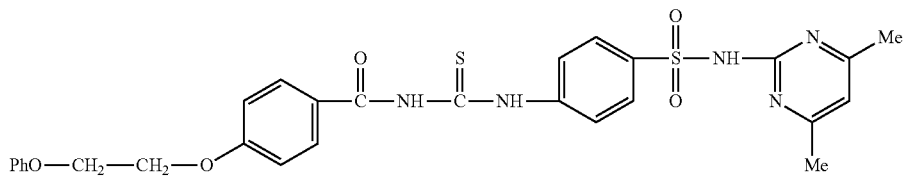
Answer 79:
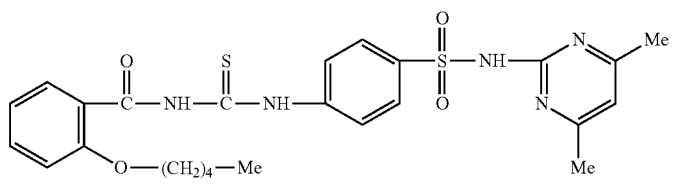
Answer 80:
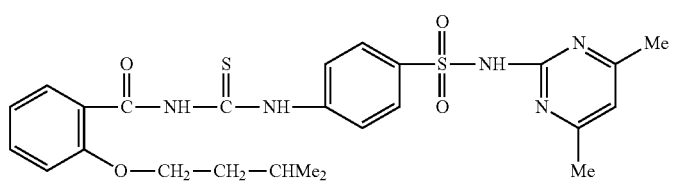
Answer 81:
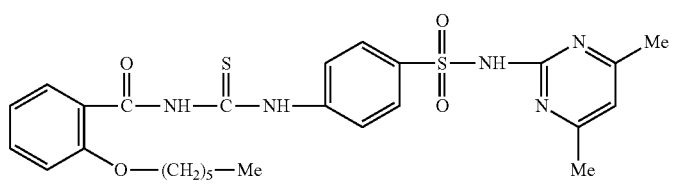
Answer 82:
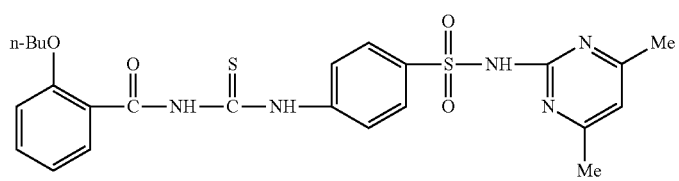

Answer 83:
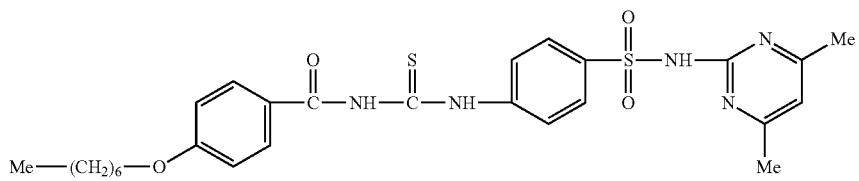
Answer 84:
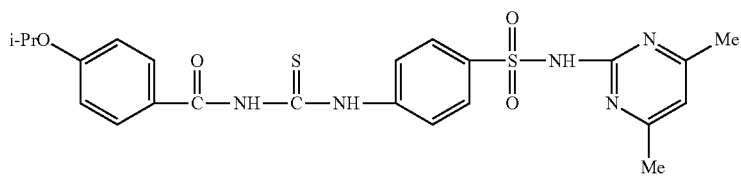
Answer 85:
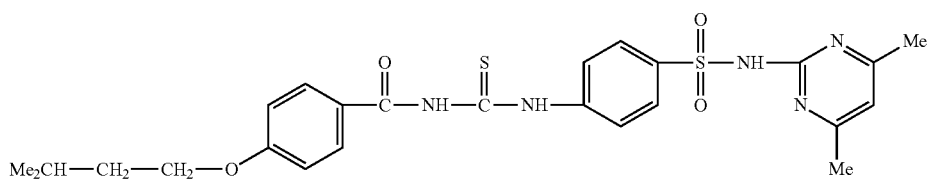
Answer 86:
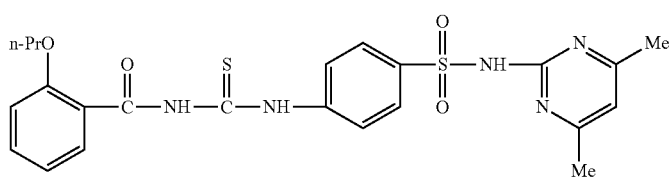
Answer 87:
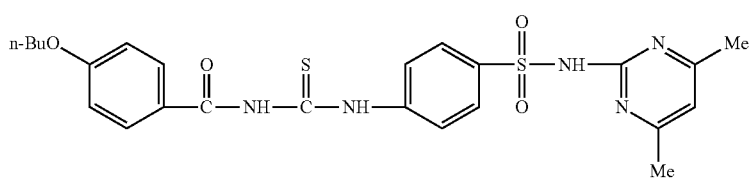
Answer 88:
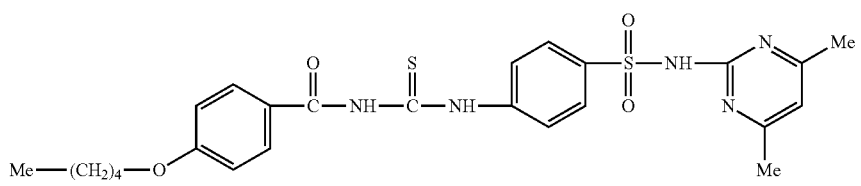
Answer 89:
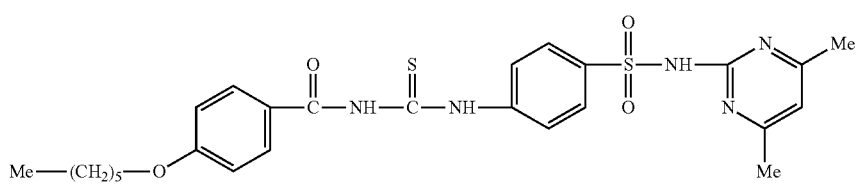

Answer 90:
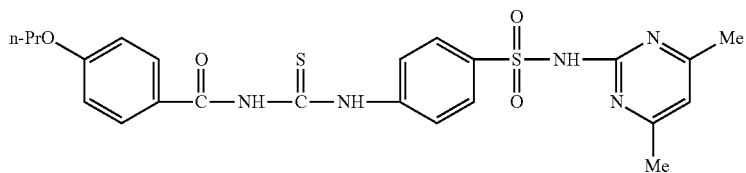
Answer 91:
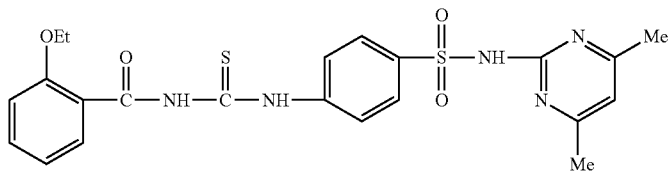
Answer 92:
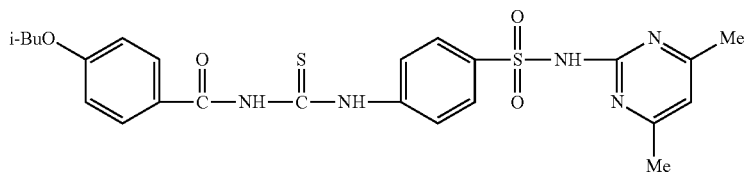
Answer 93:
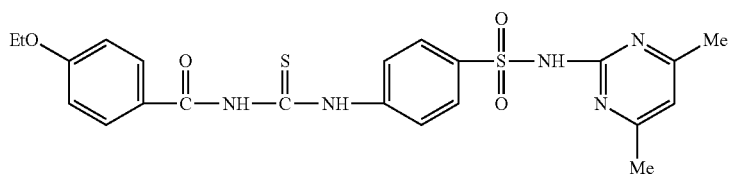
Answer 94:
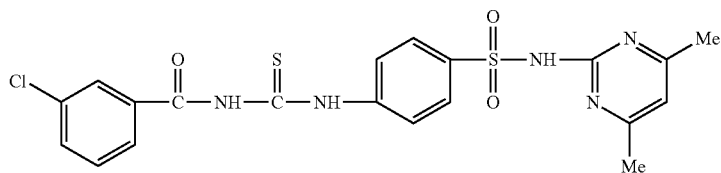
Answer 95:
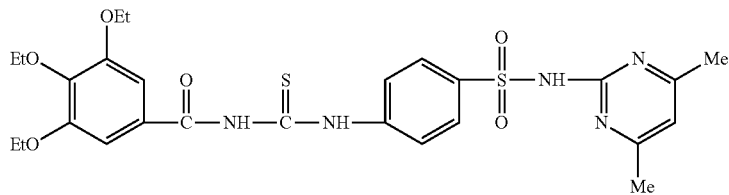
Answer 96:
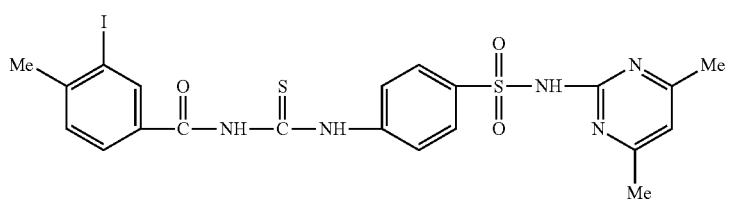

Answer 97:
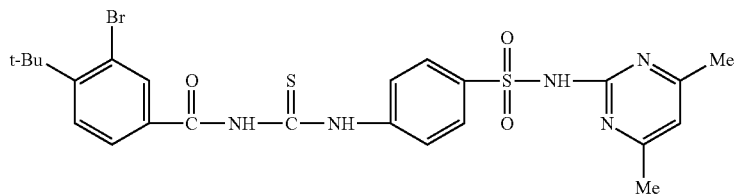
Answer 98:
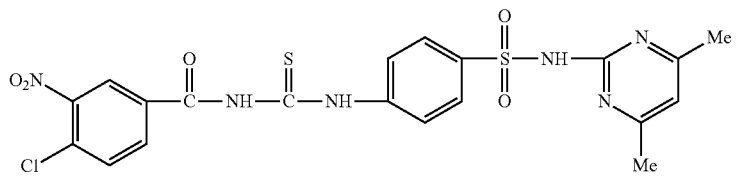
Answer 99:
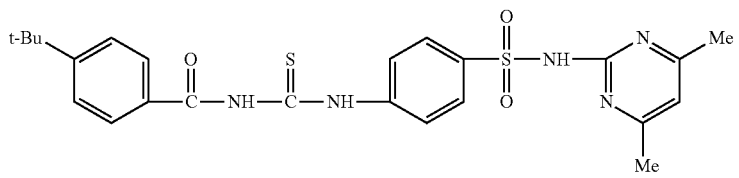
Answer 100:
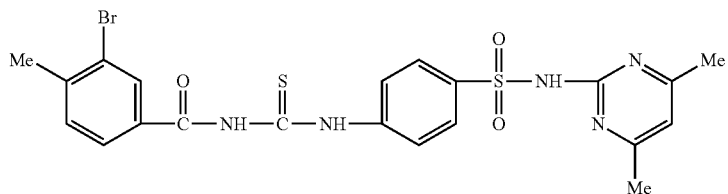
Answer 101:
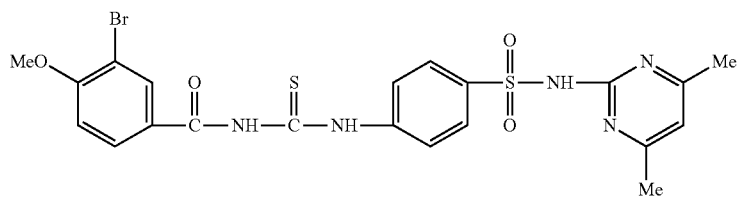
Answer 102:
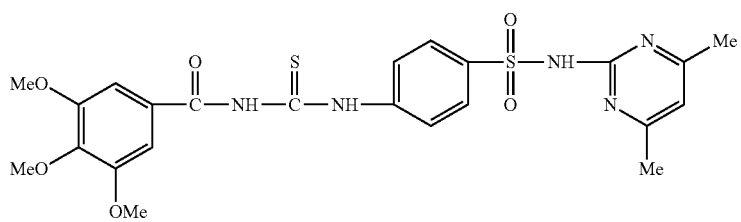
Answer 103:
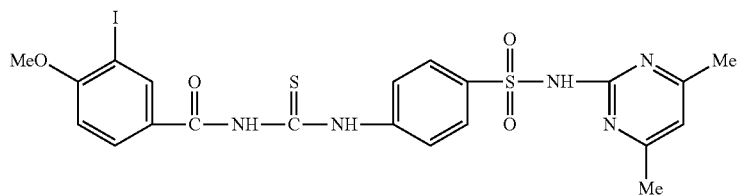

Answer 104:
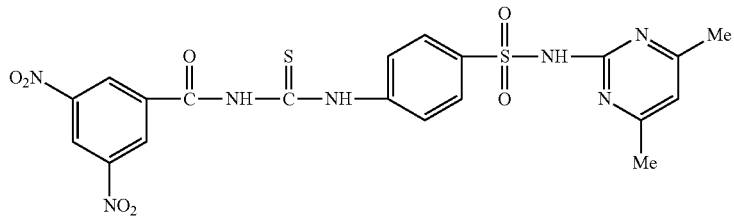
Answer 105:
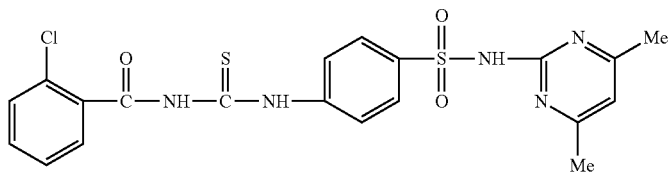
Answer 106:
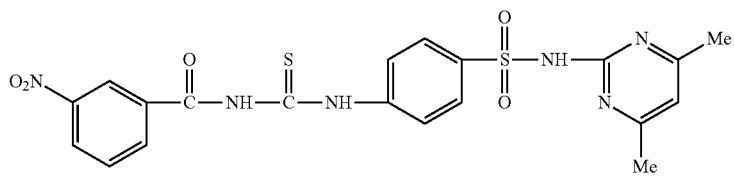
Answer 107:
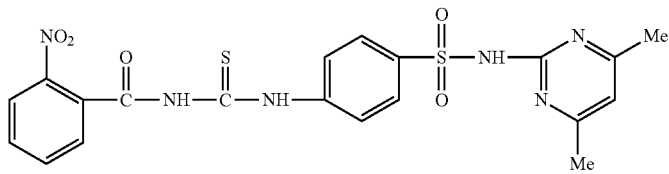
Answer 108:
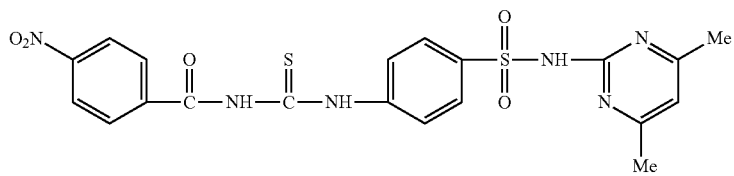
Answer 109:
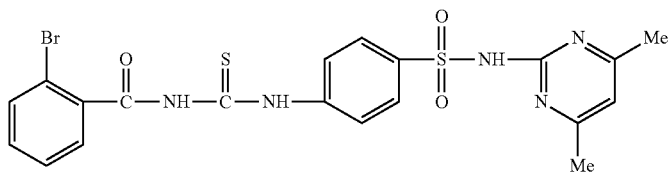
Answer 110:
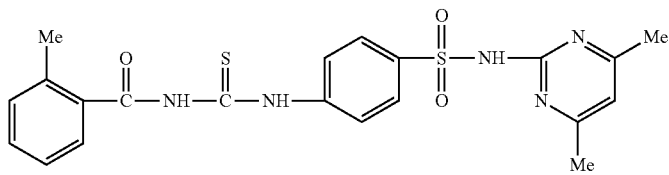

Answer 111:
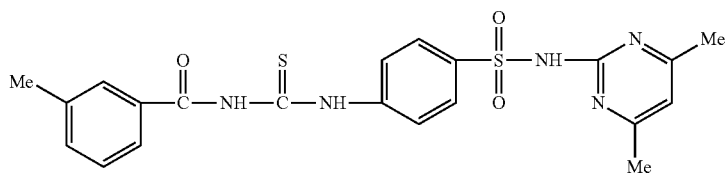
Answer 112:
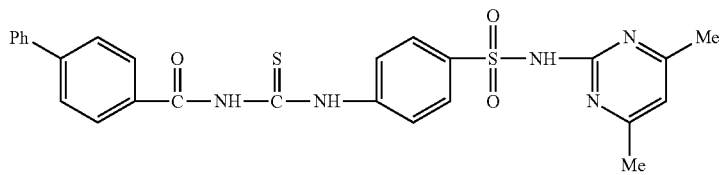
Answer 113:
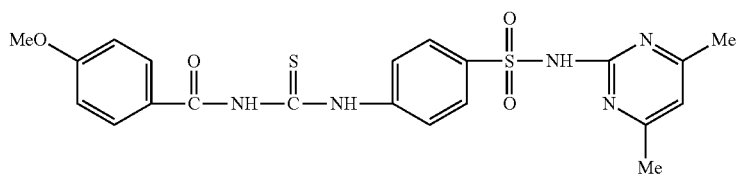
Answer 114:
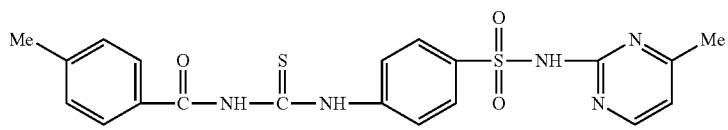
Answer 115:
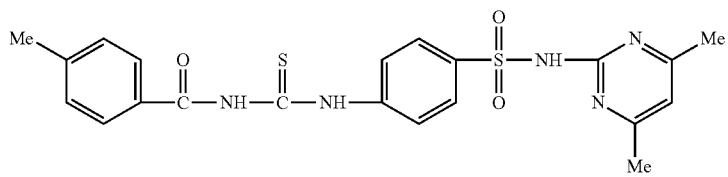
Answer 116:
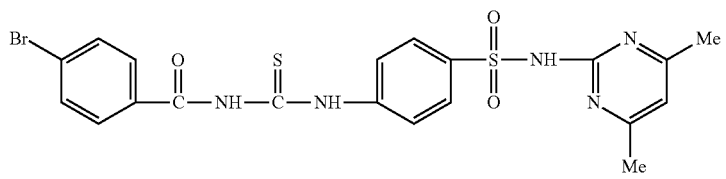
Answer 117:
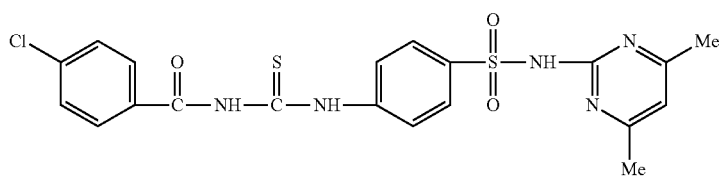

Answer 118:
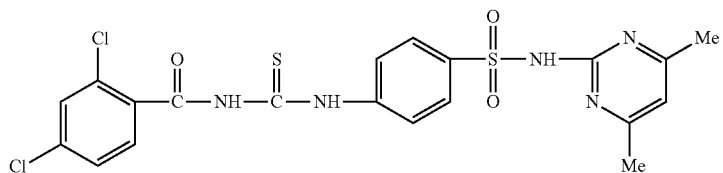
Answer 119:
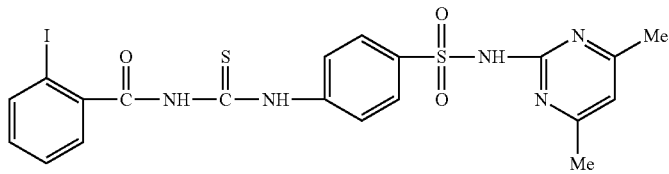
Answer 120:
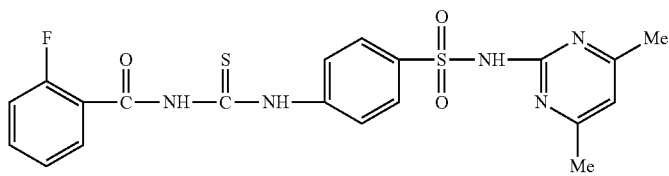
Answer 121:
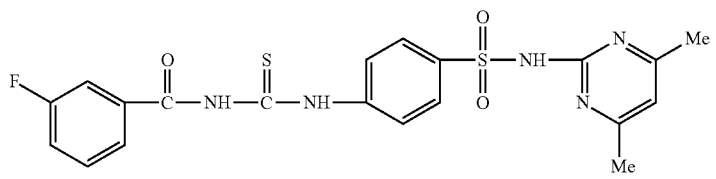
Answer 122:
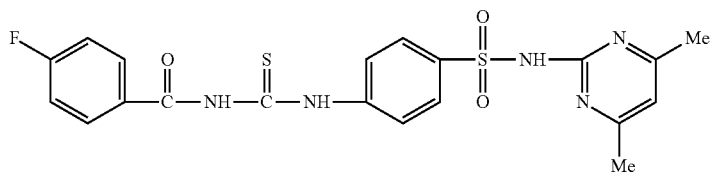
Answer 123:
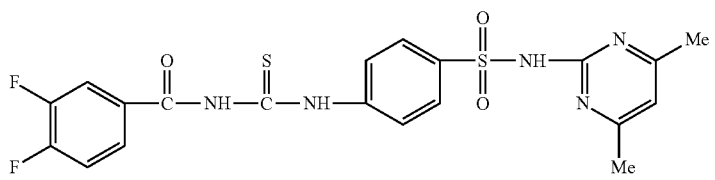
Answer 124:
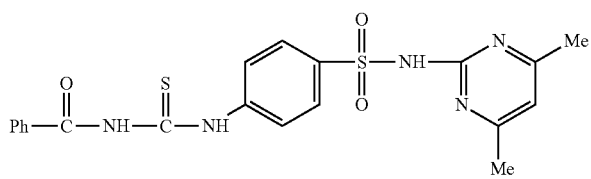

Answer 125:
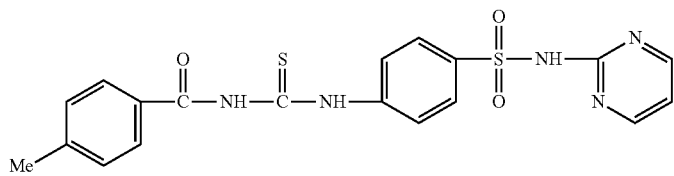
Answer 126:
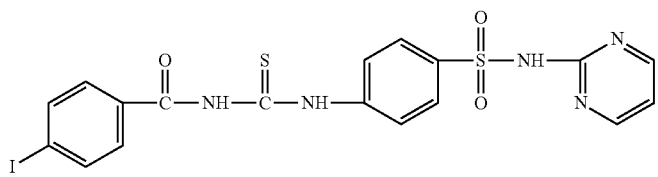
Answer 127:
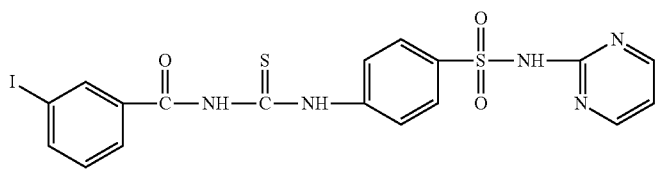
Answer 128:
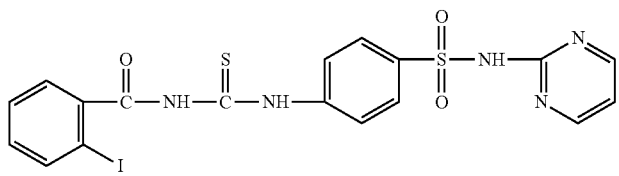
Answer 129:
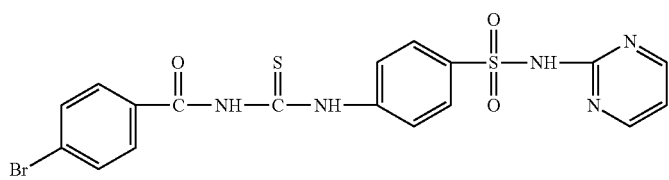
Answer 130:
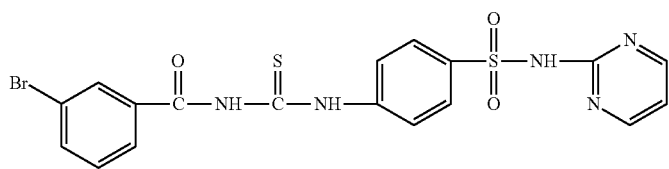
Answer 131:
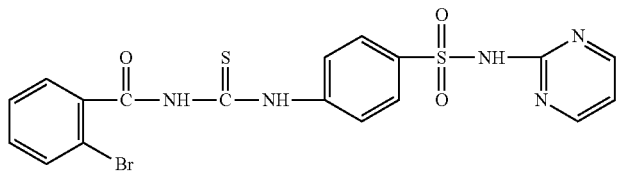

Answer 132:
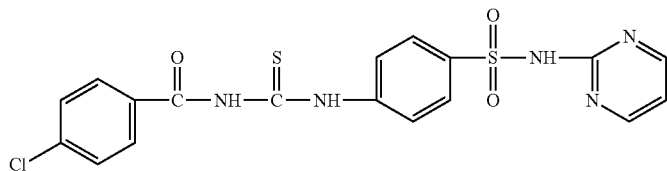
Answer 133:
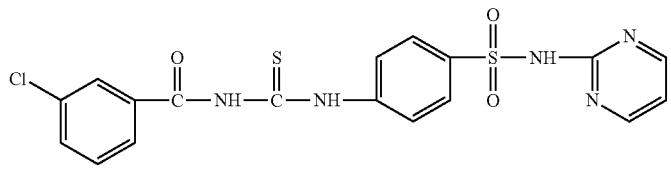
Answer 134:
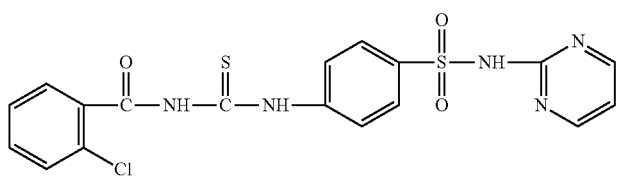
Answer 135:
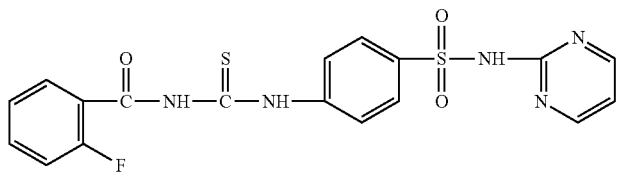
Answer 136:
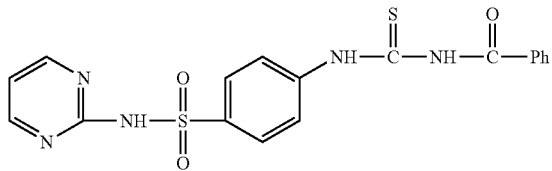
Answer 1:
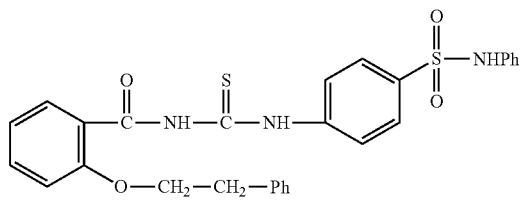
Answer 2:
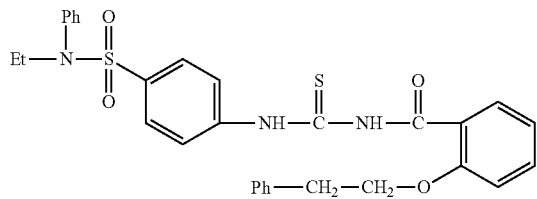

Answer 3:
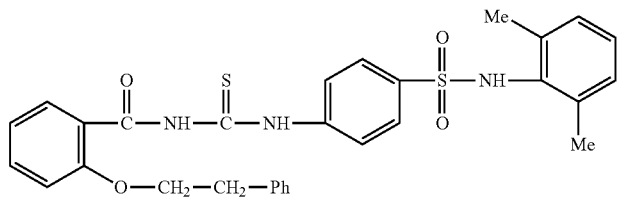
Answer 4:
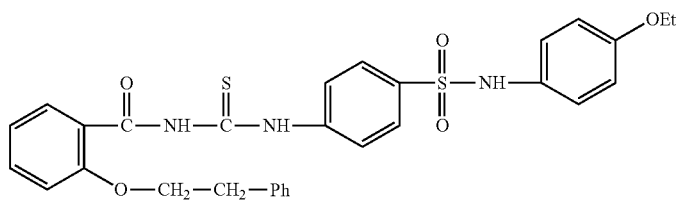
Answer 5:
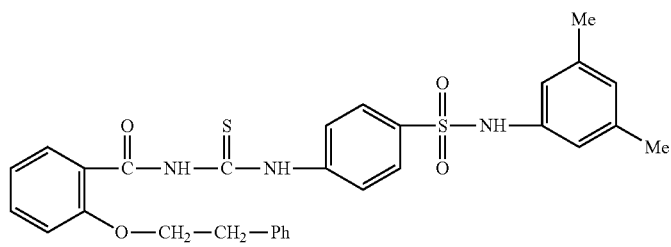
Answer 6:
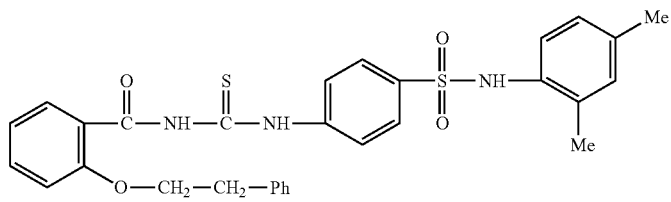
Answer 7:
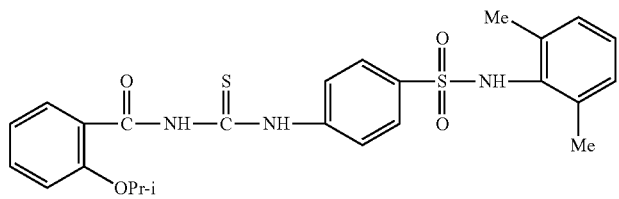
Answer 8:
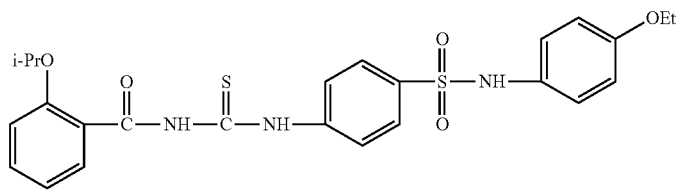

-continued
Answer 9:
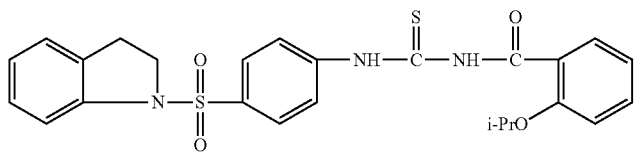
Answer 10:
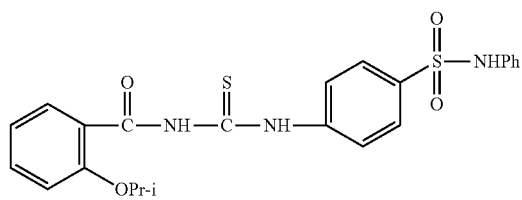
Answer 11:
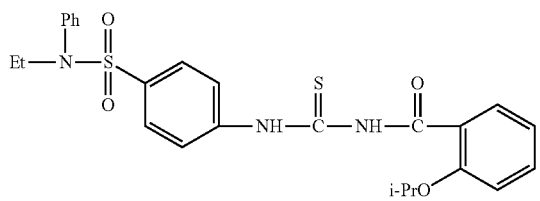
Answer 12:
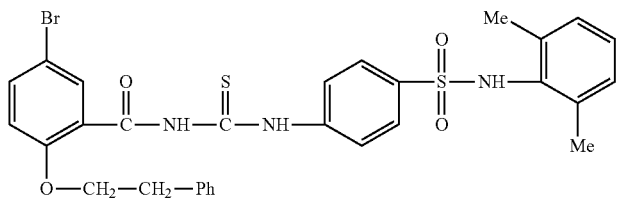
Answer 13:
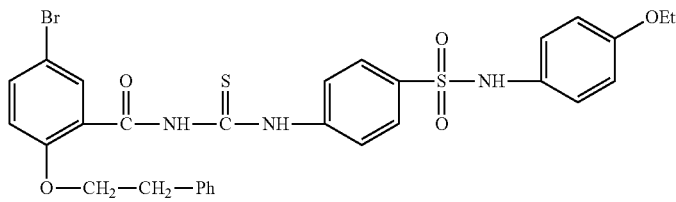
Answer 14:
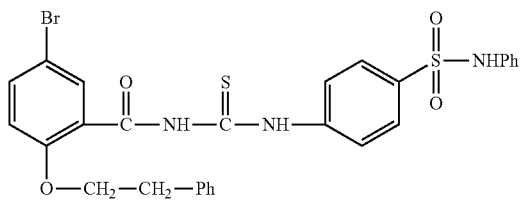

Answer 15:
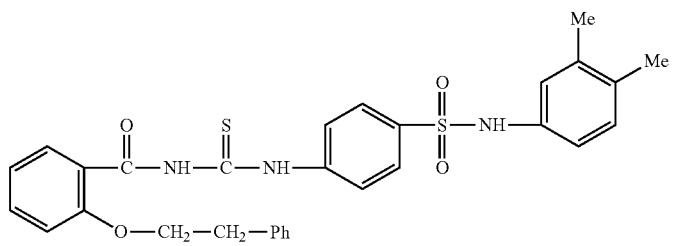
Answer 16:
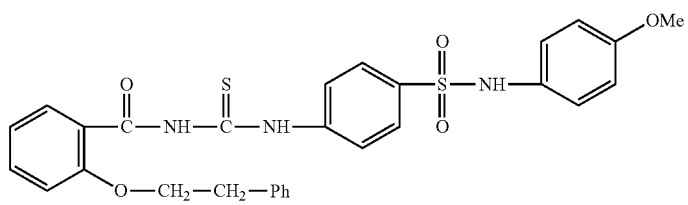
Answer 17:
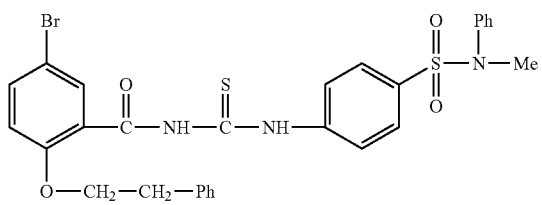
Answer 18:
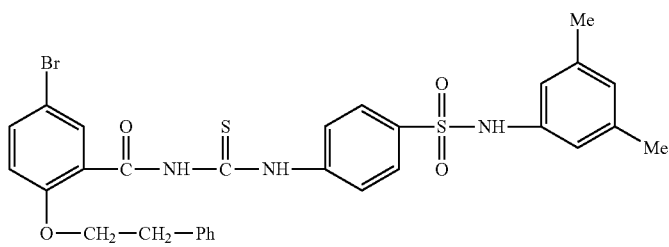
Answer 19:
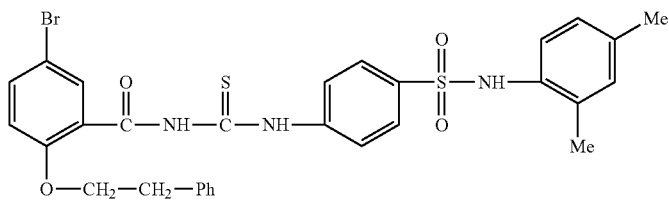
Answer 20:
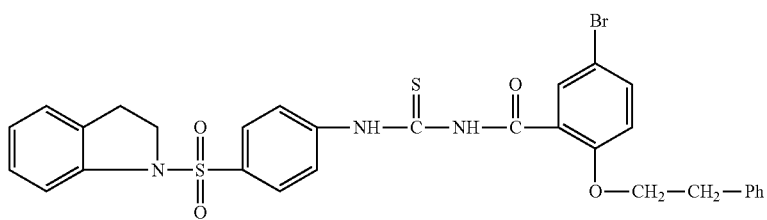

-continued
Answer 21:
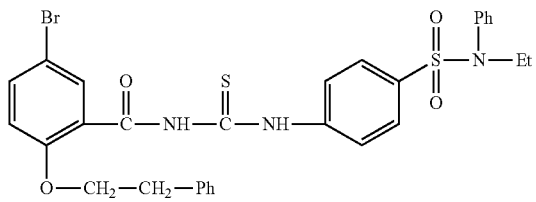
Answer 22:
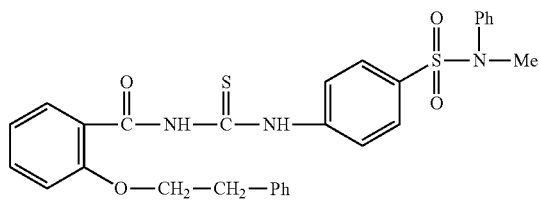
Answer 23:
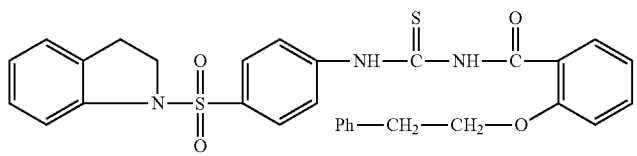
Answer 24:
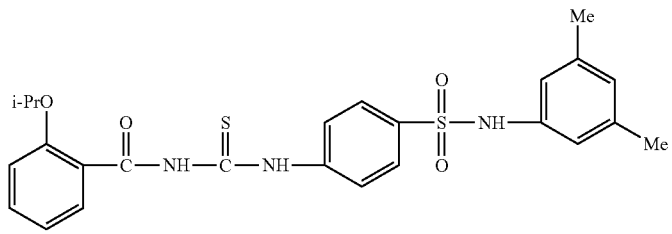
Answer 25:
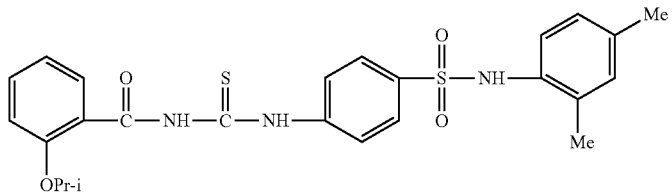
REGISTRY (Copyright (C) 2009 ACS)
Answer 26:
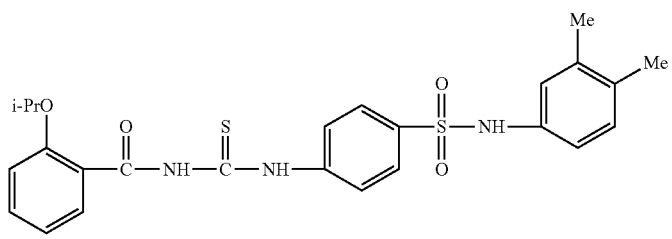

-continued
Answer 27:
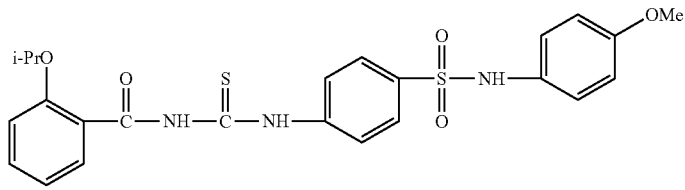
Answer 28:
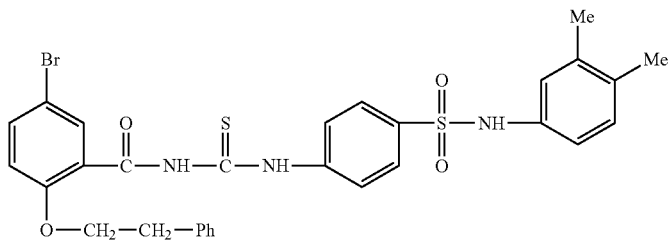
Answer 29:
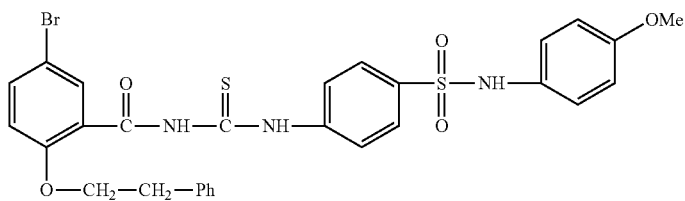
Answer 30:
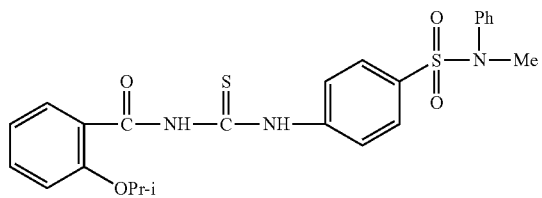
Answer 31:
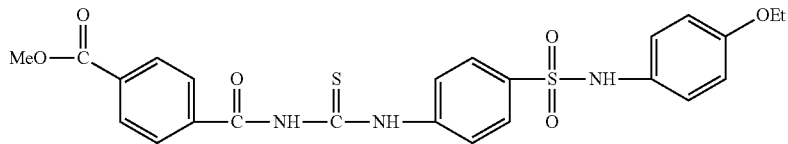
Answer 32:
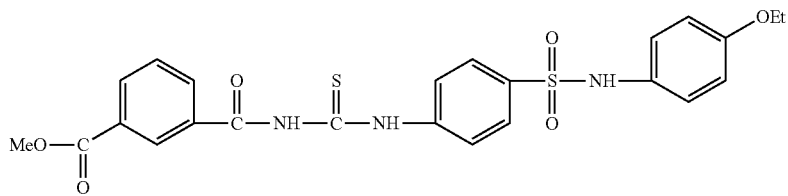
Answer 33:
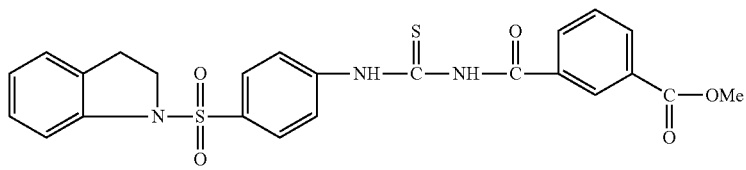

Answer 34:
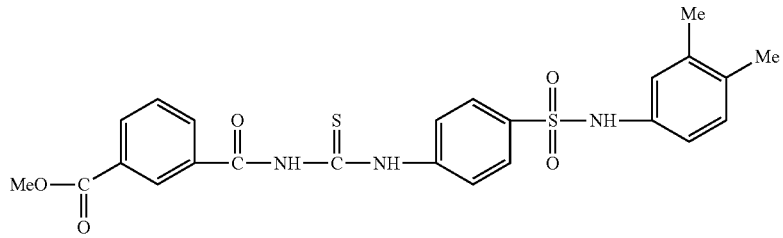
Answer 35:
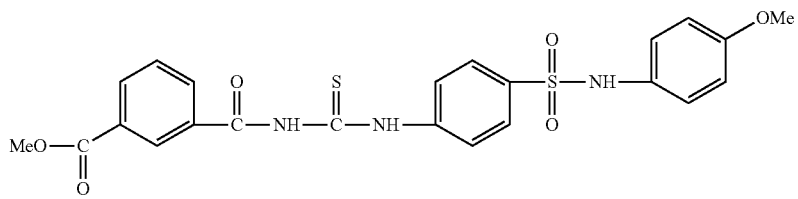
Answer 36:
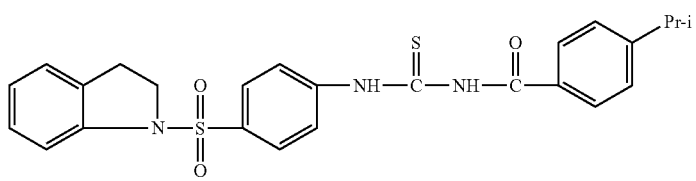
Answer 37:
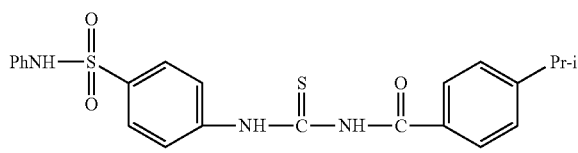
Answer 38:
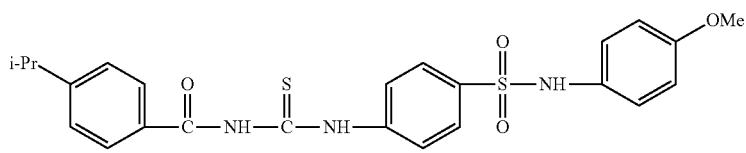
Answer 39:
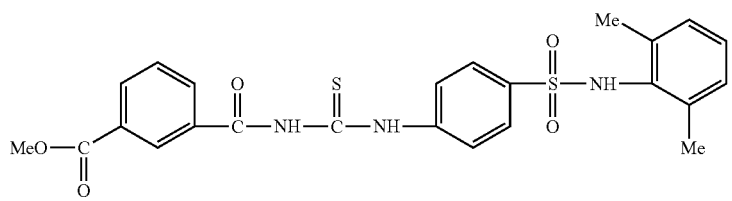
Answer 40:
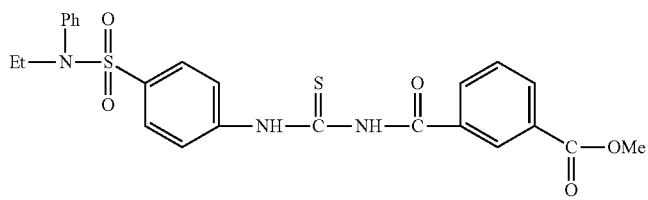

-continued
Answer 41:
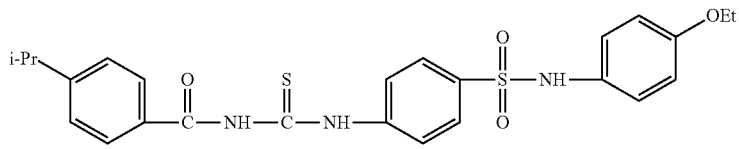
Answer 42:
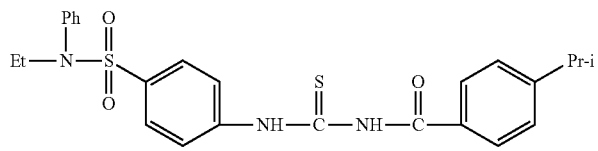
REGISTRY (Copyright (C) 2009 ACS)
Answer 43:
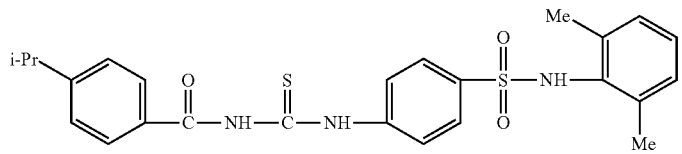
REGISTRY (Copyright (C) 2009 ACS)
Answer 44:
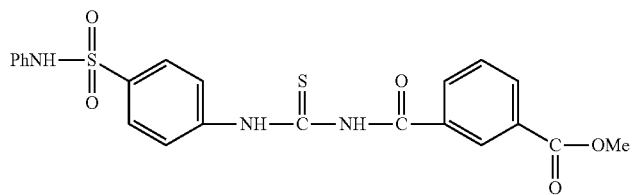
REGISTRY (Copyright (C) 2009 ACS)
Answer 45:
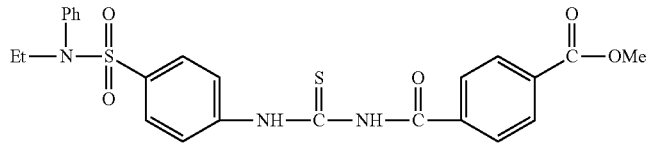
REGISTRY (Copyright (C) 2009 ACS)
Answer 46:
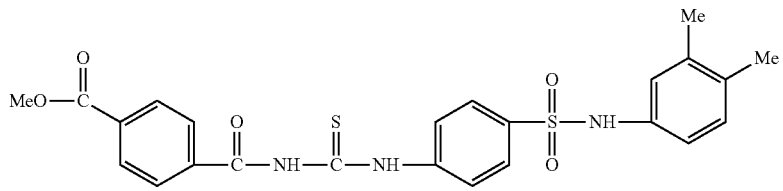
REGISTRY (Copyright (C) 2009 ACS)
Answer 47:
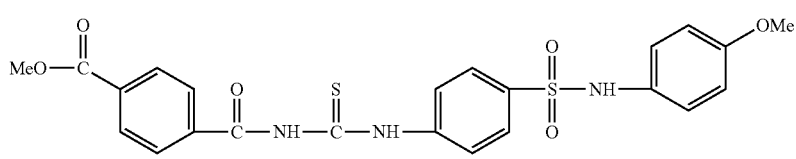
REGISTRY (Copyright (C) 2009 ACS)

Answer 48:
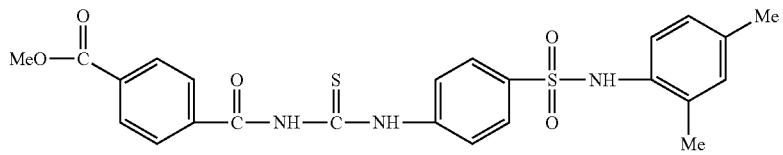
REGISTRY (Copyright (C) 2009 ACS)
Answer 49:
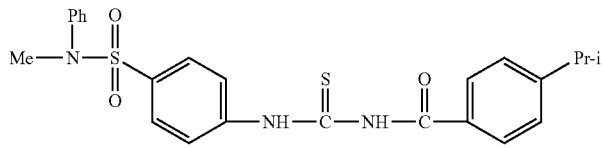
REGISTRY (Copyright (C) 2009 ACS)
Answer 50:
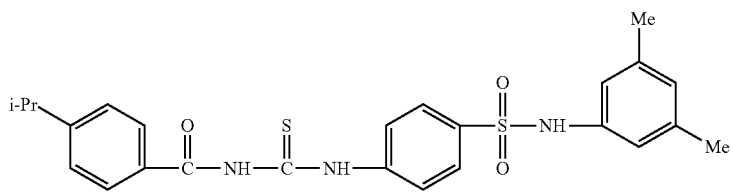
Answer 51:
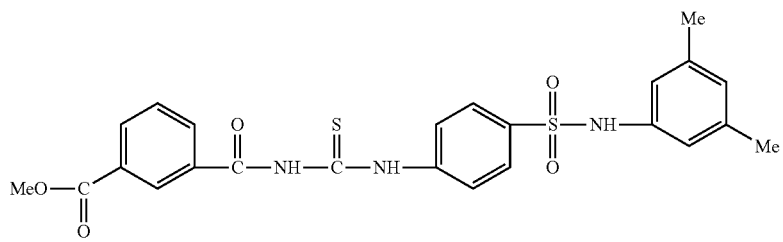
Answer 52:
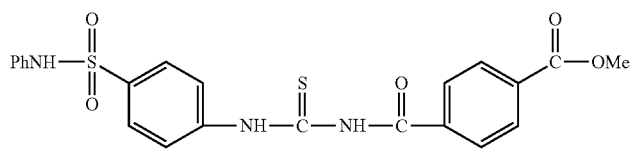
Answer 53:
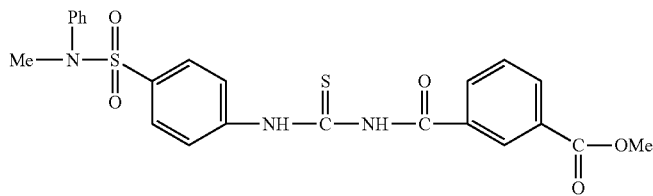
Answer 54:
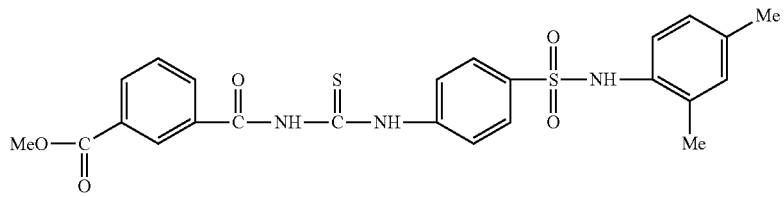

Answer 55:
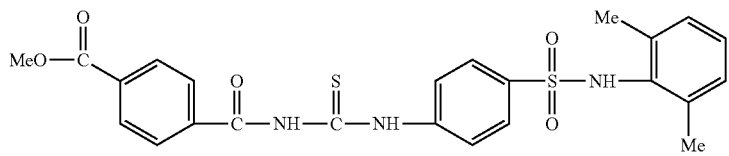
Answer 56:
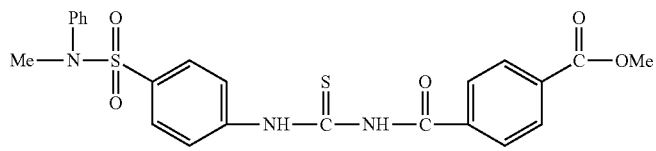
Answer 57:
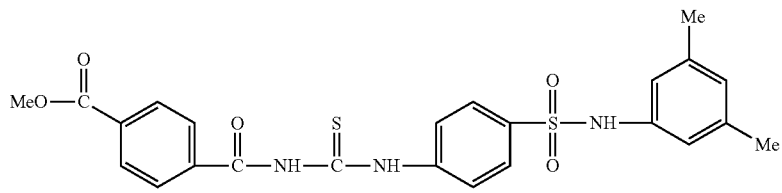
Answer 58:
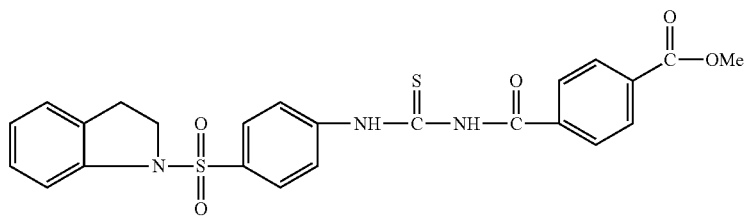
Answer 59:
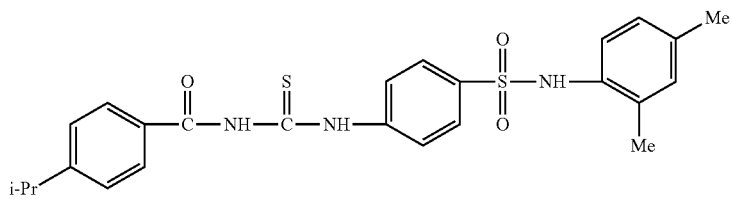
Answer 60:
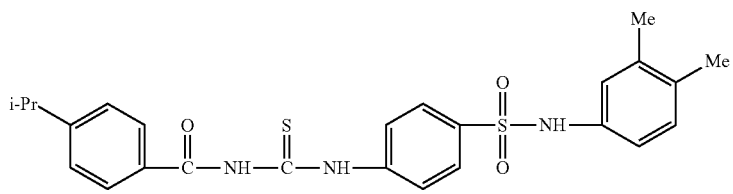
Answer 61:
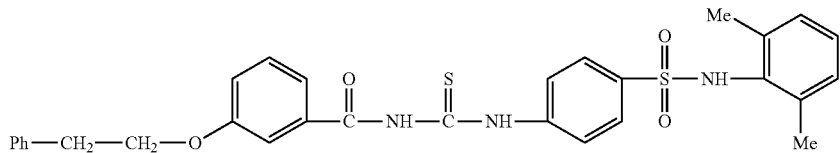

Answer 62:
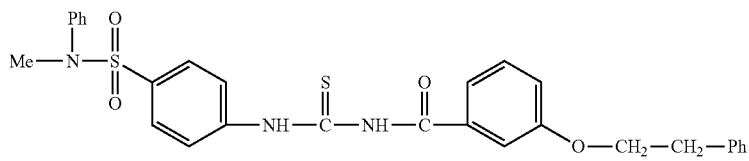
Answer 63:
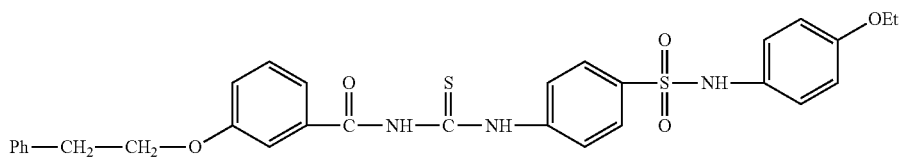
Answer 64:
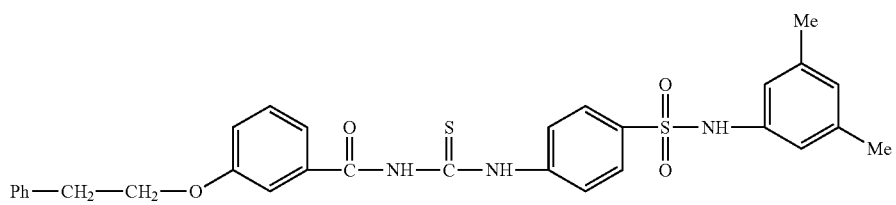
Answer 65:
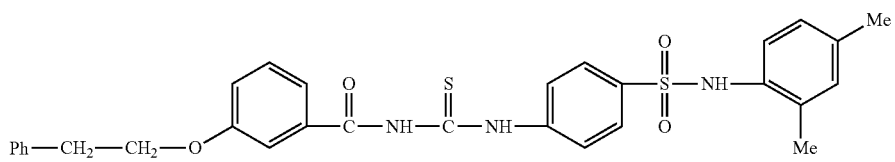
Answer 66:
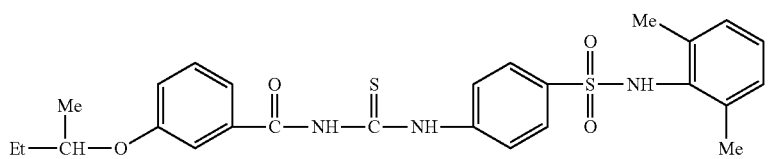
Answer 67:
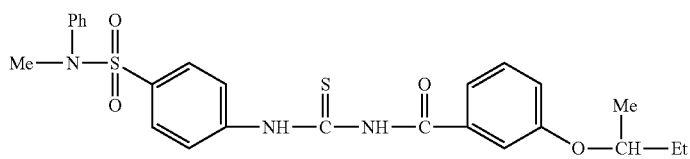
Answer 68:
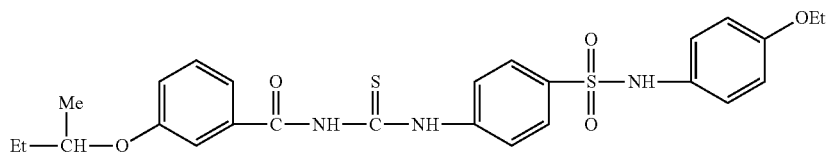

Answer 69:
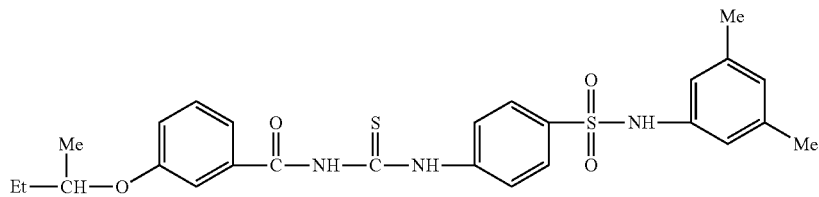
Answer 70:
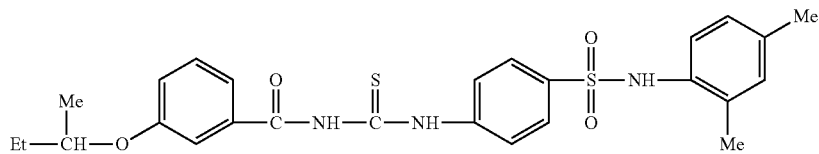
Answer 71:
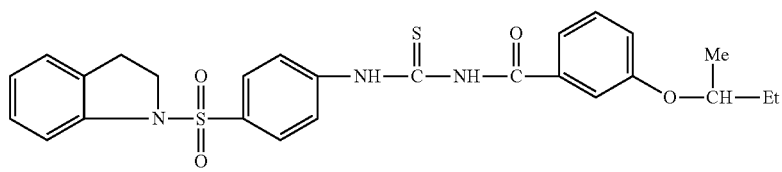
Answer 72:
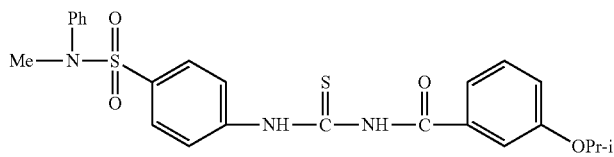
Answer 73:
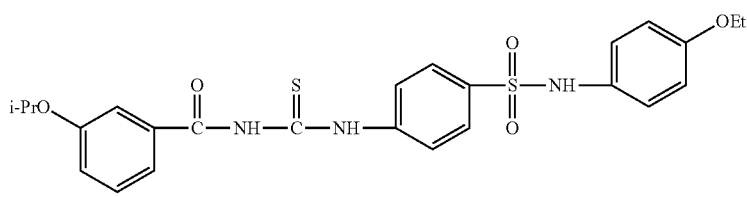
Answer 74:
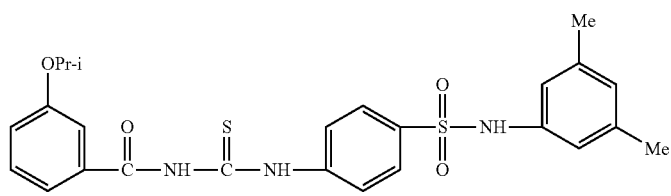
Answer 75:
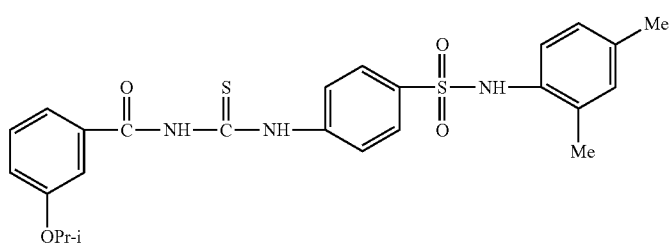

Answer 76:
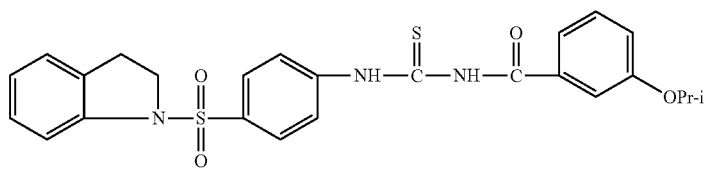
Answer 77:
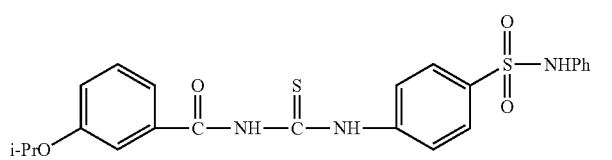
Answer 78:
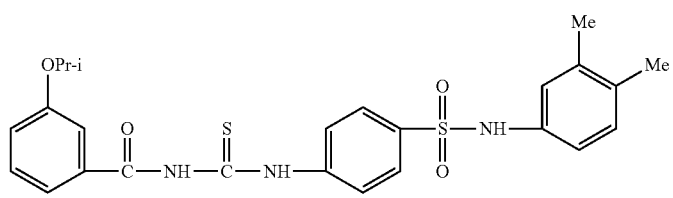
Answer 79:
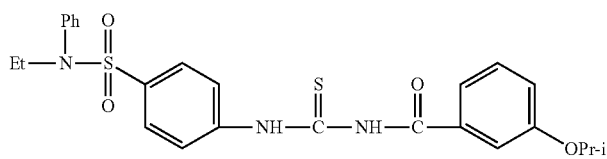
Answer 80:
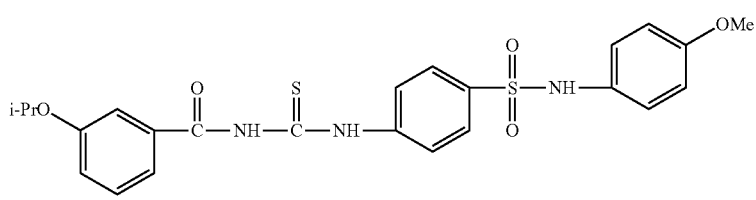
Answer 81:
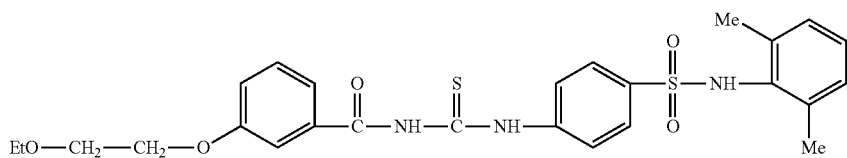
Answer 82:
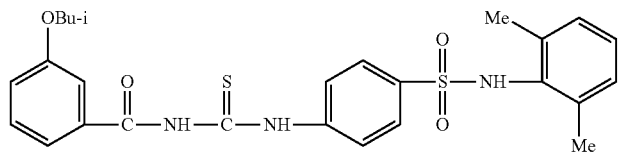

Answer 83:
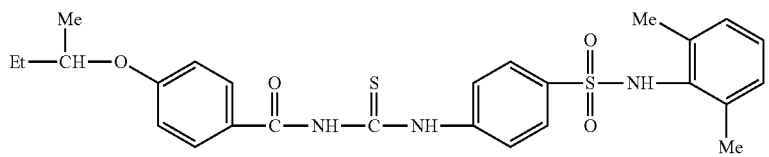
Answer 84:
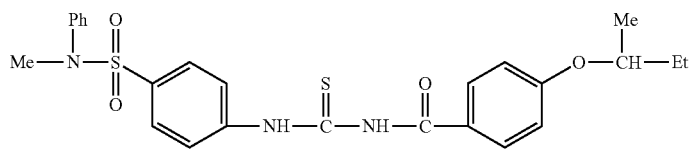
Answer 85:
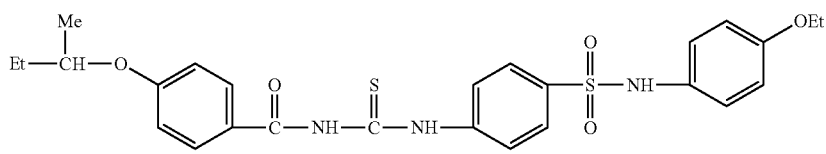
Answer 86:
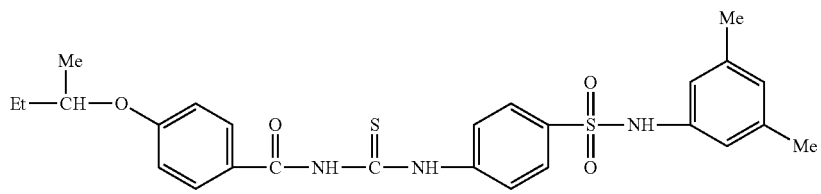
Answer 87:
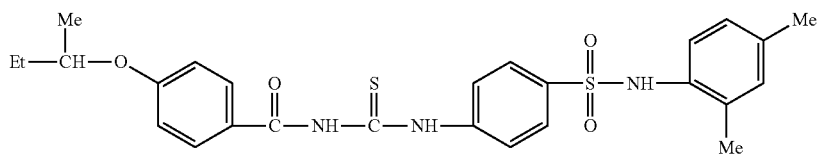
Answer 88:
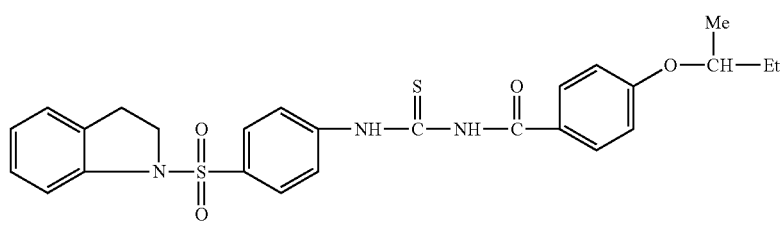
Answer 89:
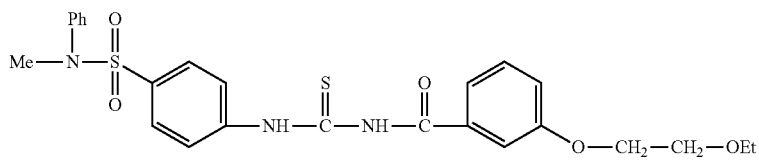

Answer 90:
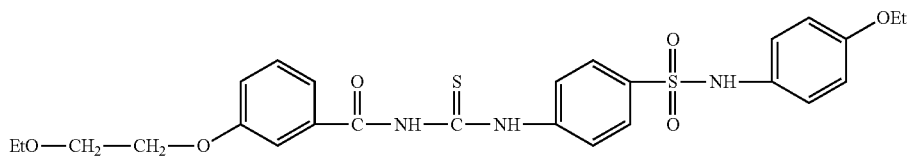
Answer 91:
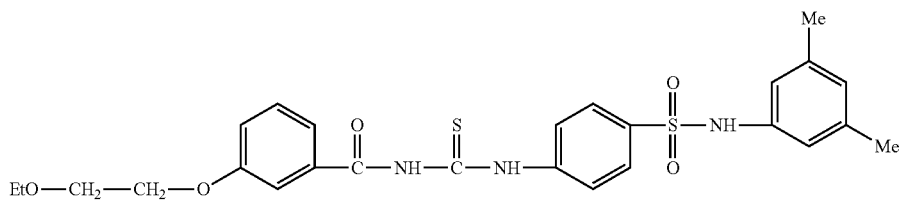
Answer 92:
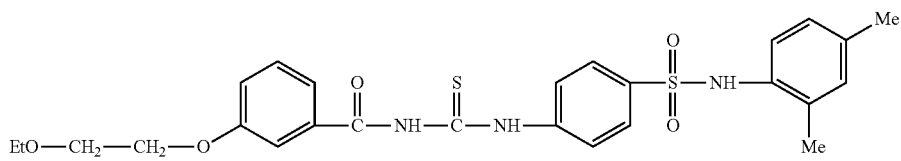
Answer 93:
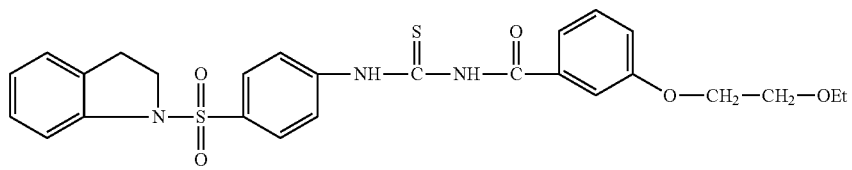
Answer 94:
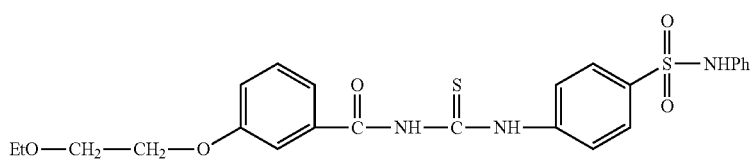
Answer 95:
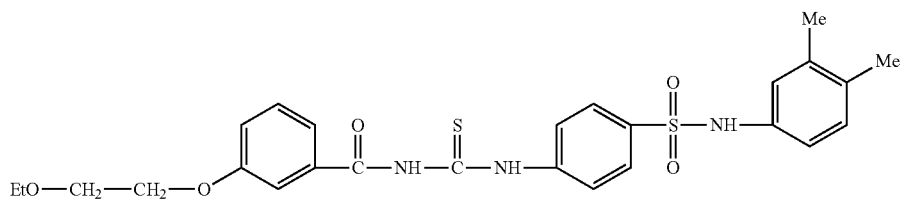
Answer 96:
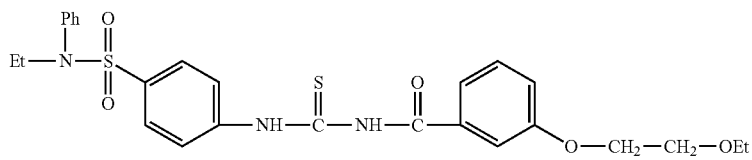

Answer 97:
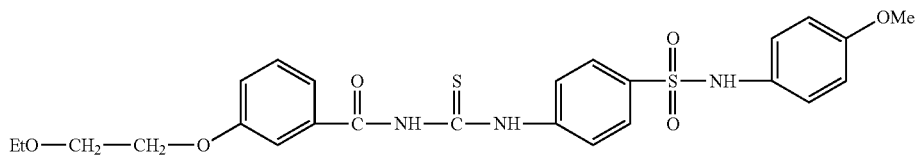
Answer 98:
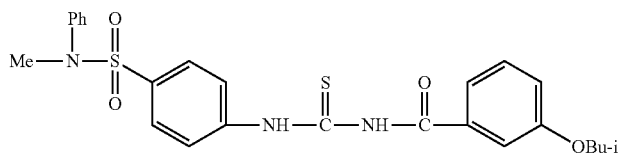
Answer 99:
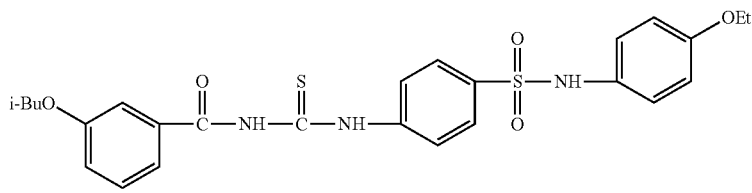
Answer 100:
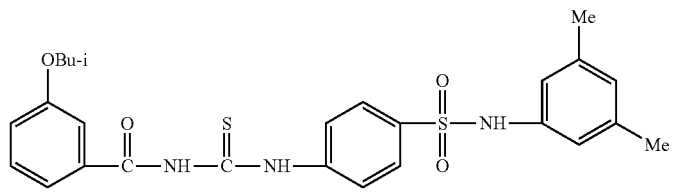
Answer 101:
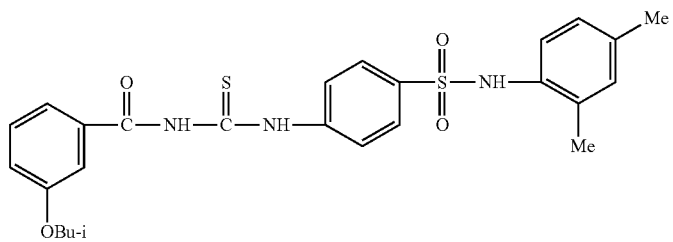
Answer 102:
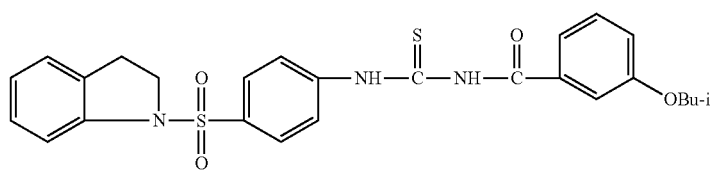
Answer 103:
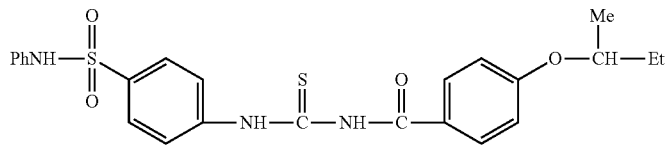

Answer 104:
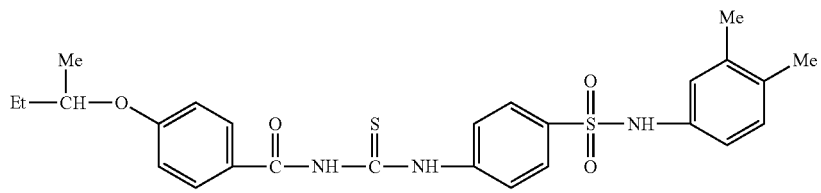
Answer 105:
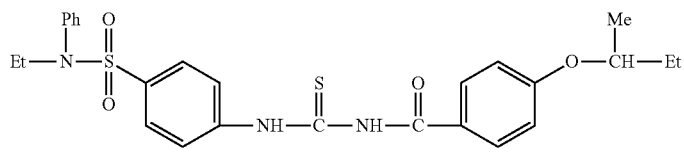
Answer 106:
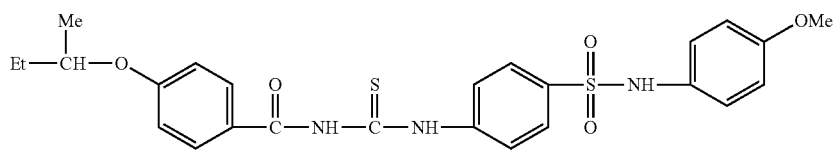
Answer 107:
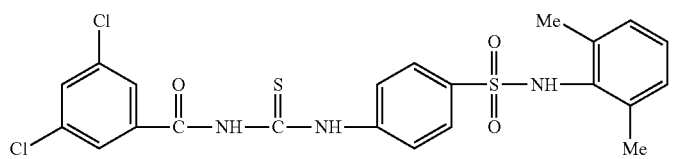
Answer 108:
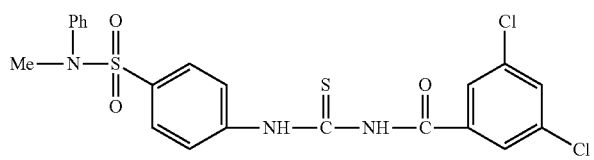
Answer 109:
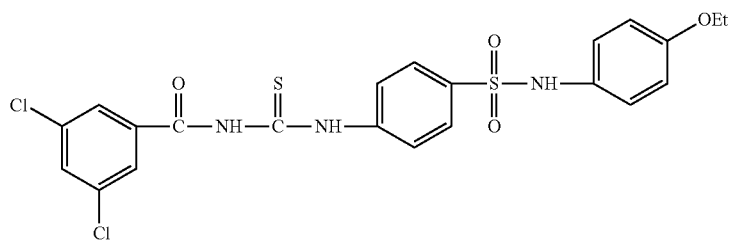
Answer 110:
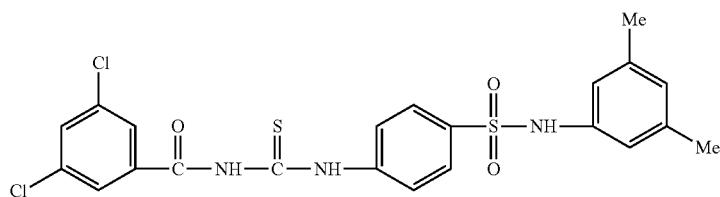

Answer 111:
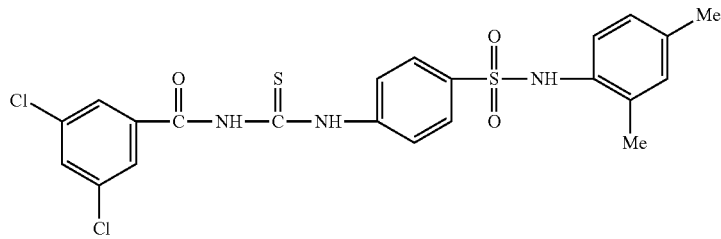
Answer 112:
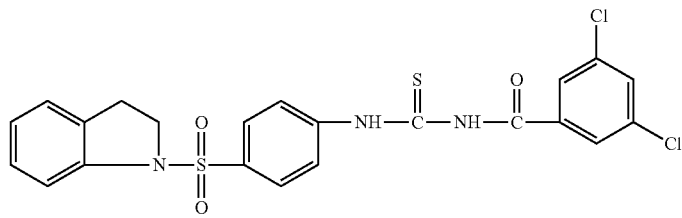
Answer 113:
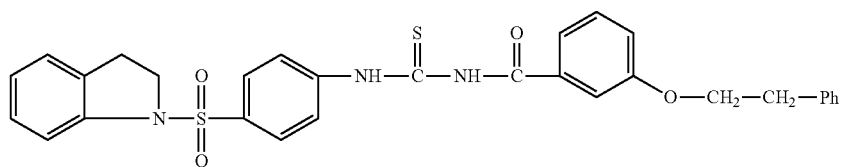
Answer 114:
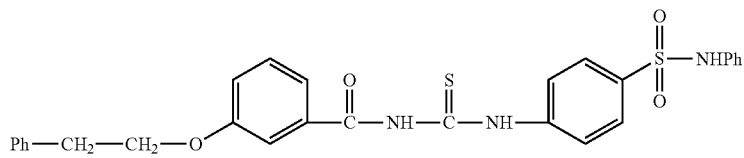
Answer 115:
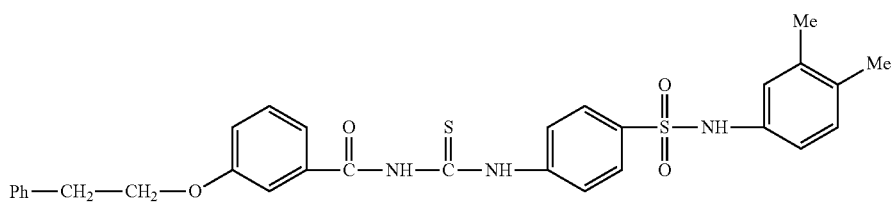
Answer 116:
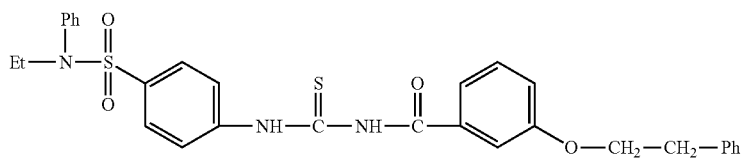
Answer 117:
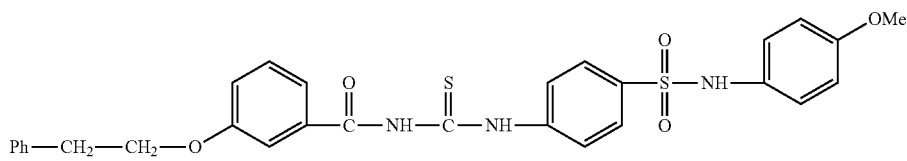

-continued
Answer 118:
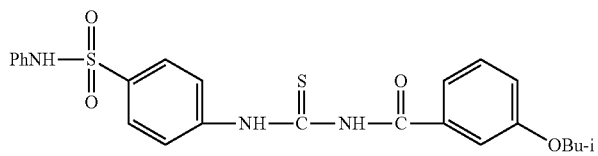
Answer 119:
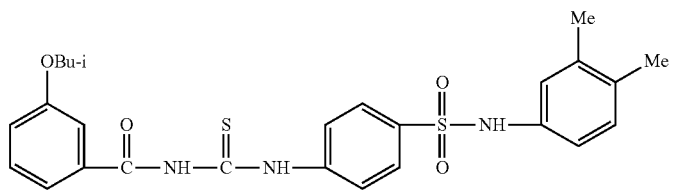
Answer 120:
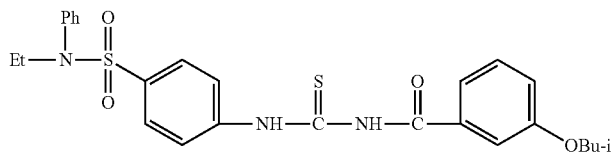
Answer 121:
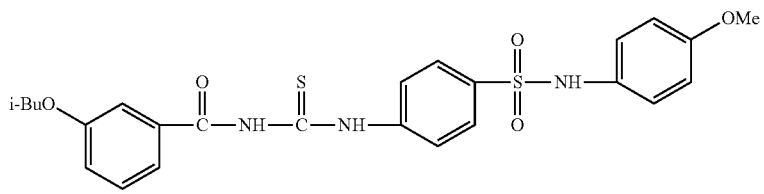
Answer 122:
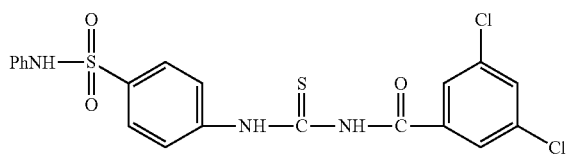
Answer 123:
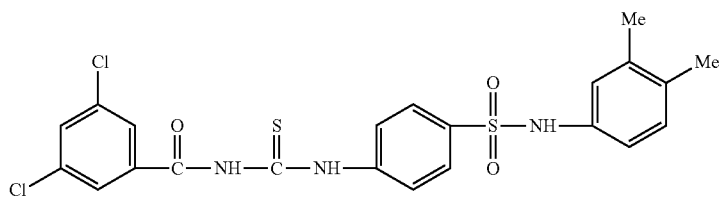
Answer 124:
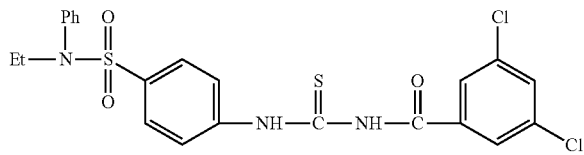

Answer 125:
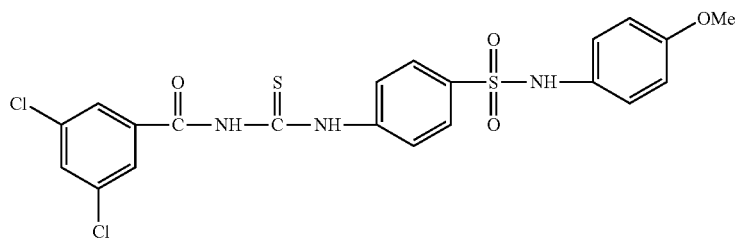
Answer 126:
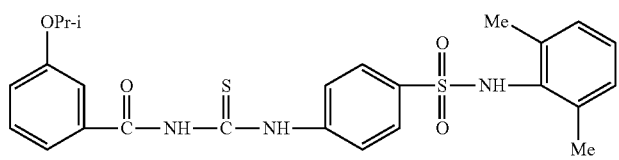
Answer 127:
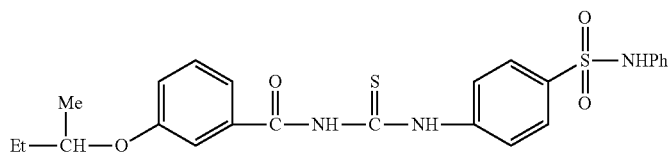
Answer 128:
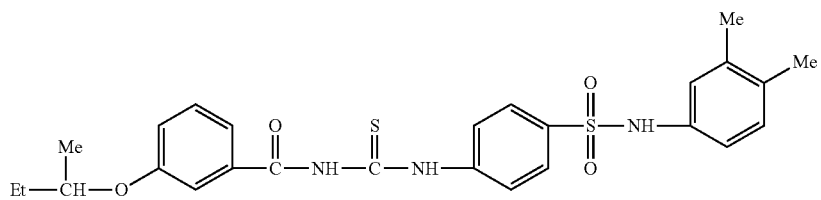
Answer 129:
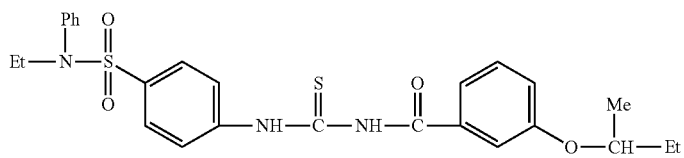
Answer 130:
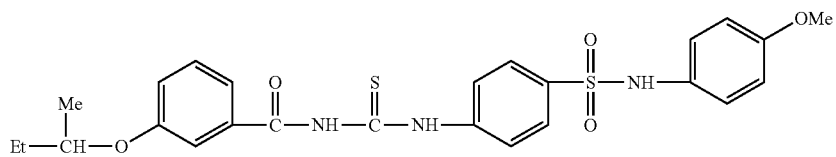
Answer 131:
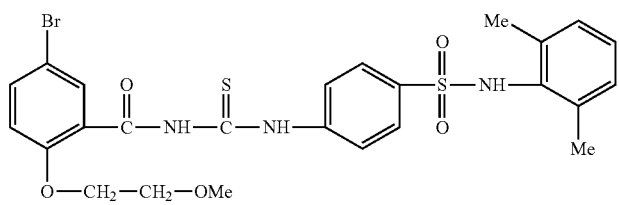

Answer 132:
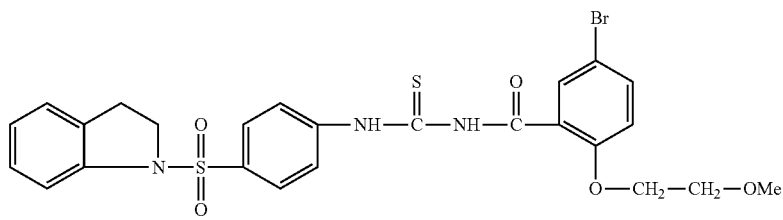
Answer 133:
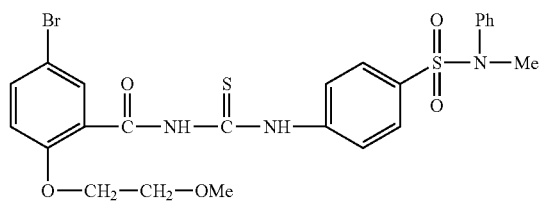
Answer 134:
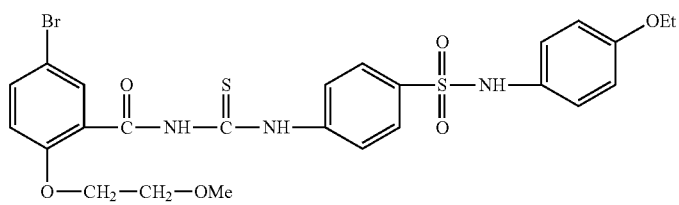
Answer 135:
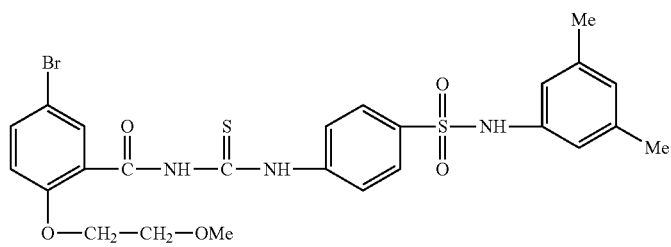
Answer 136:
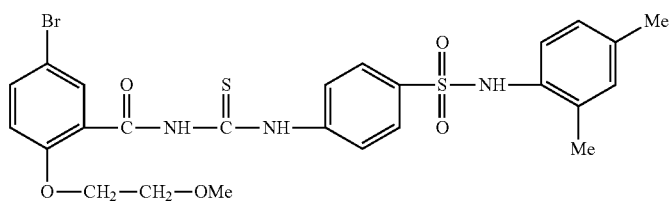
Answer 137:
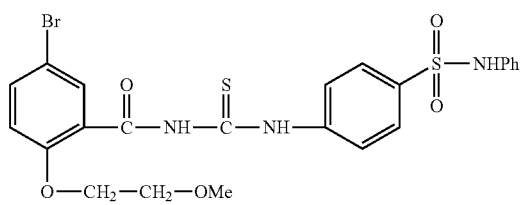

Answer 138:
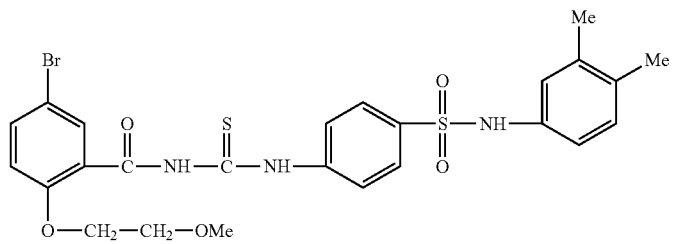
Answer 139:
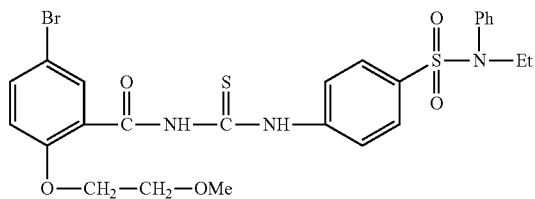
Answer 140:
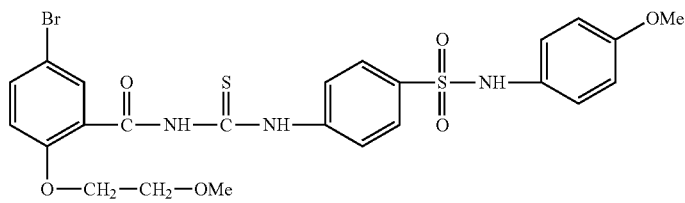
Answer 141:
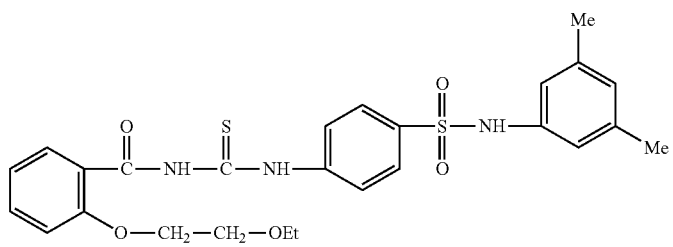
Answer 142:
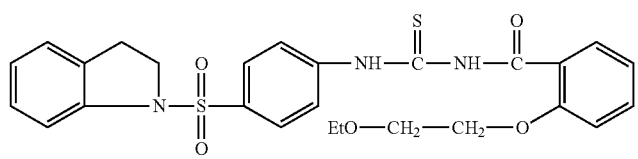
Answer 143:
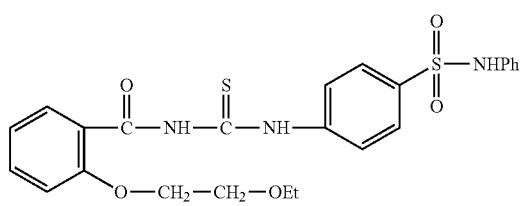

Answer 144:
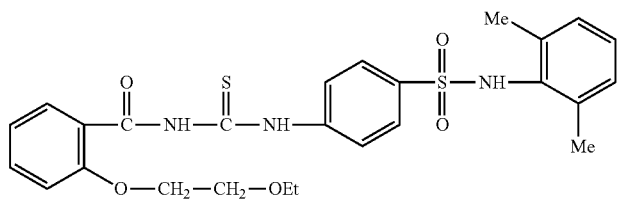
Answer 145:
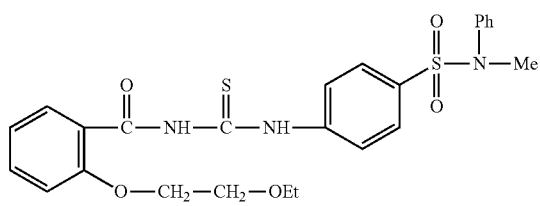
Answer 146:
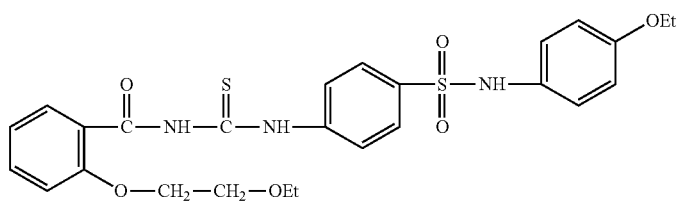
Answer 147:
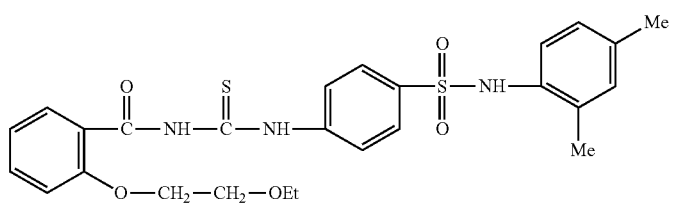
Answer 148:
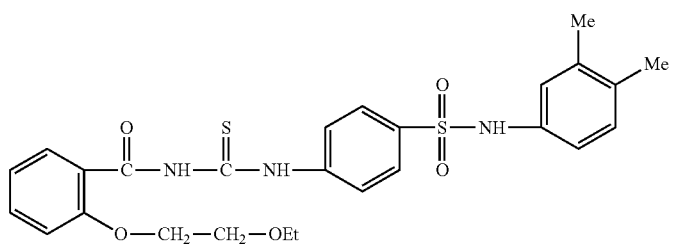
Answer 149:
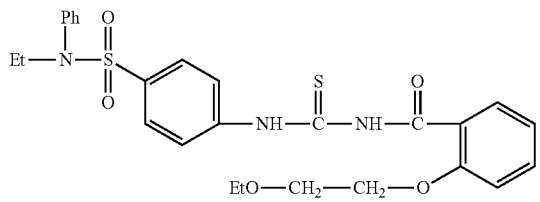

Answer 150:
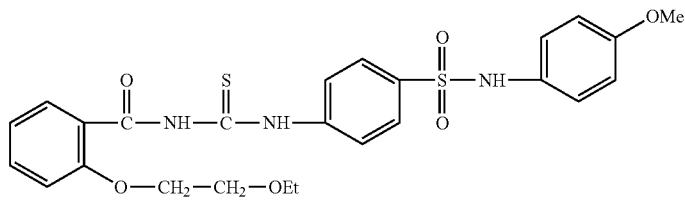
Answer 151:
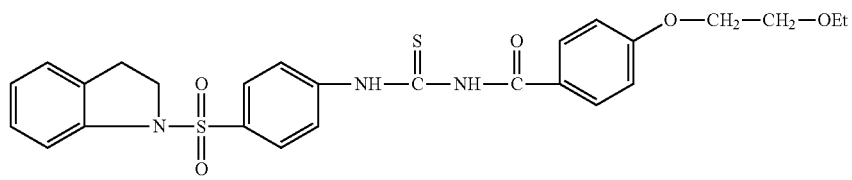
Answer 152:
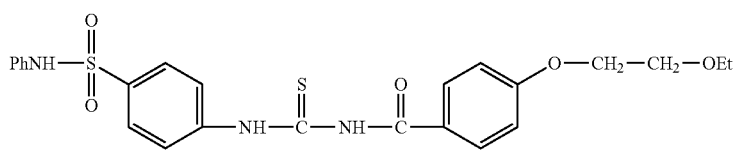
Answer 153:
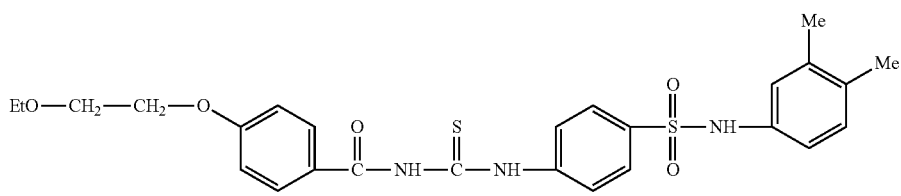
Answer 154:
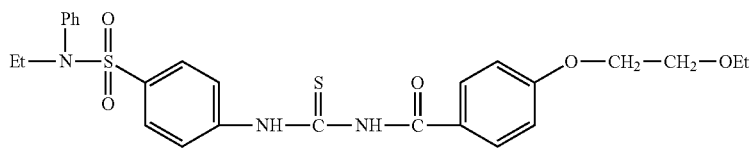
Answer 155:
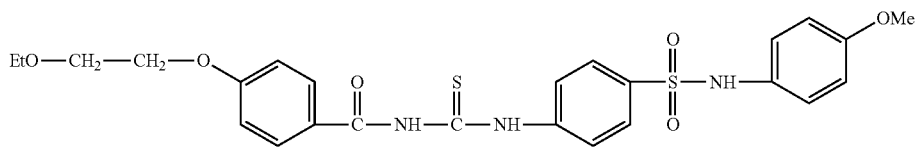
Answer 156:
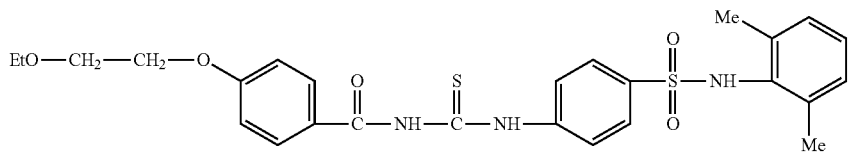

-continued
Answer 157:
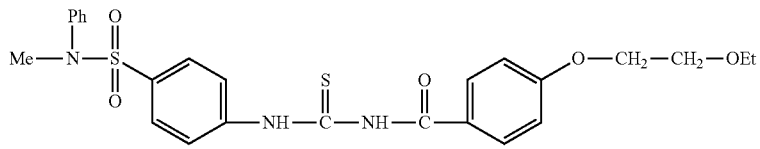
Answer 158:
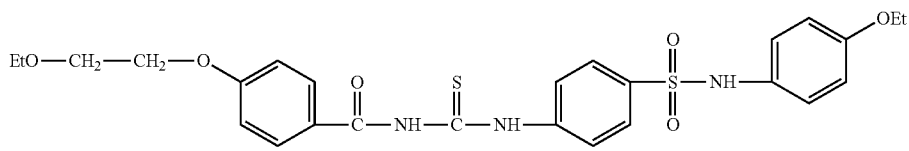
Answer 159:
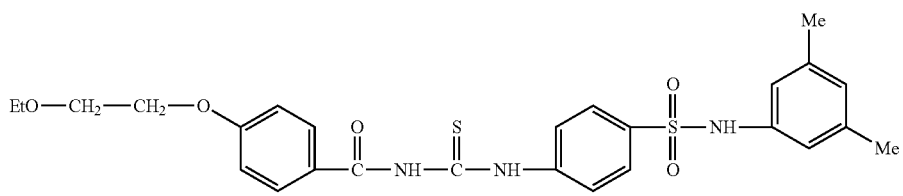
Answer 160:
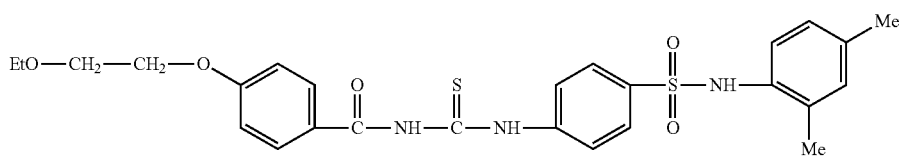
Answer 161:
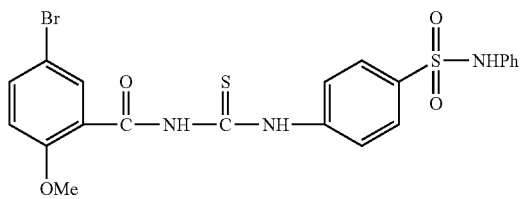
Answer 162:
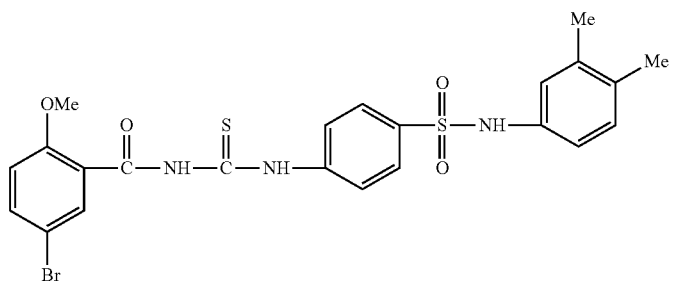
Answer 163:
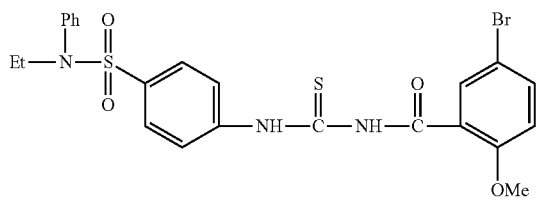

Answer 164:
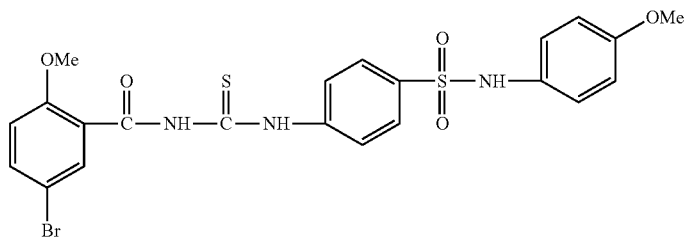
Answer 165:
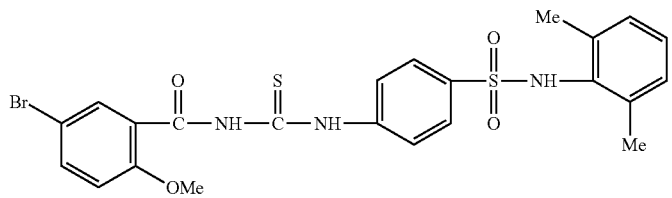
Answer 166:
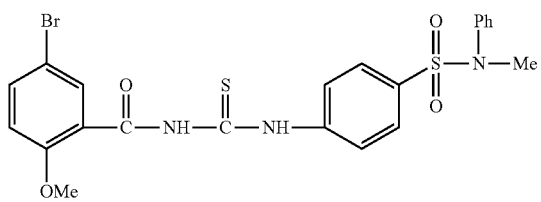
Answer 167:
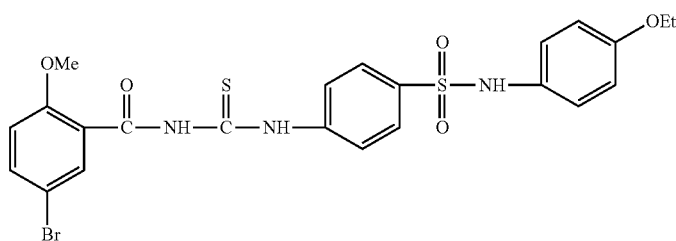
Answer 168:
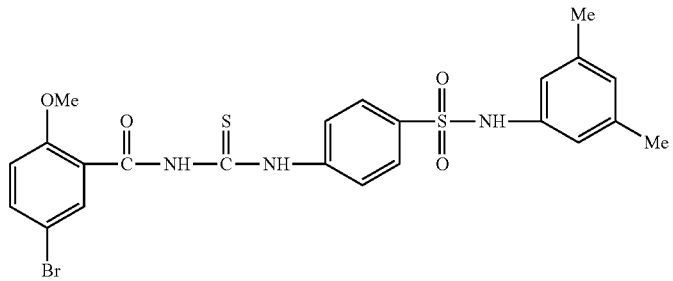
Answer 169:
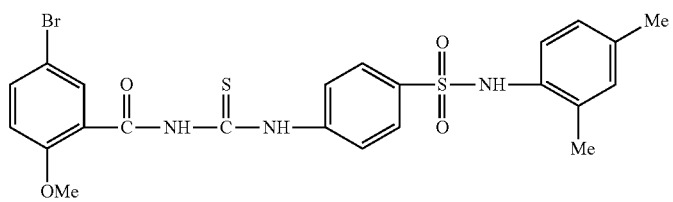

Answer 170:
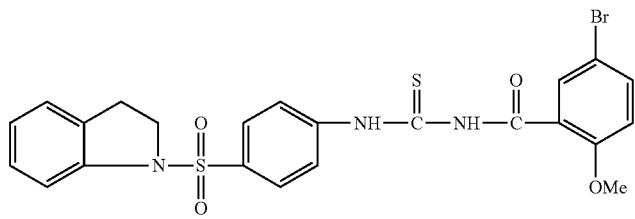
Answer 171:
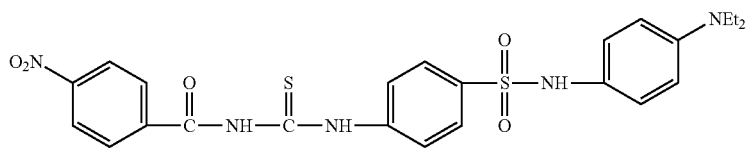
Answer 172:
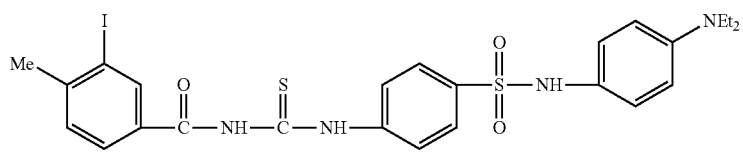
Answer 173:
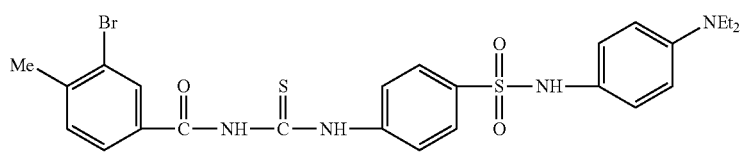
Answer 174:
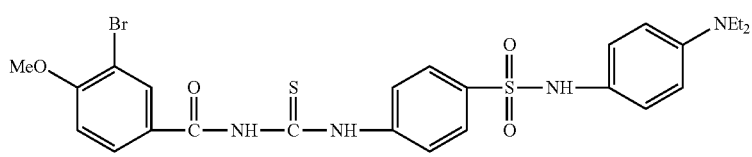
Answer 175:
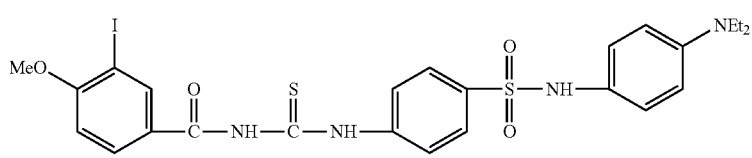
Answer 176:
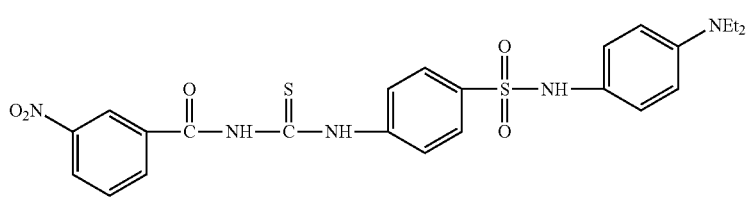

Answer 177:
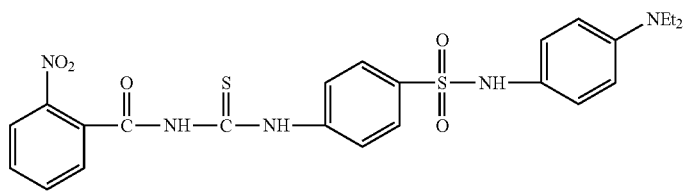
Answer 178:
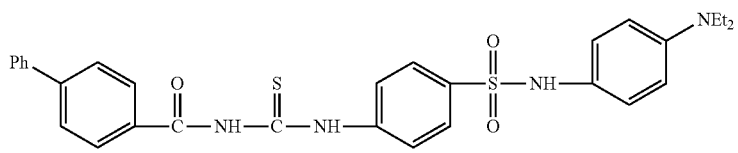
Answer 179:
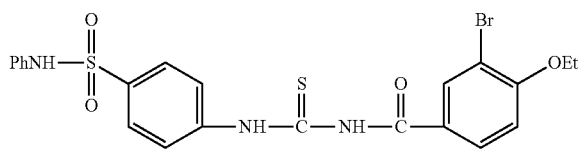
Answer 180:
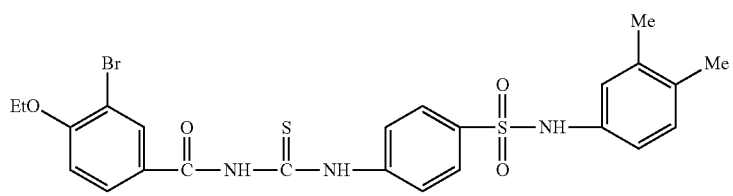
Answer 181:
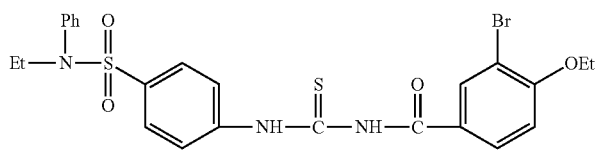
Answer 182:
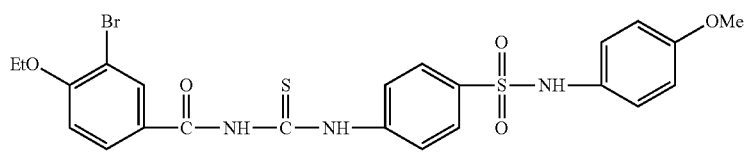
Answer 183:
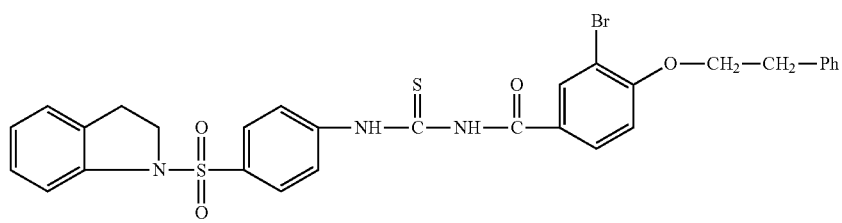

Answer 184:
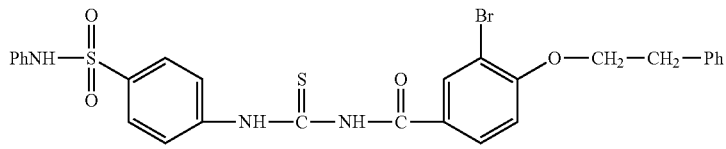
Answer 185:
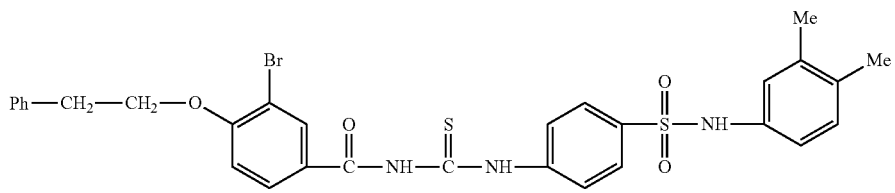
Answer 186:
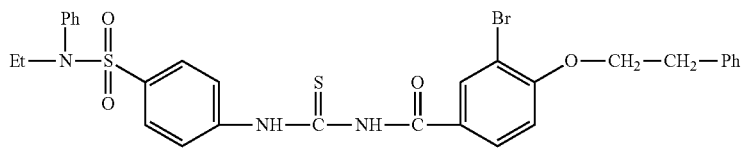
Answer 187:
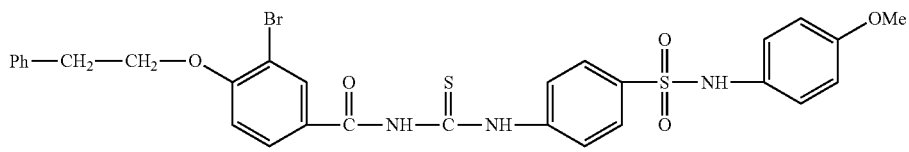
Answer 188:
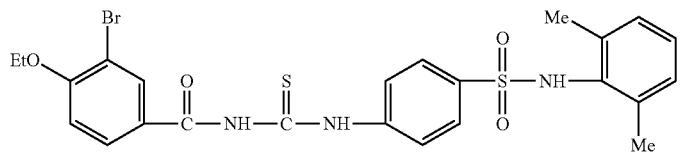
Answer 189:
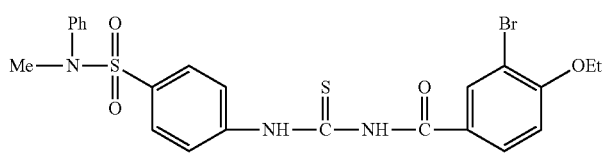
Answer 190:
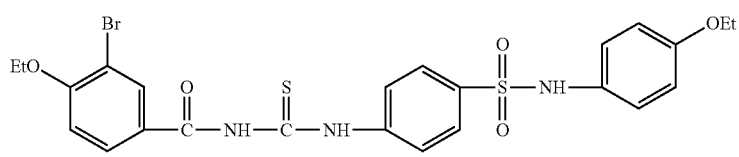
Answer 191:
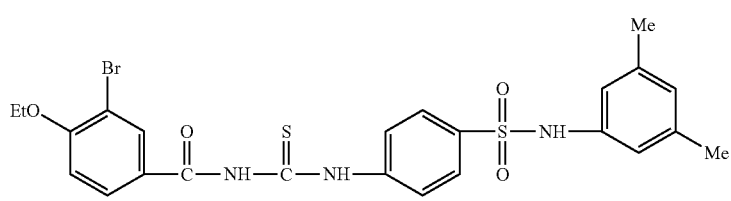

Answer 192:
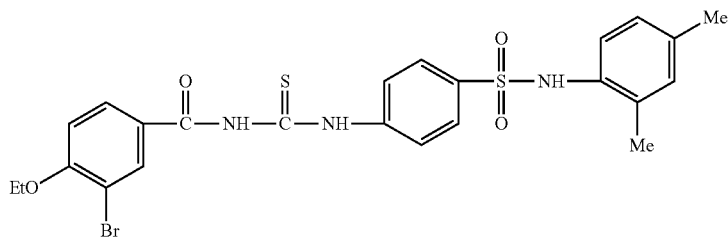
Answer 193:
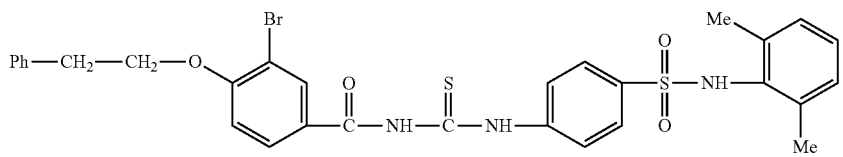
Answer 194:
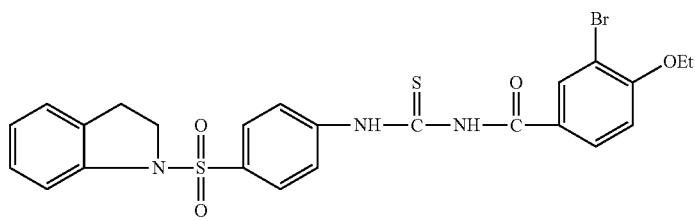
Answer 195:
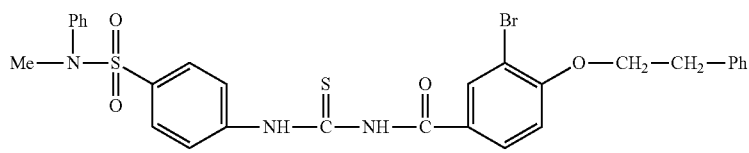
Answer 196:
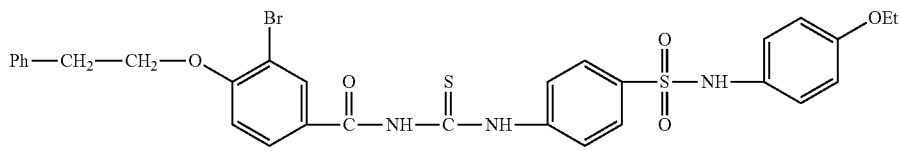
Answer 197:
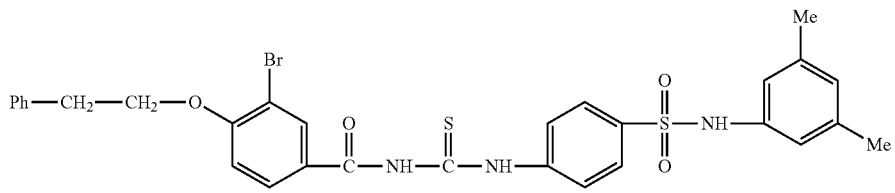
Answer 198:
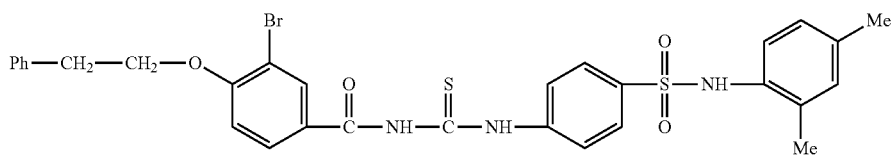

Answer 199:
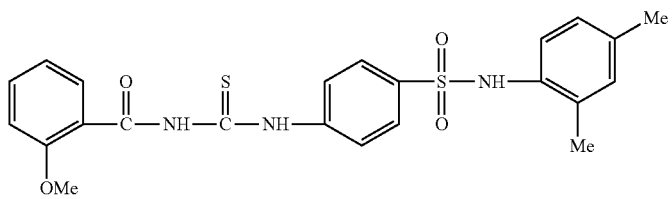
Answer 200:
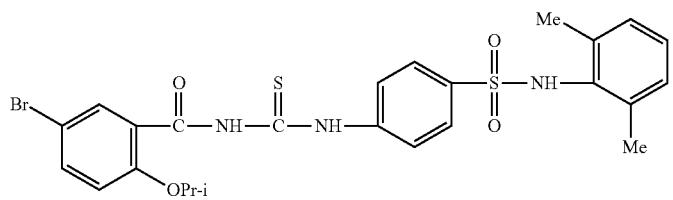
Answer 201:
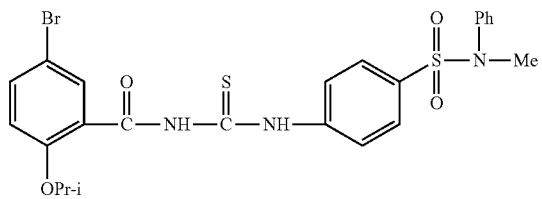
Answer 202:
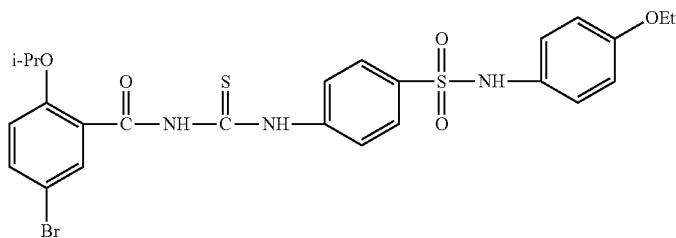
Answer 203:
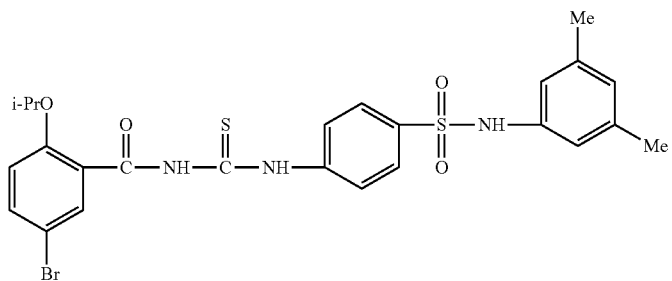
Answer 204:
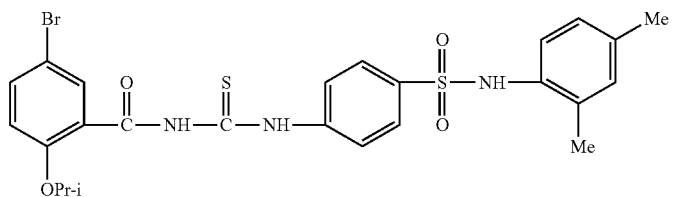

-continued
Answer 205:
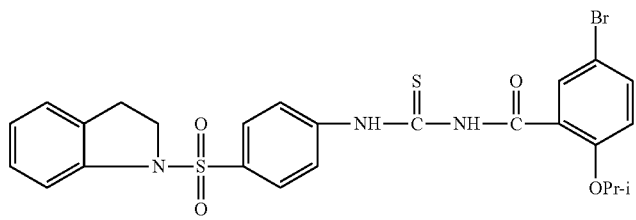
Answer 206:
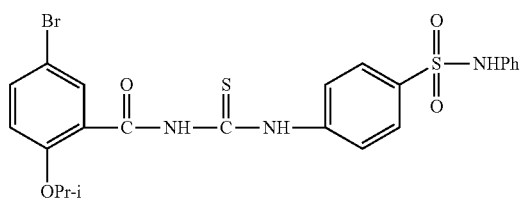
Answer 207:
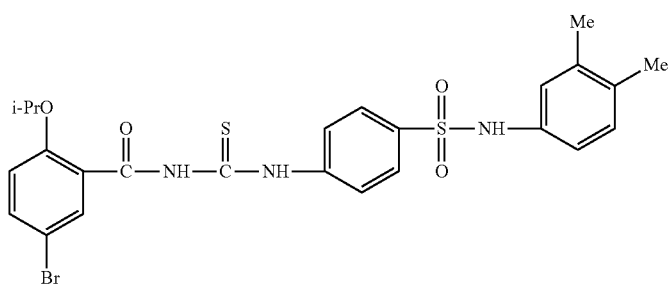
Answer 208:
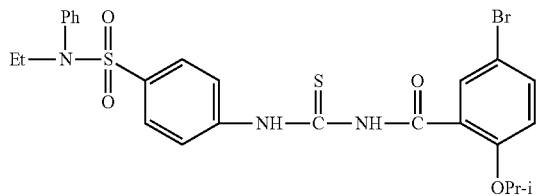
Answer 209:
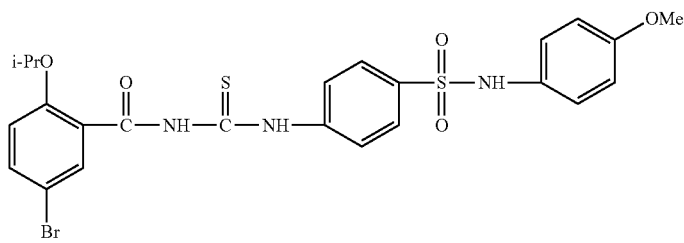
Answer 210:
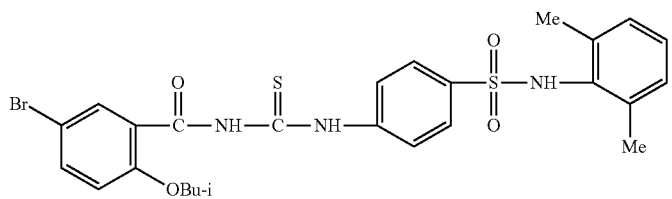

Answer 211:
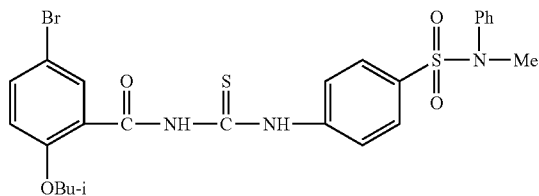
Answer 212:
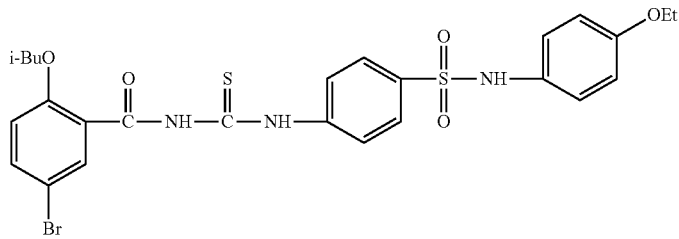
Answer 213:
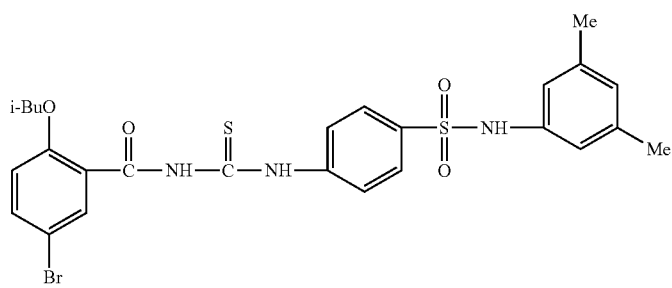
Answer 214:
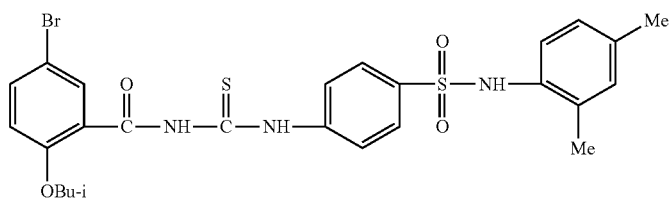
Answer 215:
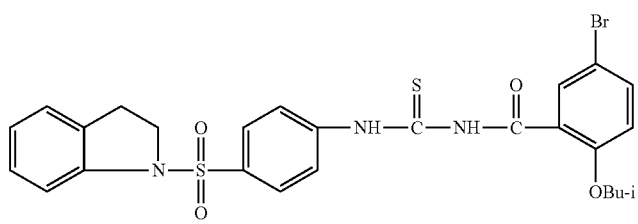
Answer 216:
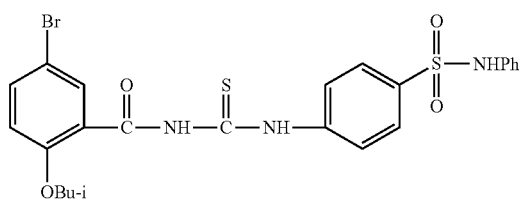

Answer 217:
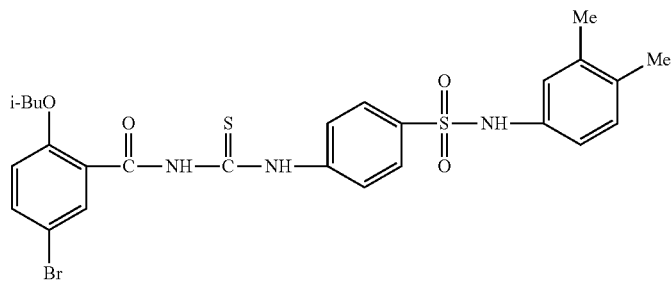
Answer 218:
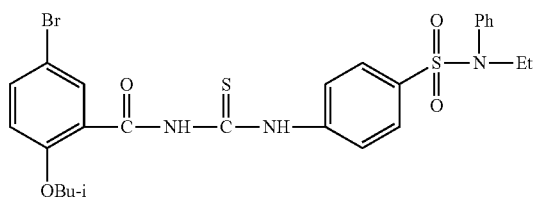
Answer 219:
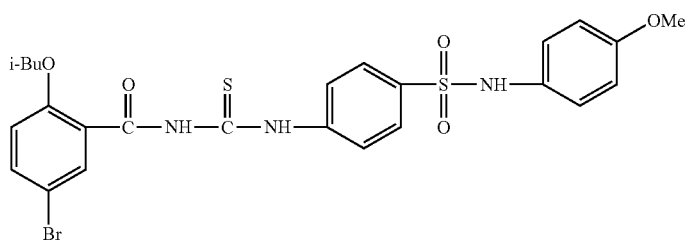
Answer 220:
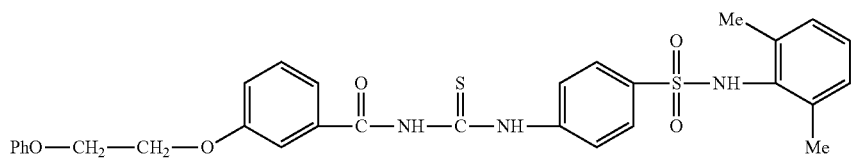
Answer 221:
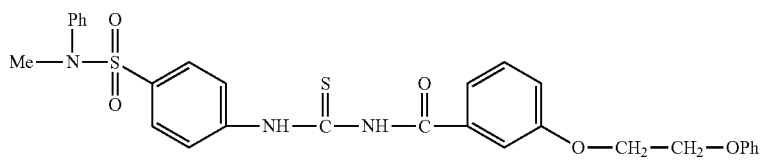
Answer 222:
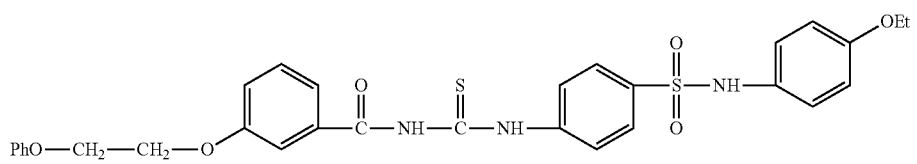

Answer 223:
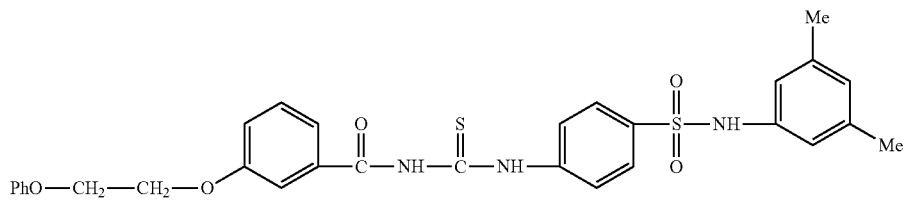
Answer 224:
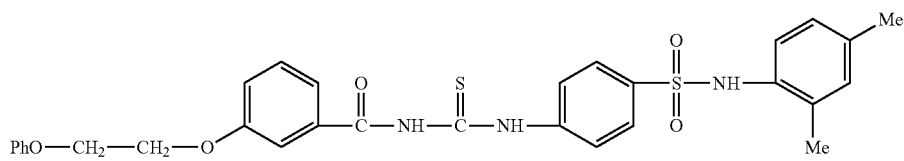
Answer 225:
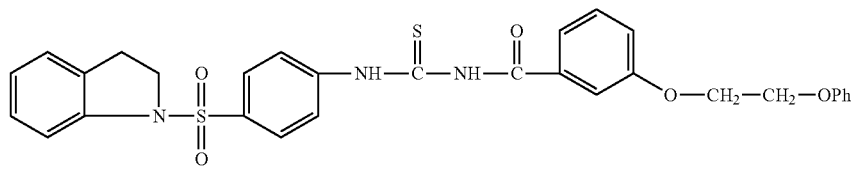
Answer 226:
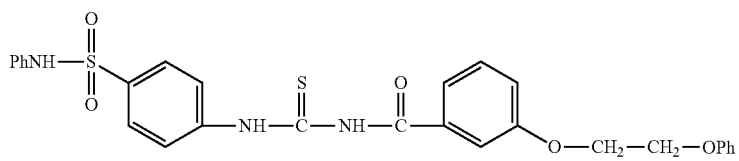
Answer 227:
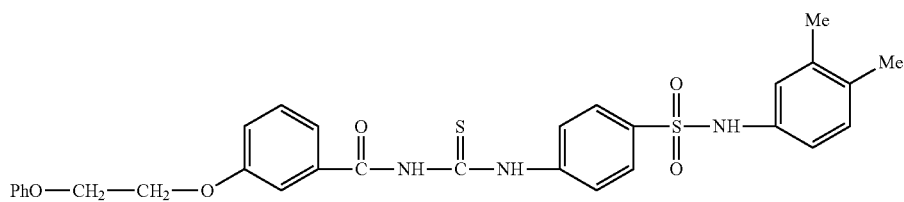
Answer 228:
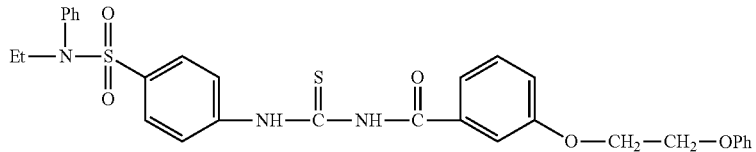
Answer 229:
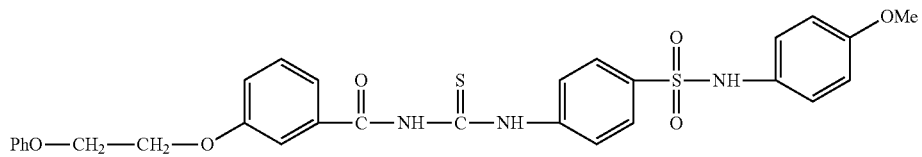

Answer 230:
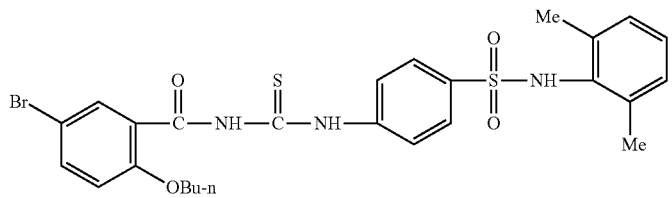
Answer 231:
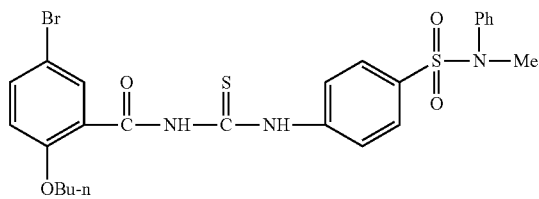
Answer 232:
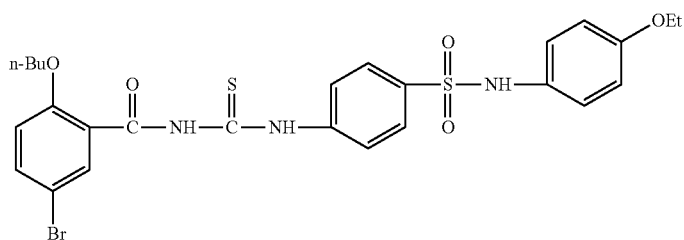
Answer 233:
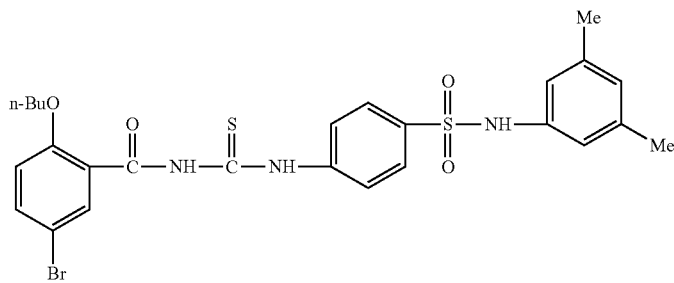
Answer 234:
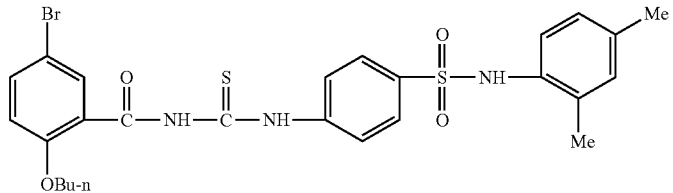
Answer 235:
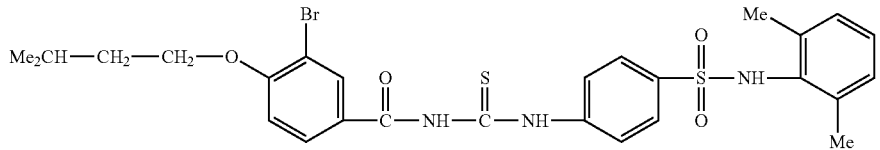

Answer 236:
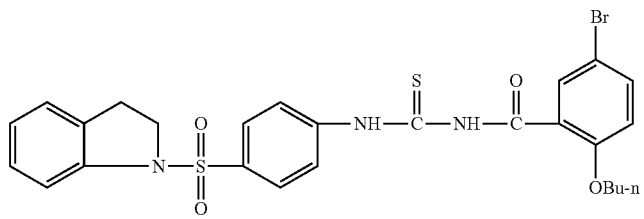
Answer 237:
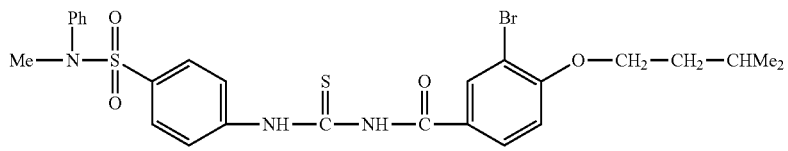
Answer 238:
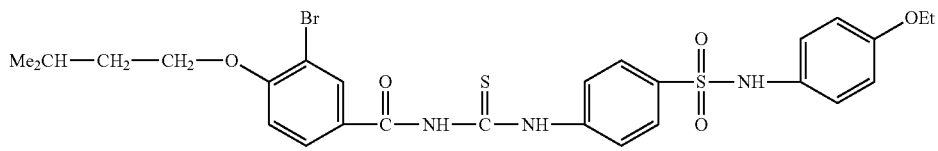
Answer 239:
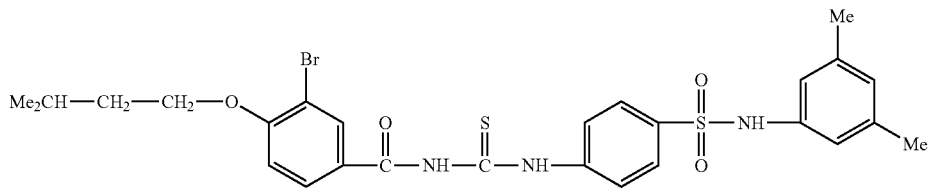
Answer 240:
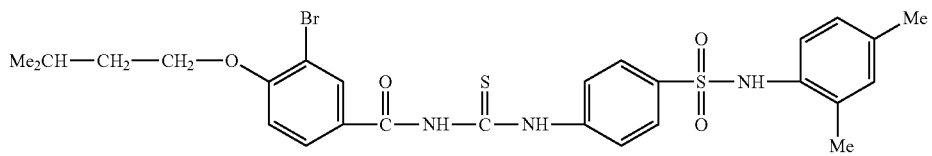
Answer 241:
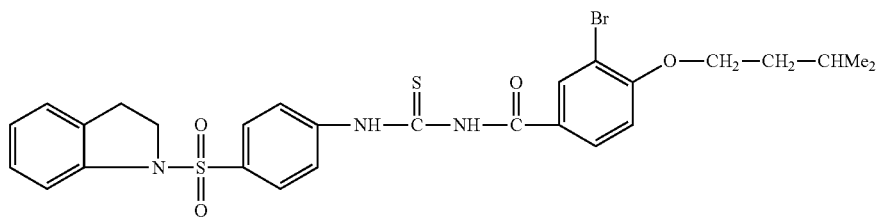
Answer 242:
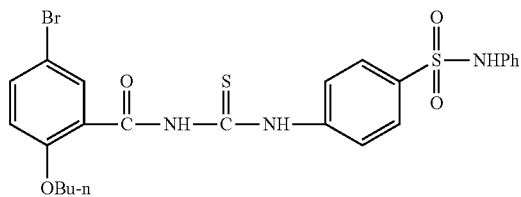

Answer 243:
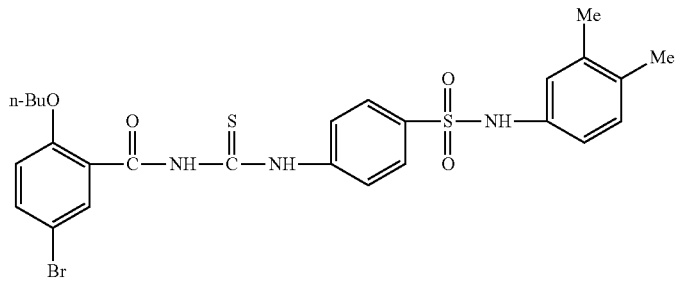
Answer 244:
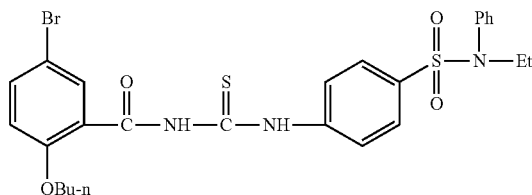
Answer 245:
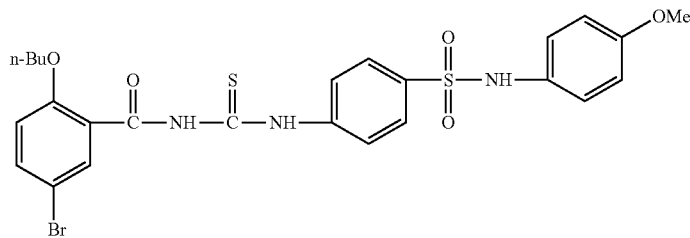
Answer 246:
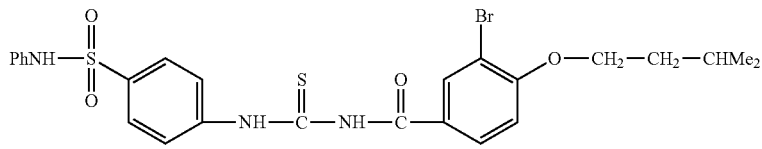
Answer 247:
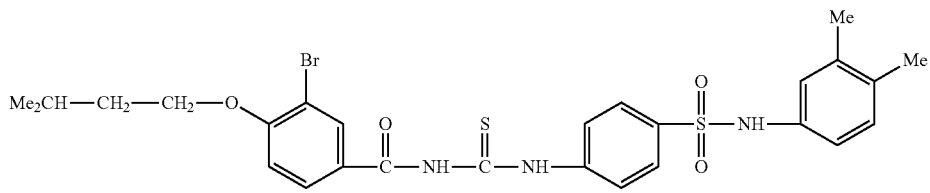
Answer 248:
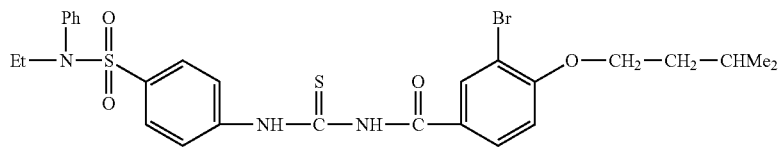
Answer 249:
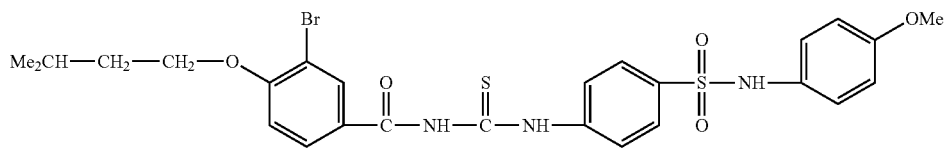

Answer 250:
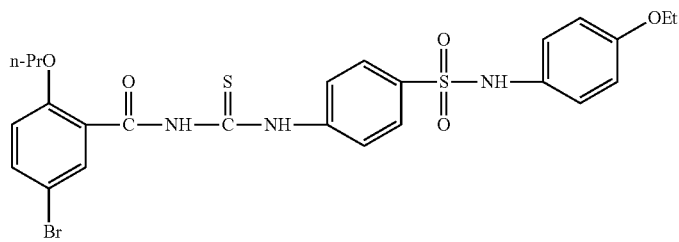
Answer 251:
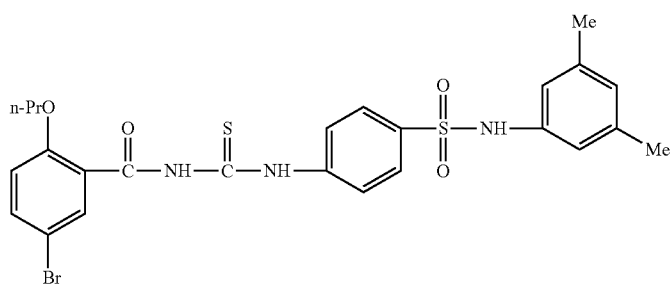
Answer 252:
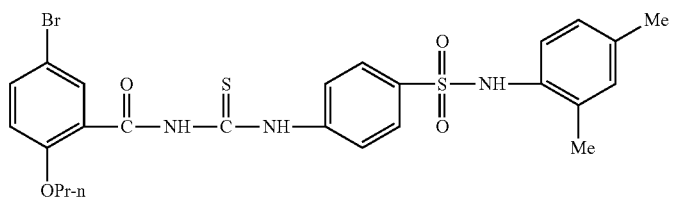
Answer 253:
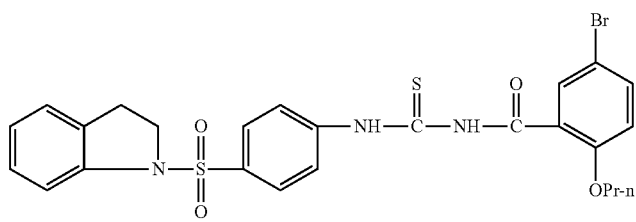
Answer 254:
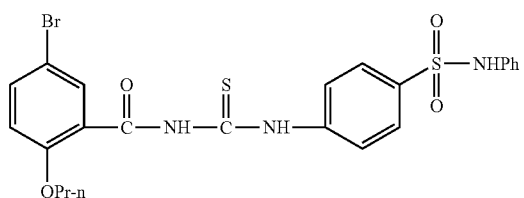

-continued
Answer 255:
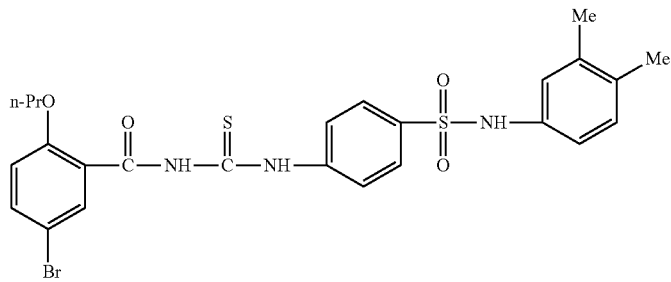
Answer 256:
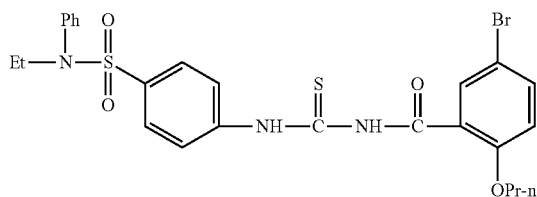
Answer 257:
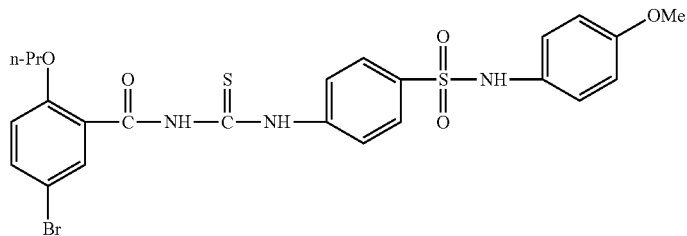
Answer 258:
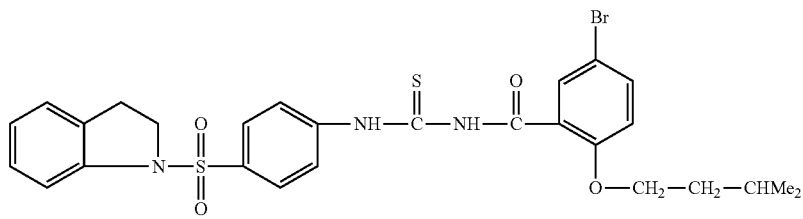
Answer 259:
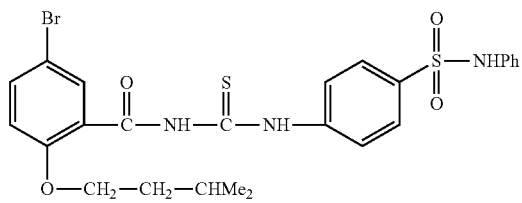
Answer 260:
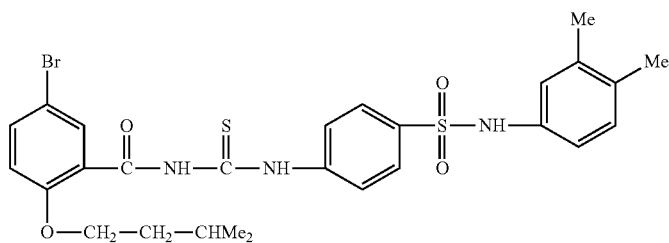

-continued
Answer 261:
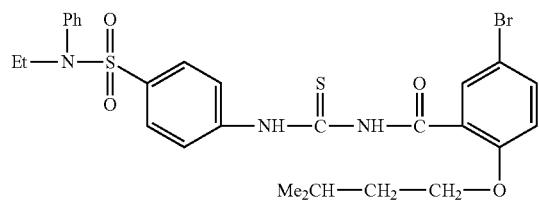
Answer 262:
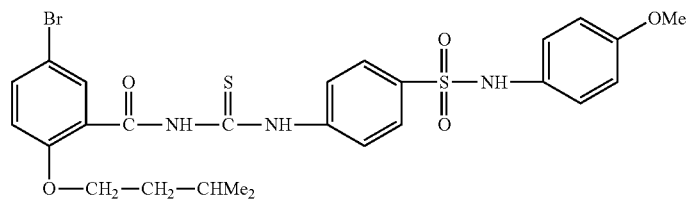
Answer 263:
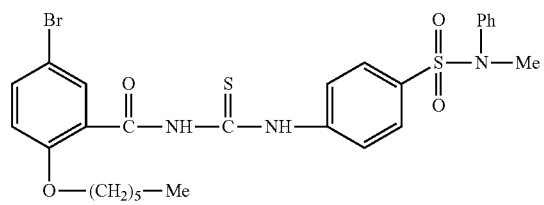
Answer 264:
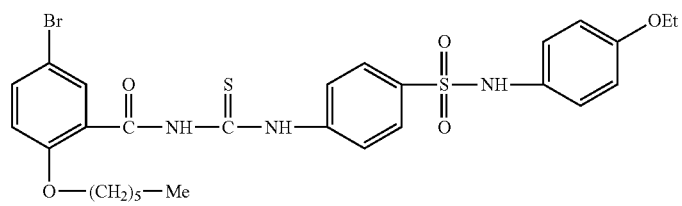
Answer 265:
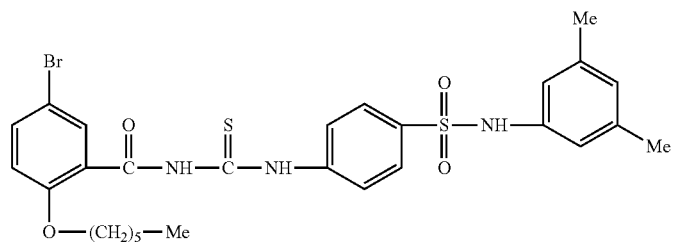
Answer 266:
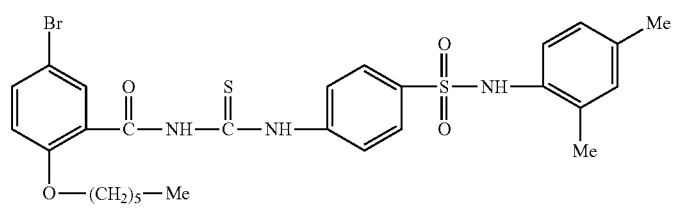

-continued
Answer 267:
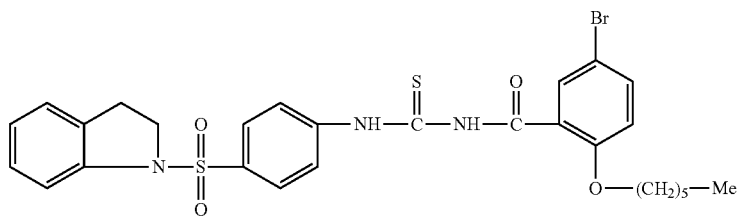
Answer 268:
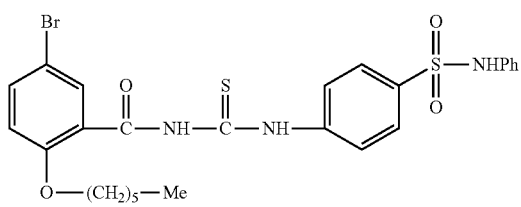
Answer 269:
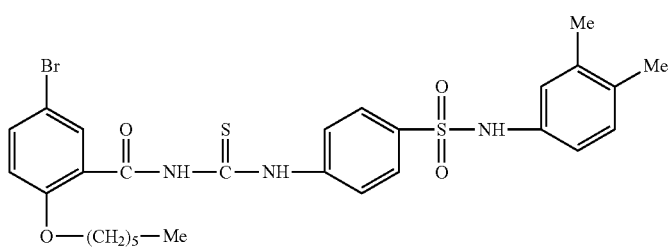
Answer 270:
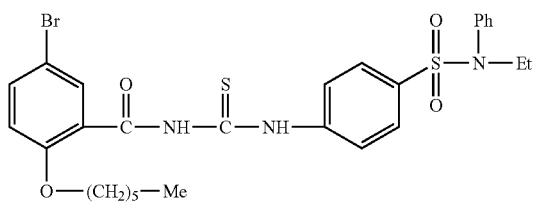
Answer 271:
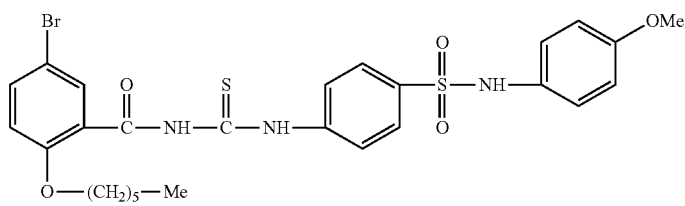
Answer 272:
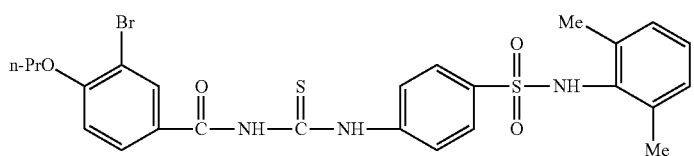

Answer 273:
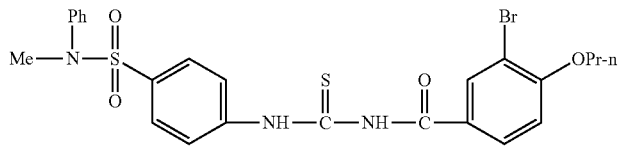
Answer 274:
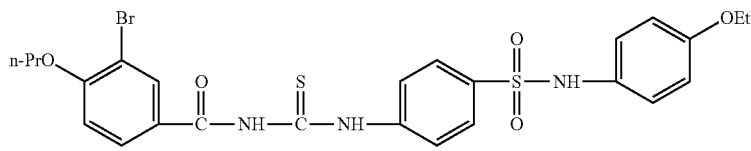
Answer 275:
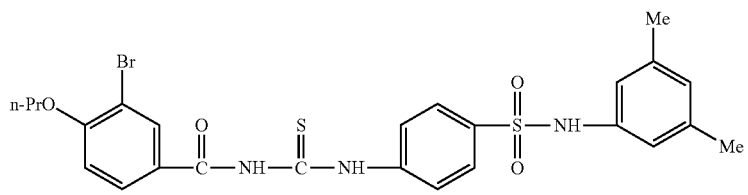
Answer 276:
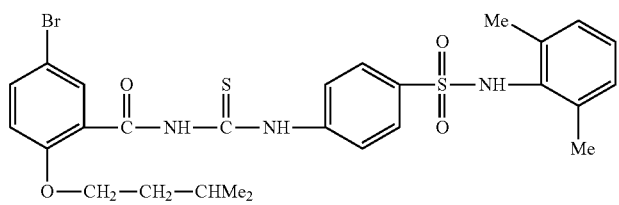
Answer 277:
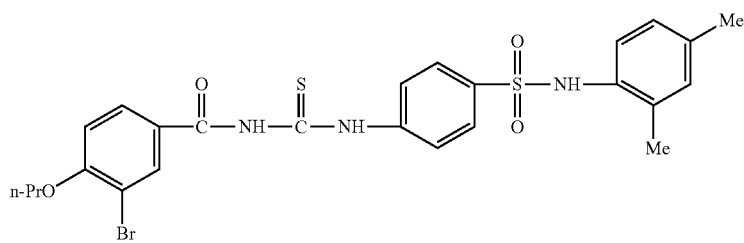
Answer 278:
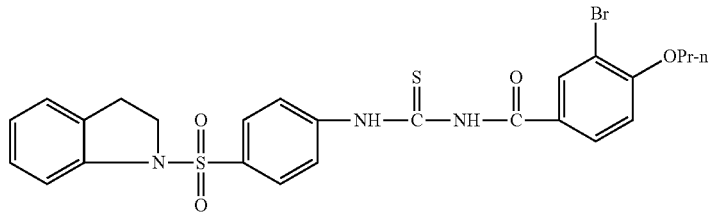
Answer 279:
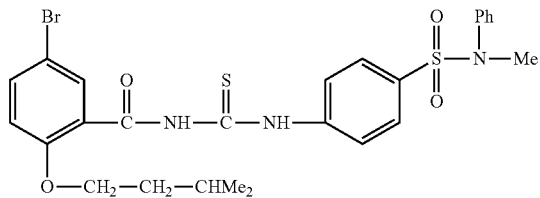

Answer 280:
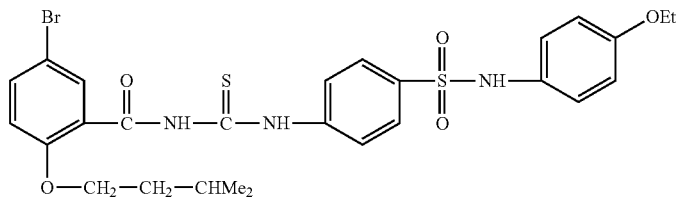
Answer 281:
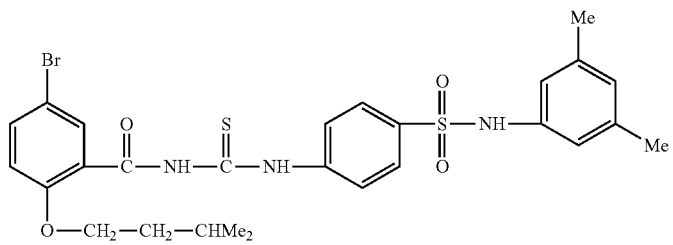
Answer 282:
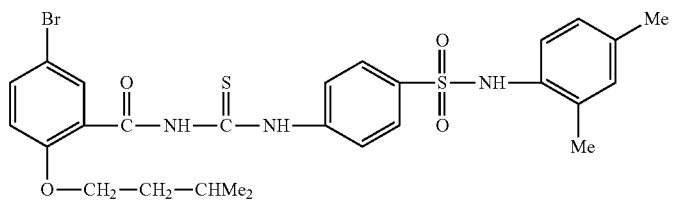
Answer 283:
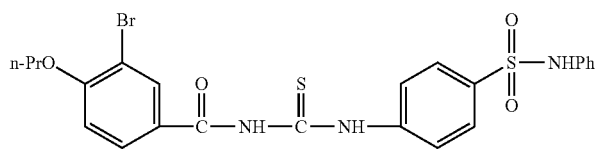
Answer 284:
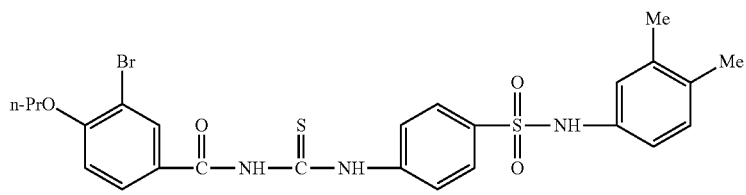
Answer 285:
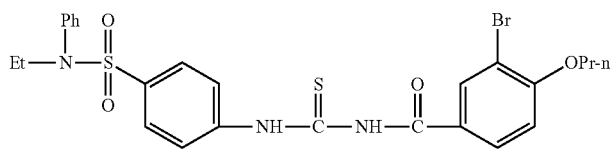
Answer 286:
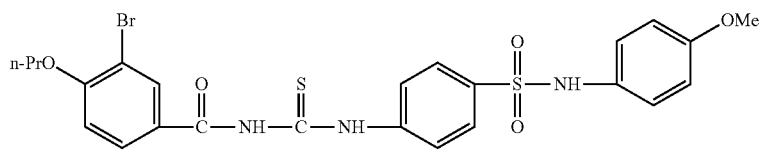

Answer 287:
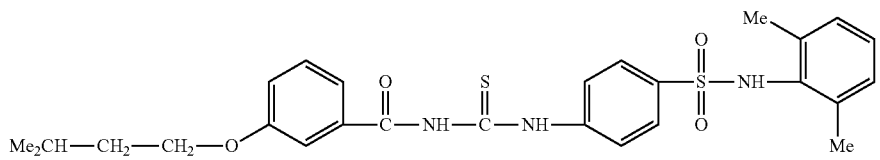
Answer 288:
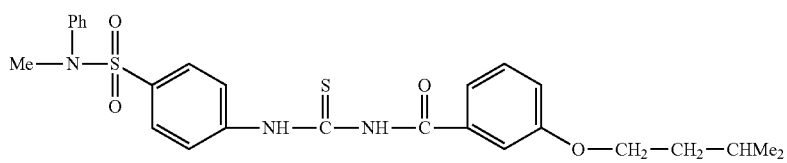
Answer 289:
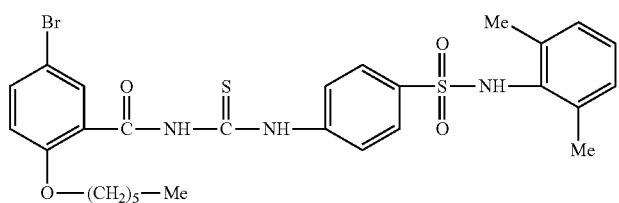
Answer 290:
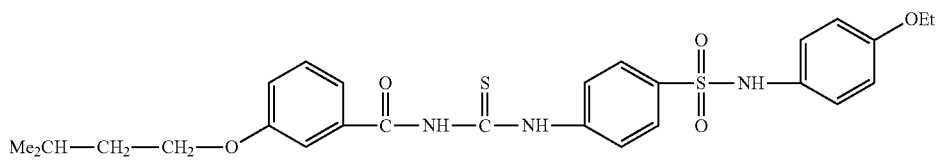
Answer 291:
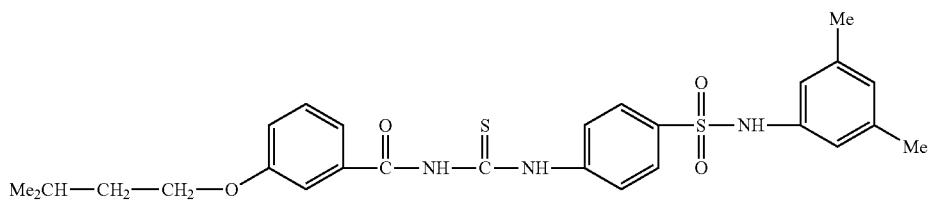
Answer 292:
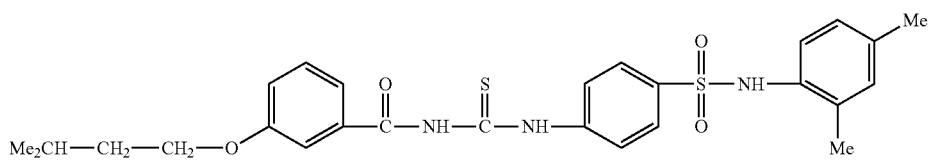
Answer 293:
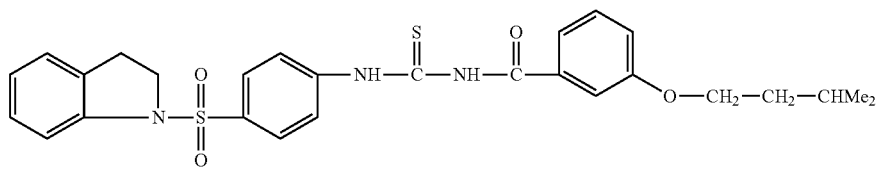

Answer 294:
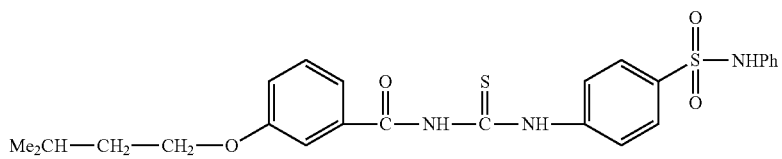
Answer 295:
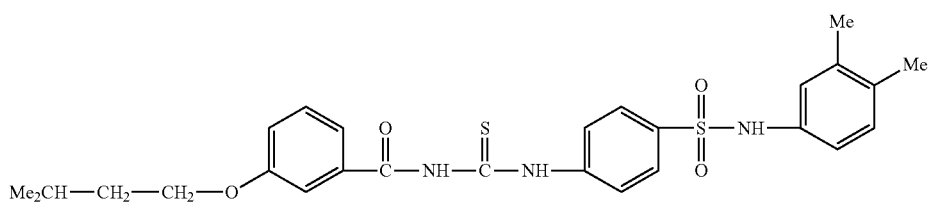
Answer 296:
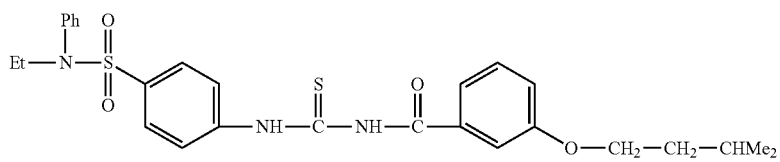
Answer 297:
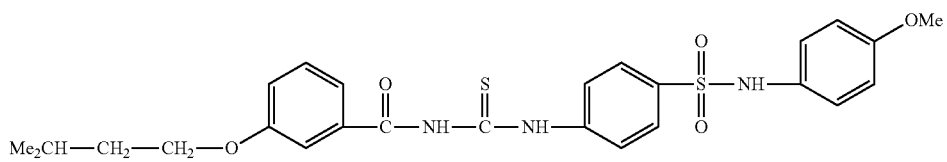
Answer 298:
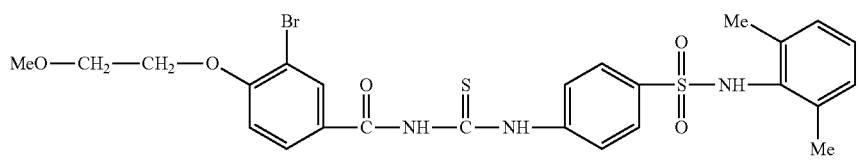
Answer 299:
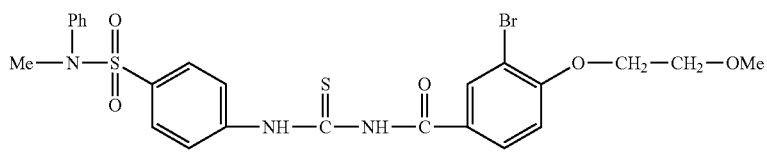
Answer 300:
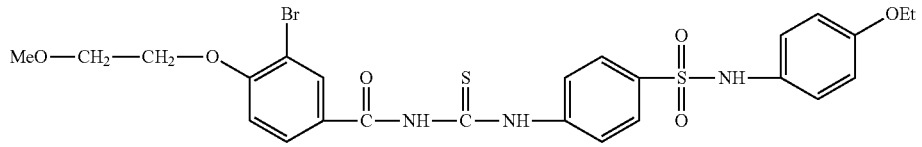

Answer 301:
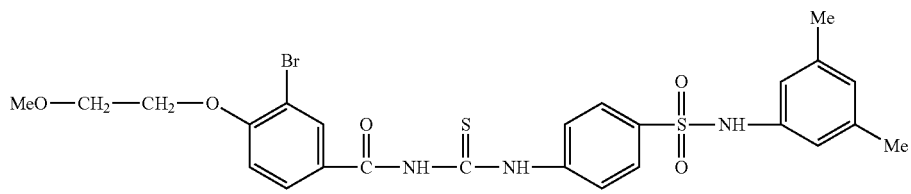
Answer 302:
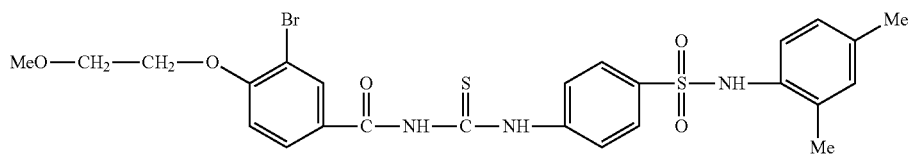
Answer 303:
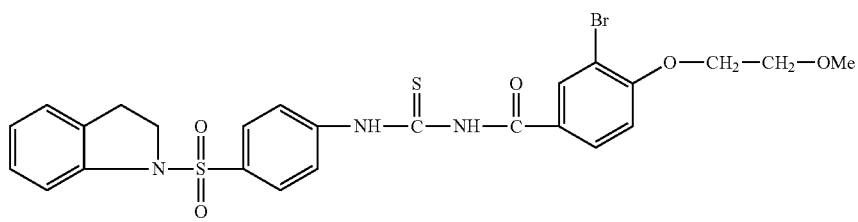
Answer 304:
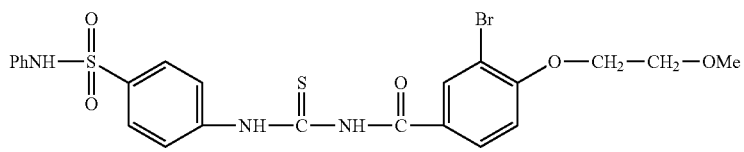
Answer 305:
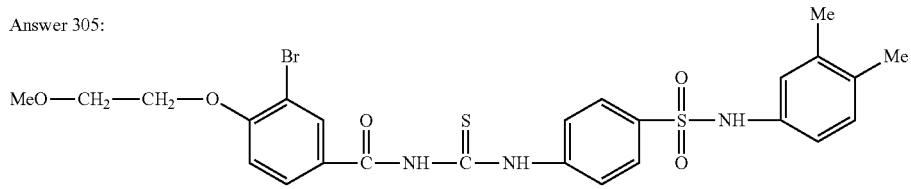 [SMILES: COCCOc1ccc(C(=O)NC(=S)Nc2ccc(S(=O)(=O)Nc3ccc(C)c(C)c3)cc2)cc1Br]
Answer 306:
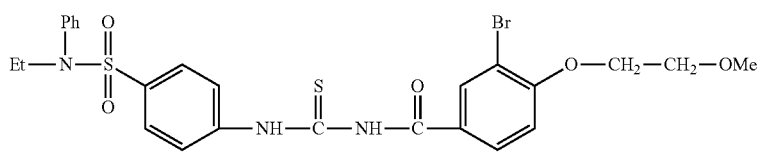
Answer 307:
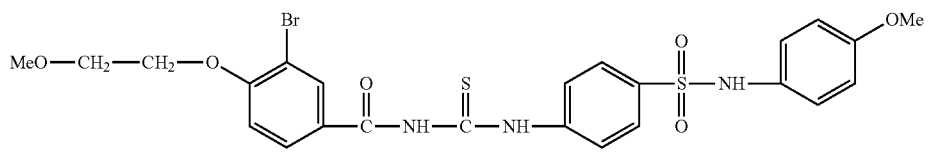

Answer 308:
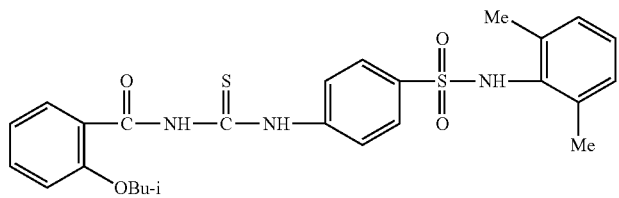
Answer 309:
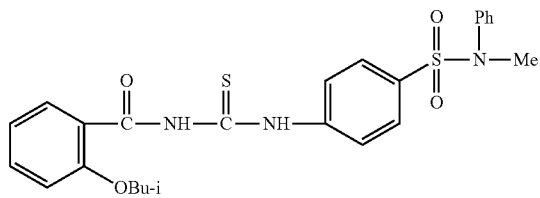
Answer 310:
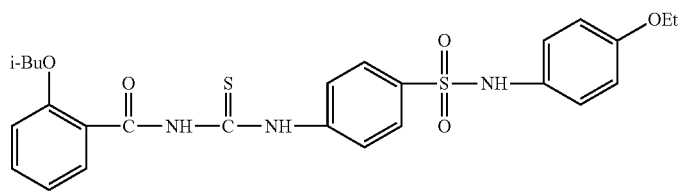
Answer 311:
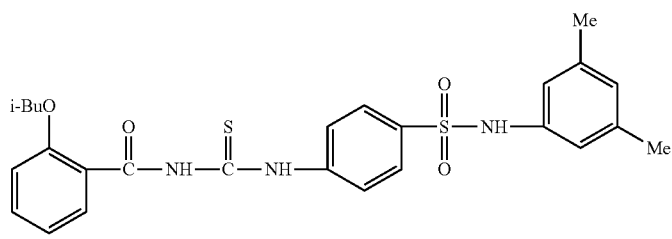
Answer 312:
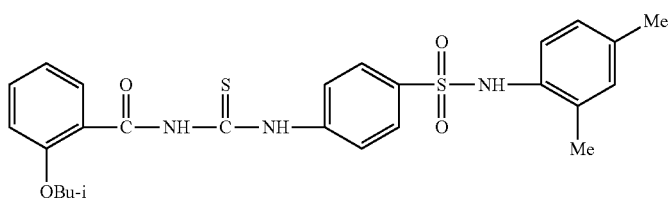
Answer 313:
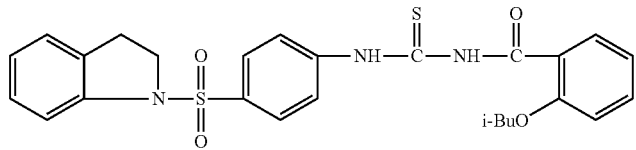

Answer 314:
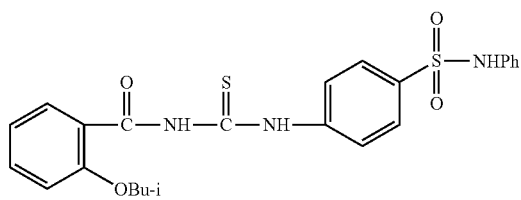
Answer 315:
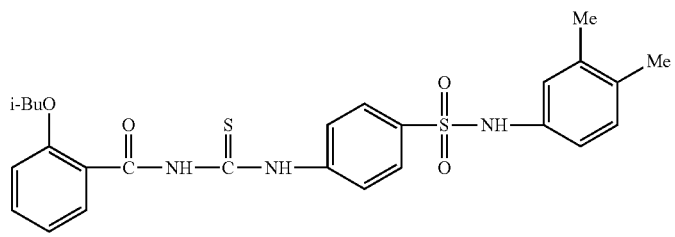
Answer 316:
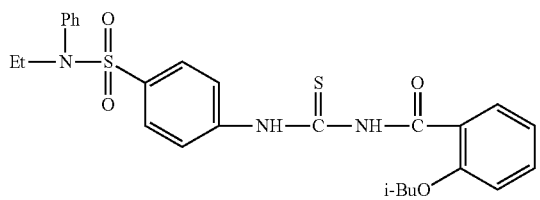
Answer 317:
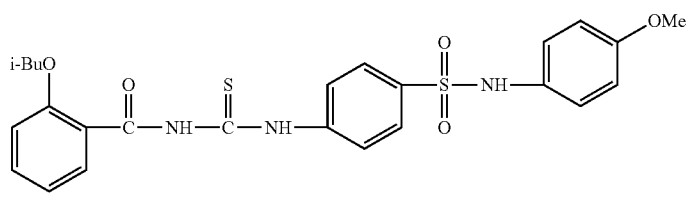
Answer 318:
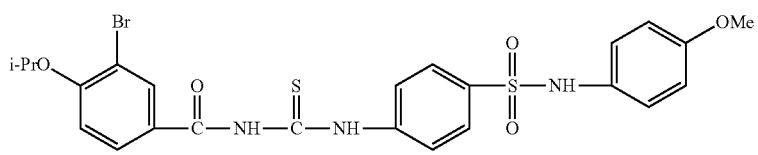
Answer 319:
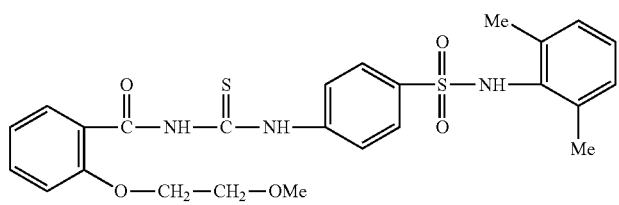

-continued
Answer 320:
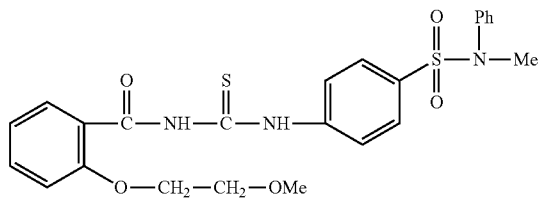
Answer 321:
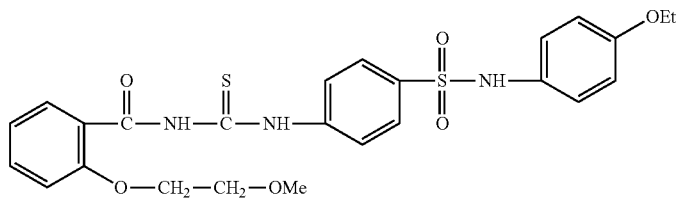
Answer 322:
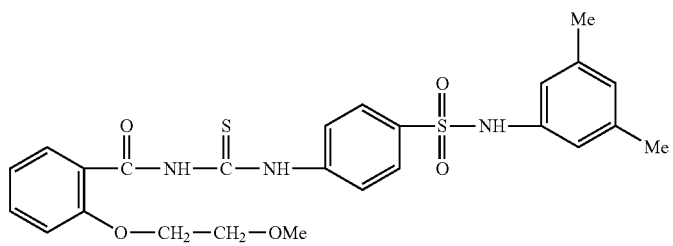
Answer 323:
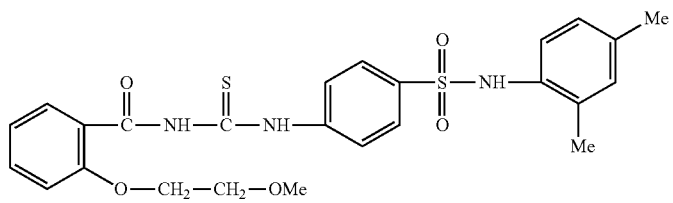
Answer 324:
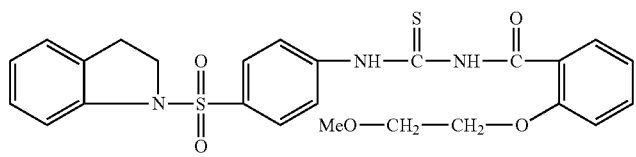
Answer 325:
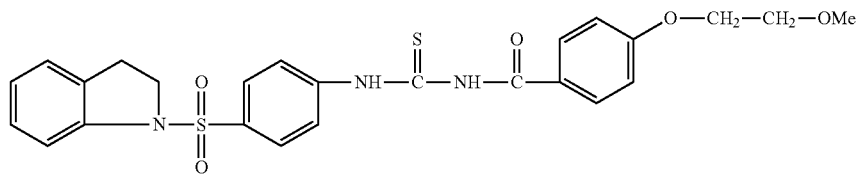

-continued
Answer 326:
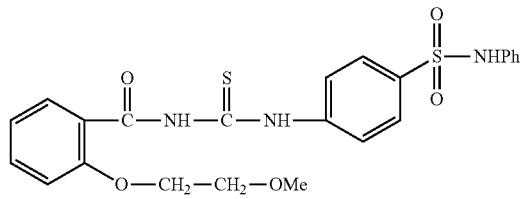
Answer 327:
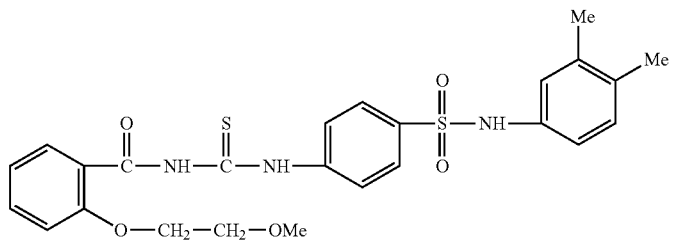
Answer 328:
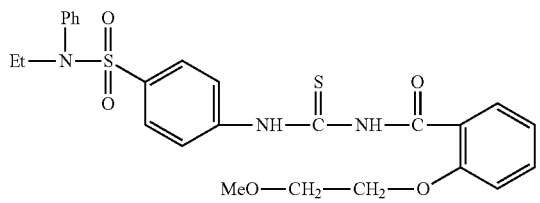
Answer 329:
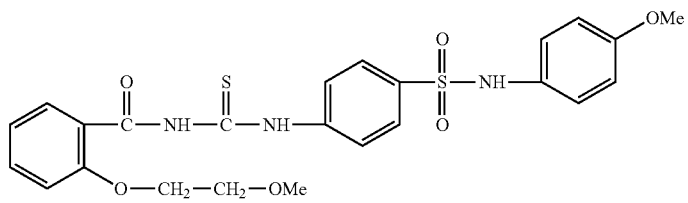
Answer 330:
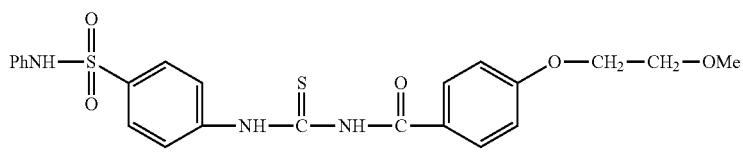
Answer 331:
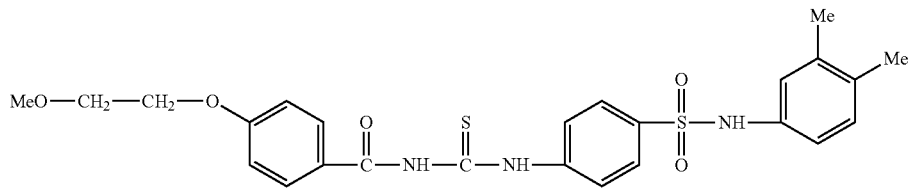
Answer 332:
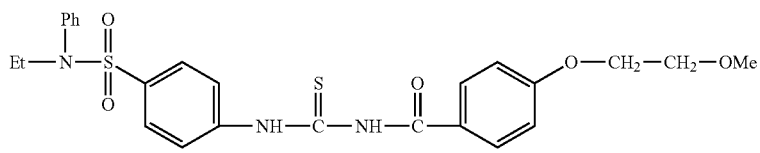

Answer 333:
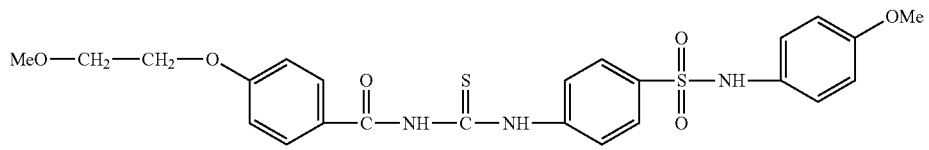
Answer 334:
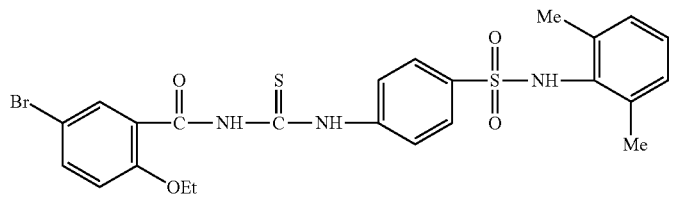
Answer 335:
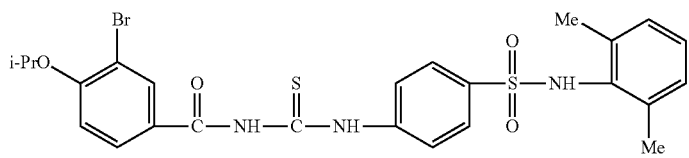
Answer 336:
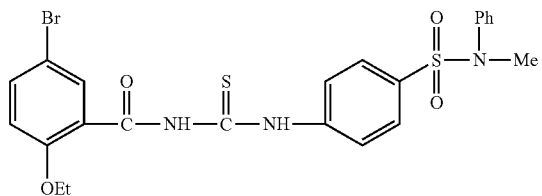
Answer 337:
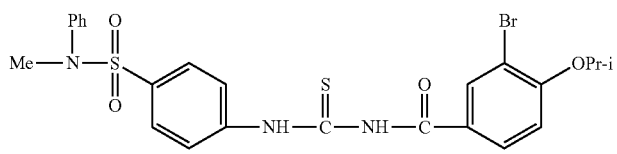
Answer 338:
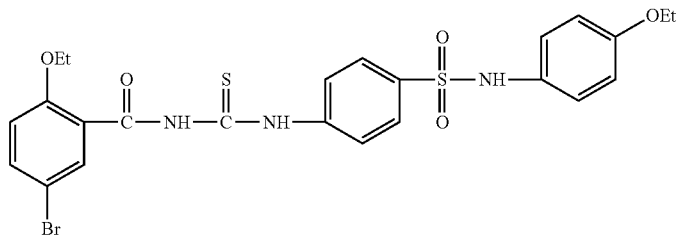
Answer 339:
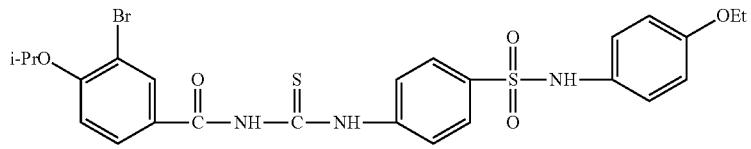

Answer 340:
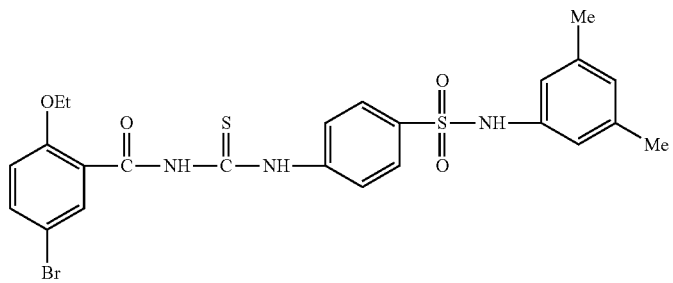
Answer 341:
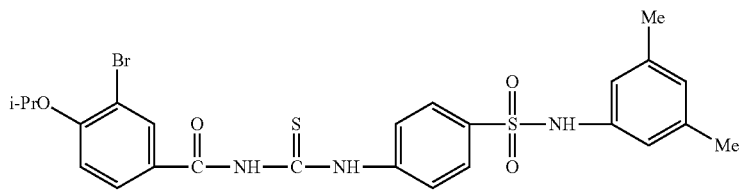
Answer 342:
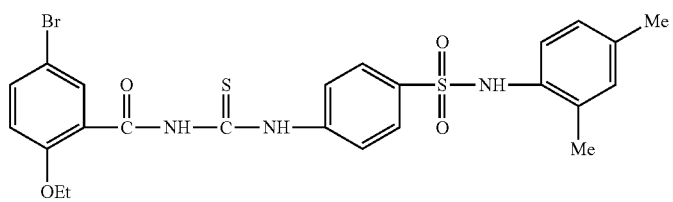
Answer 343:
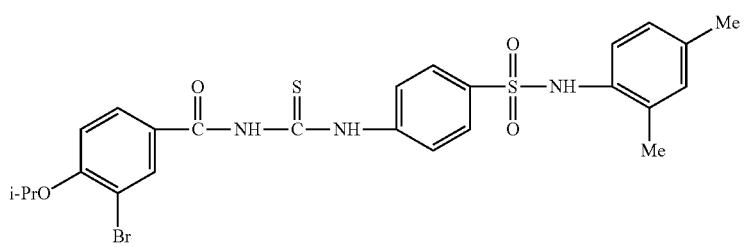
Answer 344:
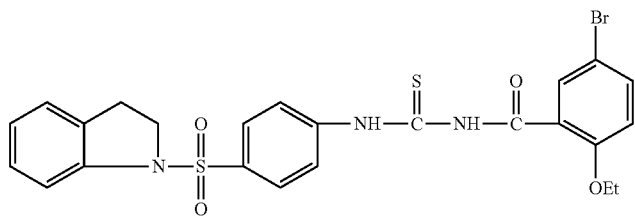
Answer 345:
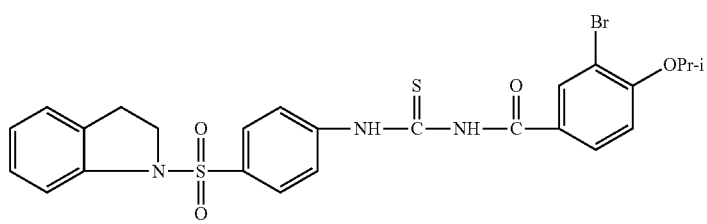

-continued
Answer 346:
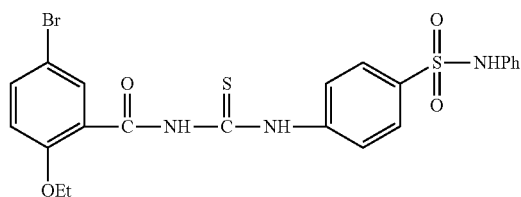
Answer 347:
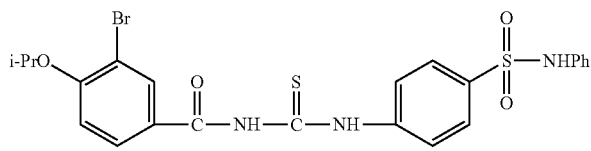
Answer 348:
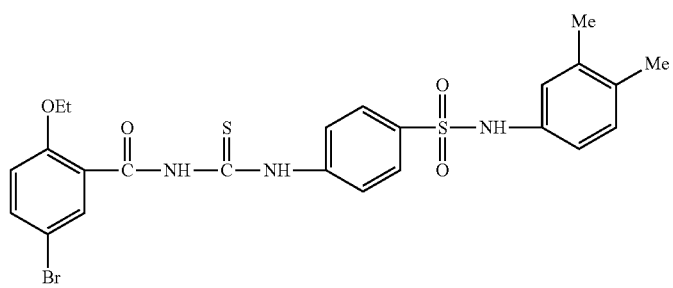
Answer 349:
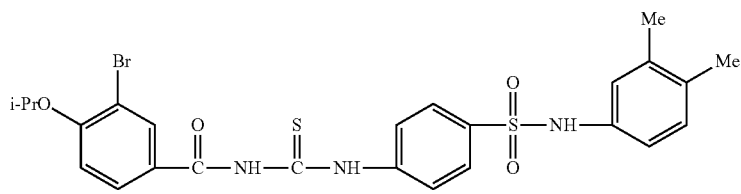
Answer 350:
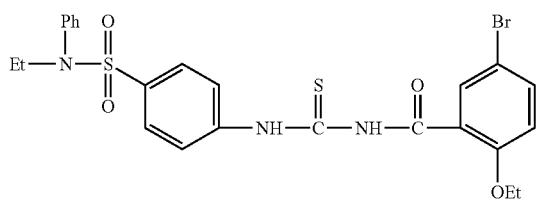
Answer 351:
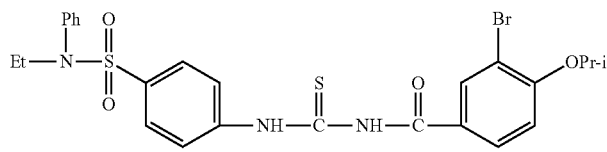

Answer 352:
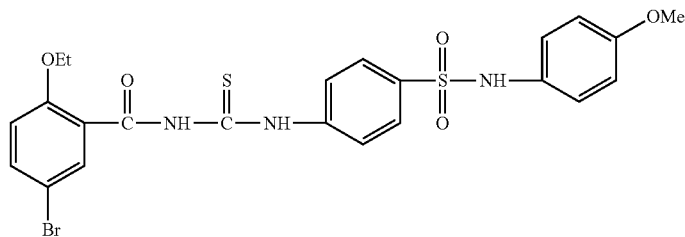
Answer 353:
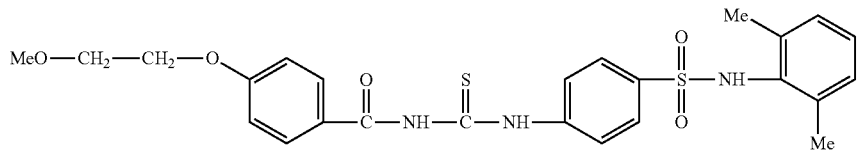
Answer 354:
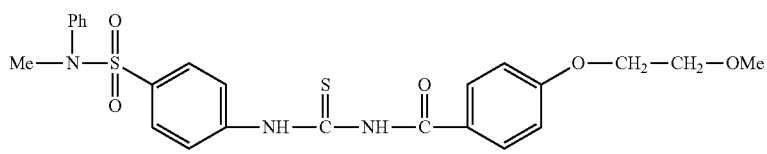
Answer 355:
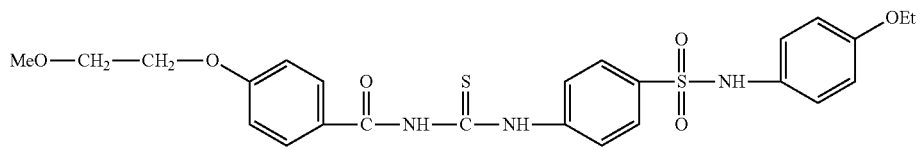
Answer 356:
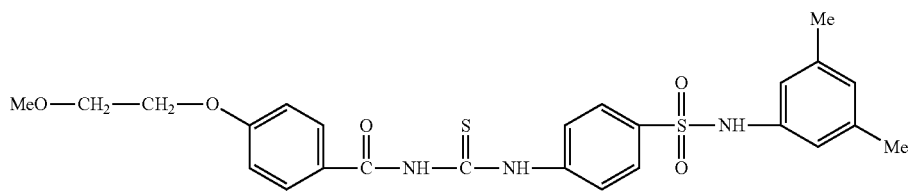
Answer 357:
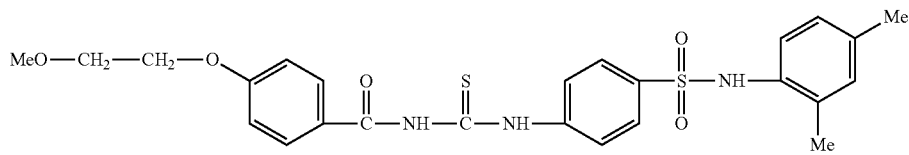
Answer 358:
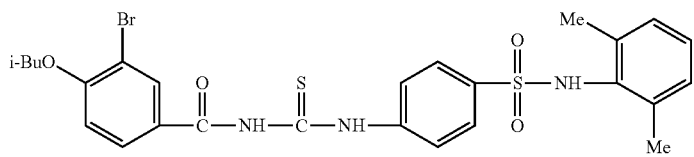

-continued
Answer 359:
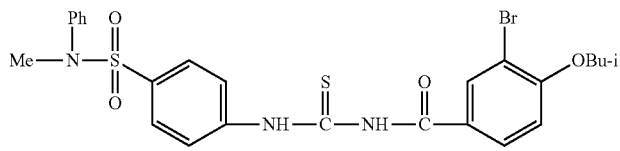
Answer 360:
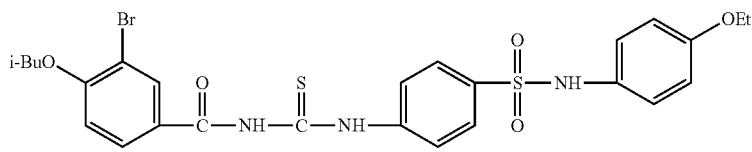
Answer 361:
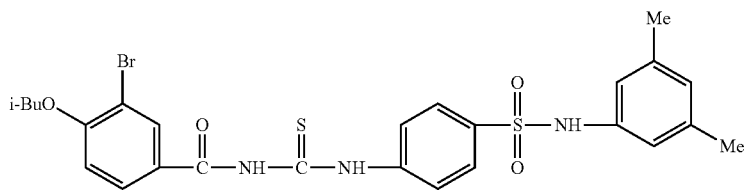
Answer 362:
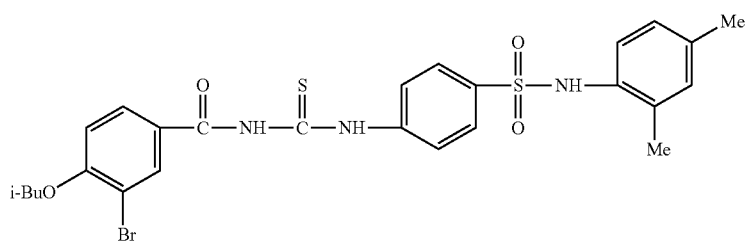
Answer 363:
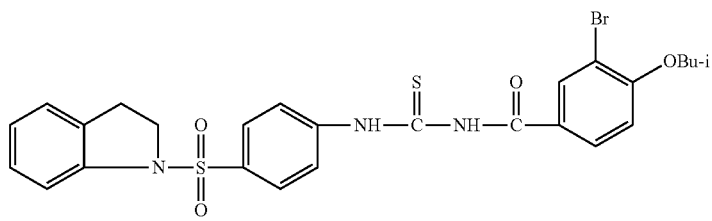
Answer 364:
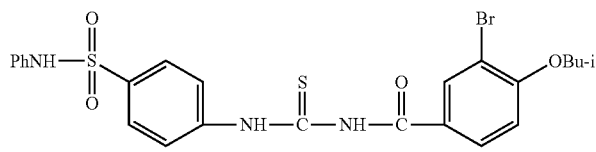
Answer 365:
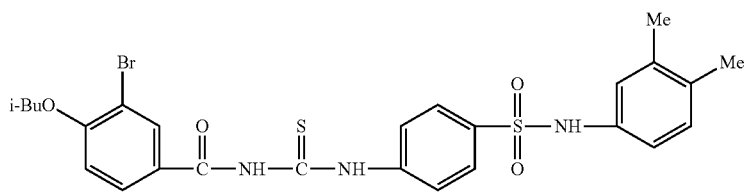

Answer 366:
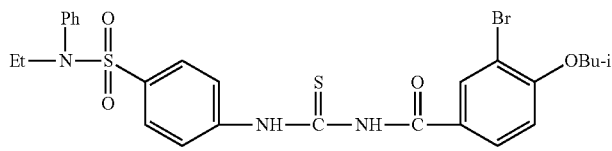
Answer 367:
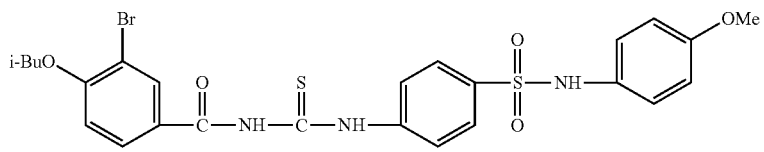
Answer 368:
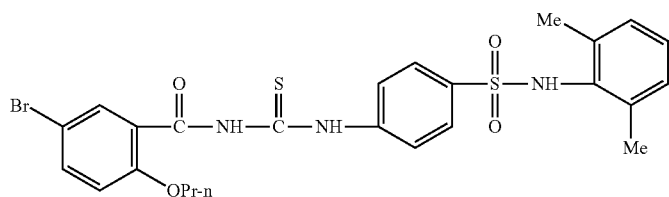
Answer 369:
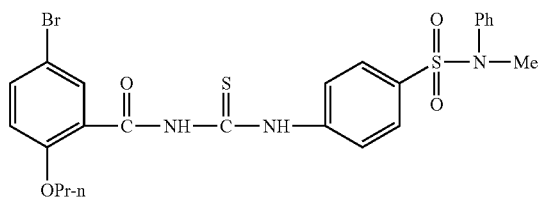
Answer 370:
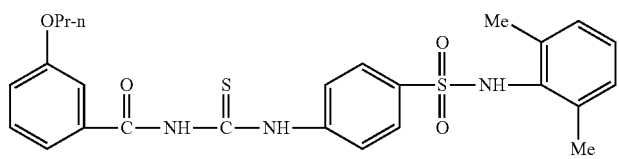
Answer 371:
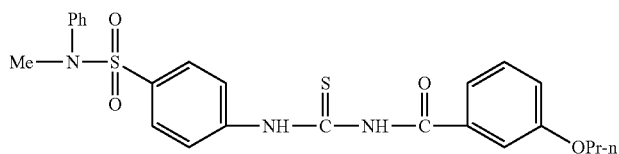
Answer 372:
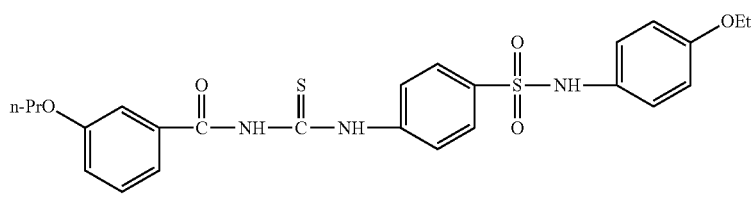

Answer 373:
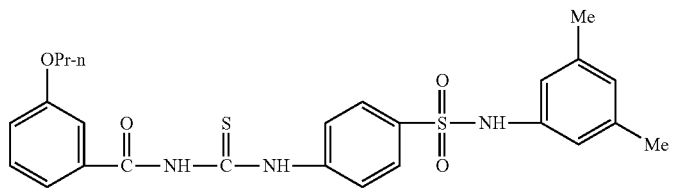
Answer 374:
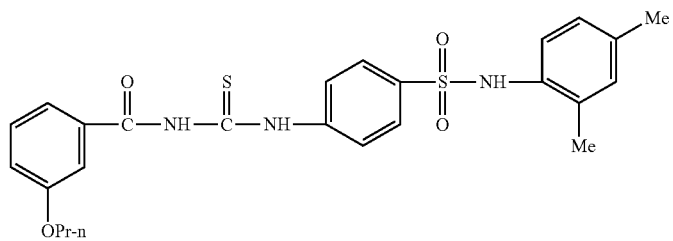
Answer 375:
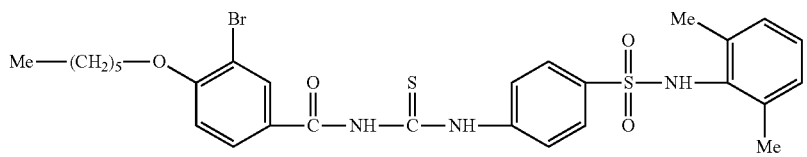
Answer 376:
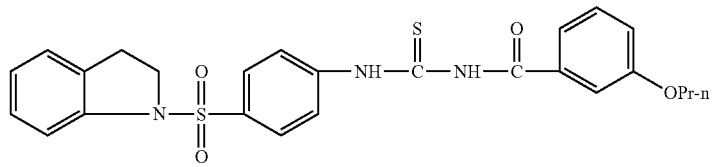
Answer 377:
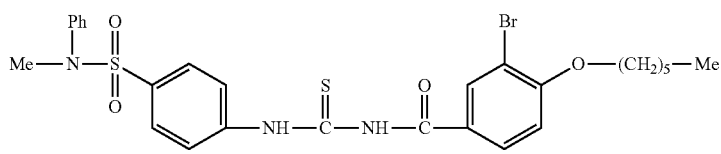
Answer 378:
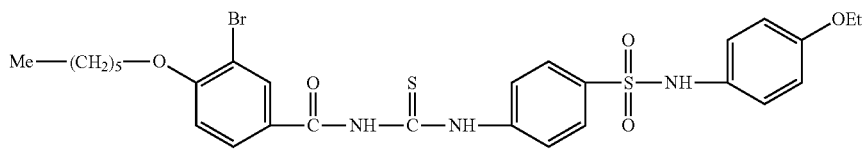
Answer 379:
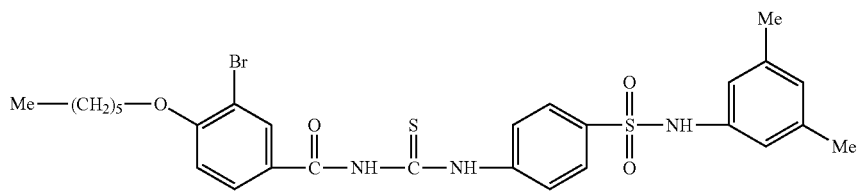

Answer 380:
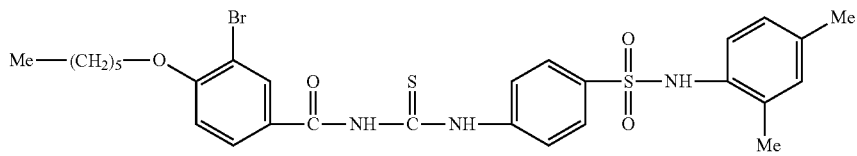
Answer 381:
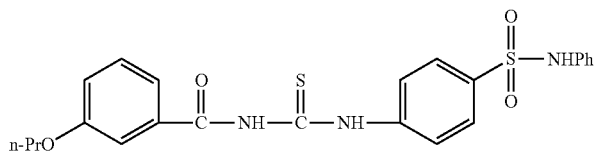
Answer 382:
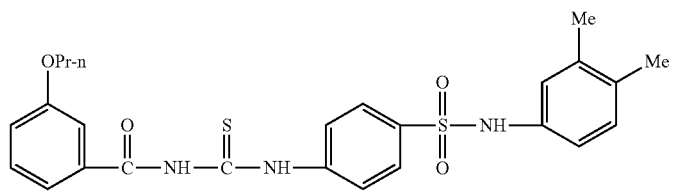
Answer 383:
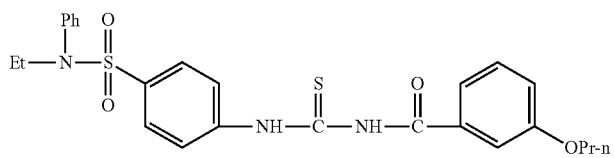
Answer 384:
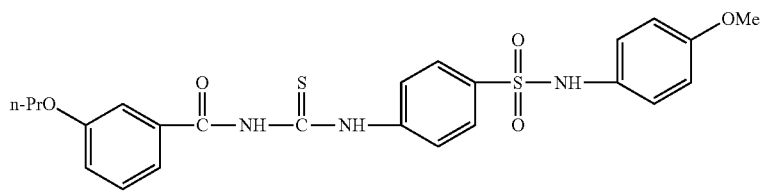
Answer 385:
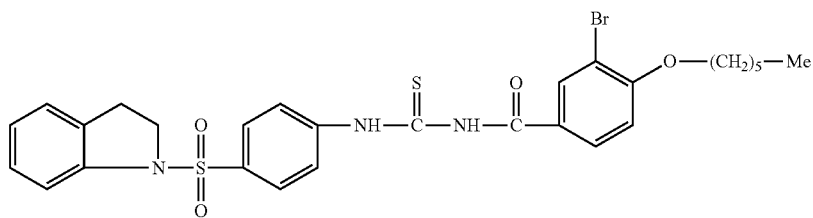
Answer 386:
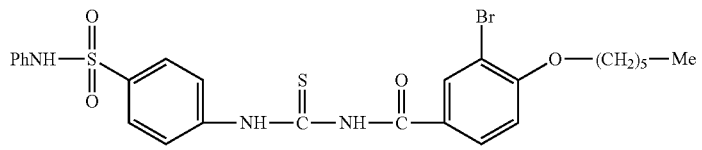

Answer 387:
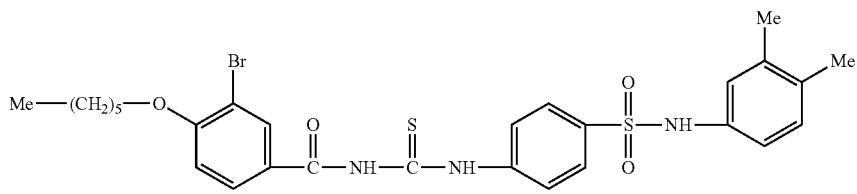
Answer 388:
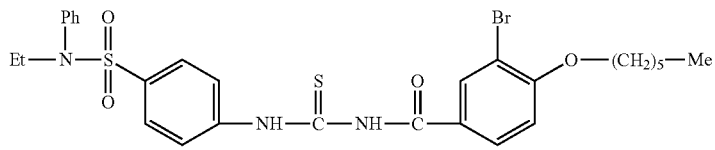
Answer 389:
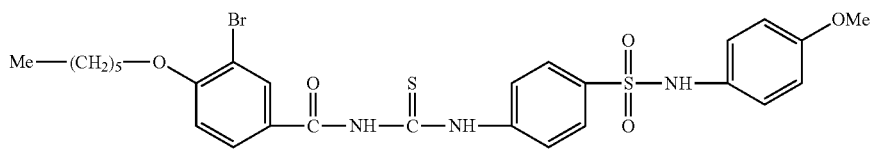
Answer 390:
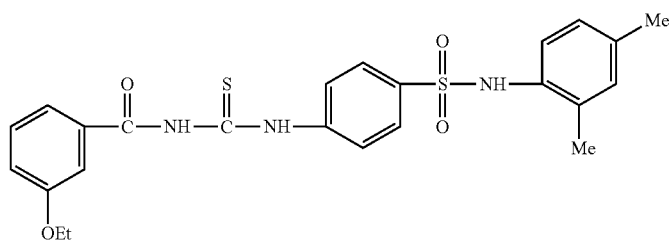
Answer 391:
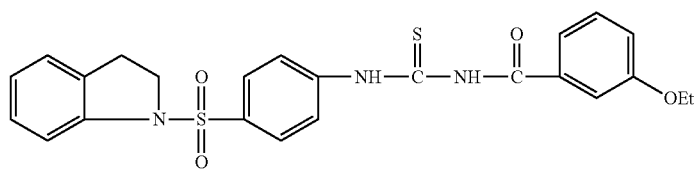
Answer 392:
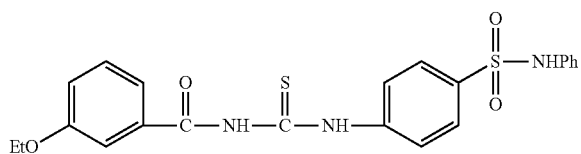
Answer 393:
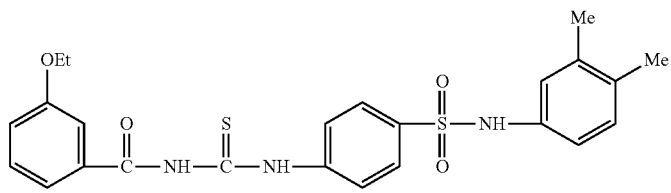

Answer 394:
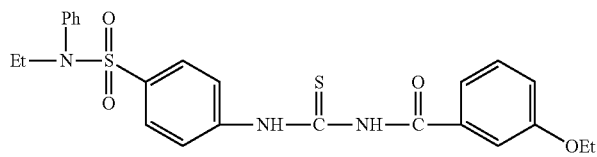
Answer 395:
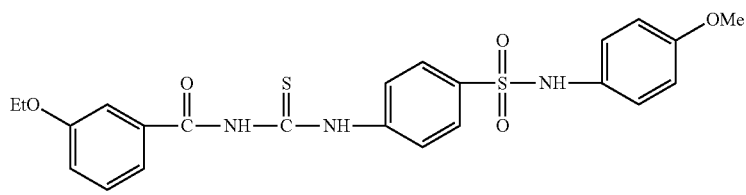
Answer 396:
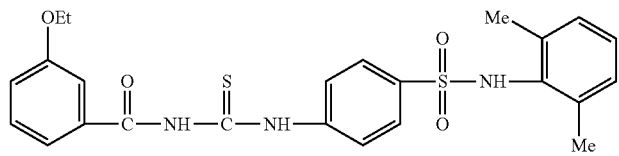
Answer 397:
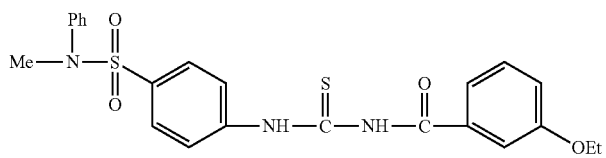
Answer 398:
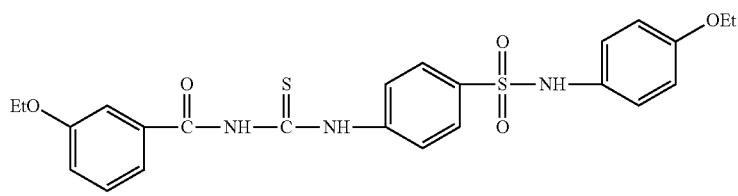
Answer 399:
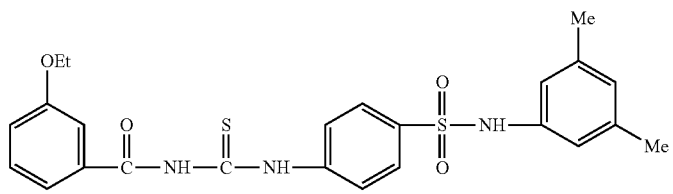
Answer 400:
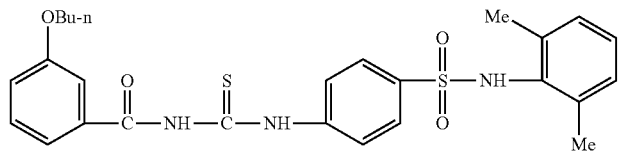

Answer 401:
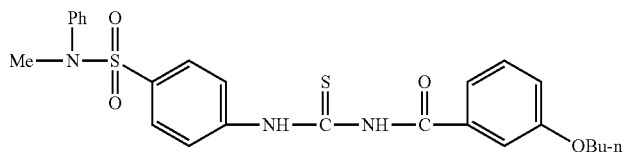
Answer 402:
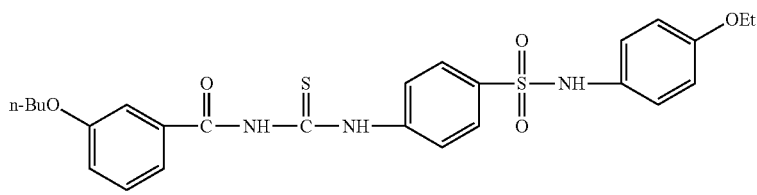
Answer 403:
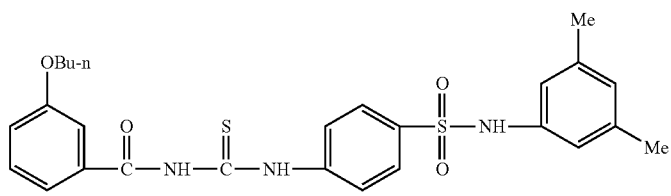
Answer 404:
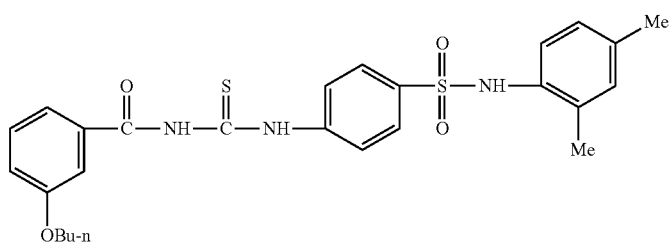
Answer 405:
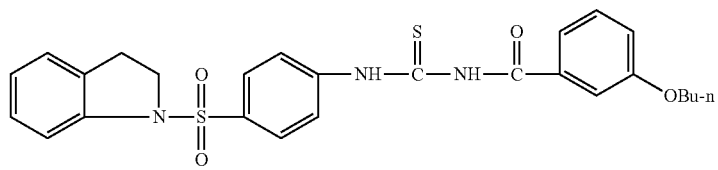
Answer 406:
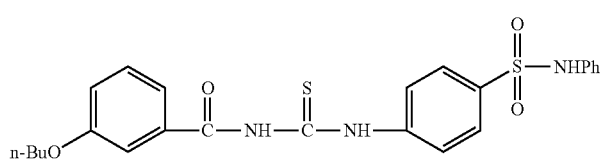
Answer 407:
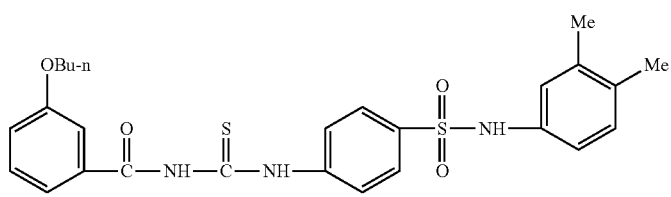

Answer 408:
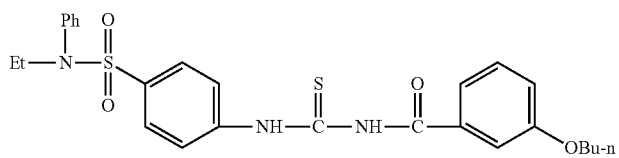
Answer 409:
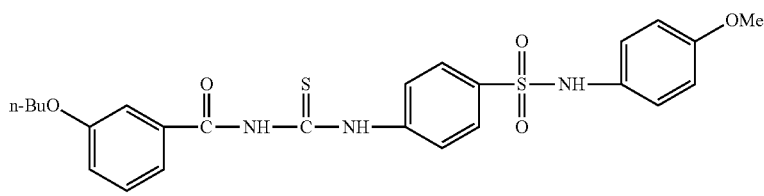
Answer 410:
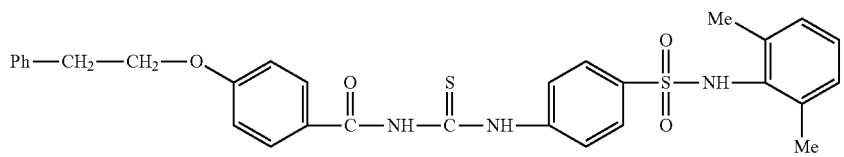
Answer 411:
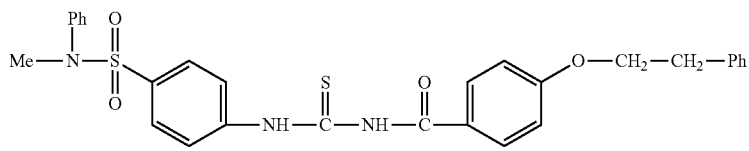
Answer 412:
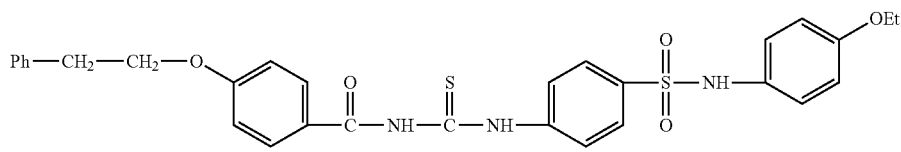
Answer 413:
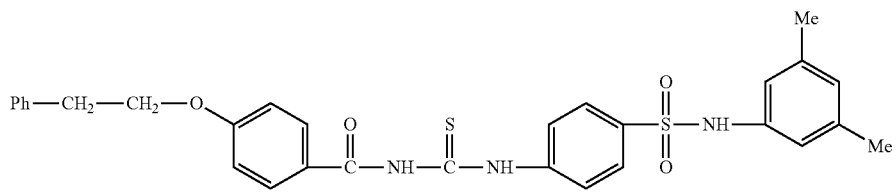
Answer 414:
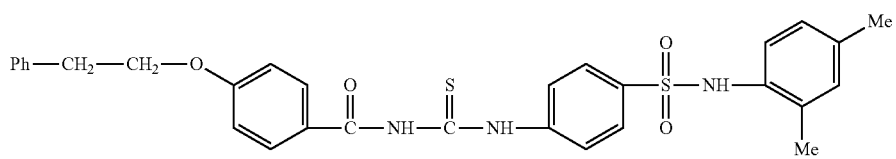

-continued
Answer 415:
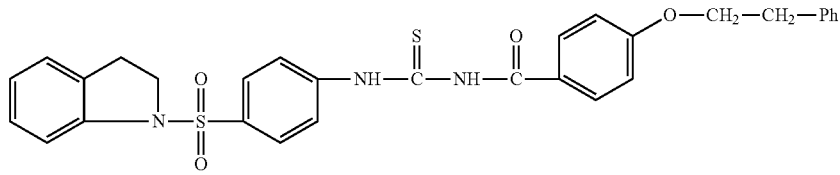
Answer 416:
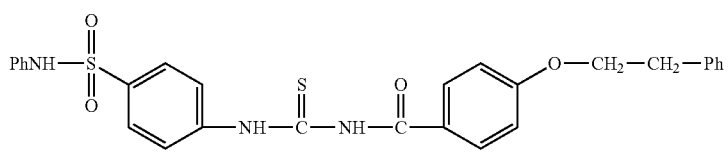
Answer 417:
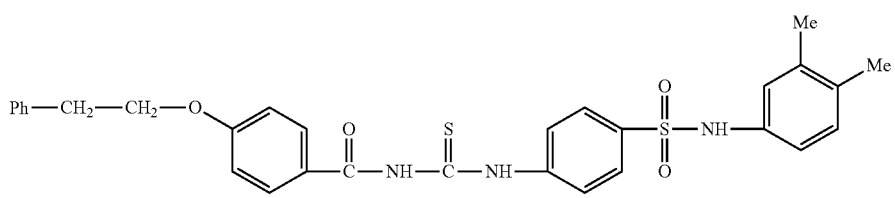
Answer 418:
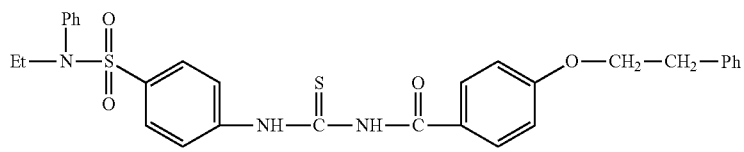
Answer 419:
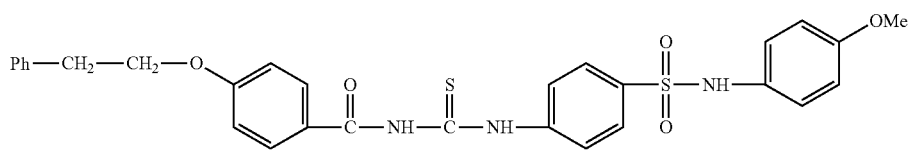
Answer 420:
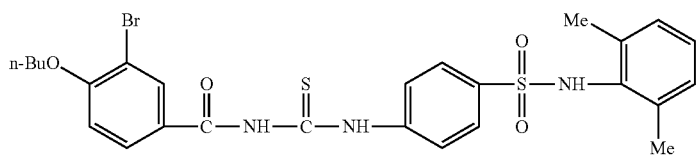
Answer 421:
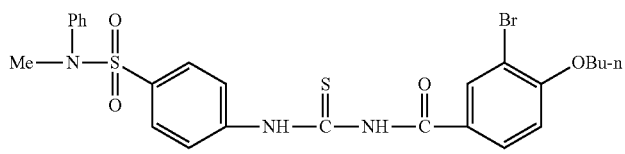
Answer 422:
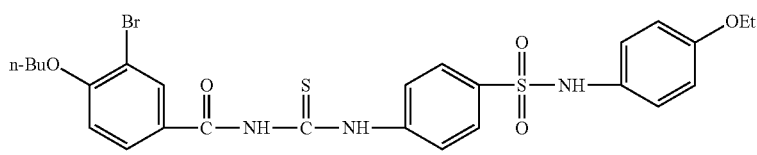

Answer 423:
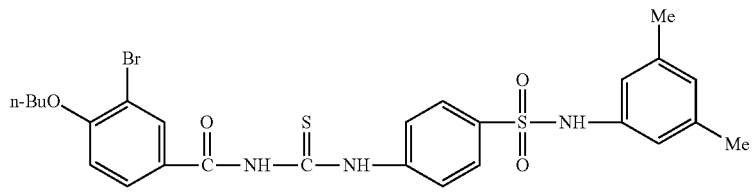
Answer 424:
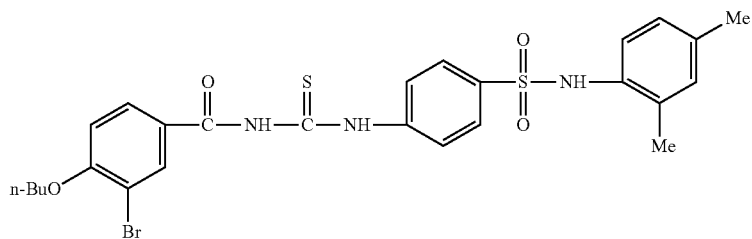
Answer 425:
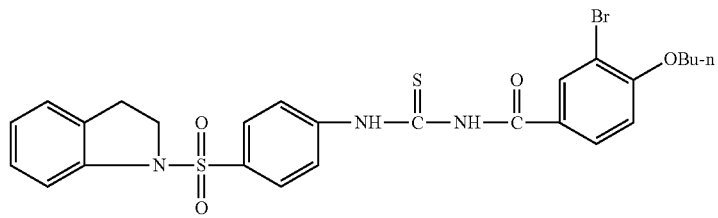
Answer 426:
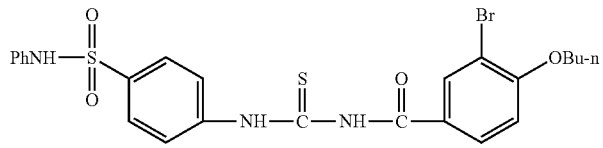
Answer 427:
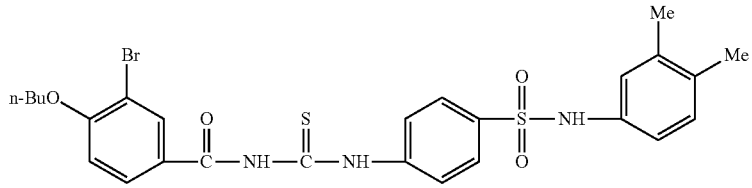
Answer 428:
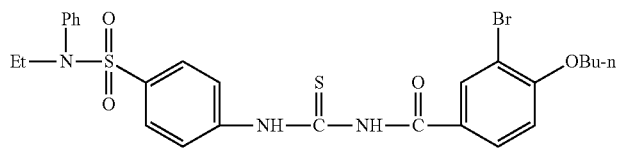
Answer 429:
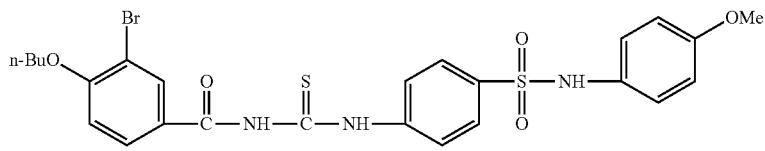

Answer 430:
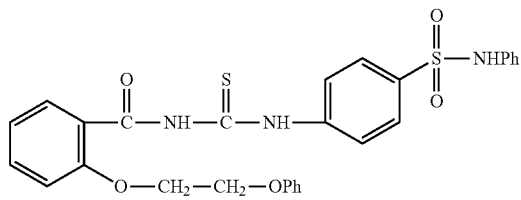
Answer 431:
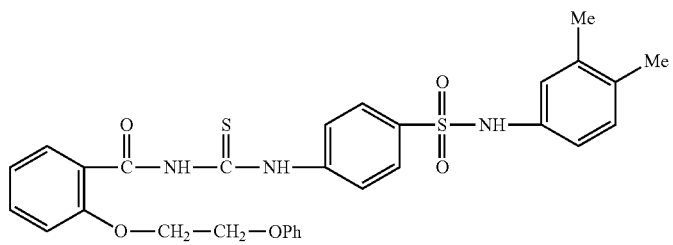
Answer 432:
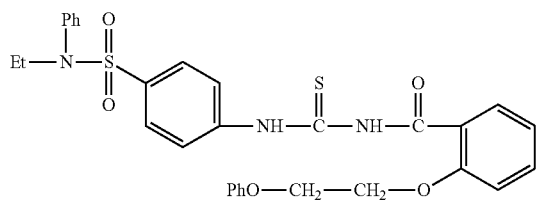
Answer 433:
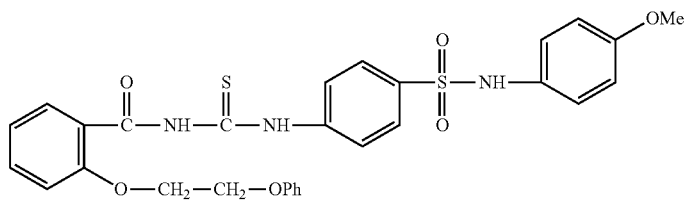
Answer 434:
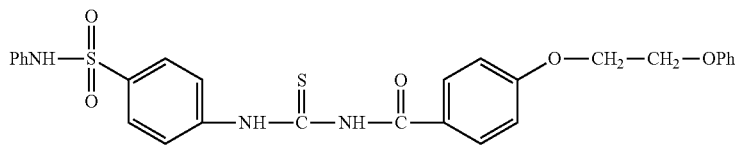
Answer 435:
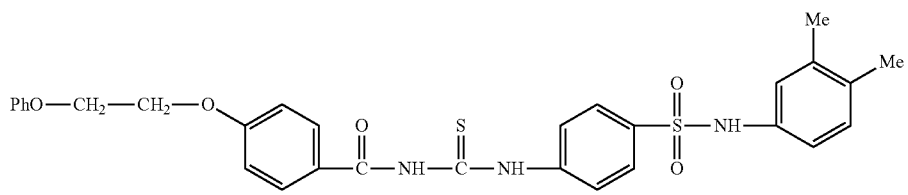
Answer 436:
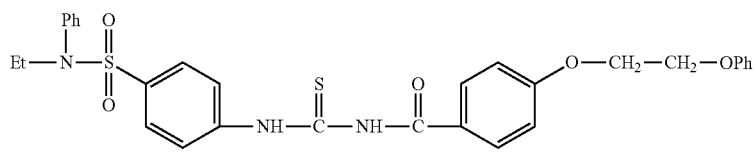

Answer 437:
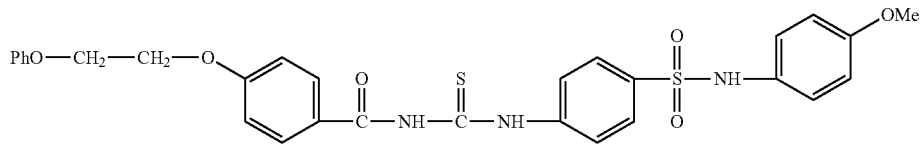
Answer 438:
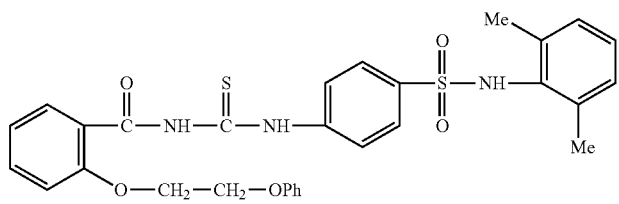
Answer 439:
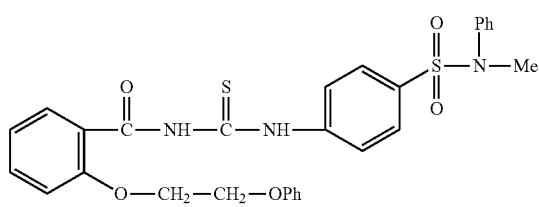
Answer 440:
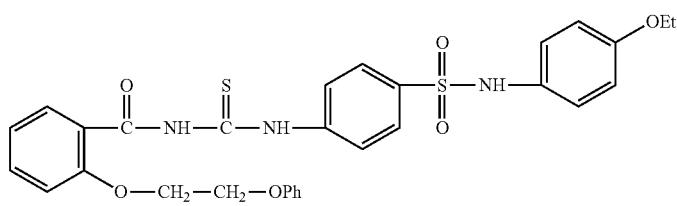
Answer 441:
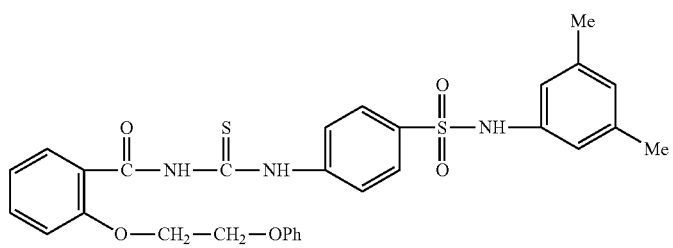
Answer 442:
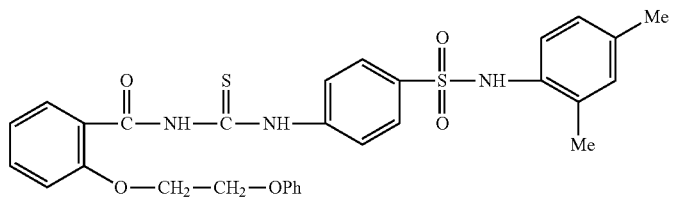
Answer 443:
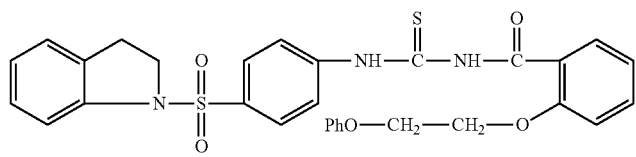

Answer 444:
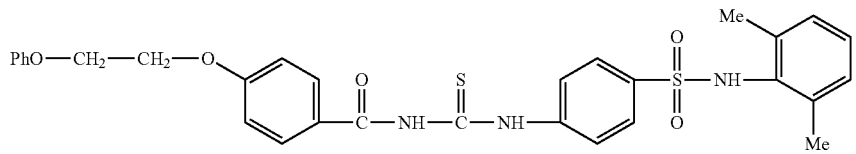
Answer 445:
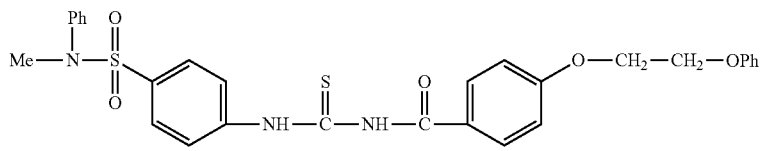
Answer 446:
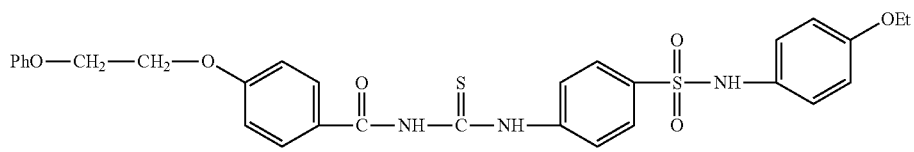
Answer 447:
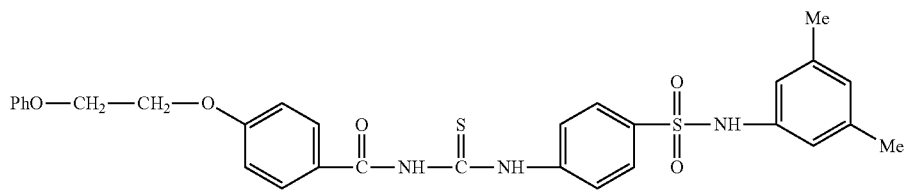
Answer 448:
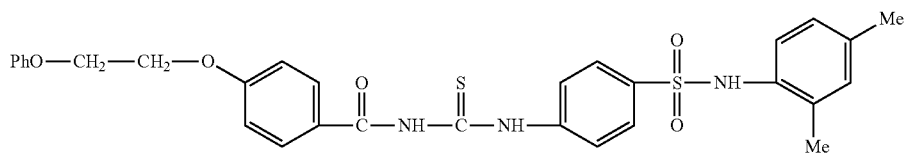
Answer 449:
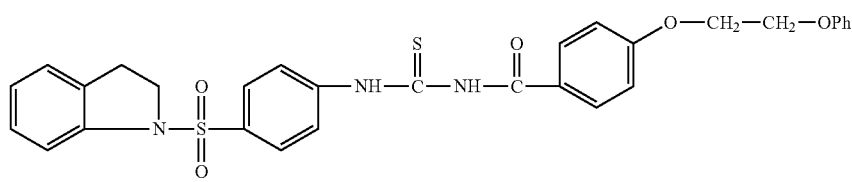
Answer 450:
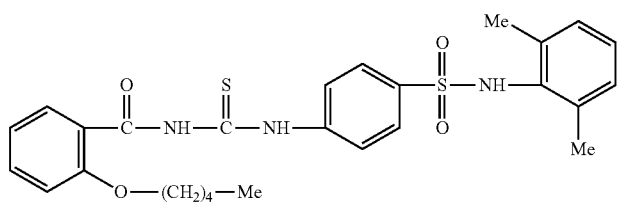

Answer 451:
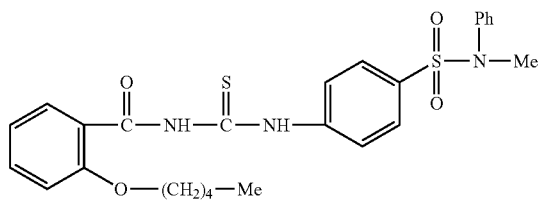
Answer 452:
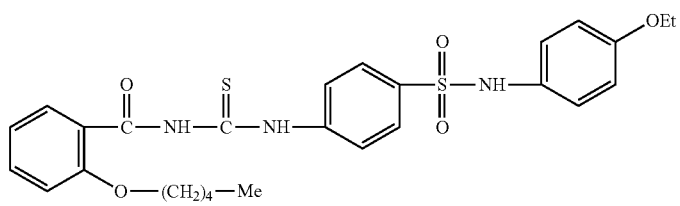
Answer 453:
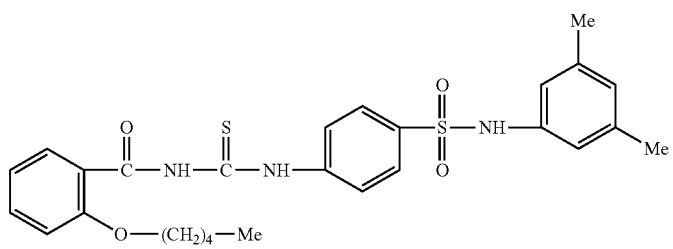
Answer 454:
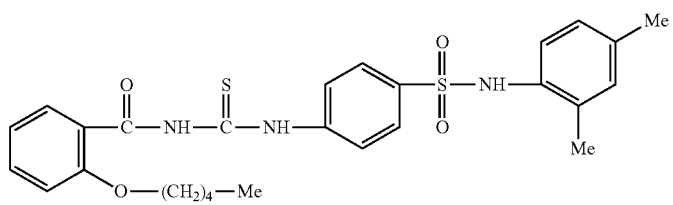
Answer 455:
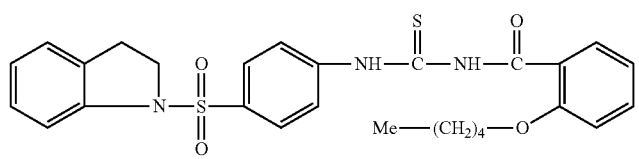
Answer 456:
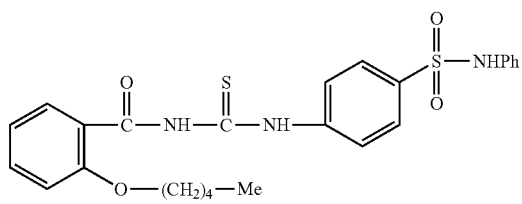

Answer 457:
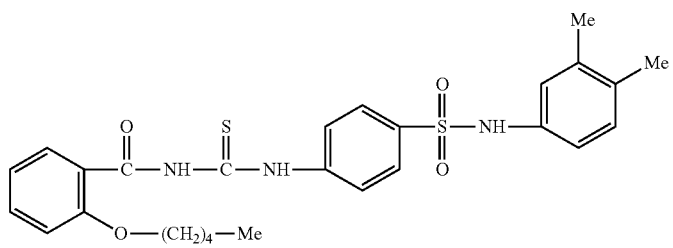
Answer 458:
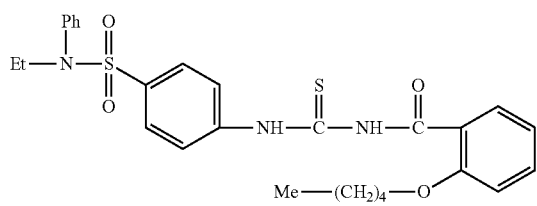
Answer 459:
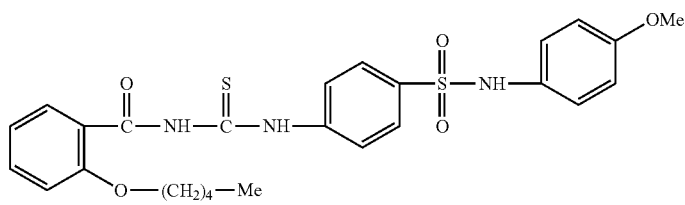
Answer 460:
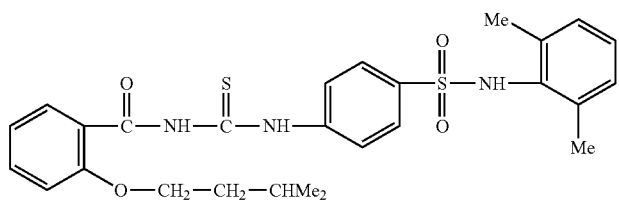
Answer 461:
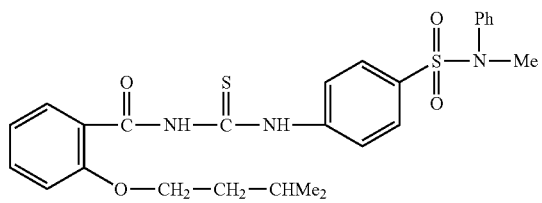
Answer 462:
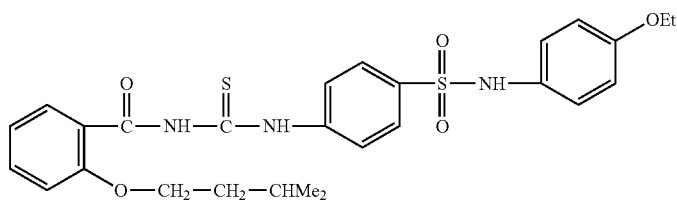

Answer 463:
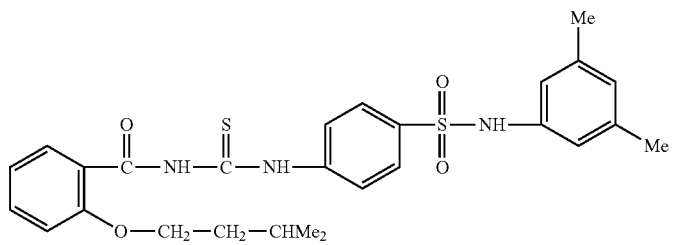
Answer 464:
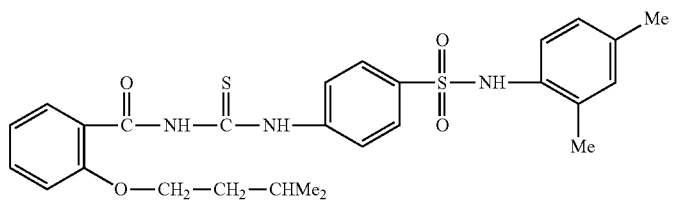
Answer 465:
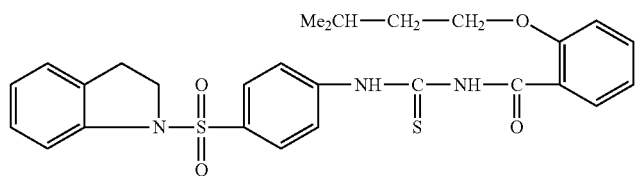
Answer 466:
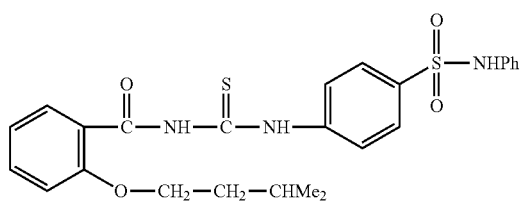
Answer 467:
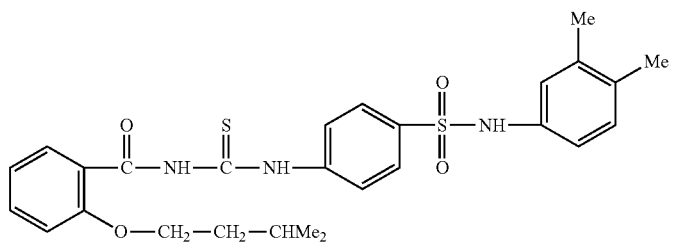
Answer 468:
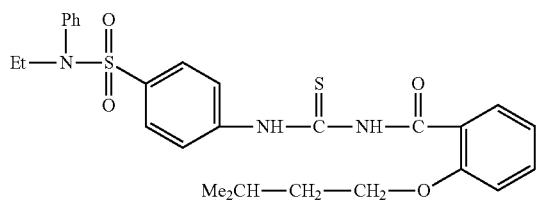

Answer 469:
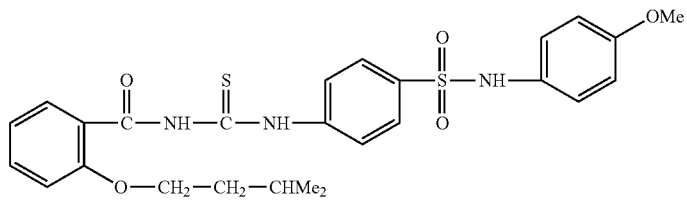
Answer 470:
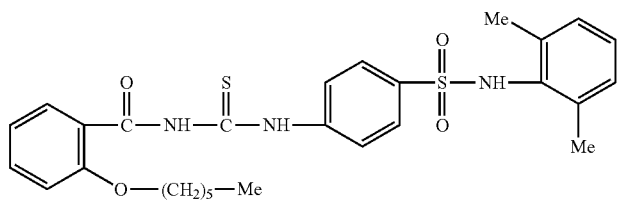
Answer 471:
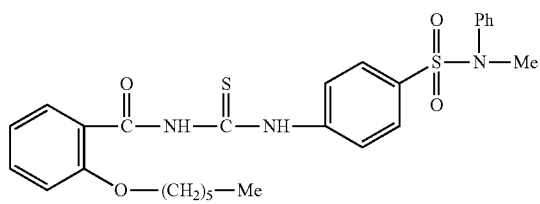
Answer 472:
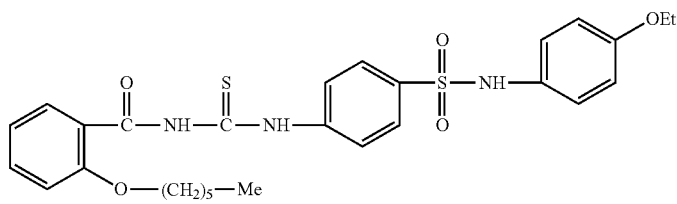
Answer 473:
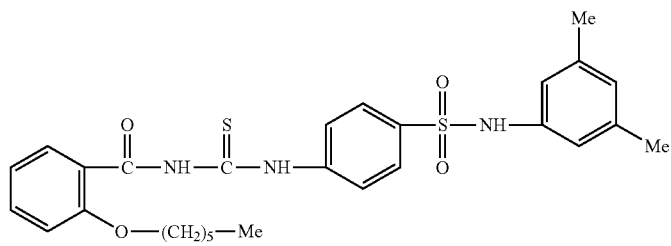
Answer 474:
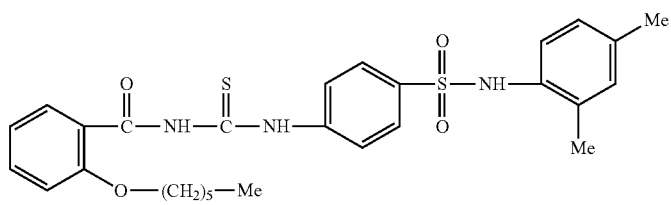

Answer 475:
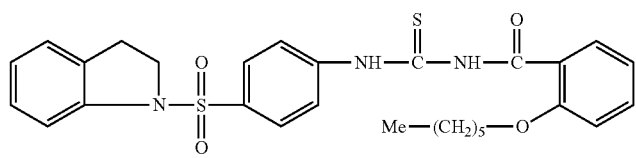
Answer 476:
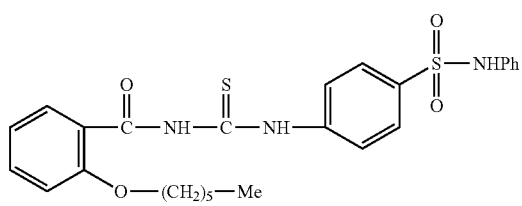
Answer 477:
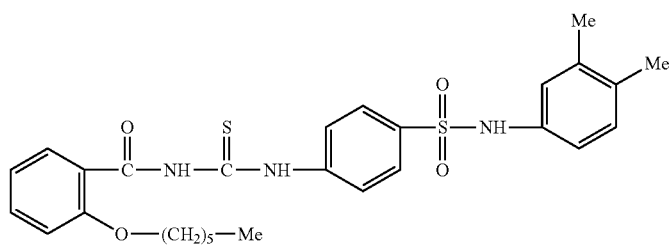
Answer 478:
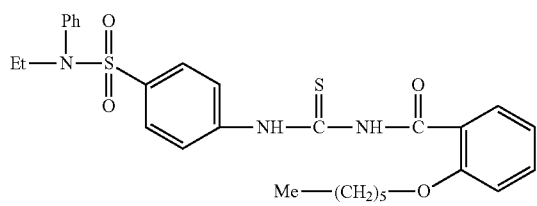
Answer 479:
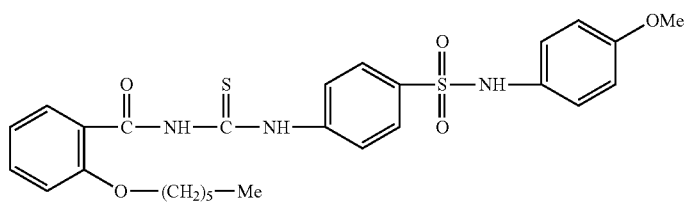
Answer 480:
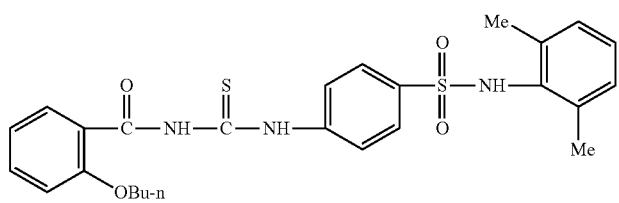

Answer 481:
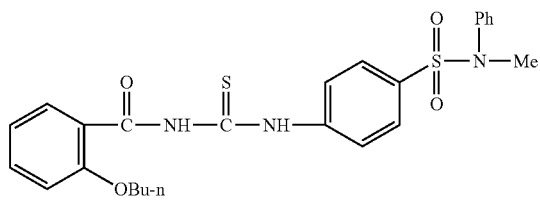
Answer 482:
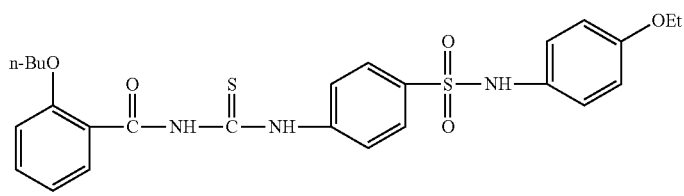
Answer 483:
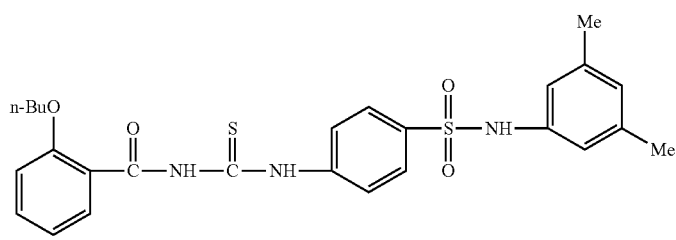
Answer 484:
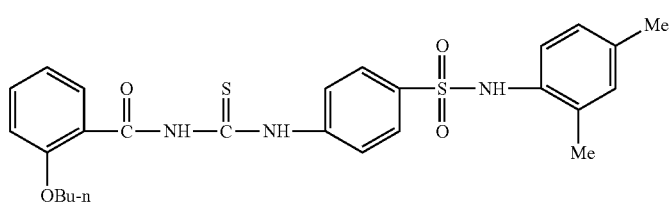
Answer 485:
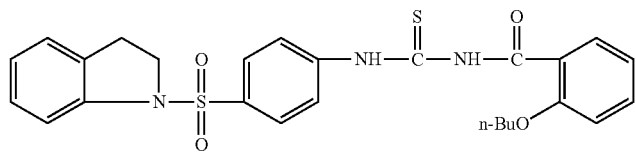
Answer 486:
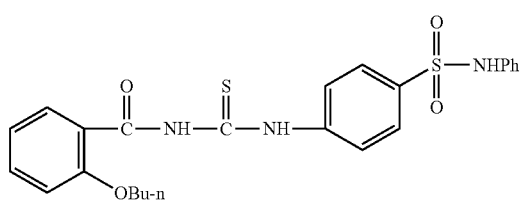

Answer 487:
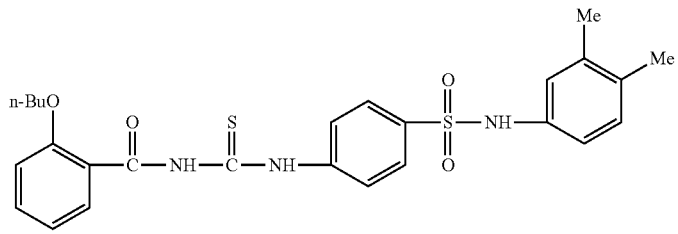
Answer 488:
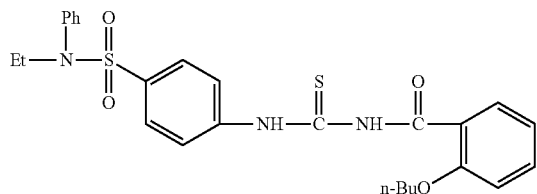
Answer 489:
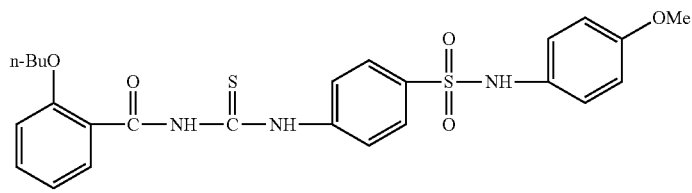
Answer 490:
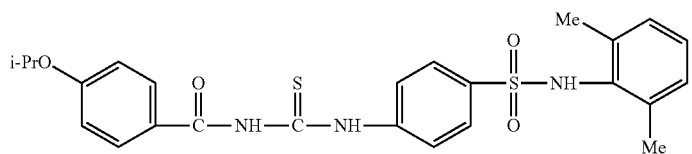
Answer 491:
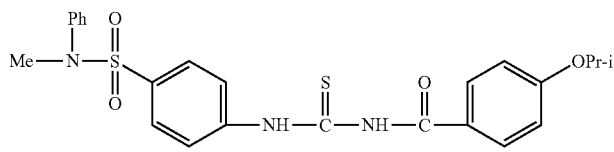
Answer 492:
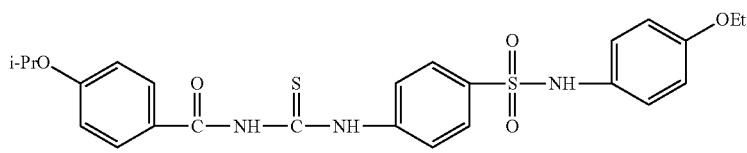
Answer 493:
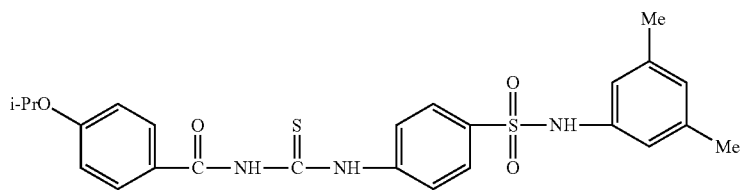

Answer 494:
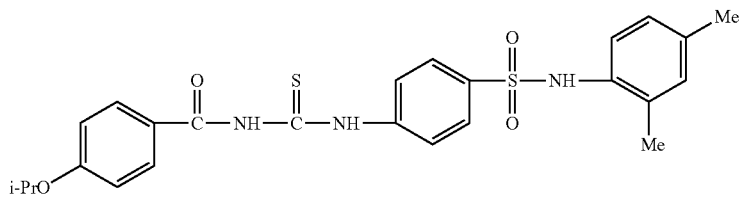
Answer 495:
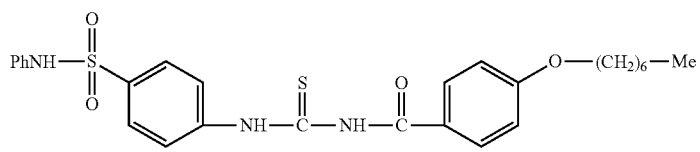
Answer 496:
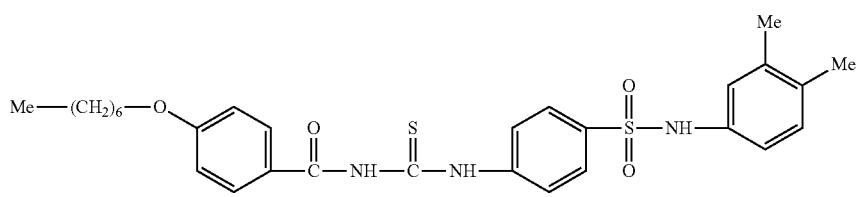
Answer 497:
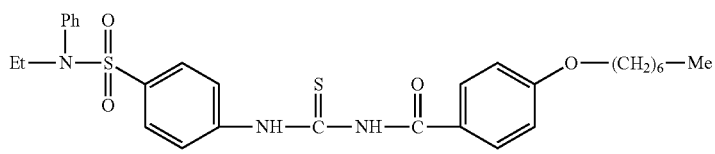
Answer 498:
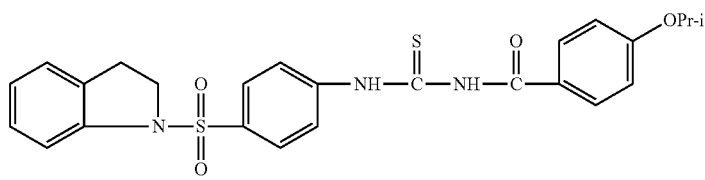
Answer 499:
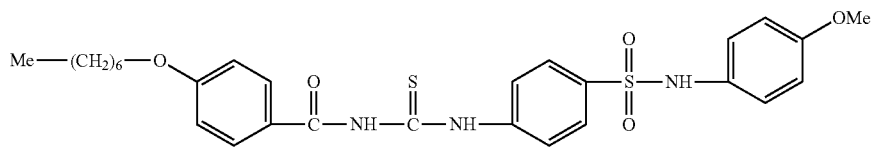
Answer 500:
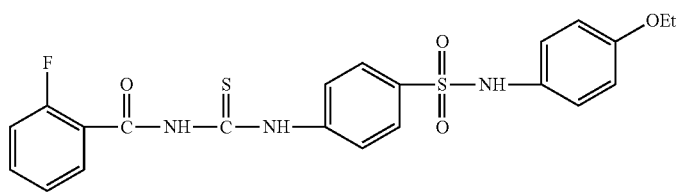

Answer 501:
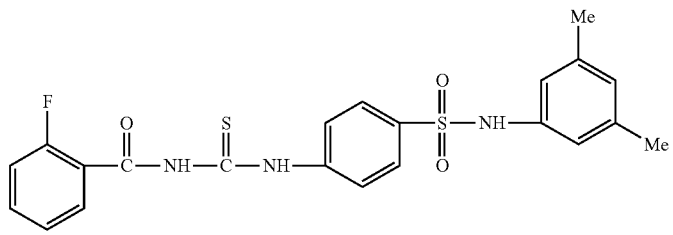
Answer 502:
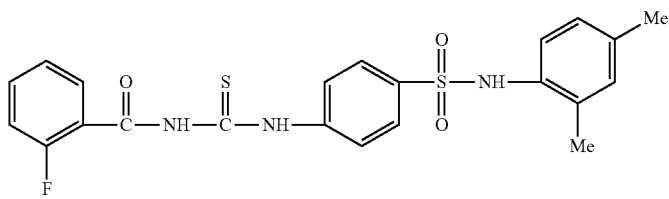
Answer 503:
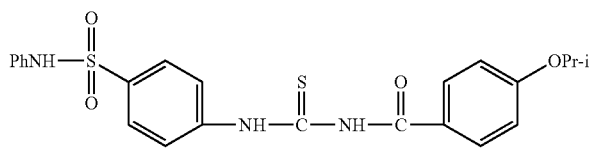
Answer 504:
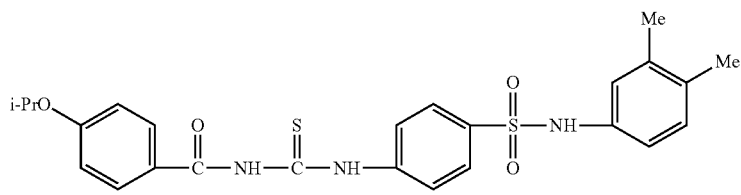
Answer 505:
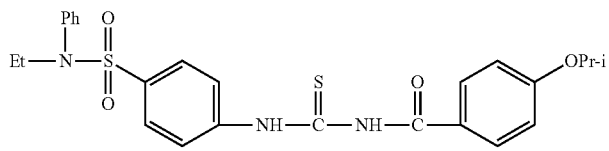
Answer 506:
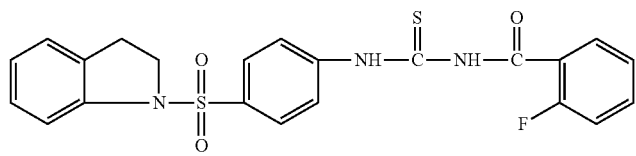
Answer 507:
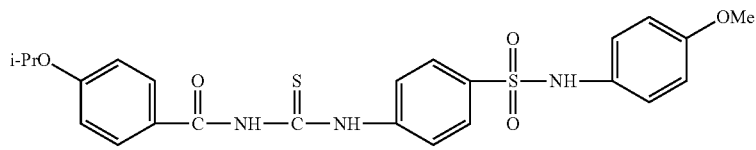

Answer 508:
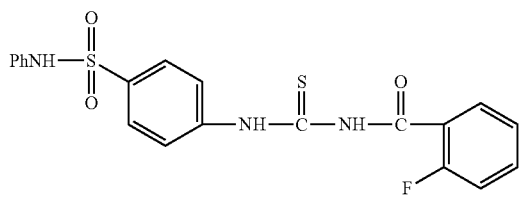
Answer 509:
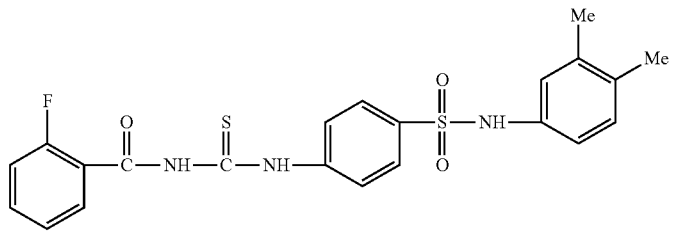
Answer 510:
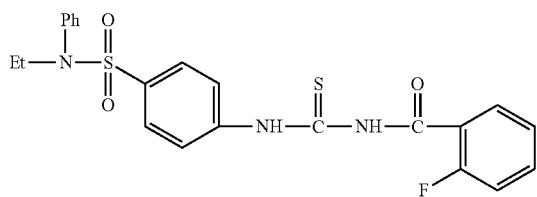
Answer 511:
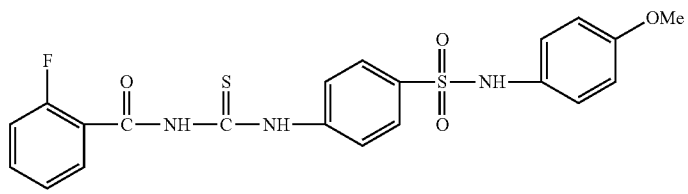
Answer 512:
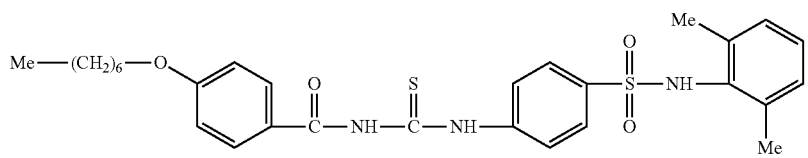
Answer 513:
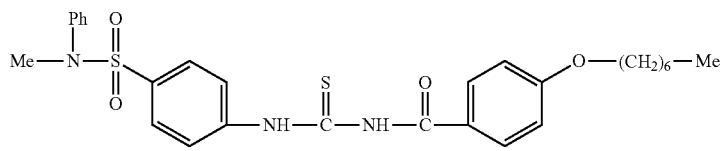
Answer 514:
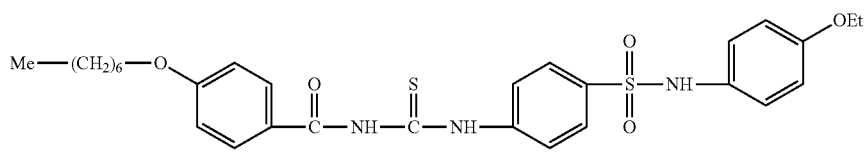

Answer 515:
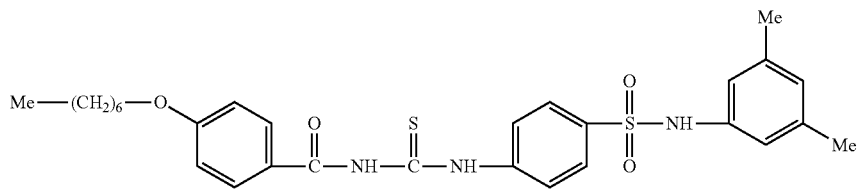
Answer 516:
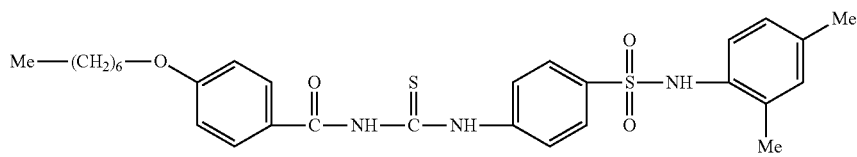
Answer 517:
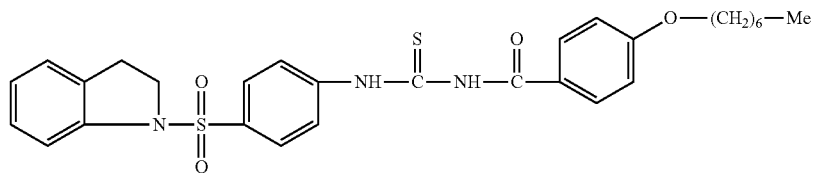
Answer 518:
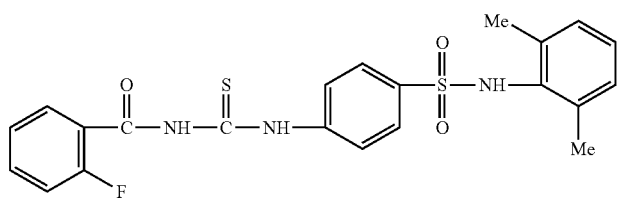
Answer 519:
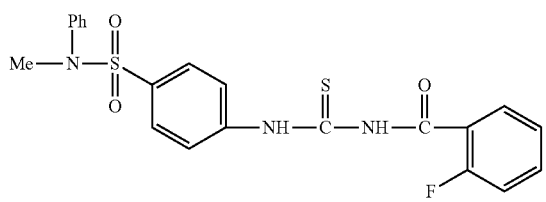
Answer 520:
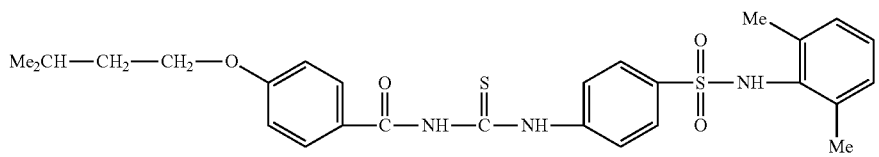
Answer 521:
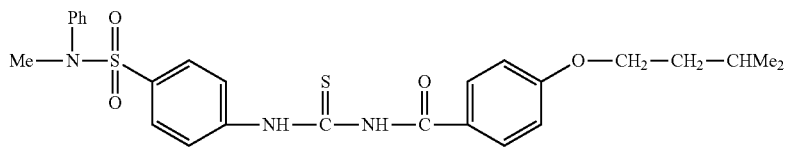

Answer 522:
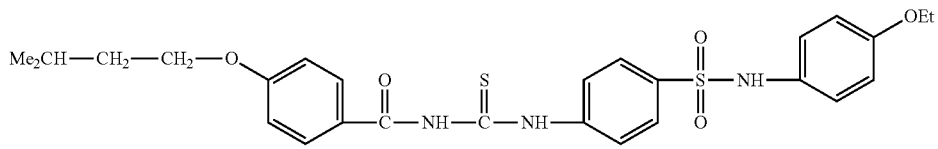
Answer 523:
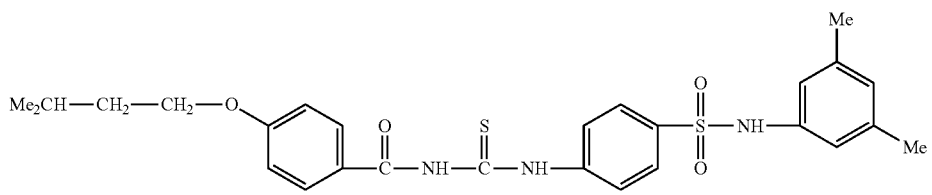
Answer 524:
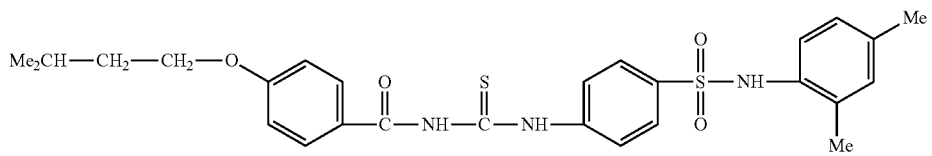
Answer 525:
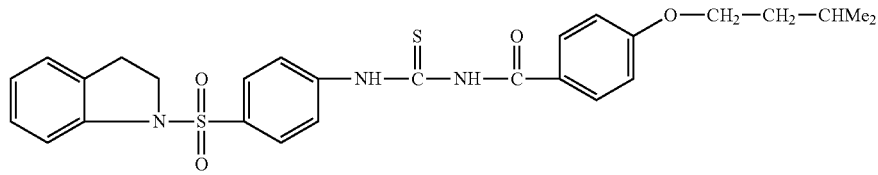
Answer 526:
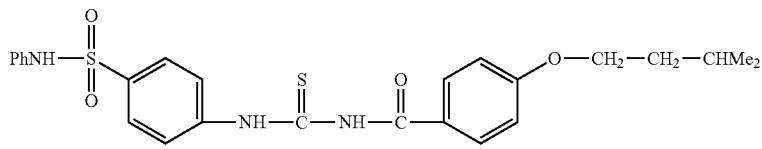
Answer 527:
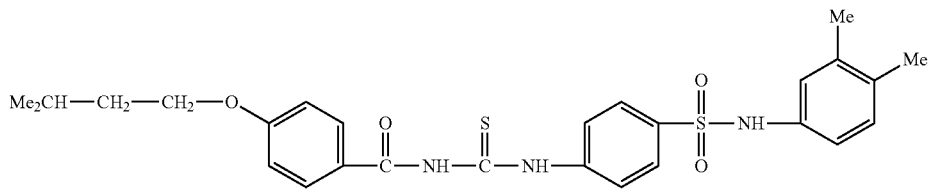
Answer 528:
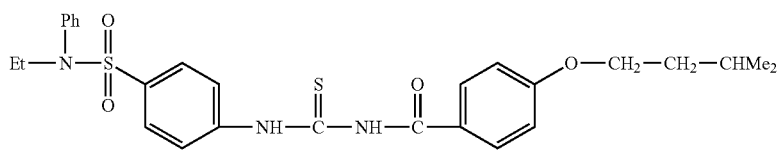
Answer 529:
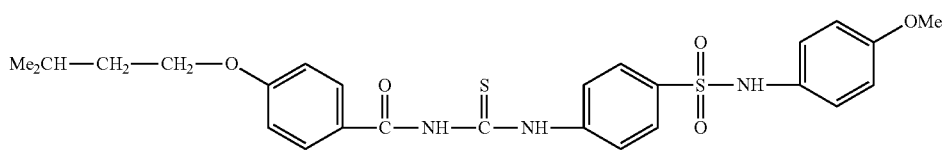

-continued
Answer 530:
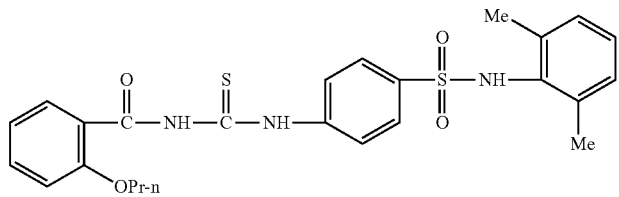
Answer 531:
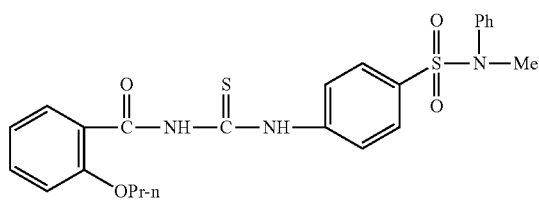
Answer 532:
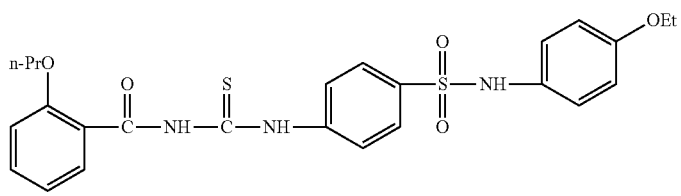
Answer 533:
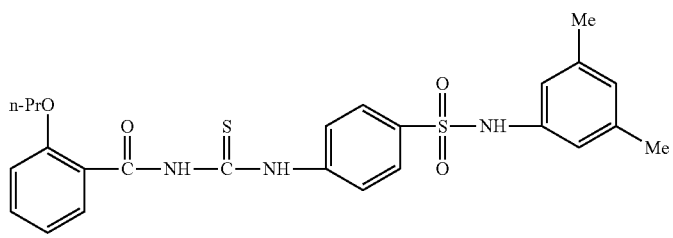
Answer 534:
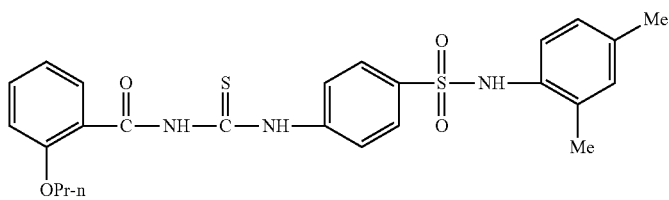
Answer 535:
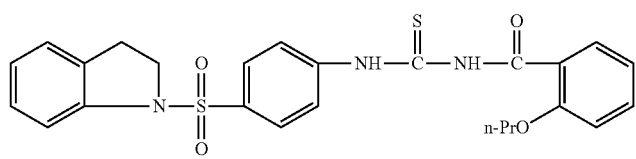

Answer 536:
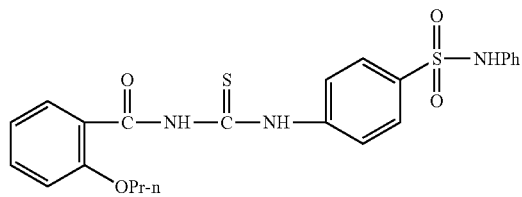
Answer 537:
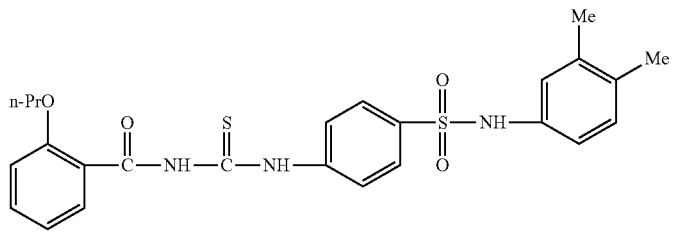
Answer 538:
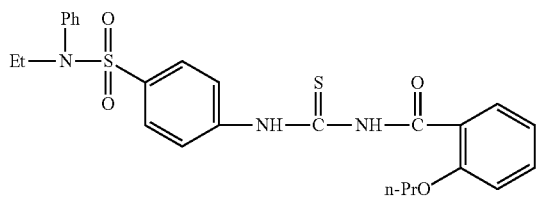
Answer 539:
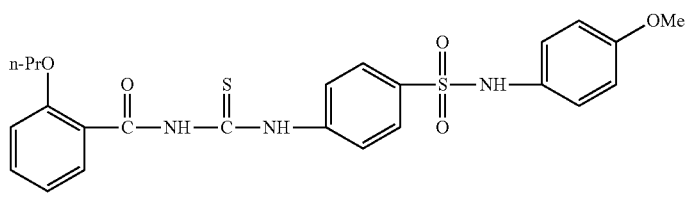
Answer 540:
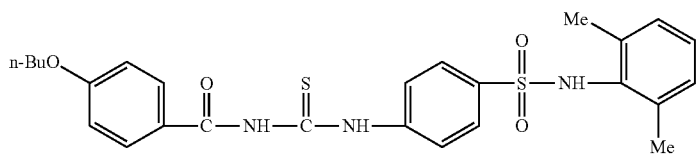
Answer 541:
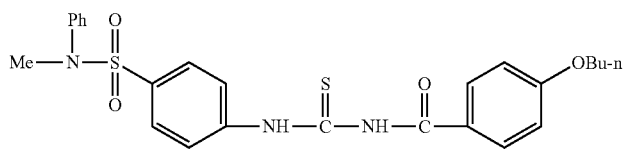
Answer 542:
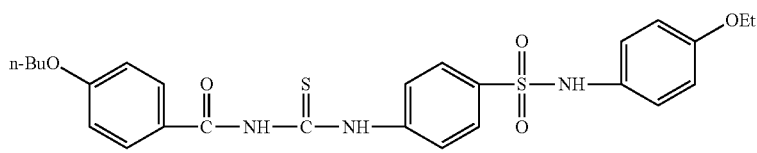

Answer 543:
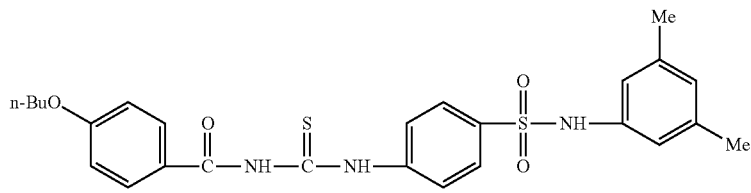
Answer 544:
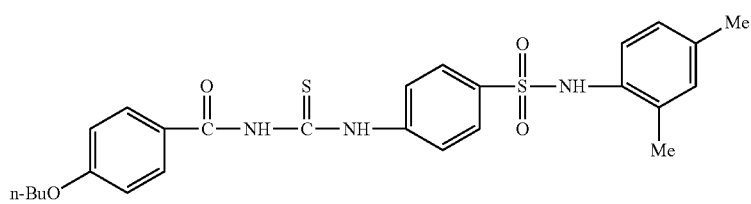
Answer 545:
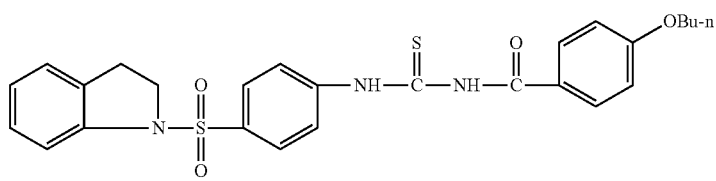
Answer 546:
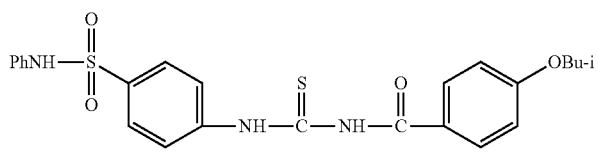
Answer 547:
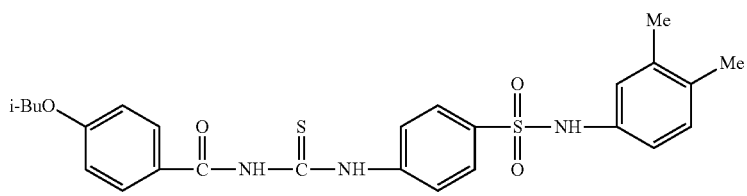
Answer 548:
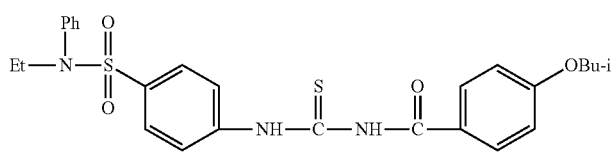
Answer 549:
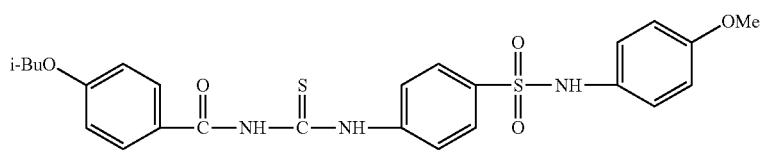

Answer 550:
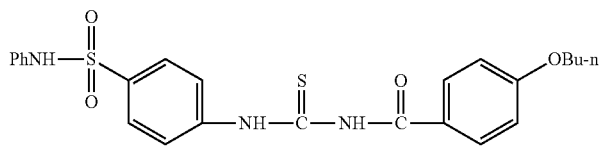
Answer 551:
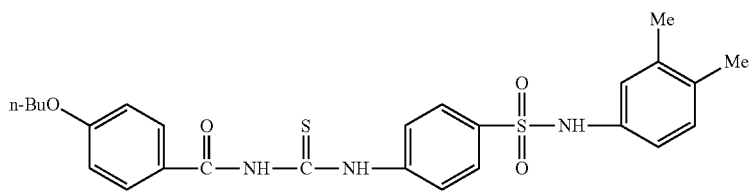
Answer 552:
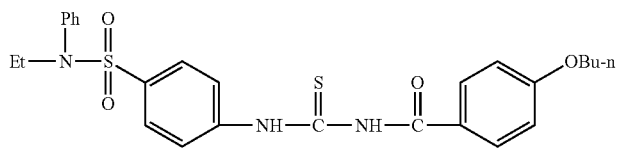
Answer 553:
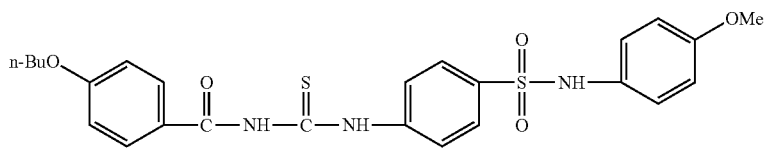
Answer 554:
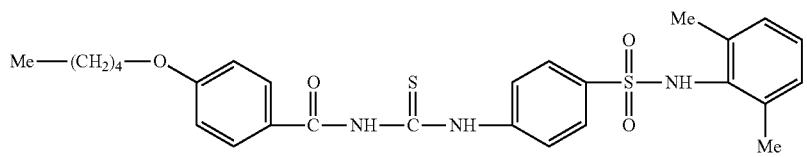
Answer 555:
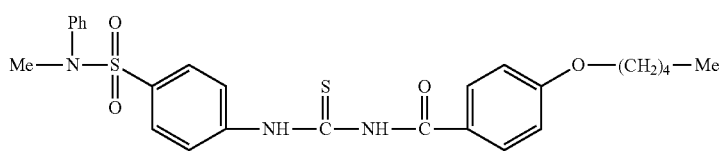
Answer 556:
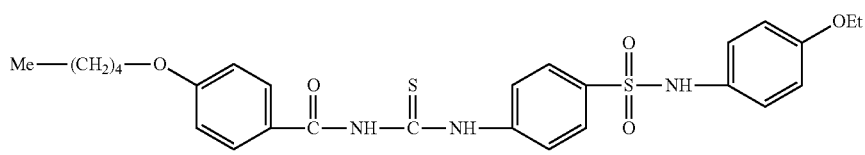
Answer 557:
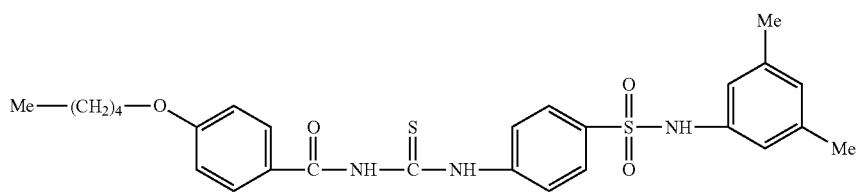

-continued
Answer 558:
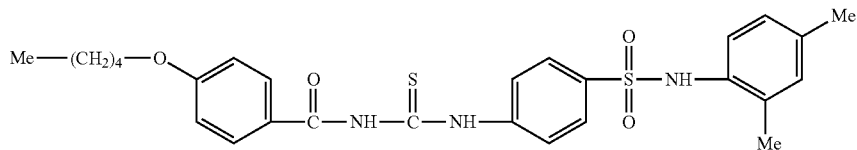
Answer 559:
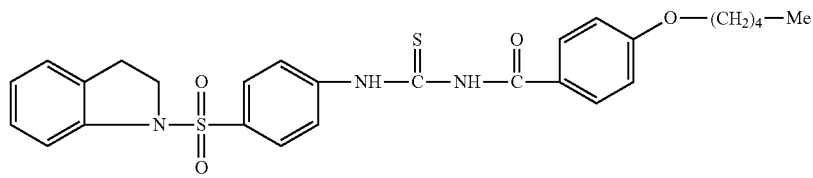
Answer 560:
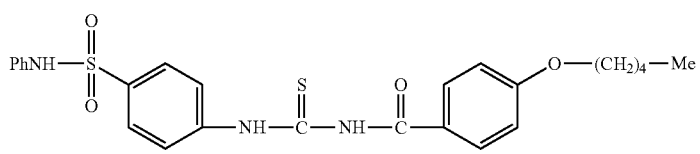
Answer 561:
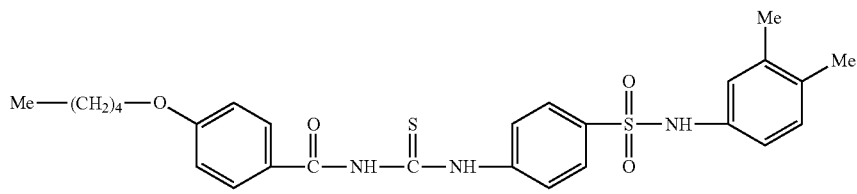
Answer 562:
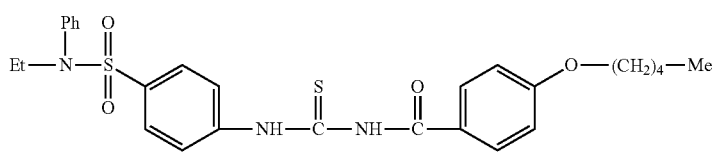
Answer 563:
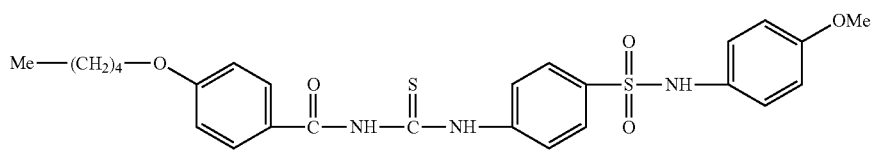
Answer 564:
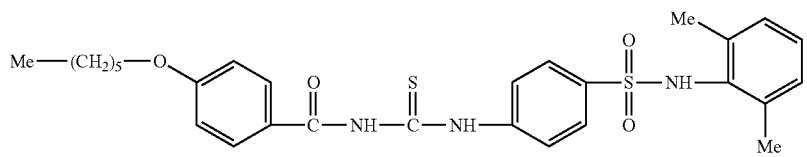
Answer 565:
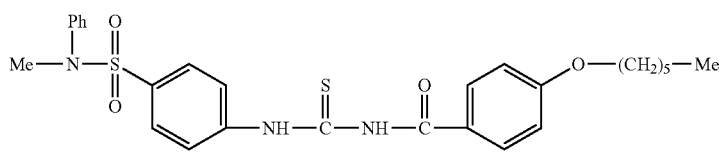

Answer 566:
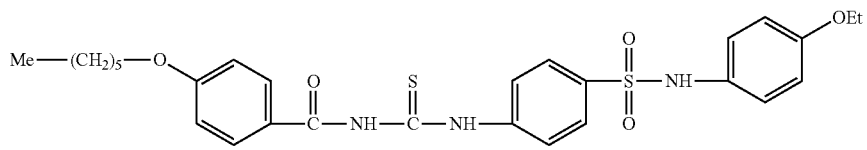
Answer 567:
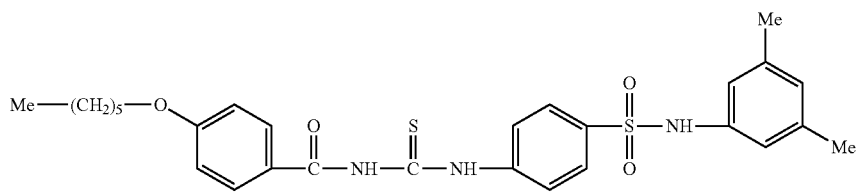
REGISTRY (Copyright (C) 2009 ACS)
Answer 568:
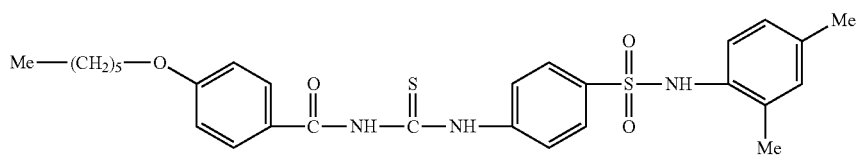
REGISTRY (Copyright (C) 2009 ACS)
Answer 569:
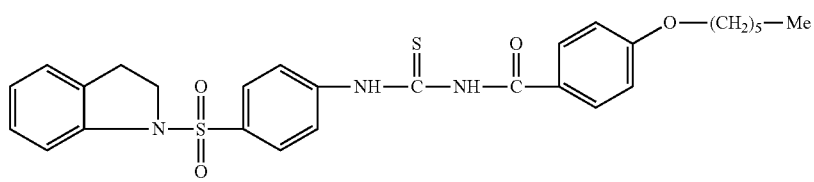
REGISTRY (Copyright (C) 2009 ACS)
Answer 570:
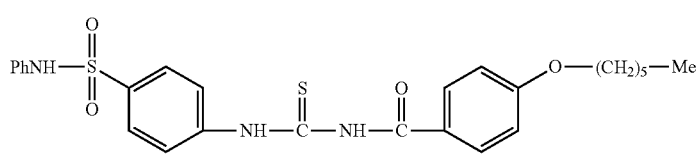
REGISTRY (Copyright (C) 2009 ACS)
Answer 571:
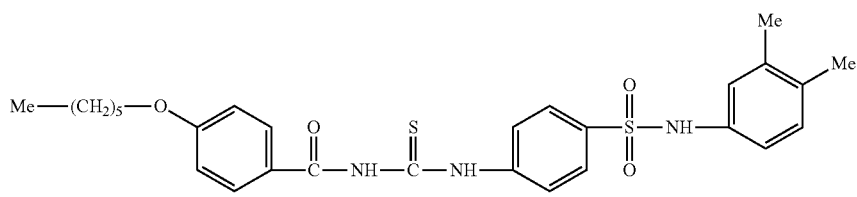
REGISTRY (Copyright (C) 2009 ACS)
Answer 572:
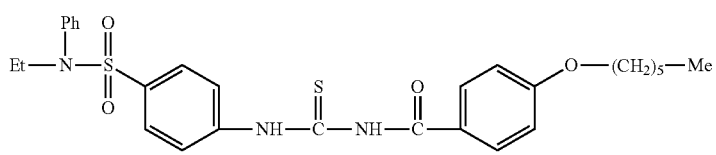
REGISTRY (Copyright (C) 2009 ACS)

Answer 573:
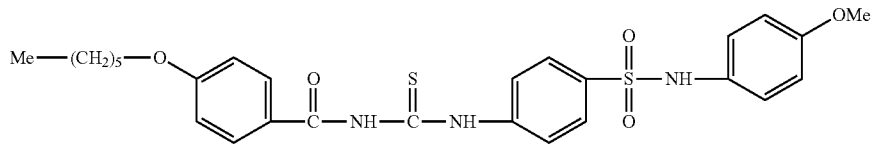
REGISTRY (Copyright (C) 2009 ACS)
Answer 574:
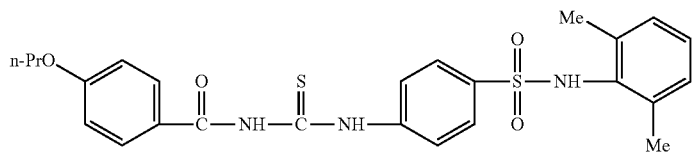
REGISTRY (Copyright (C) 2009 ACS)
Answer 575:
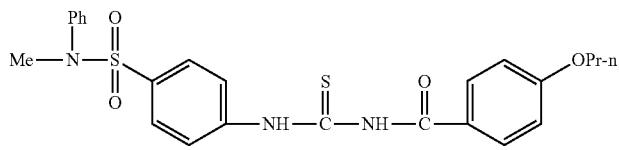
Answer 576:
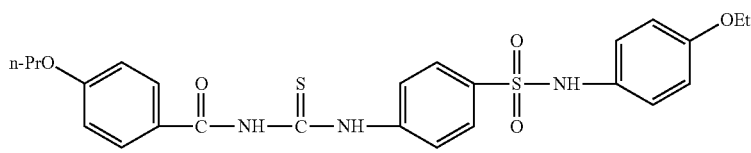
Answer 577:
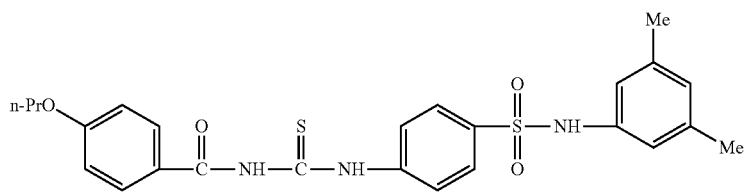
Answer 578:
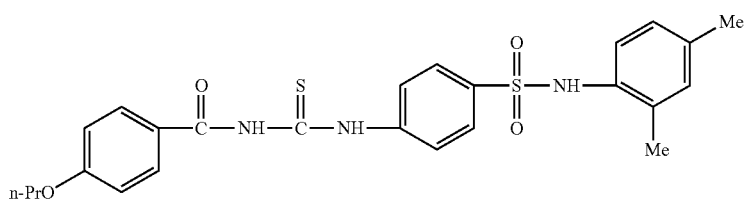
Answer 579:
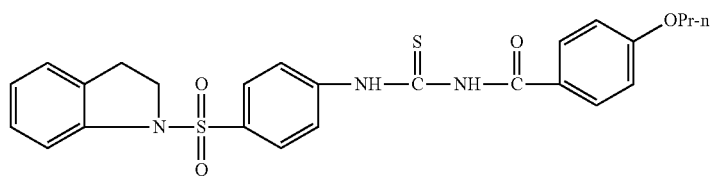

Answer 580:
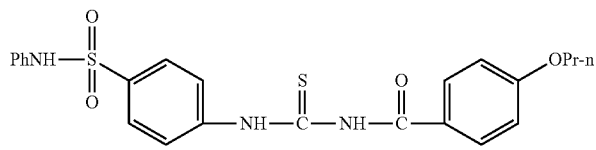
Answer 581:
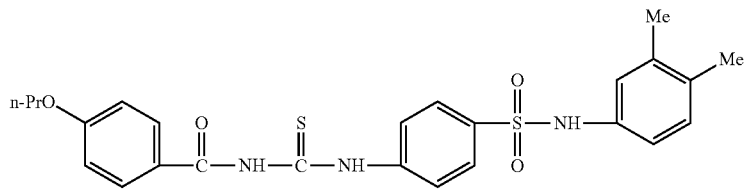
Answer 582:
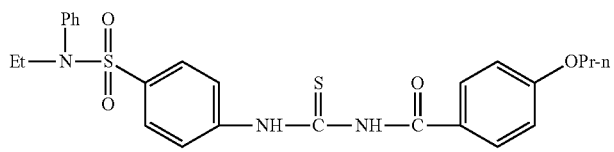
Answer 583:
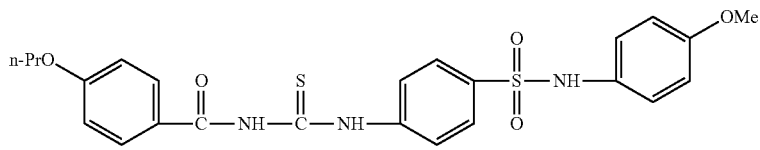
Answer 584:
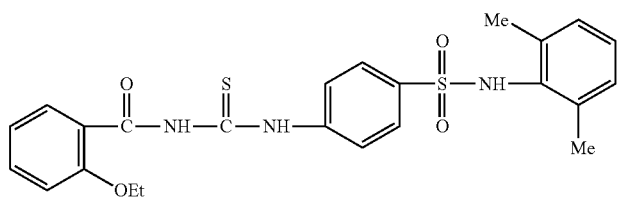
Answer 585:
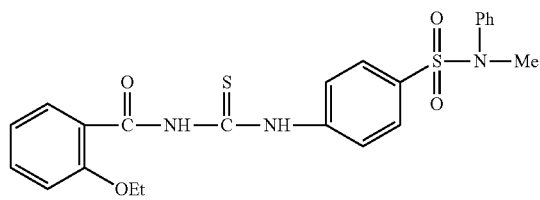
Answer 586:
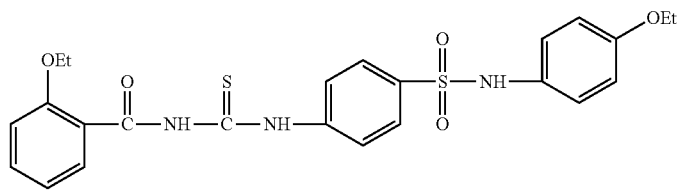

Answer 587:
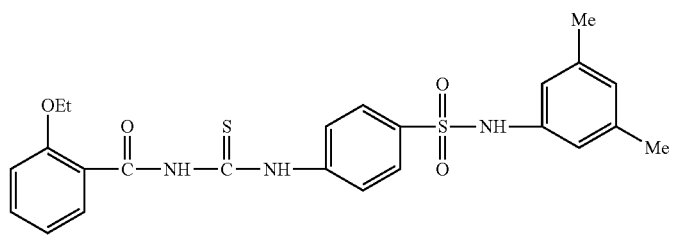
Answer 588:
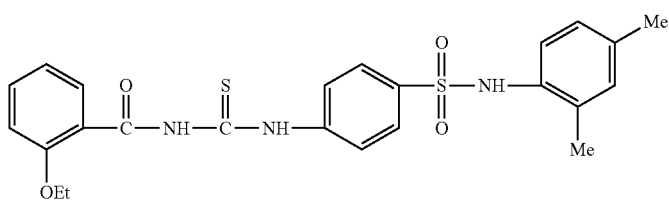
Answer 589:
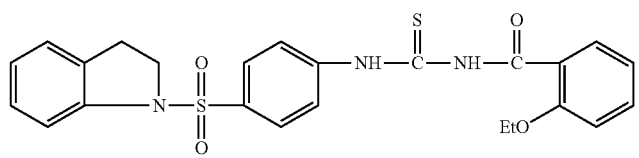
Answer 590:
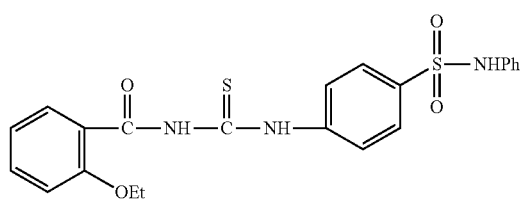
Answer 591:
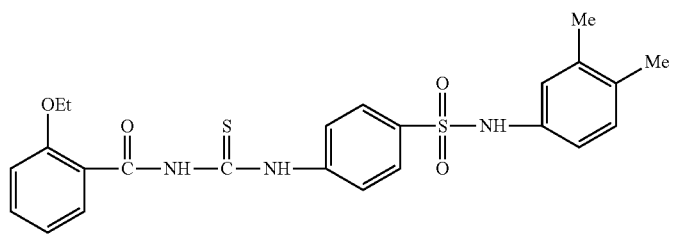
Answer 592:
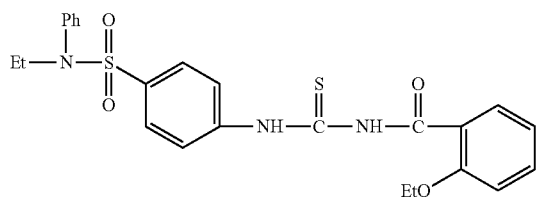

Answer 593:
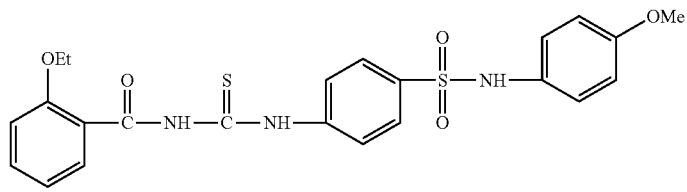
Answer 594:
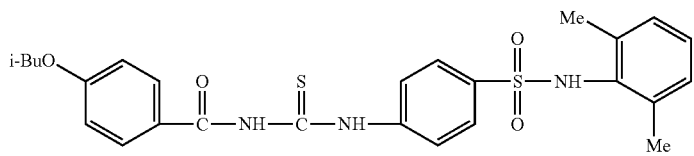
Answer 595:
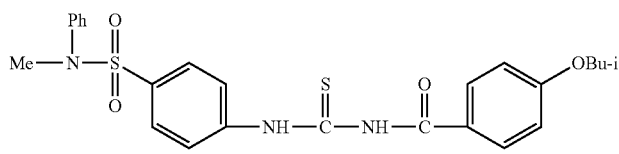
Answer 596:
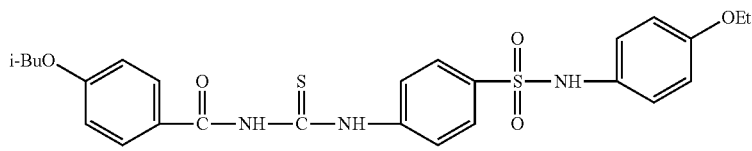
Answer 597:
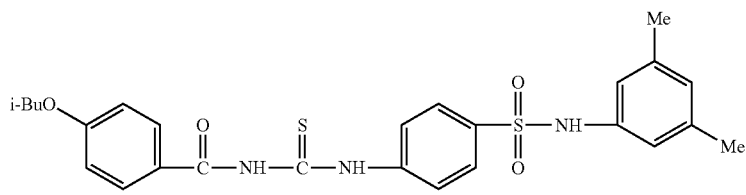
Answer 598:
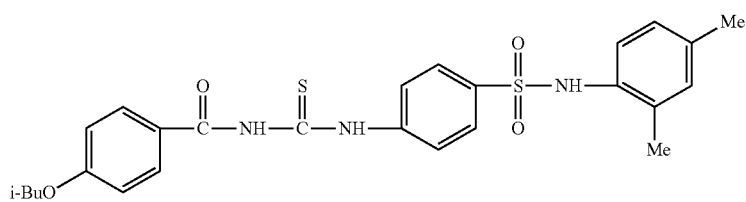
Answer 599:
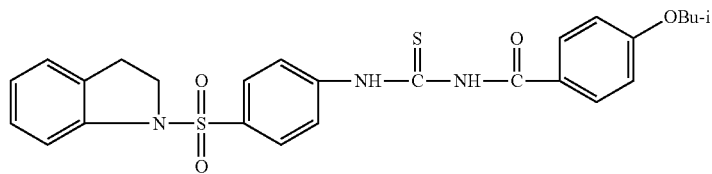

Answer 600:
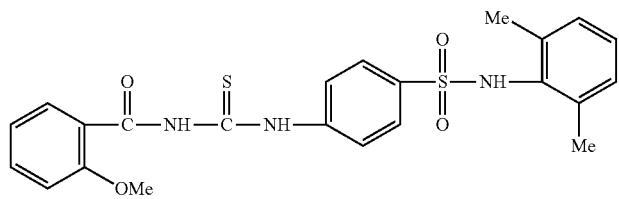
Answer 601:
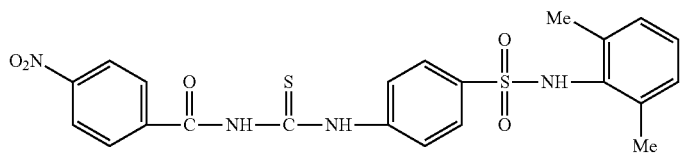
Answer 602:
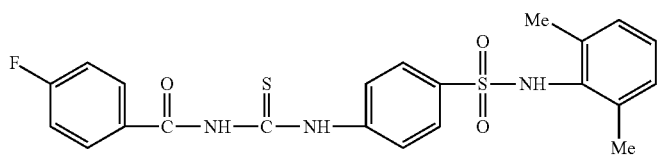
Answer 603:
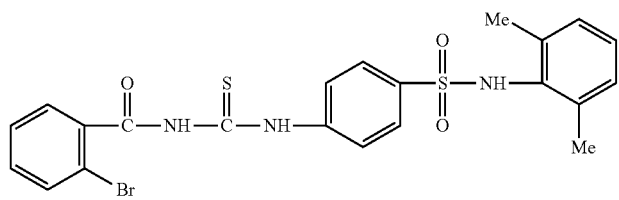
Answer 604:
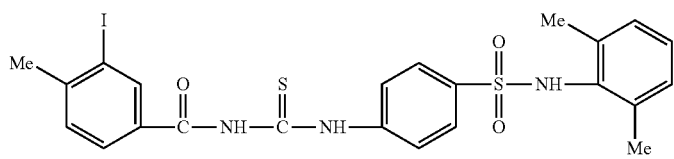
Answer 605:
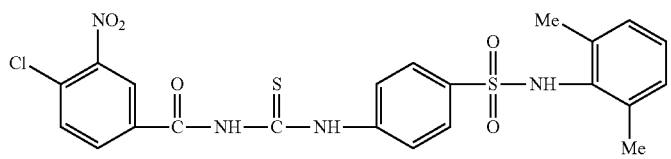
Answer 606:
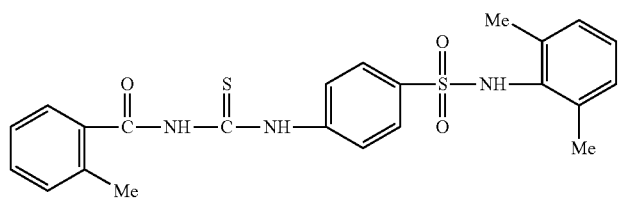

-continued
Answer 607:
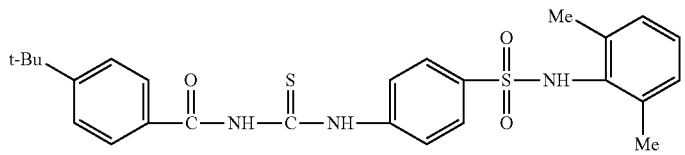
Answer 608:
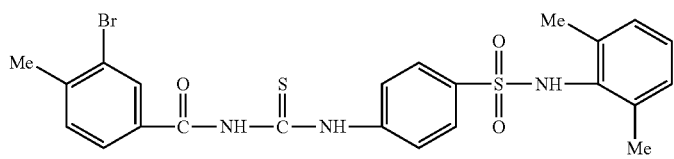
Answer 609:
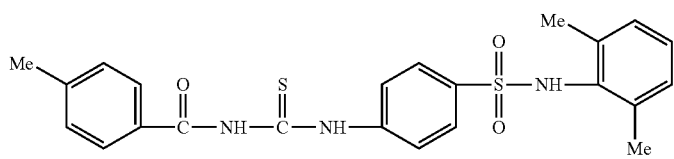
Answer 610:
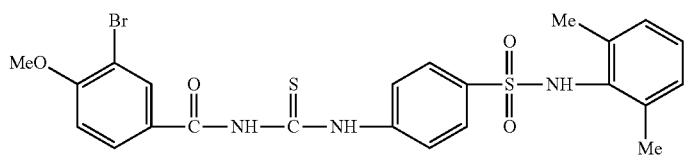
Answer 611:
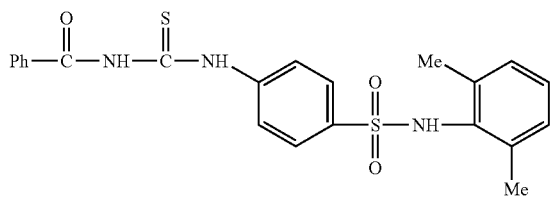
Answer 612:
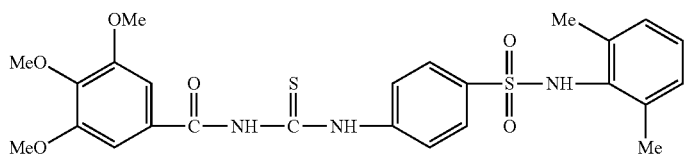
Answer 613:
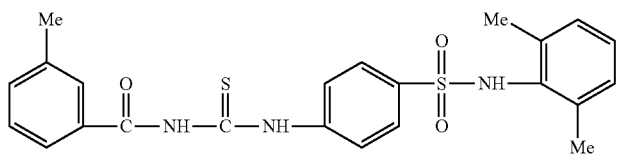
Answer 614:
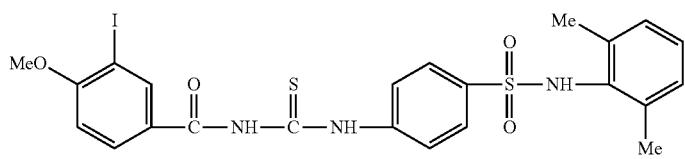

Answer 615:
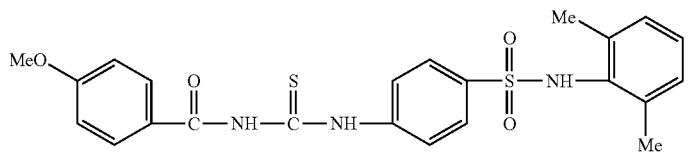
Answer 616:
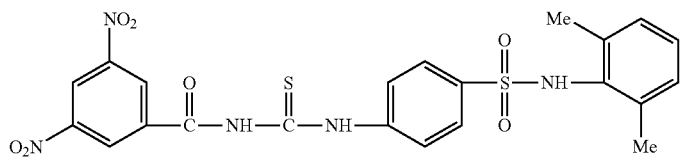
Answer 617:
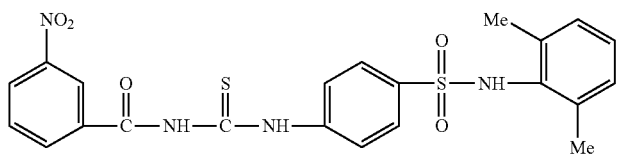
Answer 618:
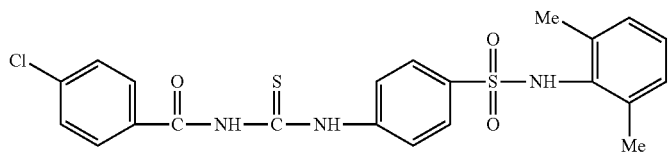
Answer 619:
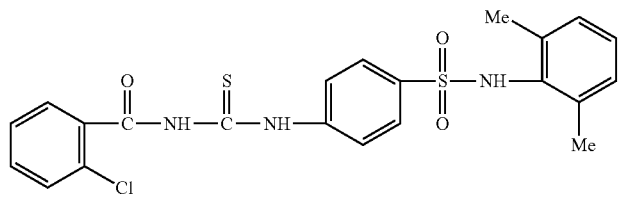
Answer 620:
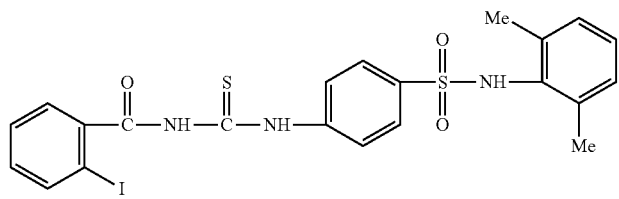
Answer 621:
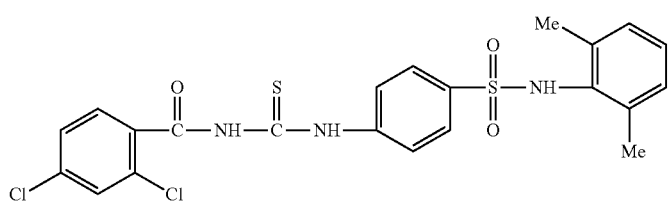

Answer 622:
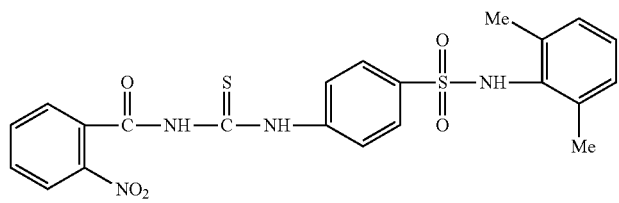
Answer 623:
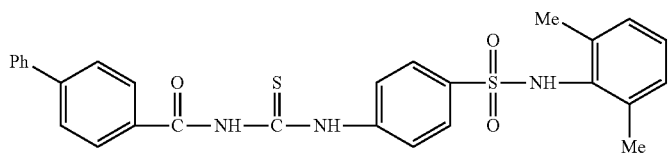
Answer 624:
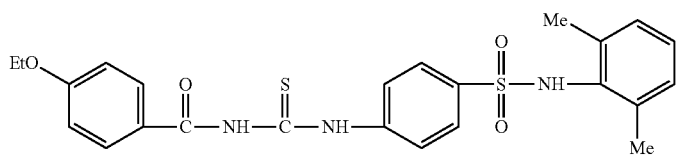
Answer 625:
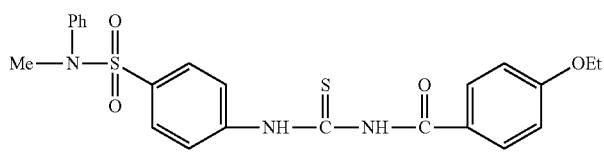
Answer 626:
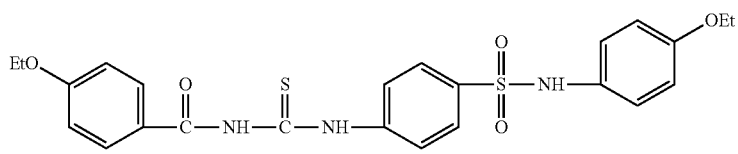
Answer 627:
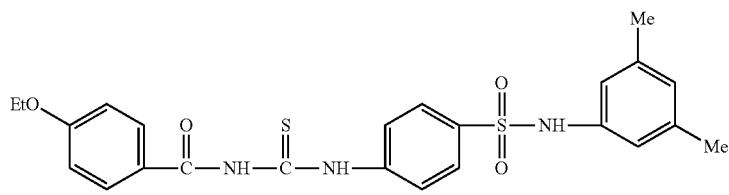
Answer 628:
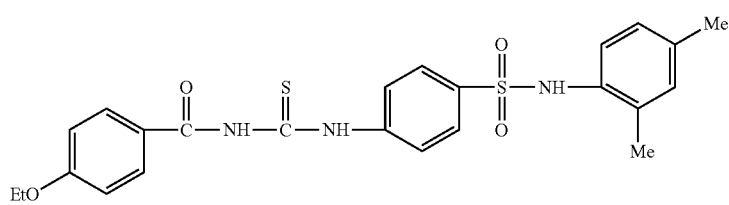

Answer 629:
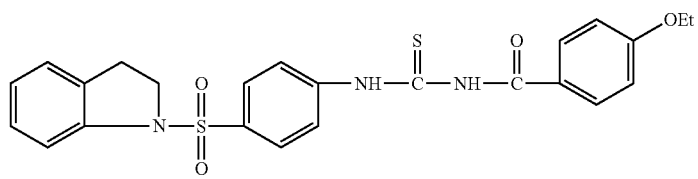
Answer 630:
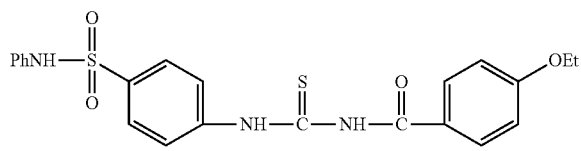
Answer 631:
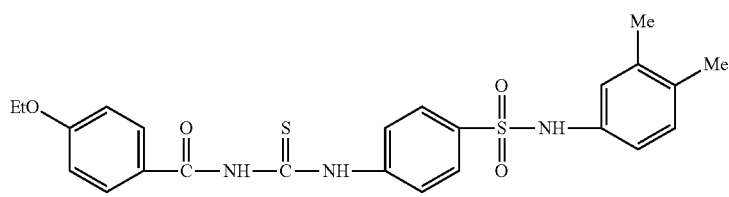
Answer 632:
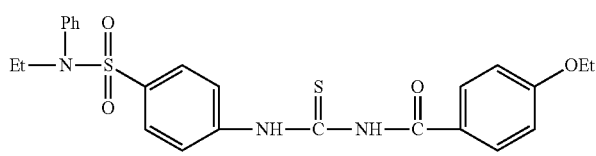
Answer 633:
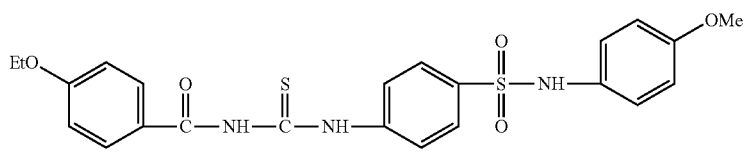
Answer 634:
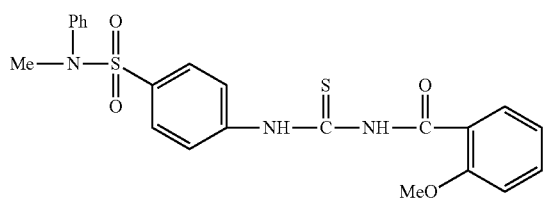
Answer 635:
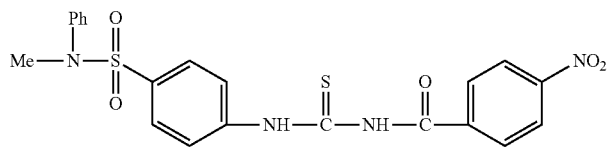

Answer 636:
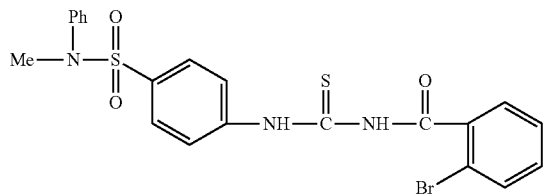
Answer 637:
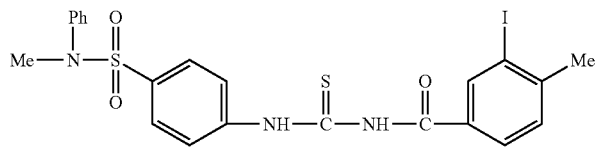
Answer 638:
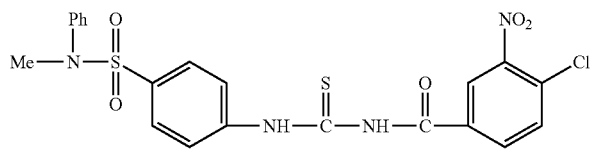
Answer 639:
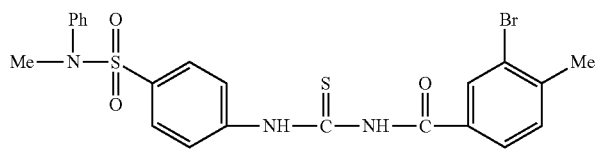
Answer 640:
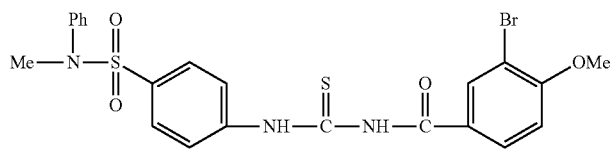
Answer 641:
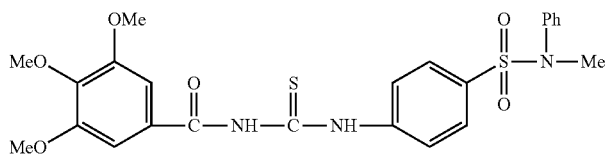
Answer 642:
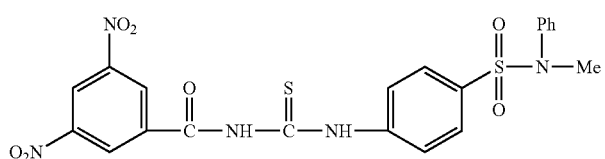
Answer 643:
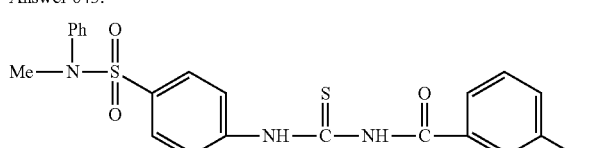

Answer 644:
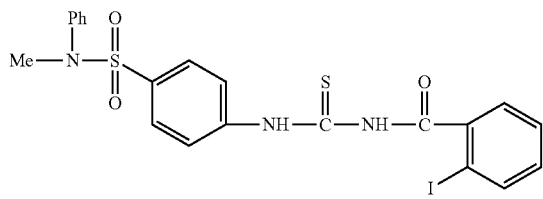
Answer 645:
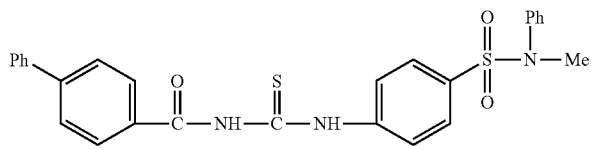
Answer 646:
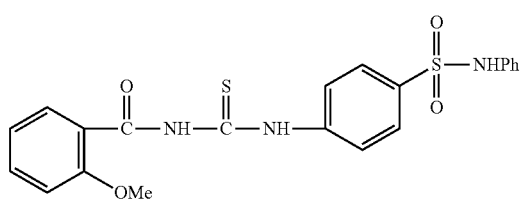
Answer 647:
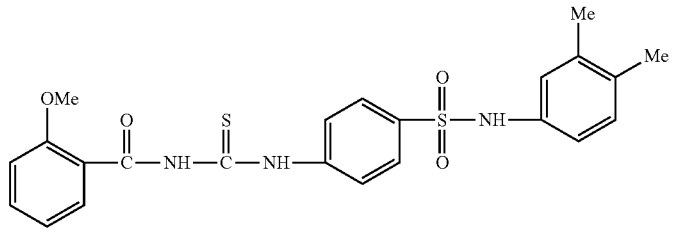
Answer 648:
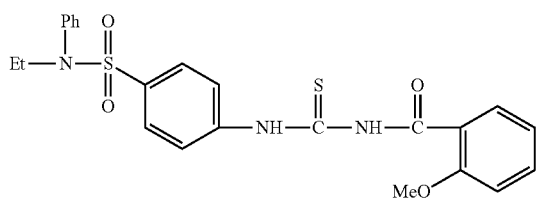
Answer 649:
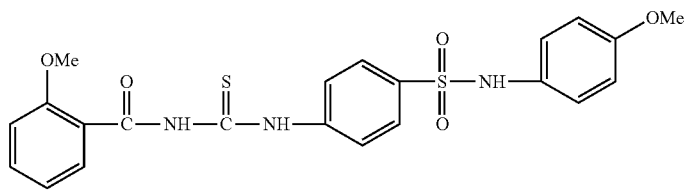
Answer 650:
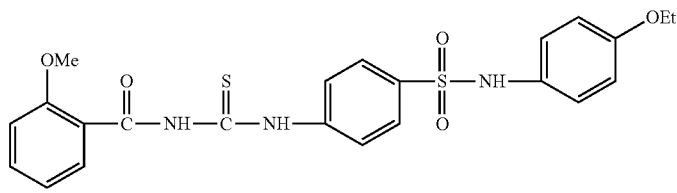

Answer 651:
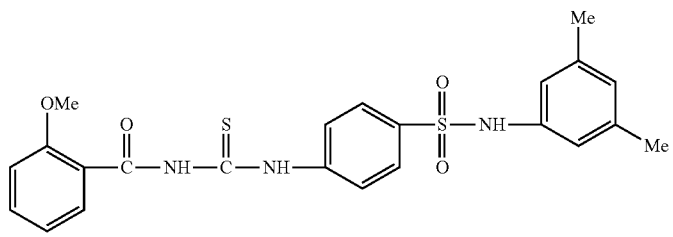
Answer 652:
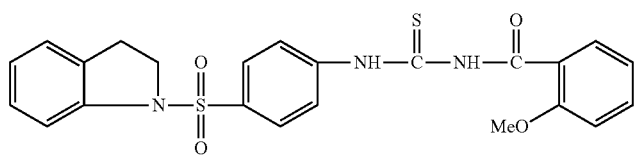
Answer 653:
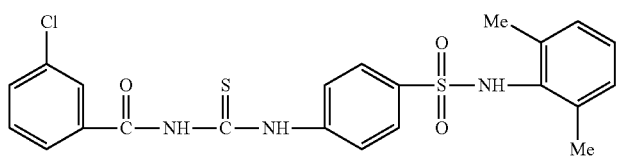
Answer 654:
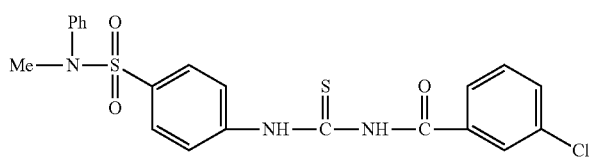
Answer 655:
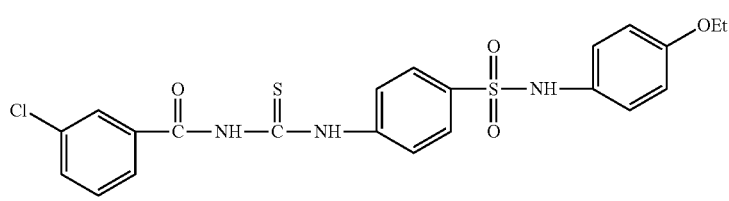
Answer 656:
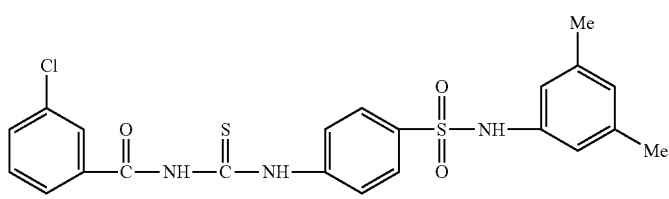
Answer 657:
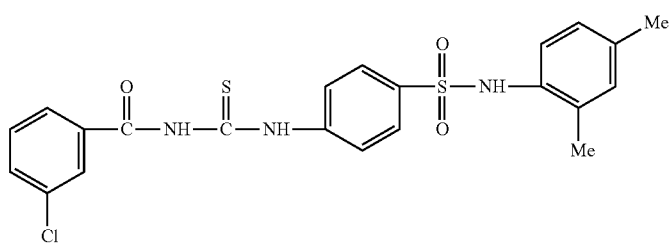

Answer 658:
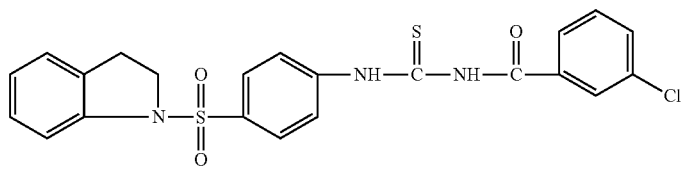
Answer 659:
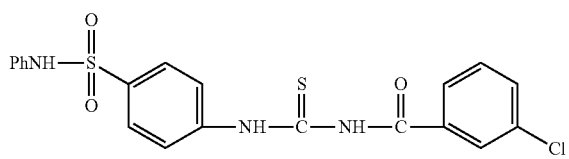
Answer 660:
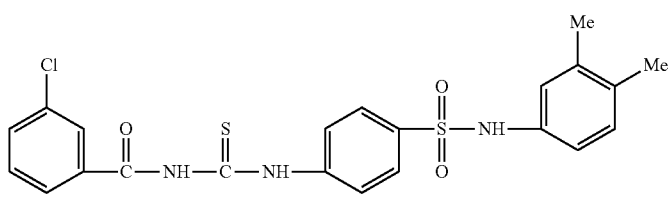
Answer 661:
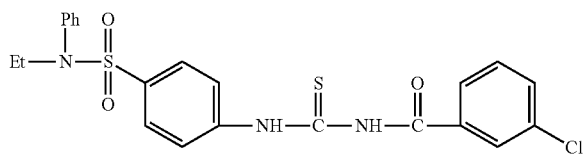
Answer 662:
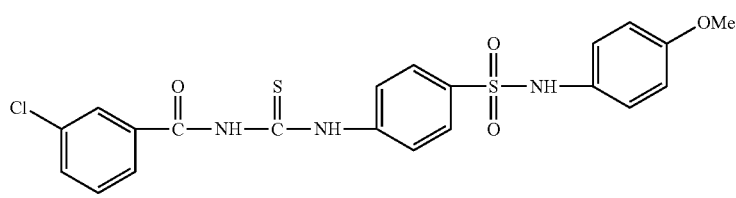
Answer 663:
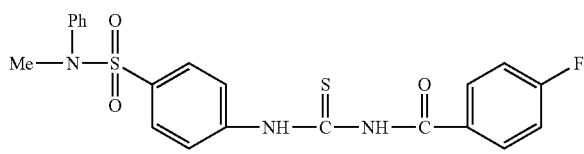
Answer 664:
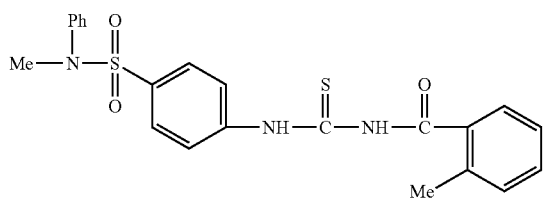

Answer 665:
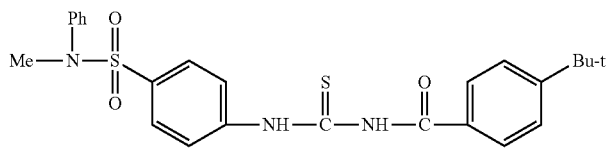
Answer 666:
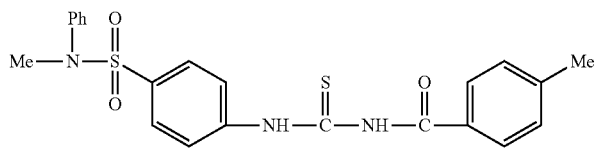
Answer 667:
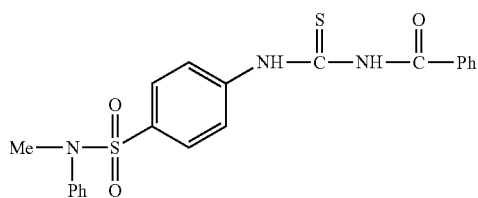
Answer 668:
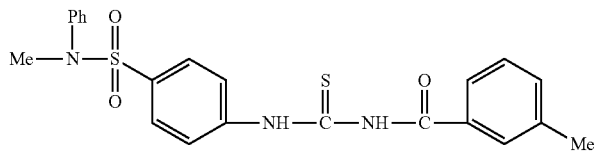
Answer 669:
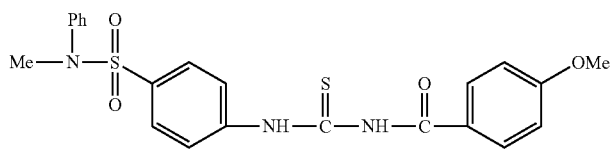
Answer 670:
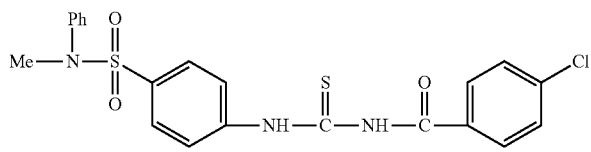
Answer 671:
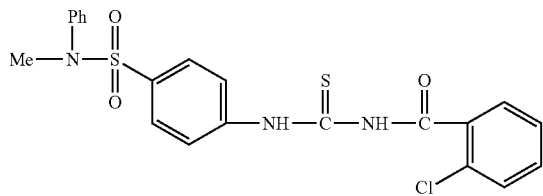

-continued
Answer 672:
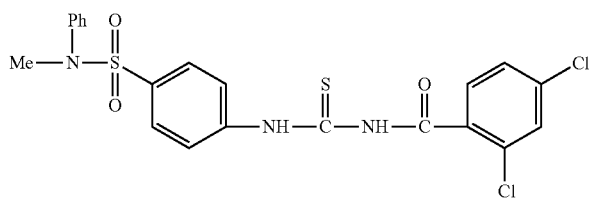
Answer 673:
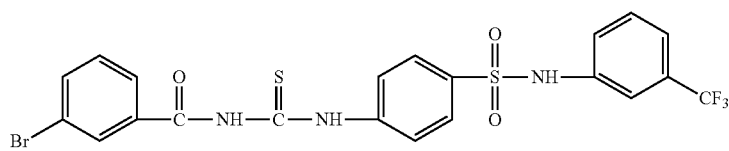
Answer 674:
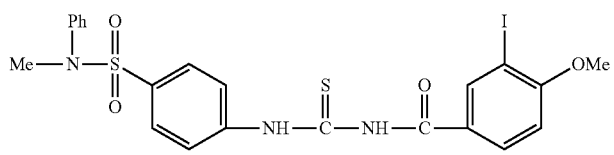
Answer 675:
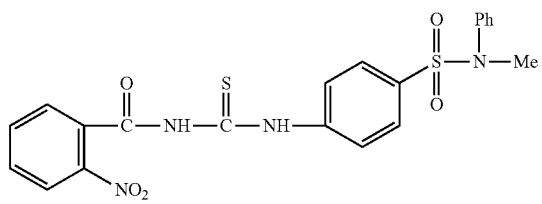
Answer 676:
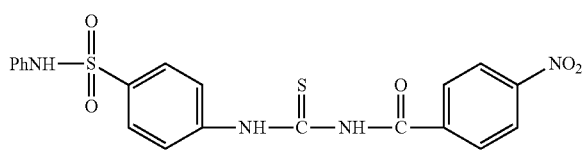
Answer 677:
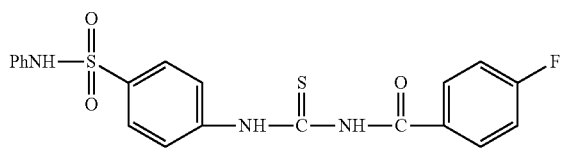
Answer 678:
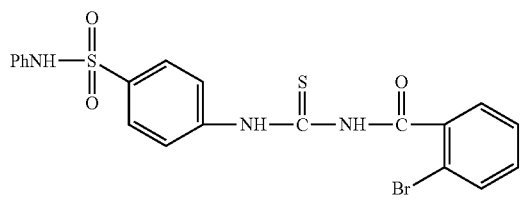

Answer 679:
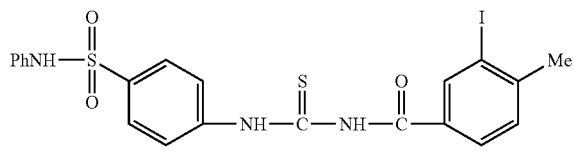
Answer 680:
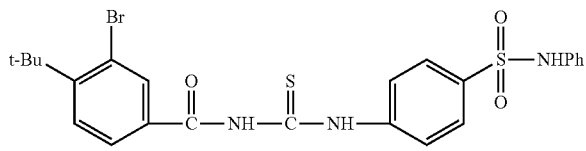
Answer 681:
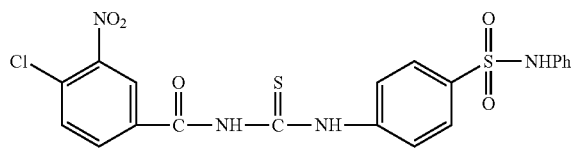
Answer 682:
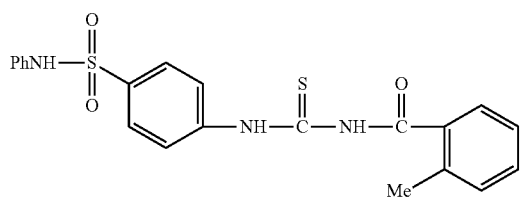
Answer 683:
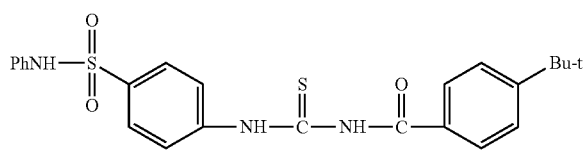
Answer 684:
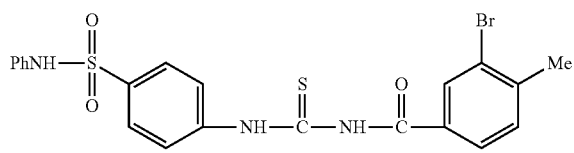
Answer 685:
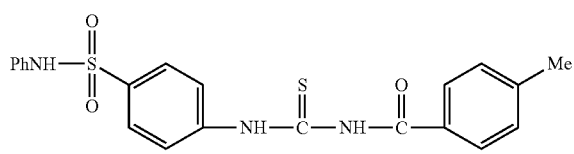
Answer 686:
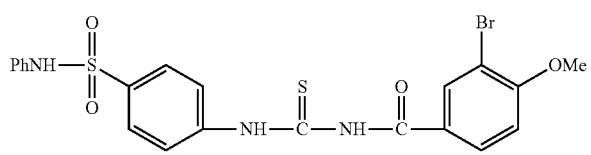

Answer 687:
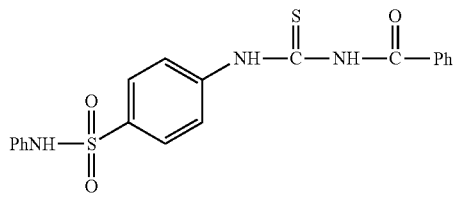
Answer 688:
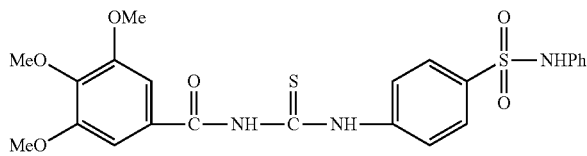
Answer 689:
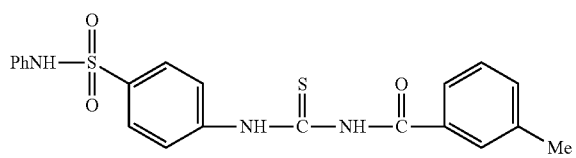
Answer 690:
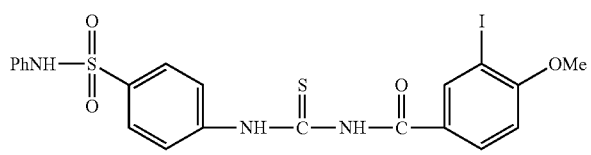
Answer 691:
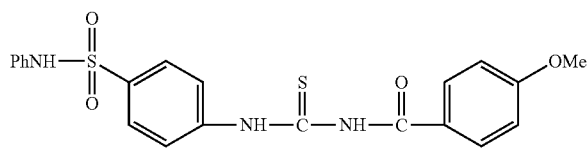
Answer 692:
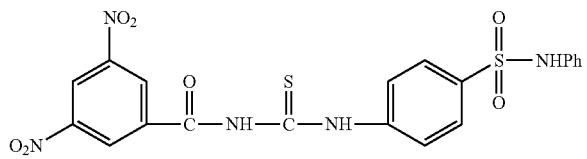
Answer 693:
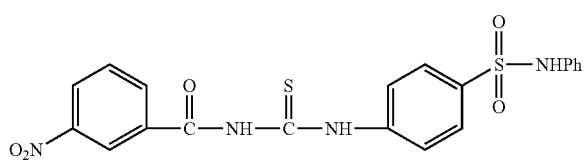
Answer 694:
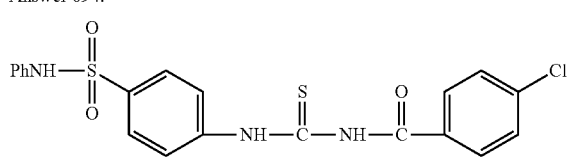

Answer 695:
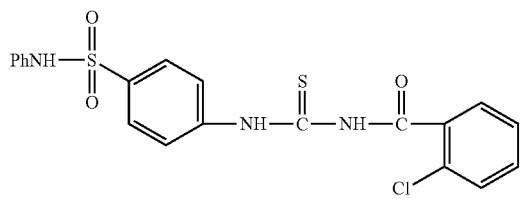
Answer 696:
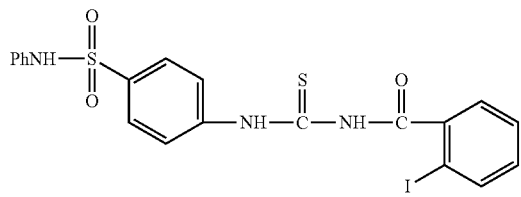
Answer 697:
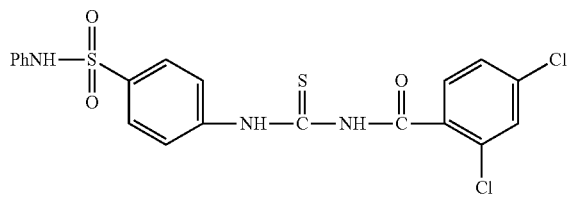
Answer 698:
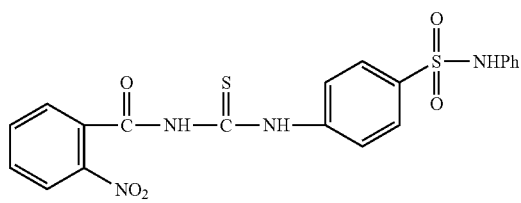
Answer 699:
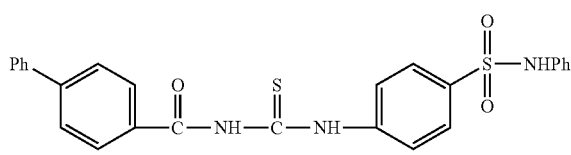
Answer 700:
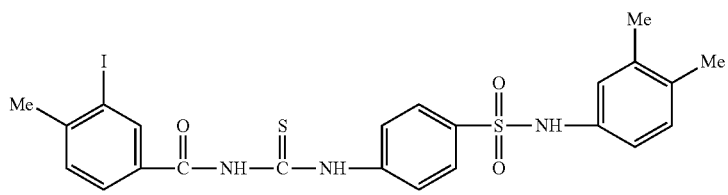
Answer 701:
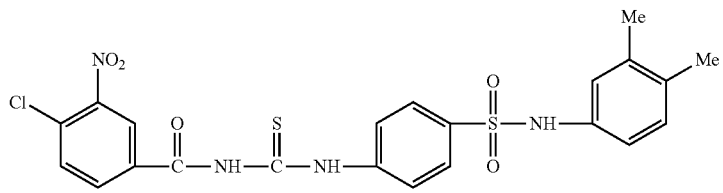

Answer 702:
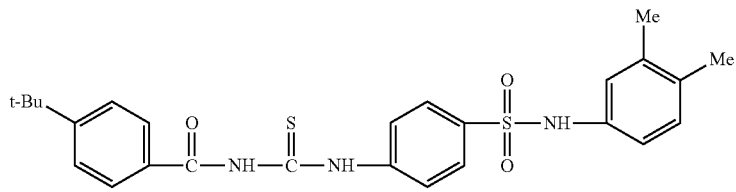
Answer 703:
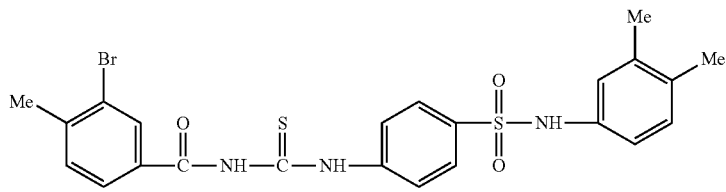
Answer 704:
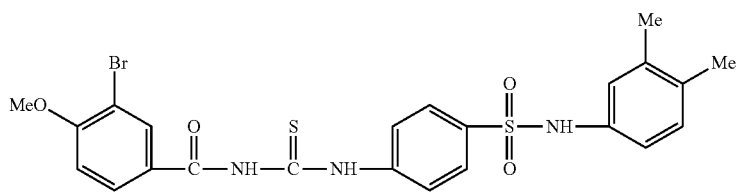
Answer 705:
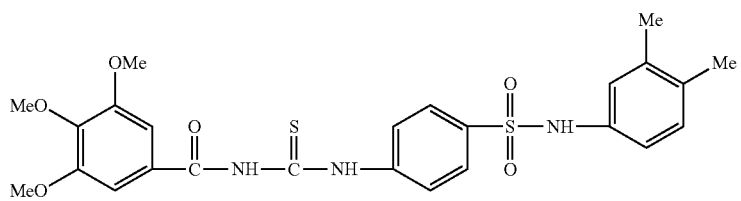
Answer 706:
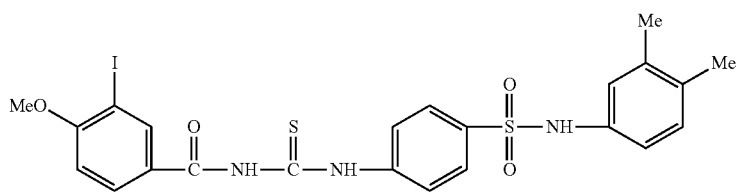
Answer 707:
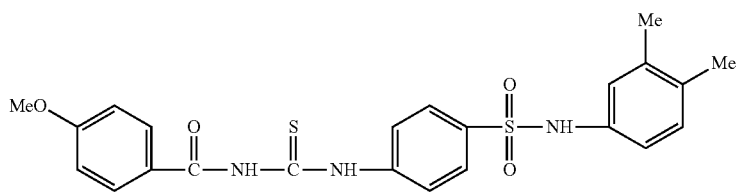
Answer 708:
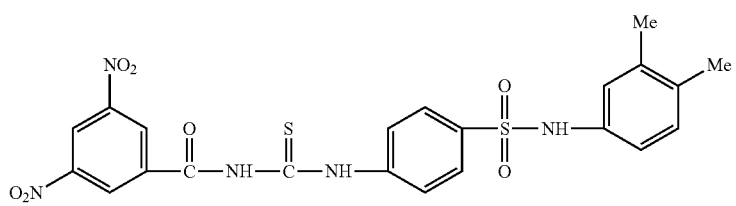

-continued
Answer 709:
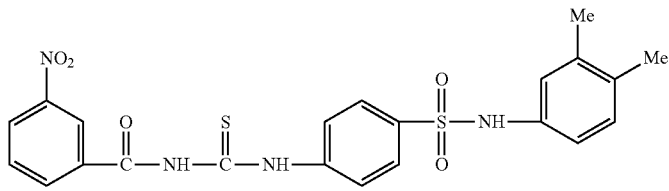
Answer 710:
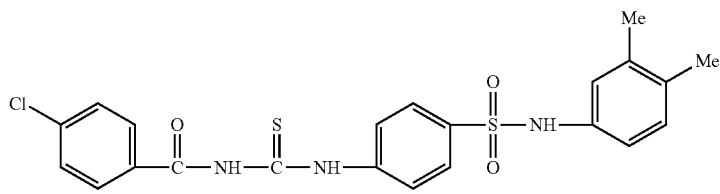
Answer 711:
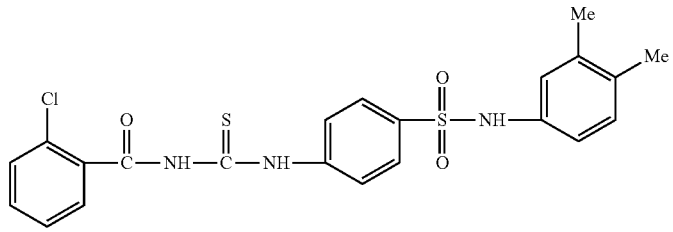
Answer 712:
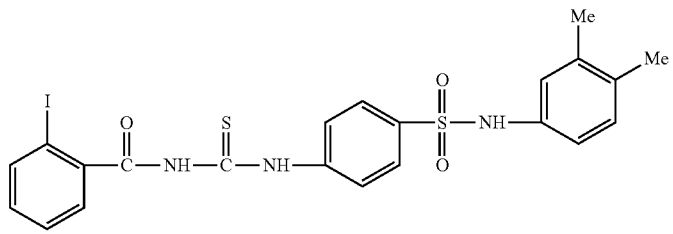
Answer 713:
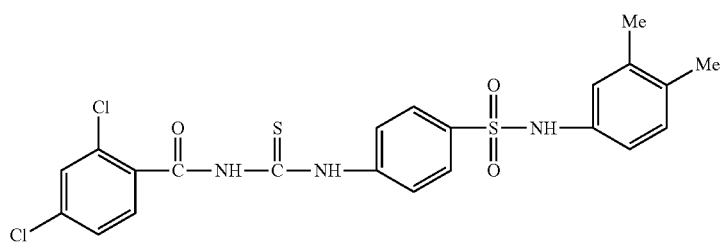
Answer 714:
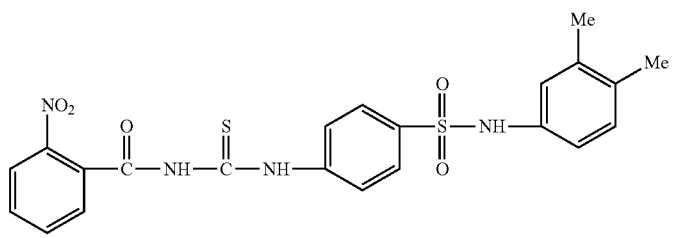

Answer 715:
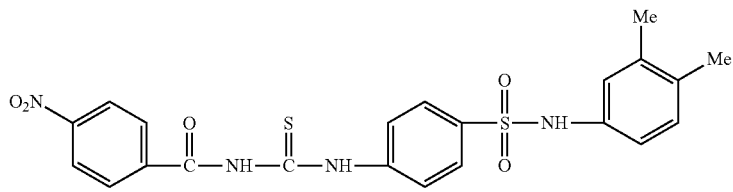
Answer 716:
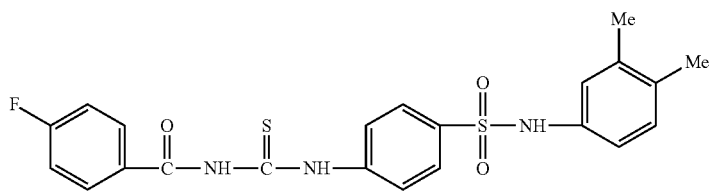
Answer 717:
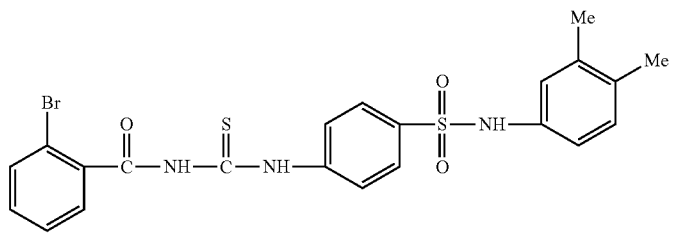
Answer 718:
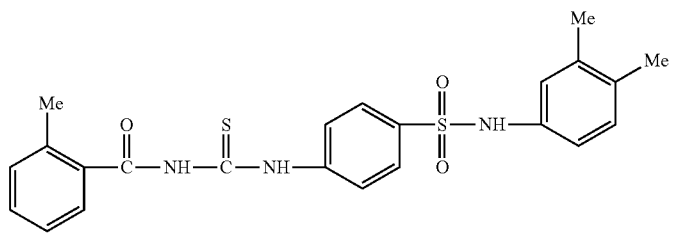
Answer 719:
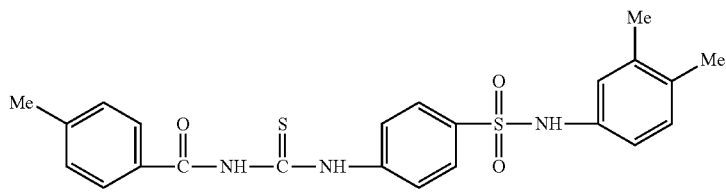
Answer 720:
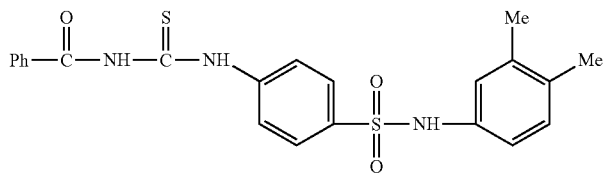

Answer 721:
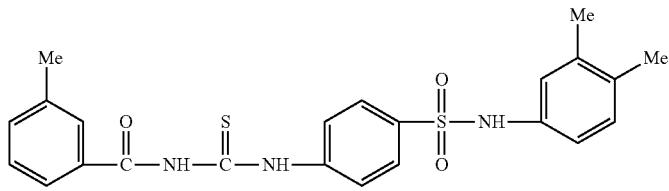
Answer 722:
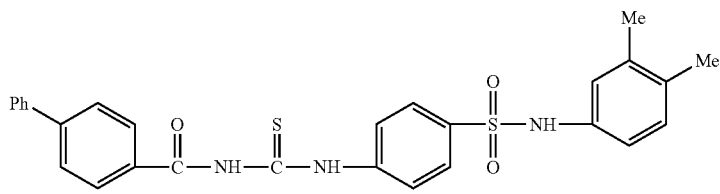
Answer 723:
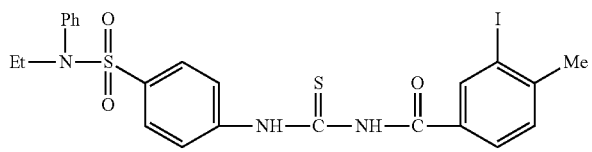
Answer 724:
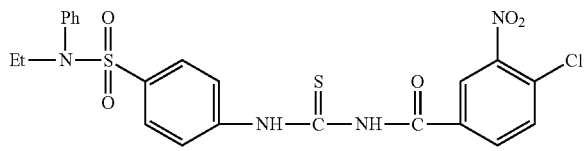
Answer 725:
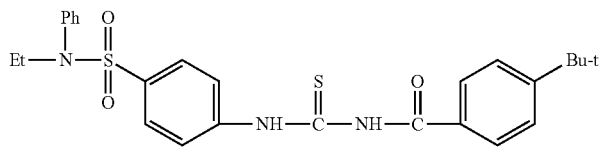
Answer 726:
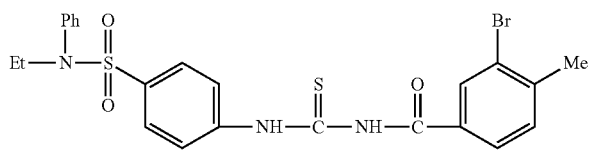
Answer 727:
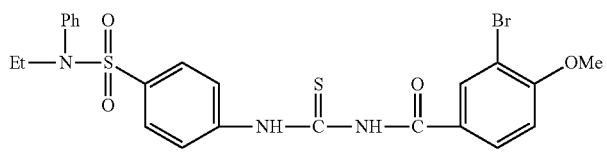
Answer 728:
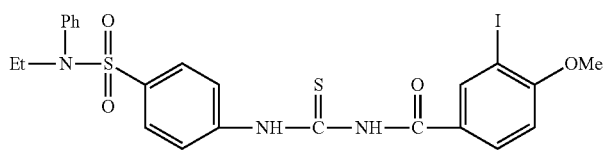

Answer 729:
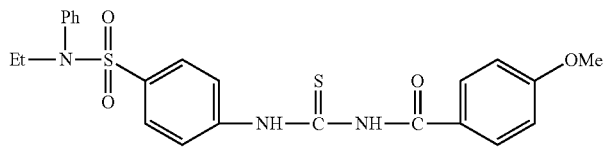
Answer 730:
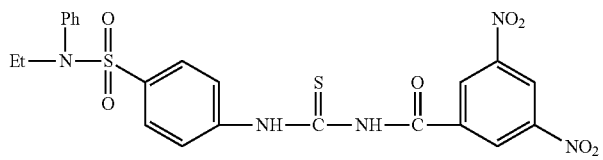
Answer 731:
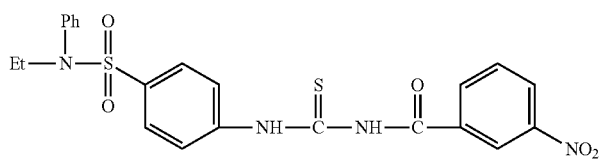
Answer 732:
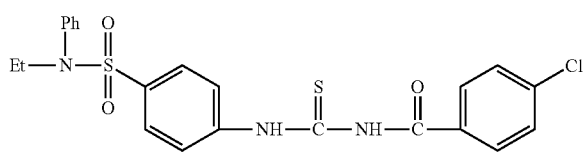
Answer 733:
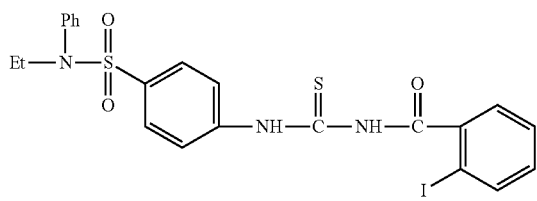
Answer 734:
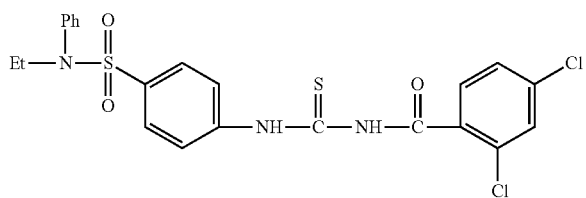
Answer 735:
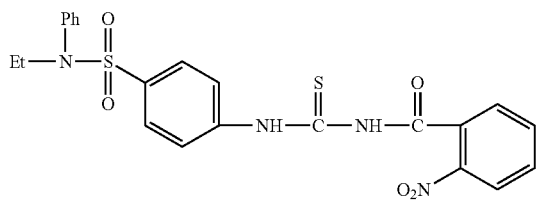

Answer 736:
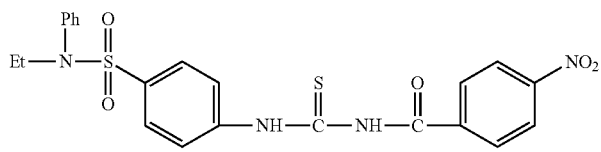
Answer 737:
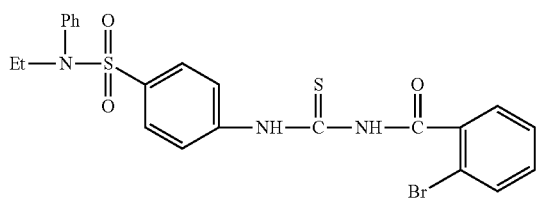
Answer 738:
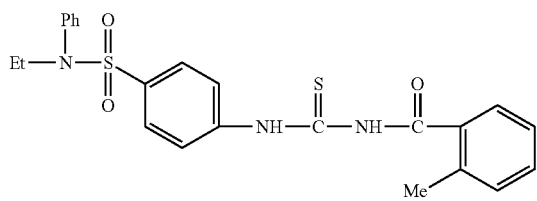
Answer 739:
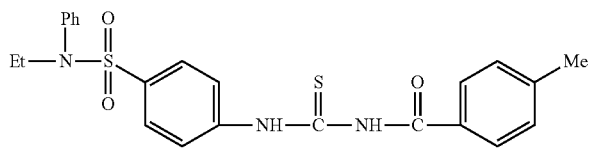
Answer 740:
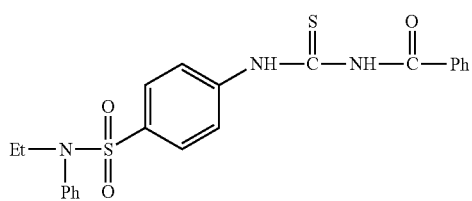
Answer 741:
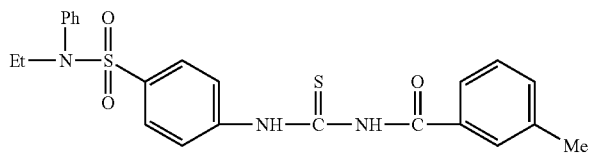
Answer 742:
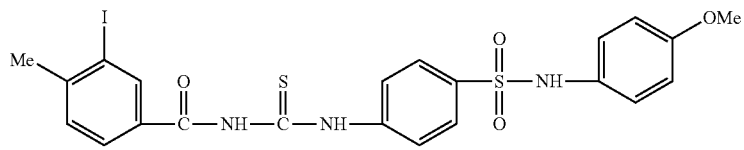

Answer 743:
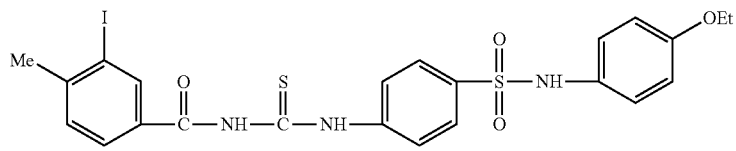
Answer 744:
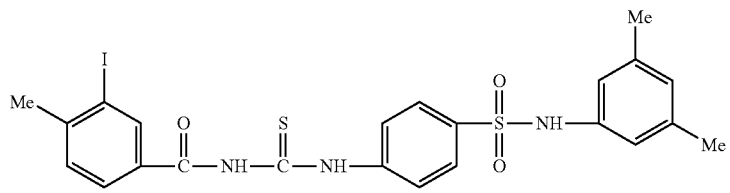
Answer 745:
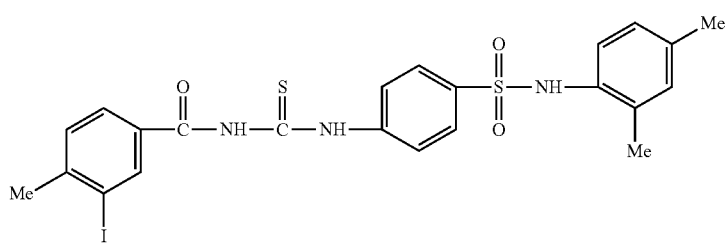
Answer 746:
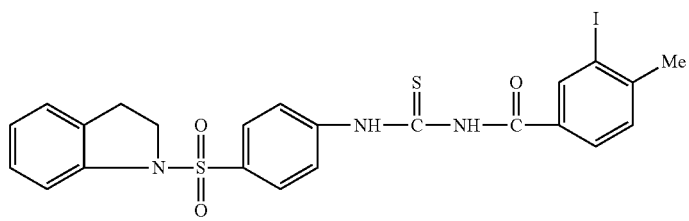
Answer 747:
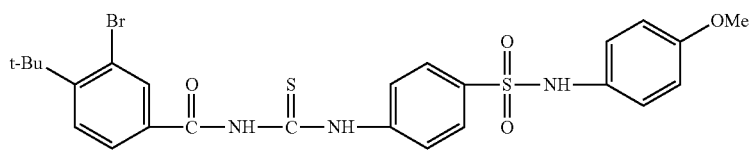
Answer 748:
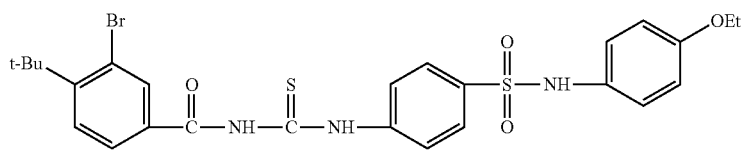
Answer 749:
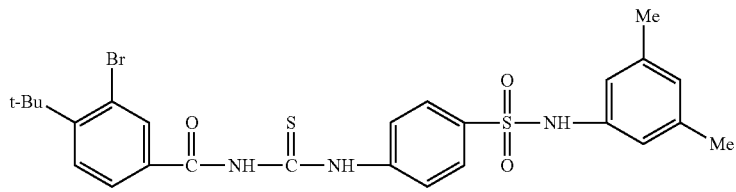

Answer 750:
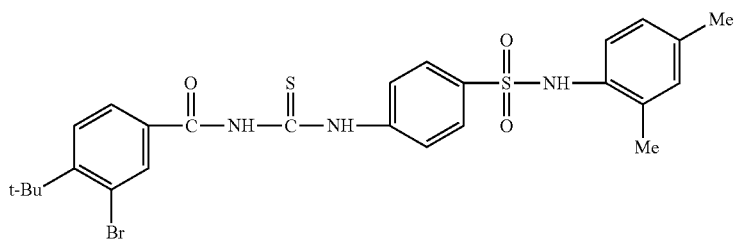
Answer 751:
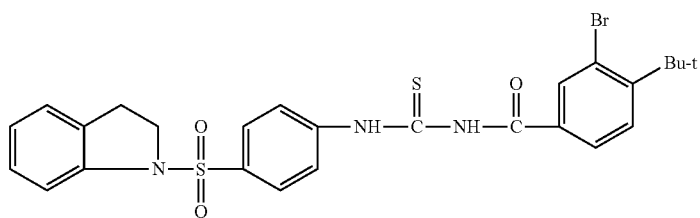
Answer 752:
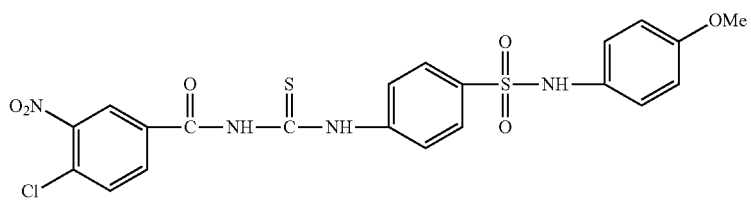
Answer 753:
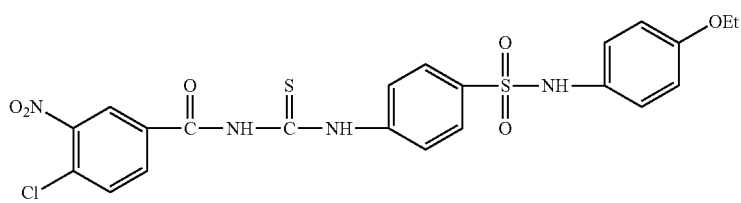
Answer 754:
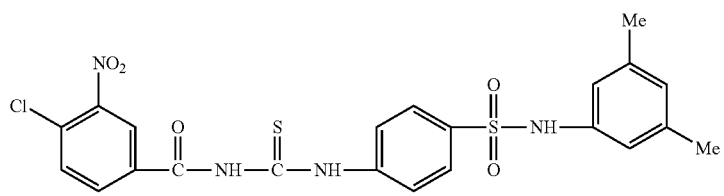
Answer 755:
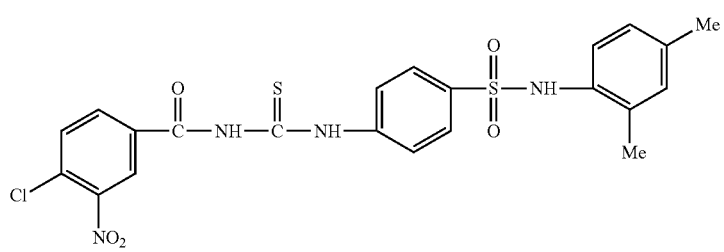

Answer 756:
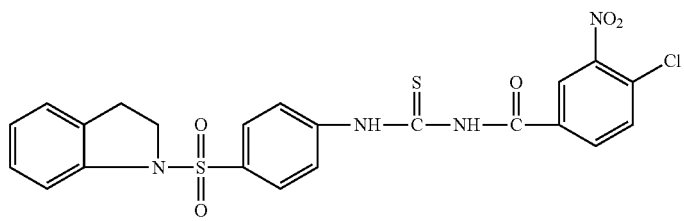
Answer 757:
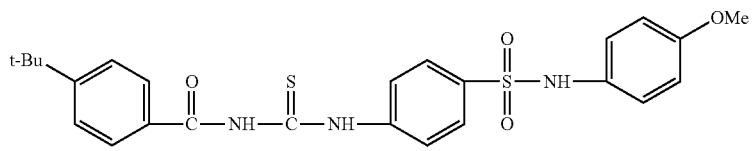
Answer 758:
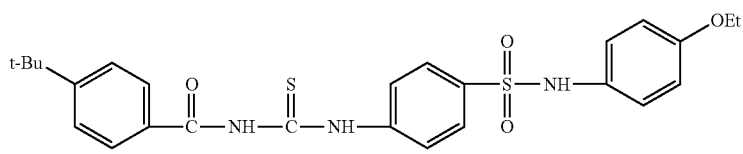
Answer 759:
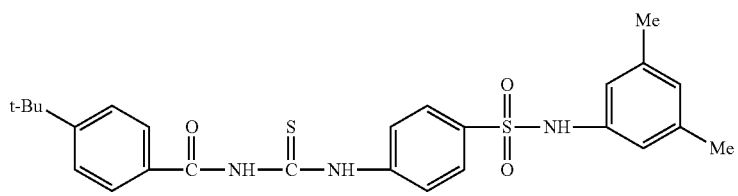
Answer 760:
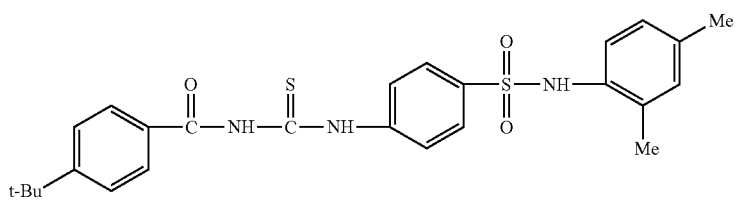
Answer 761:
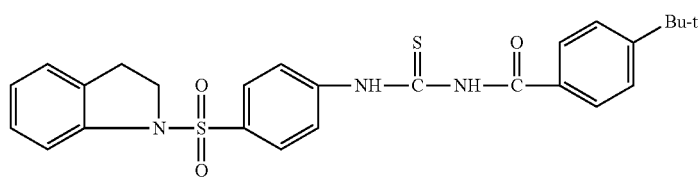
Answer 762:
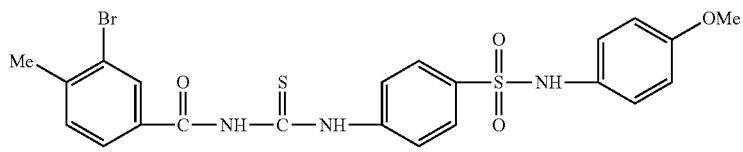

Answer 763:
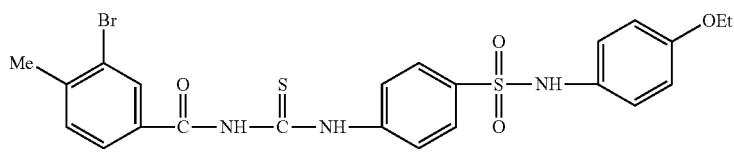
Answer 764:
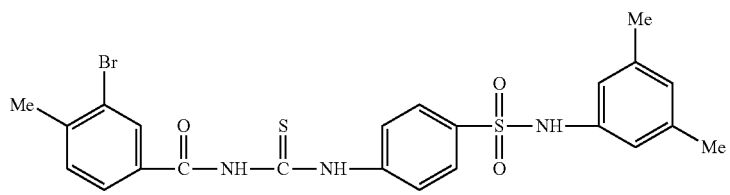
Answer 765:
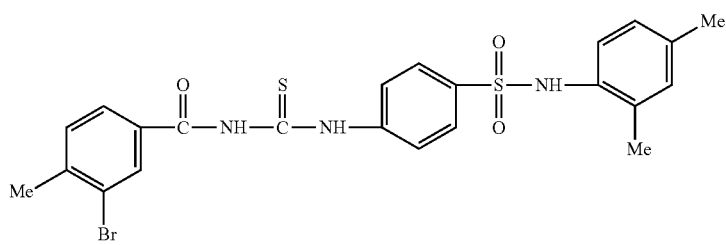
Answer 766:
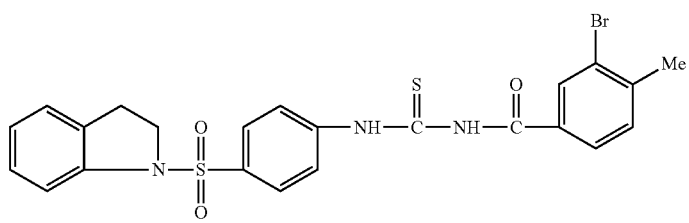
Answer 767:
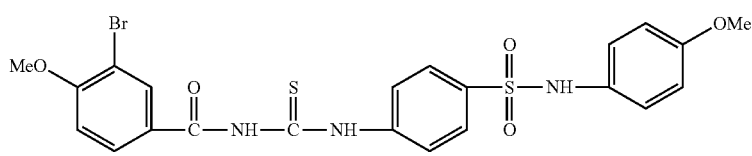
Answer 768:
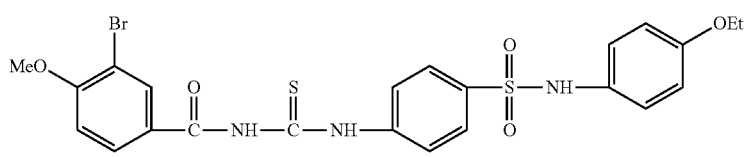
Answer 769:
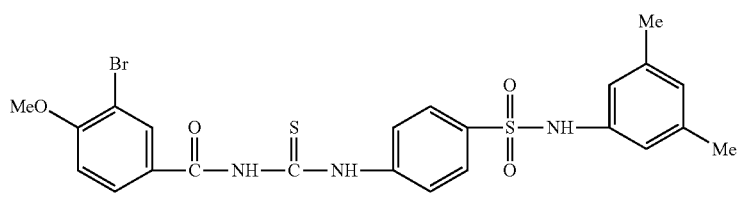

Answer 770:
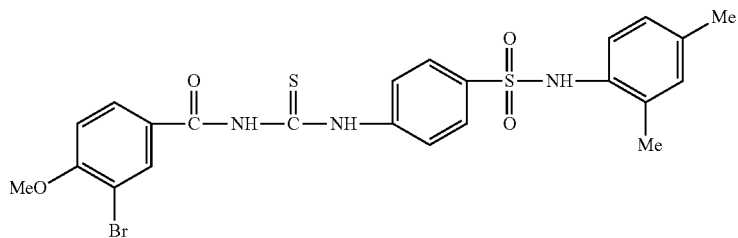
Answer 771:
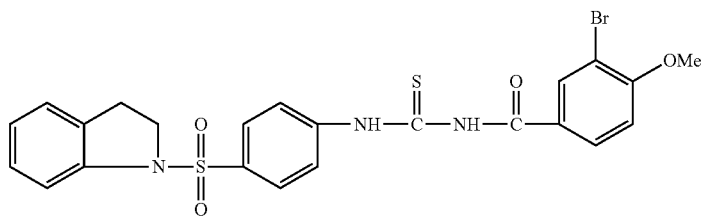
Answer 772:
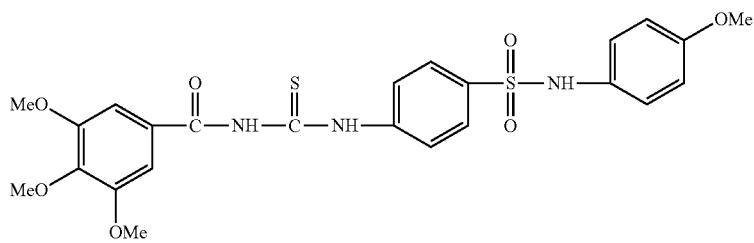
Answer 773:
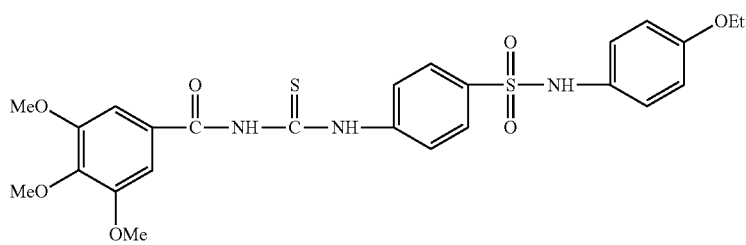
Answer 774:
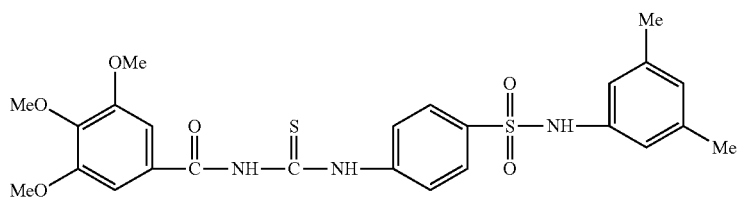
Answer 775:
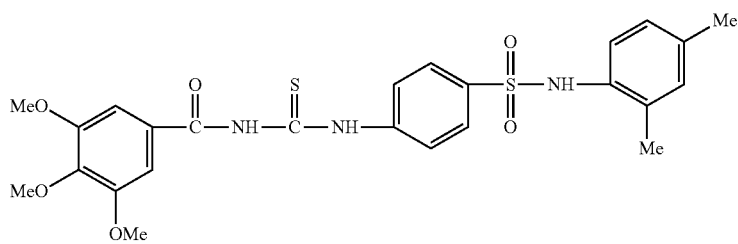

Answer 776:
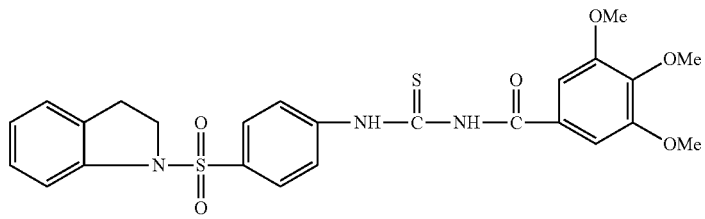
Answer 777:
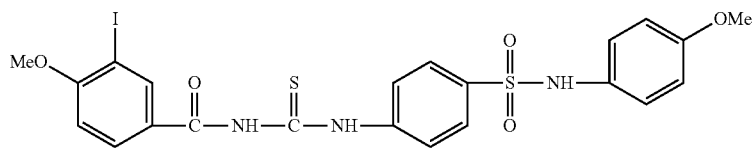
Answer 778:
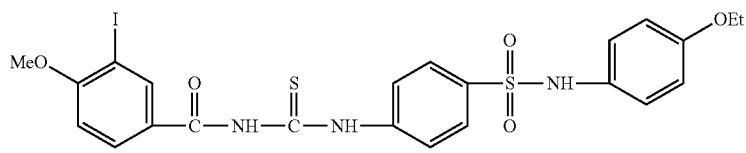
Answer 779:
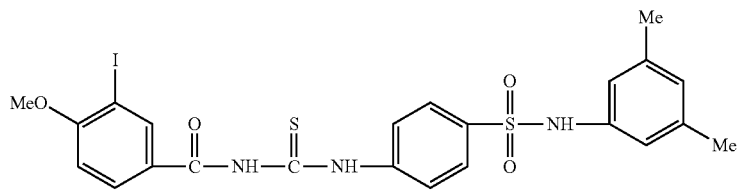
Answer 780:
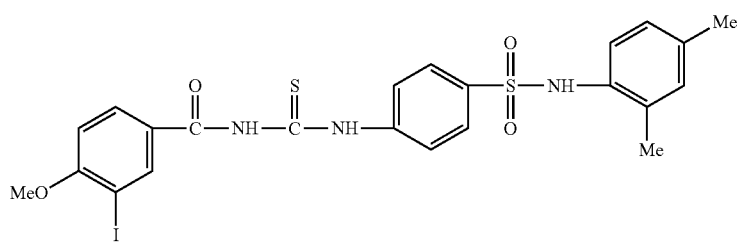
Answer 781:
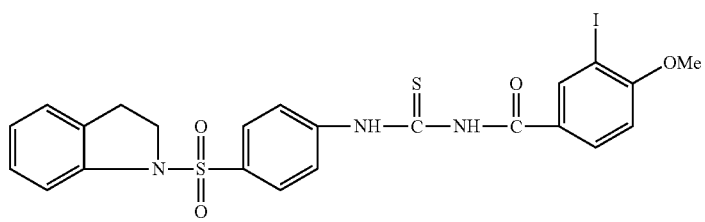
Answer 782:
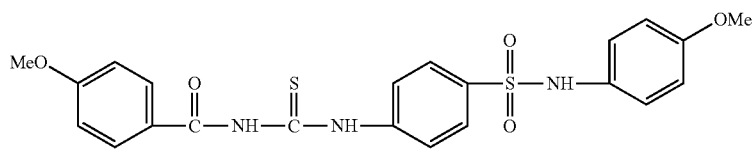

Answer 783:
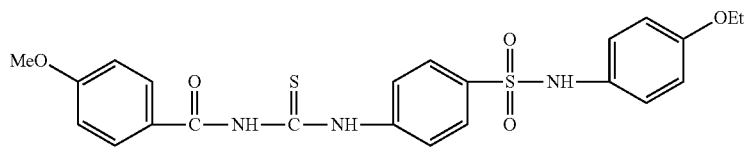
Answer 784:
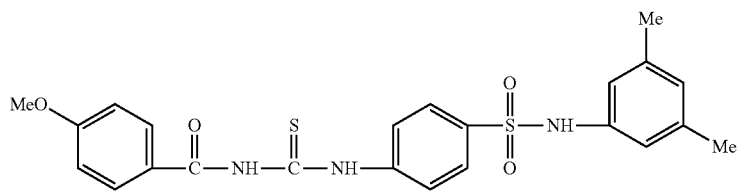
Answer 785:
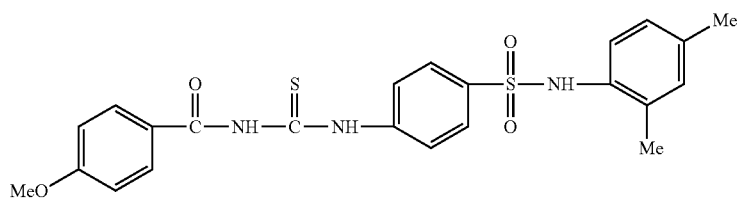
Answer 786:
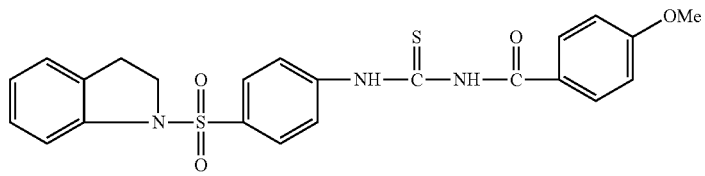
Answer 787:
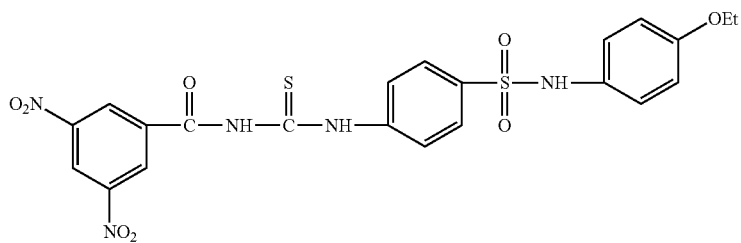
Answer 788:
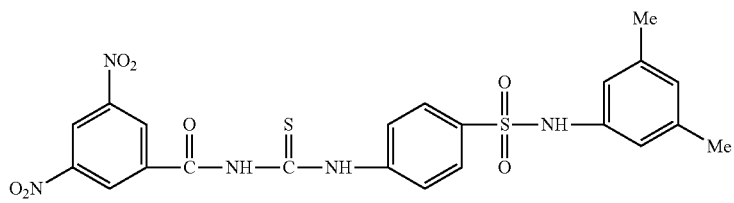

-continued
Answer 789:
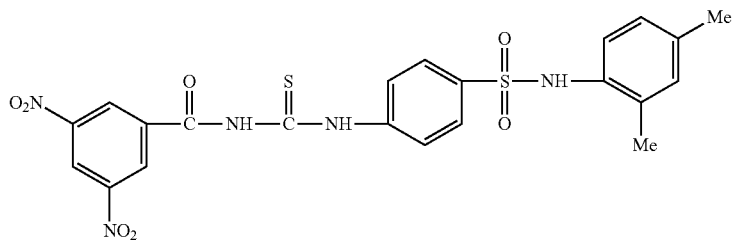
Answer 790:
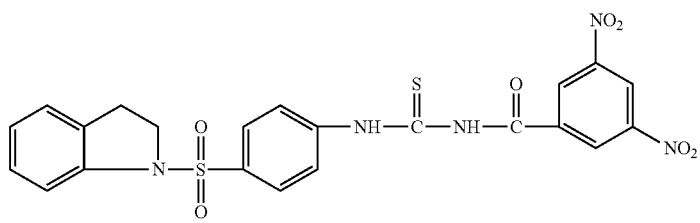
Answer 791:
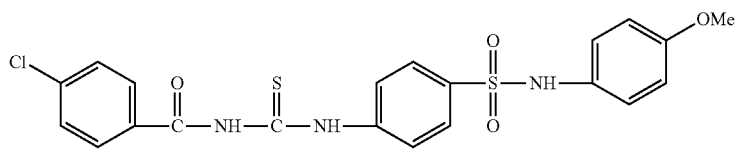
Answer 792:
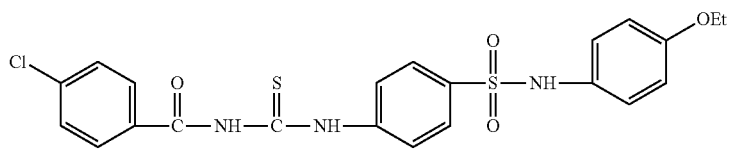
Answer 793:
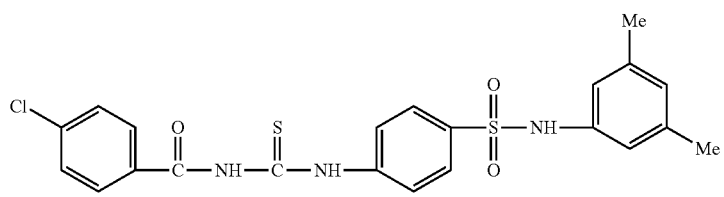
Answer 794:
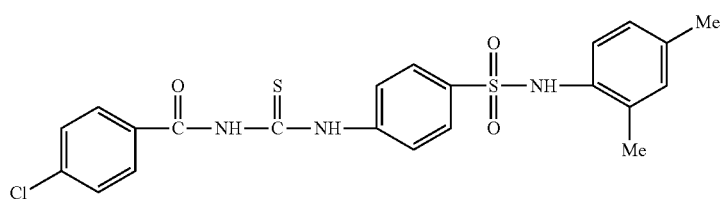
Answer 795:
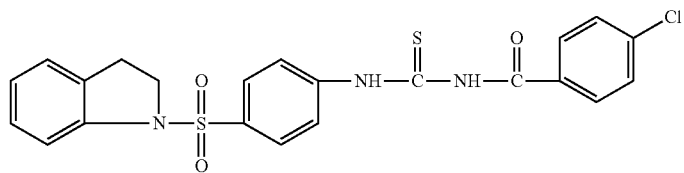

-continued
Answer 796:
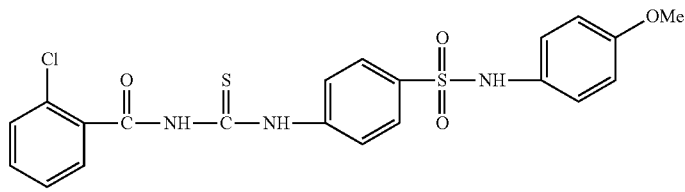
Answer 797:
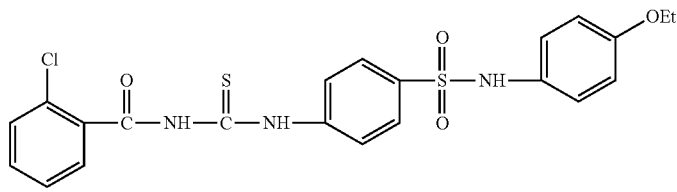
Answer 798:
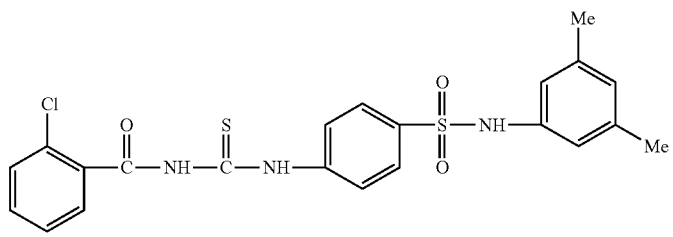
Answer 799:
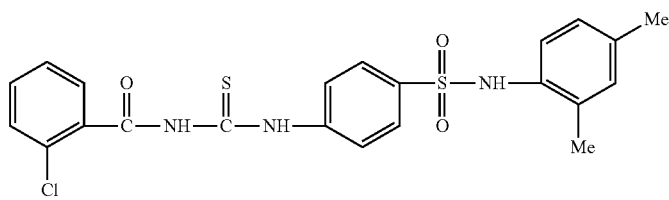
Answer 800:
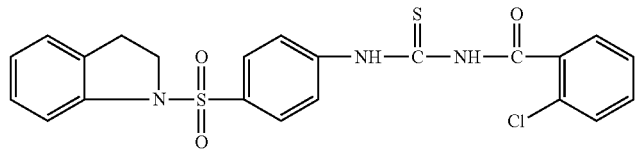
Answer 801:
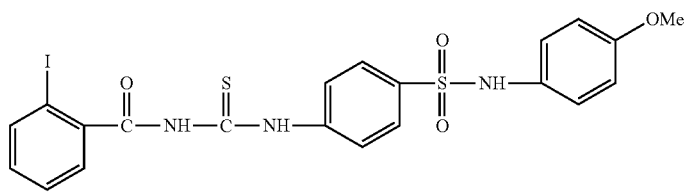
Answer 802:
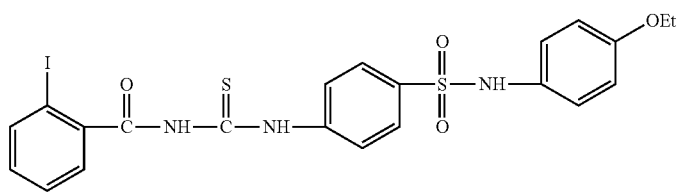

Answer 803:
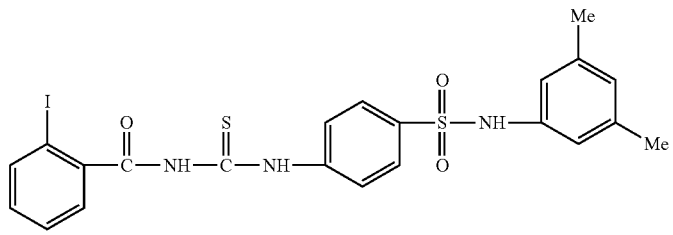
Answer 804:
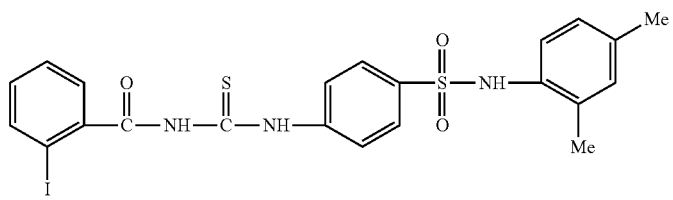
Answer 805:
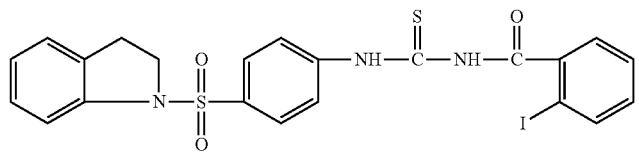
Answer 806:
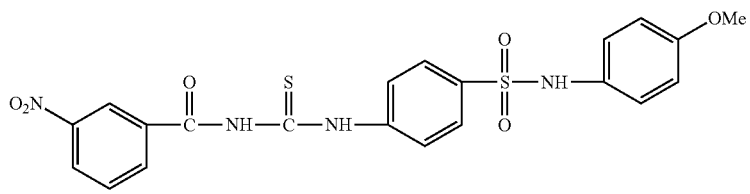
Answer 807:
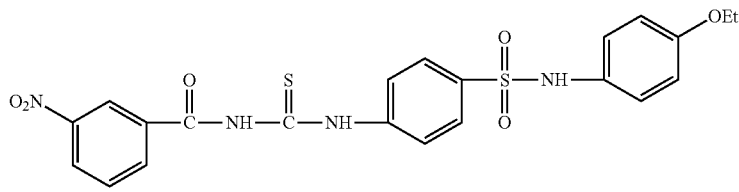
Answer 808:
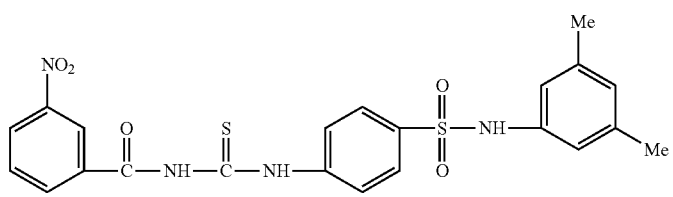

Answer 809:
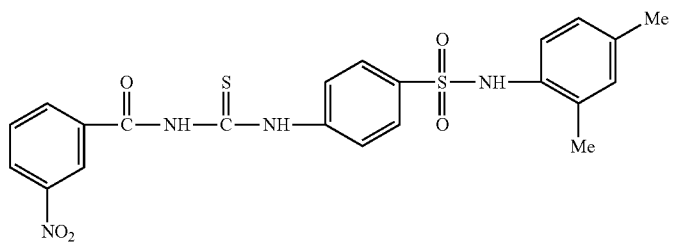
Answer 810:
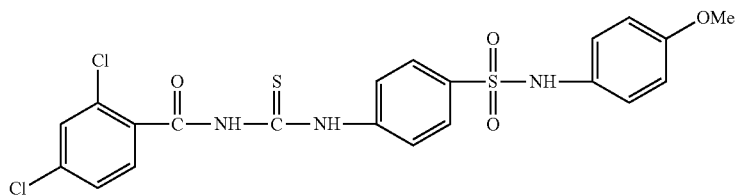
Answer 811:
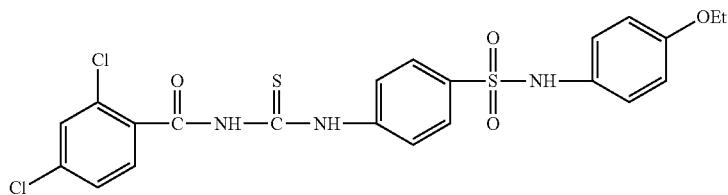
Answer 812:
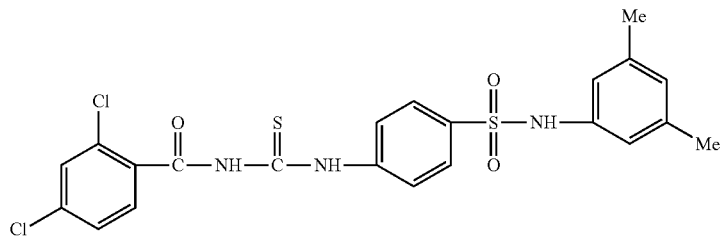
Answer 813:
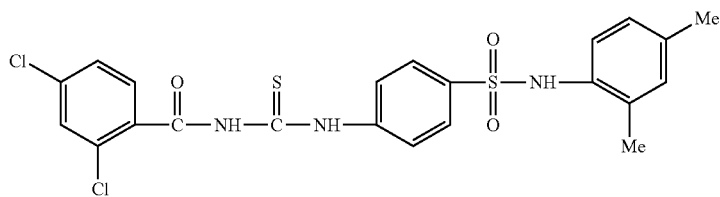
Answer 814:
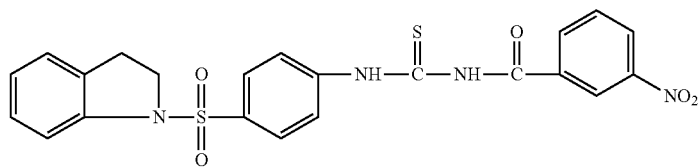

Answer 815:
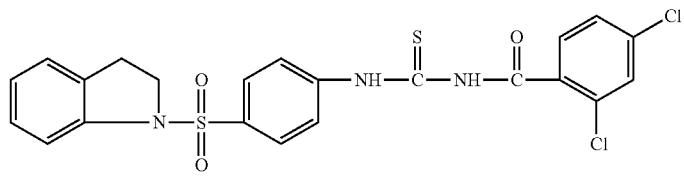
Answer 816:
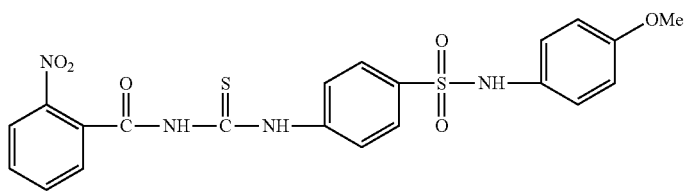
Answer 817:
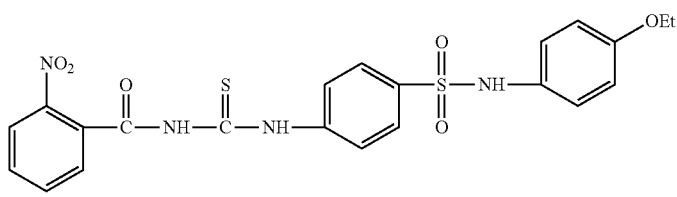
Answer 818:
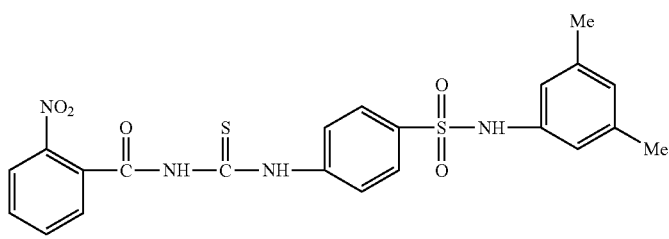
Answer 819:
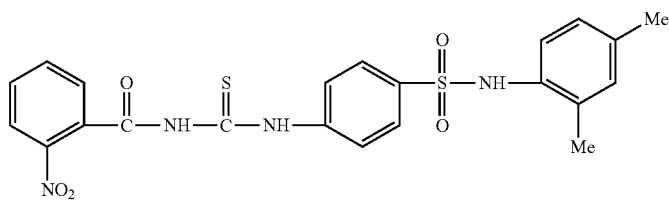
Answer 820:
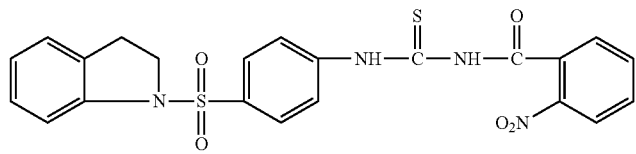
Answer 821:
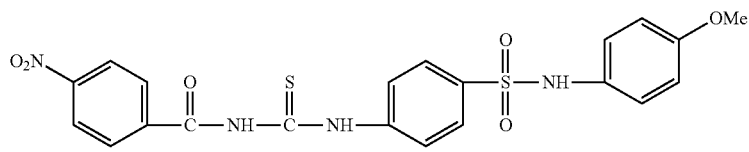

Answer 822:
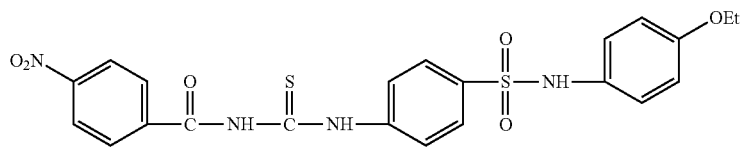
Answer 823:
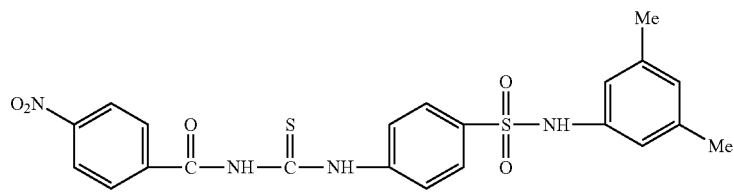
Answer 824:
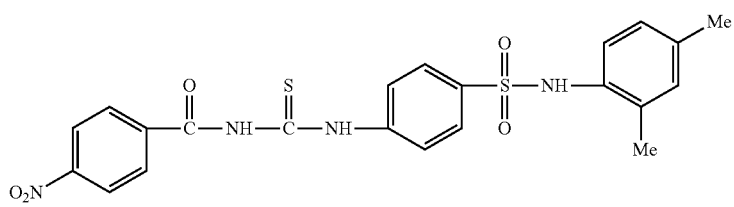
Answer 825:
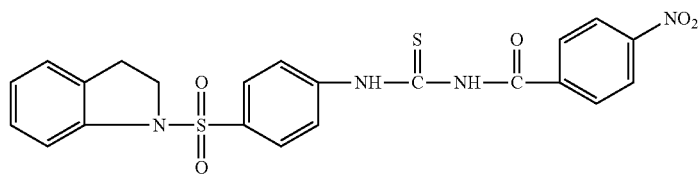
Answer 826:
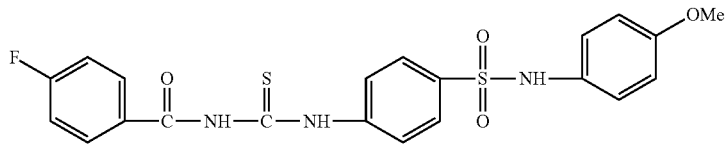
Answer 827:
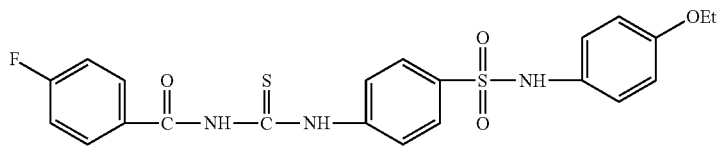
Answer 828:
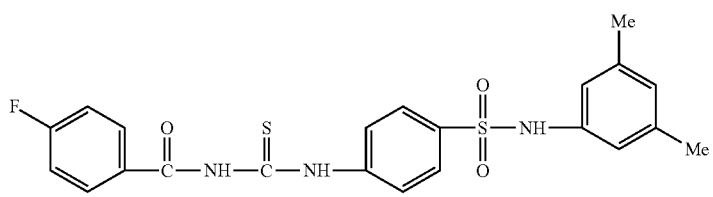

Answer 829:
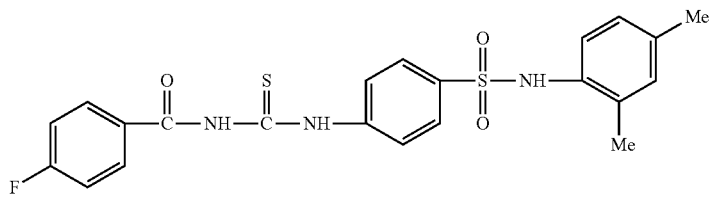
Answer 830:
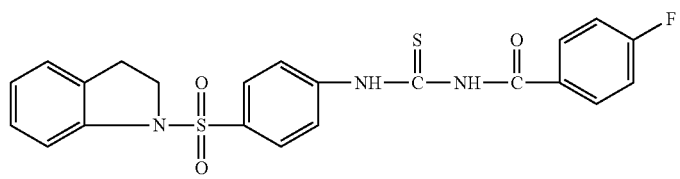
Answer 831:
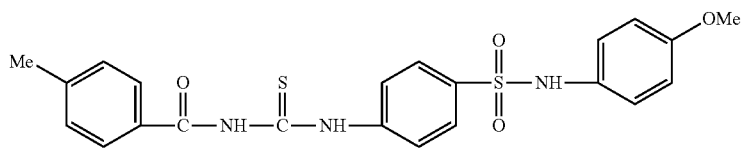
Answer 832:
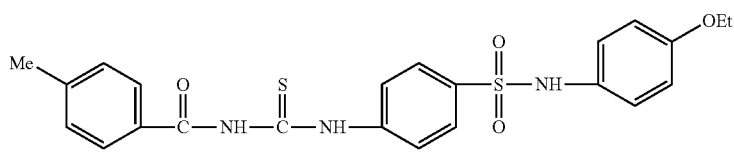
Answer 833:
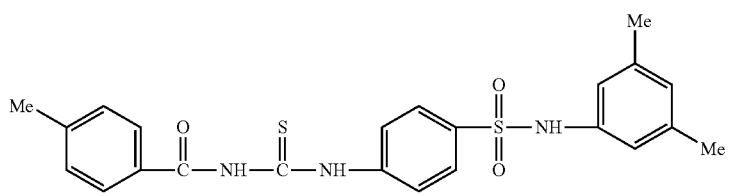
Answer 834:
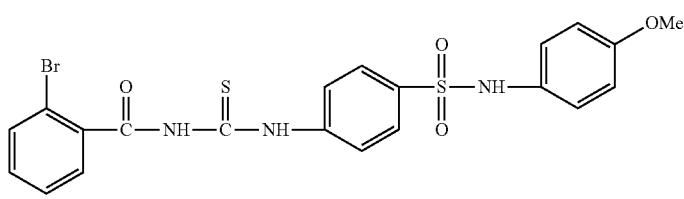
Answer 835:
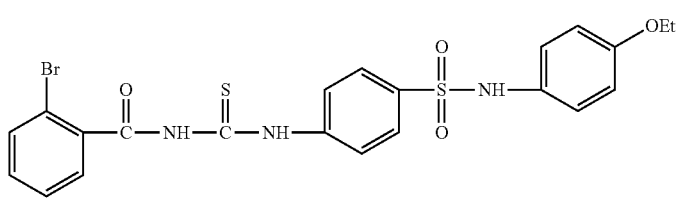

-continued
Answer 836:
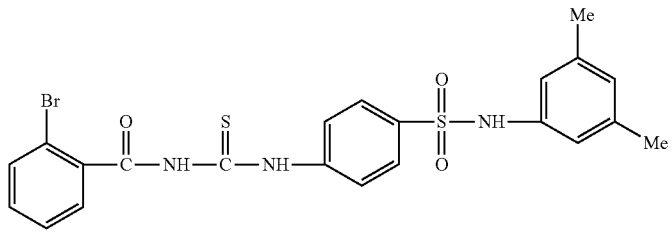
Answer 837:
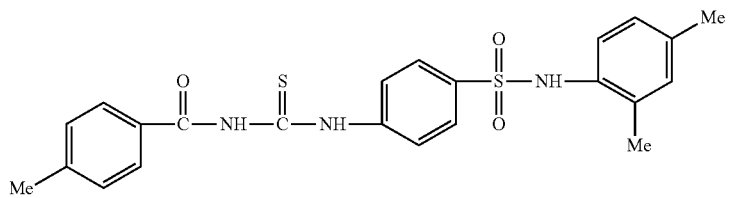
Answer 838:
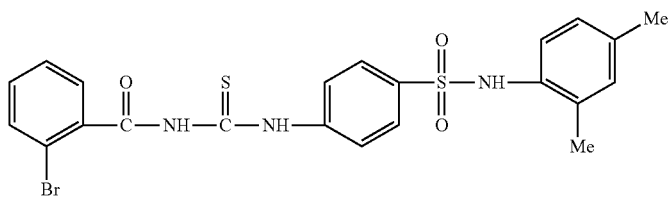
Answer 839:
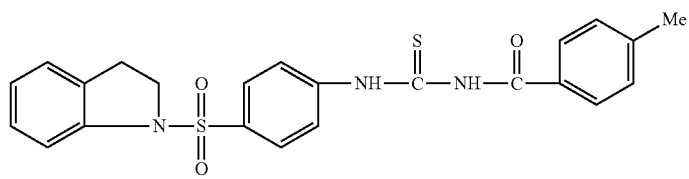
Answer 840:
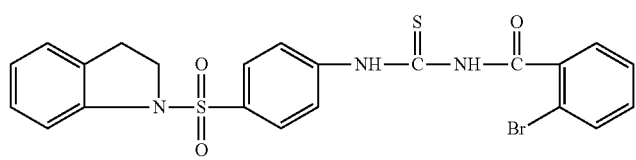
Answer 841:
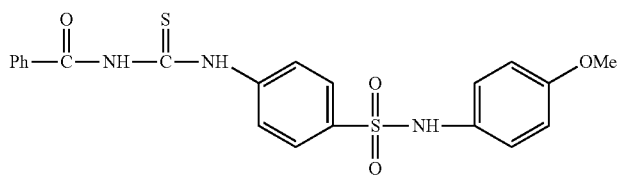
Answer 842:
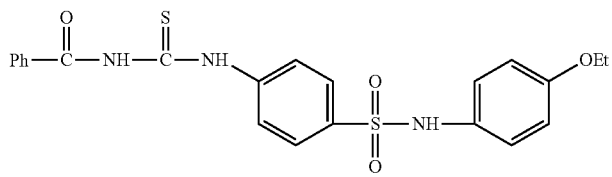

Answer 843:
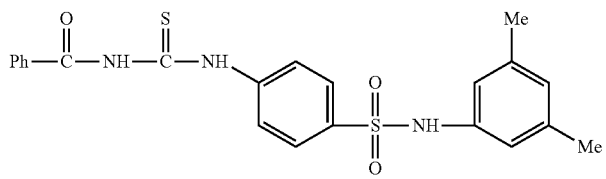
Answer 844:
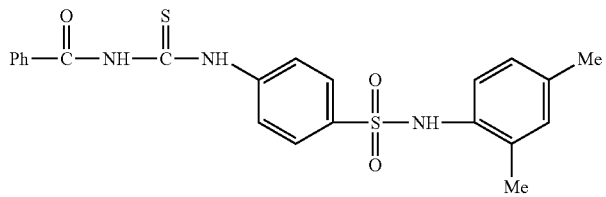
Answer 845:
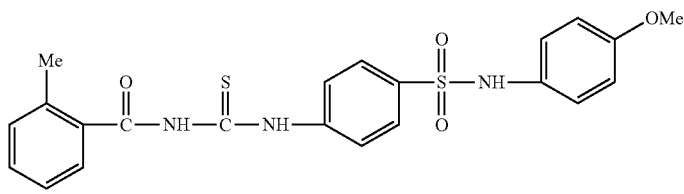
Answer 846:
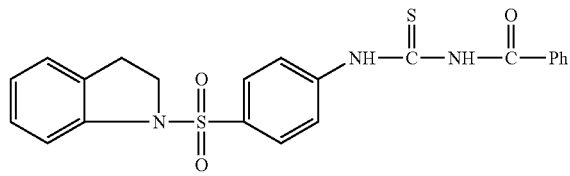
Answer 847:
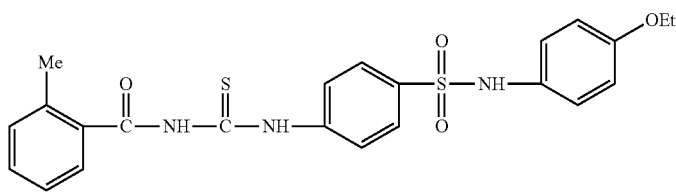
Answer 848:
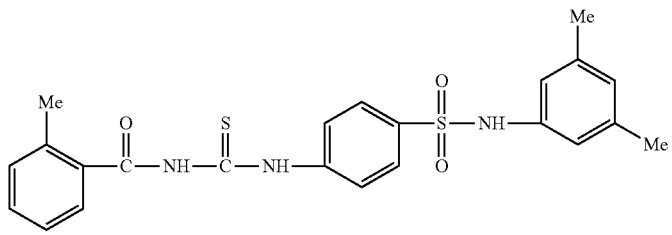

-continued
Answer 849:
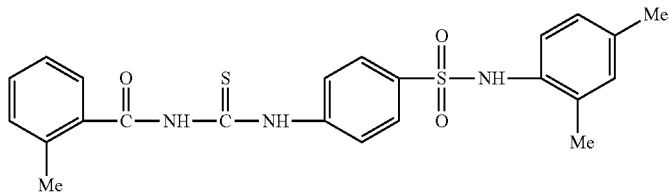
Answer 850:
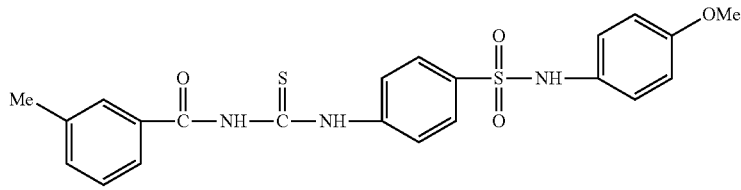
Answer 851:
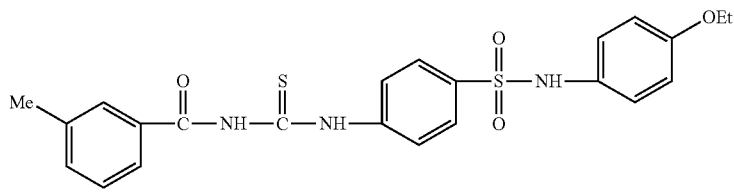
Answer 852:
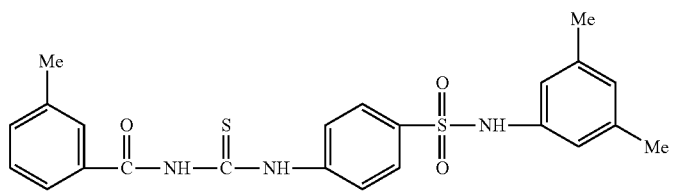
Answer 853:
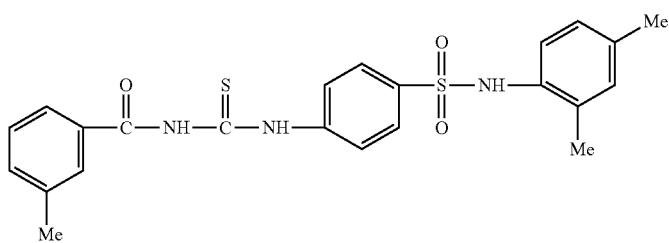
Answer 854:
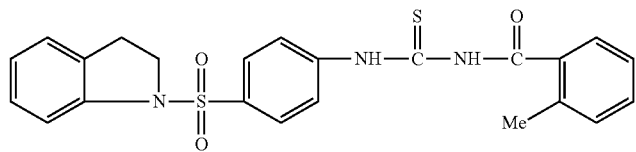
Answer 855:
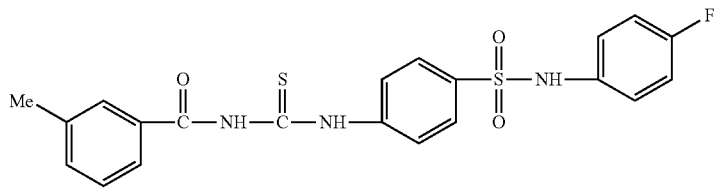

Answer 856:
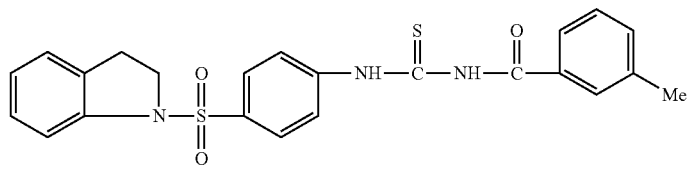
Answer 857:
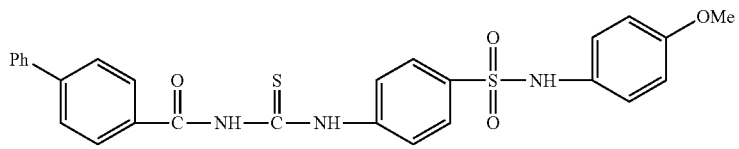
Answer 858:
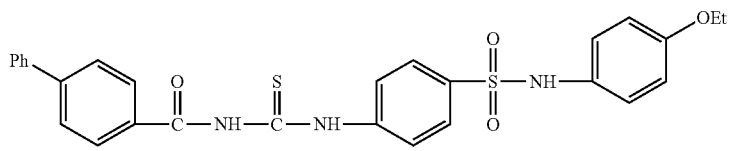
Answer 859:
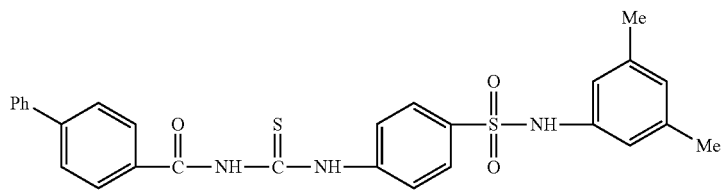
Answer 860:
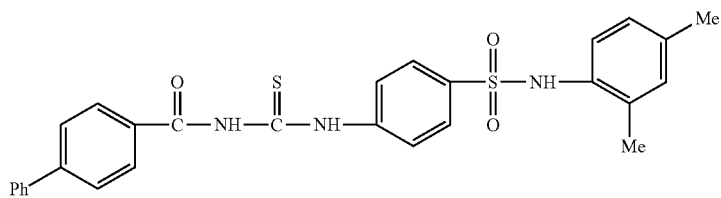
Answer 861:
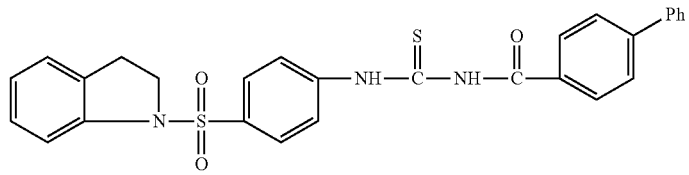
Answer 862:
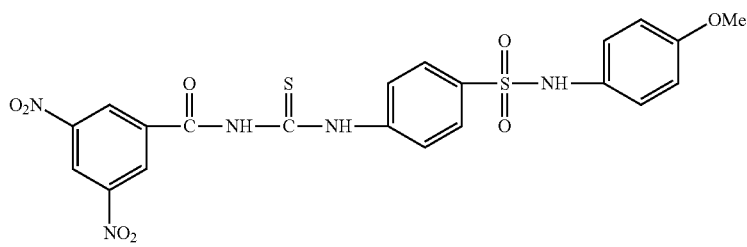

Answer 863:

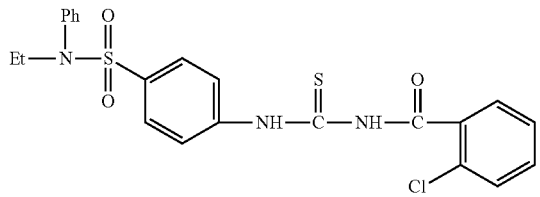

Answer 864:

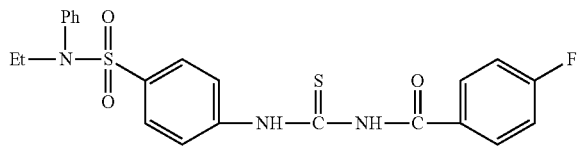

Answer 865:

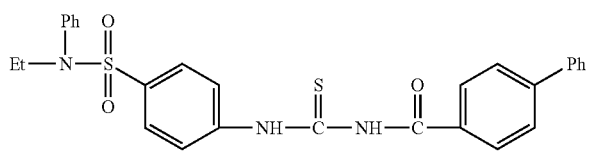

What is claimed is:

1. A compound of Formula I:

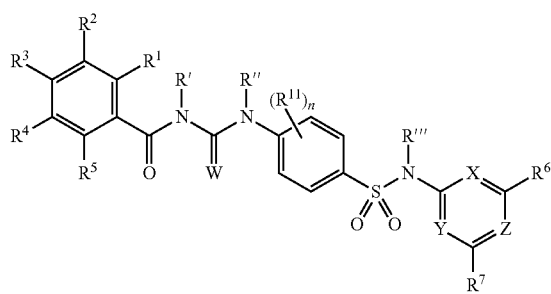

or a pharmaceutically acceptable salt thereof; wherein:
X is N, Y is N, and Z is CH;
X is N, Y is CH, and Z is N;
R', R'', and R''' are each independently selected from H and $C_{1-3}$ alkyl;
$R^1$, $R^2$, $R^3$, $R^4$, and $R^5$ are each independently selected from H, halogen, cyano, hydroxyl, carboxyl, carbamyl, $C_{1-6}$ alkyl, $C_{1-6}$ haloalkyl, $C_{2-6}$ alkenyl, $C_{2-6}$ alkenyl, $C_{1-6}$ alkoxy, $C_{1-6}$ haloalkoxy, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylthio, $C_{1-6}$ alkylsulfinyl, and $C_{1-6}$ alkylsulfonyl;
$R^6$ and $R^7$ are each $C_{1-6}$ alkyl;
n is 0;
W is O;
each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl
provided that:
when the compound has Formula I, W is O, X is N, Y is N, and Z is $CR^{10}$, then the following provisos apply:
(a) when $R^6$ and $R^7$ are each methyl, $R^{10}$ is H, and $R^1$, $R^2$, $R^4$, and $R^5$ are H, then $R^3$ is not methoxy or chloro; and
(b) when $R^6$ and $R^7$ are each methyl and $R^{10}$ is H, then at least one of $R^1$, $R^2$, $R^3$, $R^4$, and $R^5$ is other than H.

2. The compound according to claim 1, or a pharmaceutically acceptable salt thereof, wherein $R^1$, $R^2$, $R^3$, $R^4$, and $R^5$ are each independently selected from H and halogen.

3. The compound according to claim 1, or a pharmaceutically acceptable salt thereof, wherein $R^6$ and $R^7$ are each methyl.

4. The compound according to claim 1, wherein the compound is a compound of Formula Ia:

Ia or a pharmaceutically acceptable salt thereof.

5. The compound according to claim 1, which is selected from:
2,4-dichloro-N-(4-(N-(4,6-dimethylpyrimidin-2-yl)sulfamoyl)phenylcarbamoyl)benzamide;
2-chloro-N-(4-(N-(4,6-dimethylpyrimidin-2-yl)sulfamoyl)phenylcarbamoyl)benzamide;

2,3-dichloro-N-(4-(N-(4,6-dimethylpyrimidin-2-yl)sulfamoyl)phenylcarbamoyl)benzamide;

3,4-dichloro-N-(4-(N-(4,6-dimethylpyrimidin-2-yl)sulfamoyl)phenylcarbamoyl)benzamide;

2,4-dichloro-N-((4-(N-(4,6-dimethylpyrimidin-2-yl)sulfamoyl)phenyl)(methyl)carbamoyl)benzamide;

2,4-dichloro-N-(4-(N-(4,6-dimethylpyrimidin-2-yl)-N-methylsulfamoyl)phenylcarbamoyl)benzamide;

2,4-dichloro-N-(4-(N-(2,6-dimethylpyrimidin-4-yl)sulfamoyl)phenylcarbamoyl)benzamide; and 2,4-dichloro-N-(4-(N-(4,6-dimethylpyrimidin-2-yl)sulfamoyl)phenylcarbamoyl)-N-methylbenzamide;

or a pharmaceutically acceptable salt thereof.

6. A compound according to claim 1, which is selected from:

2,4-dichloro-N-(2-(diethylamino)ethyl)-N-((4-(N-(4,6-dimethylpyrimidin-2-yl)sulfamoyl)phenyl)carbamoyl)benzamide; and 2,4-dichloro-N-((4-(N-(2-(diethylamino)ethyl)-N-(4,6-dimethylpyrimidin-2-yl)sulfamoyl)phenyl)carbamoyl)benzamide;

or a pharmaceutically acceptable salt thereof.

7. A compound according to claim 1, which is 2,4-dichloro-N-(4-(N-(4,6-dimethylpyrimidin-2-yl)sulfamoyl)phenylcarbamoyl)benzamide; or a pharmaceutically acceptable salt thereof.

8. A pharmaceutical composition comprising a compound of claim 1, or a pharmaceutically acceptable salt thereof.

9. A method of treating a disorder selected from obesity, type 2 diabetes, non-alcoholic fatty liver disease, asthma, hyperlipidemia, coronary artery disease, arthritis, gallstones, and atherosclerosis in a patient in need thereof, comprising administering to said patient a compound of claim 1, or a pharmaceutically acceptable salt thereof.

10. A pharmaceutical composition comprising a compound of claim 7, or a pharmaceutically acceptable salt thereof, and a pharmaceutically acceptable carrier.

11. The pharmaceutical composition according to claim 8, wherein the compound is selected from:

4-chloro-N-(4-(N-(4,6-dimethylpyrimidin-2-yl)sulfamoyl)phenylcarbamoyl)benzamide; and 2,4-dichloro-N-(3-(N-(4,6-dimethylpyrimidin-2-yl)sulfamoyl)phenylcarbamoyl)benzamide;

or a pharmaceutically acceptable salt thereof.

12. A method of treating obesity, type 2 diabetes, non-alcoholic fatty liver disease, asthma, hyperlipidemia, coronary artery disease, arthritis, gallstones, and atherosclerosis in a patient in need thereof, comprising administering to said patient a compound of Formula I:

I or a pharmaceutically acceptable salt thereof, wherein:

X is N, Y is N, and Z is CH; or

X is N, Y is CH, and Z is N; or

R', R", and R'" are each independently selected from H and $C_{1-3}$ alkyl;

$R^1$, $R^2$, $R^3$, $R^4$, and $R^5$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylthio, $C_{1-6}$ alkylsulfinyl, and $C_{1-6}$ alkylsulfonyl;

$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylthio, and $C_{1-6}$ alkylsulfinyl, and $C_{1-6}$ alkylsulfonyl;

n is 0; and

W is O;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl.

13. The compound of claim 1, or a pharmaceutically acceptable salt thereof, wherein:

R', R", and R'" are each independently selected from H and methyl; and $R^1$, $R^2$, $R^3$, $R^4$, and $R^5$ are each independently selected from H and halogen.

14. The compound of claim 1, or a pharmaceutically acceptable salt thereof, wherein:

R', R", and R'" are each independently selected from H and methyl; and $R^1$, $R^2$, $R^3$, $R^4$, and $R^5$ are each independently selected from H and chloro.

15. The compound of claim 1, or a pharmaceutically acceptable salt thereof, having Formula Ib:

Ib or a pharmaceutically acceptable salt thereof.

16. The method of claim 9, wherein the compound is the compound of claim 7, or a pharmaceutically acceptable salt thereof.

17. The method of claim 9, wherein the disorder is obesity.

18. The method of claim 9, wherein the disorder is type 2 diabetes.-

19. The method of claim 9, wherein the disorder is atherosclerosis.

20. The method of claim 9, wherein the disorder is non-alcoholic fatty liver disease.

21. The method of claim 9, wherein the disorder is asthma.

* * * * *

UNITED STATES PATENT AND TRADEMARK OFFICE
CERTIFICATE OF CORRECTION

PATENT NO. : 9,126,938 B2  
APPLICATION NO. : 13/390910  
DATED : September 8, 2015  
INVENTOR(S) : David Cohen et al.

Page 1 of 1

It is certified that error appears in the above-identified patent and that said Letters Patent is hereby corrected as shown below:

Claims

In Column 419, Line 55, Claim 1, delete "alkenyl," and insert -- alkynyl --,

In Column 419, Line 65, Claim 1, delete "alkylamino," and insert -- $C_{1-6}$ alkylamino, --, In Column 422, Line 28, Claim 12, delete "alkylamino," and insert -- $C_{1-6}$ alkylamino, --.

Signed and Sealed this
Twenty-sixth Day of July, 2016

Michelle K. Lee
*Director of the United States Patent and Trademark Office*